United States Patent
Takahashi et al.

(10) Patent No.: US 11,839,153 B2
(45) Date of Patent: *Dec. 5, 2023

(54) COMPOUND, MATERIAL FOR ORGANIC ELECTROLUMINESCENT ELEMENT, ORGANIC ELECTROLUMINESCENT ELEMENT, AND ELECTRONIC DEVICE

(71) Applicant: IDEMITSU KOSAN CO.,LTD., Tokyo (JP)

(72) Inventors: Ryota Takahashi, Sodegaura (JP); Hidetsugu Ikeda, Sodegaura (JP); Yuki Nakano, Sodegaura (JP)

(73) Assignee: IDEMITSU KOSAN CO.,LTD., Tokyo (JP)

( * ) Notice: Subject to any disclaimer, the term of this patent is extended or adjusted under 35 U.S.C. 154(b) by 445 days.

This patent is subject to a terminal disclaimer.

(21) Appl. No.: 16/651,478

(22) PCT Filed: Oct. 9, 2018

(86) PCT No.: PCT/JP2018/037604
§ 371 (c)(1),
(2) Date: Mar. 27, 2020

(87) PCT Pub. No.: WO2019/070082
PCT Pub. Date: Apr. 11, 2019

(65) Prior Publication Data
US 2020/0266361 A1 Aug. 20, 2020

(30) Foreign Application Priority Data
Oct. 6, 2017 (JP) .............................. JP2017-196430

(51) Int. Cl.
| | |
|---|---|
| *H10K 85/60* | (2023.01) |
| *C07D 487/06* | (2006.01) |
| *C07D 487/22* | (2006.01) |
| *C09K 11/06* | (2006.01) |
| *H10K 50/11* | (2023.01) |
| *H10K 50/15* | (2023.01) |
| *H10K 101/10* | (2023.01) |

(52) U.S. Cl.
CPC ....... *H10K 85/6572* (2023.02); *C07D 487/06* (2013.01); *C07D 487/22* (2013.01); *C09K 11/06* (2013.01); *H10K 50/11* (2023.02); *H10K 50/15* (2023.02); *H10K 2101/10* (2023.02)

(58) Field of Classification Search
CPC .................................................. H01L 51/0072
USPC ........................................................ 428/690
See application file for complete search history.

(56) References Cited

U.S. PATENT DOCUMENTS

2014/0319507 A1   10/2014   Yamamoto et al.

FOREIGN PATENT DOCUMENTS

| CN | 108026106 A | | 5/2018 |
|---|---|---|---|
| CN | 110291654 A | | 9/2019 |
| EP | 3 584 850 A1 | | 12/2019 |
| KR | 2014-0034710 A | | 3/2014 |
| KR | 2017-0094771 A | | 8/2017 |
| KR | 2017-0126814 A | | 11/2017 |
| KR | 2017126814 A | * | 11/2017 |
| KR | 2018-0008336 A | | 1/2018 |
| WO | WO-2013/077344 A1 | | 5/2013 |
| WO | WO-2014/106522 A1 | | 7/2014 |
| WO | WO-2017/138755 A1 | | 8/2017 |
| WO | WO-2017/175690 A1 | | 10/2017 |
| WO | WO-2018/151065 A1 | | 8/2018 |

OTHER PUBLICATIONS

Extended European Search Report dated Apr. 13, 2021 for corresponding European Patent Application No. 18864771.3.
Notice of Reasons for Refusal issued in corresponding Japanese Patent Application No. 2019-547046 dated Jul. 5, 2022.
International Searching Authority, "International Search Report," issued in connection with International Patent Application No. PCT/JP2018/037604, dated Nov. 20, 2018.
International Searching Authority, "Written Opinion," issued in connection with International Patent Application No. PCT/JP2018/037604, dated Nov. 20, 2018.
Office Action issued in corresponding Chinese Patent Application No. 201880065063.1, dated Aug. 17, 2022.
Office Action issued in corresponding Korean Patent Application No. 10-2020-7009475, dated May 30, 2023.

\* cited by examiner

*Primary Examiner* — Taofiq A Solola
(74) *Attorney, Agent, or Firm* — Foley & Lardner LLP

(57) ABSTRACT

A compound represented by formula (1) as defined, wherein in any one pair selected from $R^4$ and $R^5$, $R^5$ and $R^6$, and $R^6$ and $R^7$, one member represents a single bond bonded to *a of a group represented by the formula (11), and the other member represents a single bond bonded to *b, in any one pair selected from $R^1$ and $R^2$, $R^2$ and $R^3$, $R^8$ and $R^9$, $R^9$ and $R^{10}$, and $R^{10}$ and $R^{11}$, one member represents a single bond bonded to *a of a group represented by the formula (11) and the other member represents a single bond bonded to *b, or one member represents a single bond bonded to *c of a group represented by the formula (21), and the other member represents a single bond bonded to *d, and $R^1$ to $R^{11}$ except for the single bonds, Ar, and $R^{21}$ to $R^{24}$ are defined.

22 Claims, 1 Drawing Sheet

COMPOUND, MATERIAL FOR ORGANIC ELECTROLUMINESCENT ELEMENT, ORGANIC ELECTROLUMINESCENT ELEMENT, AND ELECTRONIC DEVICE

CROSS-REFERENCE TO RELATED APPLICATIONS

The present application claims priority under 35 U.S.C. § 371 to International Patent Application No. PCT/JP2018/037604, filed Oct. 9, 2018, which claims priority to and the benefit of Japanese Patent Application No. 2017-196430, filed on Oct. 6, 2017. The contents of these applications are hereby incorporated by reference in their entireties.

TECHNICAL FIELD

The present invention relates to a compound, a material for an organic electroluminescent device (which may be hereinafter abbreviated an "organic EL device") containing the compound, an organic EL device using the compound, and an electronic device including the organic EL device.

BACKGROUND ART

An organic EL device is generally constituted by an anode, a cathode, and an organic layer held between the electrodes. On application of a voltage between the electrodes, electrons from the cathode and holes from the anode are injected into a light emitting region, and the injected electrons and the injected holes are recombined with each other in the light emitting region to form an excited state. Light is emitted at the time when the excited state returns to the ground state.

Various compounds have been reported that are said to be useful for the production of an organic EL device.

PTL 1 describes a compound that has an amine trisubstituted with a 6-membered aryl group or heteroaryl group, in which two of the 6-membered aryl groups or heteroaryl groups are connected to each other to form a condensed ring, and has an aryl group or a heteroaryl group as a substituent, in which the substituent is condensed to form a ring at the particular position.

PTL 2 describes an arylamine compound having two or more benzofluorene units that are connected to nitrogen.

CITATION LIST

Patent Literatures

PTL 1: WO 2013/077344
PTL 2: WO 2014/106522

SUMMARY OF INVENTION

Technical Problem

An object of the present invention is to provide a novel compound that is capable of enhancing the light emission efficiency of an organic EL device, a material for an organic EL device containing the compound, an organic EL device using the compound, and an electronic device including the organic EL device.

Solution to Problem

The present invention is based on the finding that as a result of the accumulated research and development for a compound having indolo[3,2,1-jk]carbazole as a basic skeleton, the compound that has the prescribed condensed rings at the two prescribed positions of the benzene ring of the basic skeleton is useful for the enhancement of the light emission efficiency of an organic EL device.

Specifically, the present invention provides, as one embodiment thereof, a compound represented by the following formula (1) (which may be hereinafter referred to as a "compound (1)"):

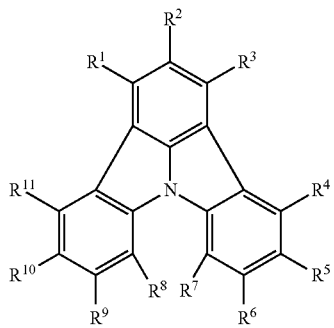

(1)

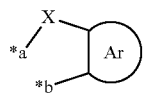

(11)

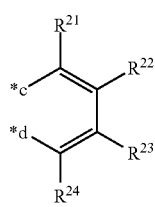

(21)

wherein in the formula (1), in any one pair selected from $R^4$ and $R^5$, $R^5$ and $R^6$, and $R^6$ and $R^7$, one member of the pair represents a single bond bonded to *a of a group represented by the formula (11), and the other member represents a single bond bonded to *b of the group represented by the formula (11), in any one pair selected from $R^1$ and $R^2$, $R^2$ and $R^3$, $R^8$ and $R^9$, $R^9$ and $R^{10}$, and $R^{10}$ and $R^{11}$, one member of the pair represents a single bond bonded to *a of a group represented by the formula (11), and the other member represents a single bond bonded to *b of the group represented by the formula (11), or one member of the pair represents a single bond bonded to *c of a group represented by the formula (21), and the other member represents a single bond bonded to *d of the group represented by the formula (21), $R^1$ to $R^{11}$ except for the single bonds each independently represent a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having from 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted alkylthio group having 1 to 20 carbon atoms, a substituted or unsubstituted aryl group having 6 to 50 ring carbon atoms, a substituted or unsubstituted aralkyl group having 7 to 51 carbon atoms, a substituted or unsubstituted aryloxy group having 6 to 50 ring carbon atoms, a substituted or unsubstituted arylthio group having 6 to 50 ring carbon atoms, a group represented by —Si(R$^{101}$)(R$^{102}$)(R$^{103}$), a group represented by —N(R$^{104}$)(R$^{105}$), or a substituted or unsubstituted heterocyclic group having 5 to 50 ring atoms, R$^{101}$ to R$^{105}$ each independently represent a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heterocyclic group having 5 to 50 ring atoms, X represents an oxygen atom (—O—), a sulfur atom (—S—), a group represented by —C(R$^{31}$)(R$^{32}$)—, or a group represented by —NR$^{33}$—, Ar represents a substituted or unsubstituted aromatic hydrocarbon ring having 6 to 18 ring carbon atoms or a substituted or unsubstituted aromatic heterocyclic group having 5 to 18 ring atoms, R$^{21}$ to R$^{24}$ each independently represent a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted alkylthio group having 1 to 20 carbon atoms, a substituted or unsubstituted aryl group having 6 to 50 ring carbon atoms, a substituted or unsubstituted aralkyl group having 7 to 51 carbon atoms, a substituted or unsubstituted aryloxy group having 6 to 50 ring carbon atoms, a substituted or unsubstituted arylthio group having 6 to 50 ring carbon atoms, a group represented by —Si(R$^{101}$)(R$^{102}$)(R$^{103}$) (wherein R$^{101}$ to R$^{103}$ have the same definitions as above), a group represented by —N(R$^{104}$)(R$^{105}$) (wherein R$^{104}$ and R$^{105}$ have the same definitions as above), or a substituted or unsubstituted heterocyclic group having 5 to 50 ring atoms, or adjacent two groups selected from R$^{21}$ to R$^{24}$ form a substituted or unsubstituted ring structure, and R$^{31}$ to R$^{33}$ each independently represent a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted alkylthio group having 1 to 20 carbon atoms, a substituted or unsubstituted aryl group having 6 to 50 ring carbon atoms, a substituted or unsubstituted aralkyl group having 7 to 51 carbon atoms, a substituted or unsubstituted aryloxy group having 6 to 50 ring carbon atoms, a substituted or unsubstituted arylthio group having 6 to 50 ring carbon atoms, a group represented by —Si(R$^{101}$)(R$^{102}$)(R$^{103}$) (wherein R$^{101}$ to R$^{103}$ have the same definitions as above), a group represented by —N(R$^{104}$)(R$^{105}$) (wherein R$^{104}$ and R$^{105}$ have the same definitions as above), or a substituted or unsubstituted heterocyclic group having 5 to 50 ring atoms, or R$^{31}$ and R$^{32}$ form a substituted or unsubstituted ring structure.

The present invention also provides, as another embodiment thereof, a compound represented by the following formula (1) (which may be hereinafter referred to as a "compound (1)"):

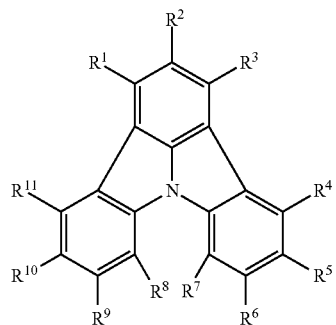

(1)

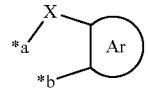

(11)

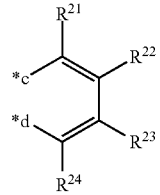

(21)

wherein in the formula (1), in any one pair selected from R$^4$ and R$^5$, R$^5$ and R$^6$, and R$^6$ and R$^7$, one member of the pair represents a single bond bonded to *a of a group represented by the formula (11), and the other member represents a single bond bonded to *b of the group represented by the formula (11), in any one pair selected from R$^1$ and R$^2$, R$^2$ and R$^3$, R$^8$ and R$^9$, R$^9$ and R$^{10}$, and R$^{10}$ and R$^{11}$, one member of the pair represents a single bond bonded to *a of a group represented by the formula (11), and the other member represents a single bond bonded to *b of the group represented by the formula (11), or one member of the pair represents a single bond bonded to *c of a group represented by the formula (21), and the other member represents a single bond bonded to *d of the group represented by the formula (21), R$^1$ to R$^{11}$ except for the single bonds each independently represent a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having from 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted alkylthio group having 1 to 20 carbon atoms, a substituted or unsubstituted aryl group having 6 to 50 ring carbon atoms, a substituted or unsubstituted aralkyl group having 7 to 51 carbon atoms, a substituted or unsubstituted aryloxy group having 6 to 50 ring carbon atoms, a substituted or unsubstituted arylthio group having 6 to 50 ring carbon atoms, a group represented by —Si(R$^{101}$)(R$^{102}$)(R$^{103}$), a group represented by —N(R$^{104}$)(R$^{105}$), or a substituted or unsubstituted heterocyclic group having 5 to 50 ring atoms, R$^{101}$ to R$^{105}$ each independently represent a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 50 ring carbon atoms, or a substituted or unsubstituted heterocyclic group having 5 to 50 ring atoms, X represents an oxygen atom (—O—), a sulfur atom (—S—), a group represented by —C($R^{31}$)($R^{32}$)—, or a group represented by —$NR^{33}$—, Ar represents a substituted or unsubstituted aromatic hydrocarbon ring having 6 to 18 ring carbon atoms or a substituted or unsubstituted aromatic heterocyclic group having 5 to 18 ring atoms, $R^{21}$ to $R^{24}$ each independently represent a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted alkylthio group having 1 to 20 carbon atoms, a substituted or unsubstituted aryl group having 6 to 50 ring carbon atoms, a substituted or unsubstituted aralkyl group having 7 to 51 carbon atoms, a substituted or unsubstituted aryloxy group having 6 to 50 ring carbon atoms, a substituted or unsubstituted arylthio group having 6 to 50 ring carbon atoms, a group represented by *Si($R^{101}$)($R^{102}$)($R^{103}$) (wherein $R^{101}$ to $R^{103}$ have the same definitions as above), a group represented by —N($R^{104}$)($R^{105}$) (wherein $R^{104}$ and $R^{105}$ have the same definitions as above), or a substituted or unsubstituted heterocyclic group having 5 to 50 ring atoms, or adjacent two groups selected from $R^{21}$ to $R^{24}$ form a substituted or unsubstituted ring structure, and $R^{31}$ to $R^{33}$ each independently represent a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted alkylthio group having 1 to 20 carbon atoms, a substituted or unsubstituted aryl group having 6 to 50 ring carbon atoms, a substituted or unsubstituted aralkyl group having 7 to 51 carbon atoms, a substituted or unsubstituted aryloxy group having 6 to 50 ring carbon atoms, a substituted or unsubstituted arylthio group having 6 to 50 ring carbon atoms, a group represented by —Si($R^{101}$)($R^{102}$)($R^{103}$) (wherein $R^{101}$ to $R^{103}$ have the same definitions as above), a group represented by —N($R^{104}$)($R^{105}$) (wherein $R^{104}$ and $R^{105}$ have the same definitions as above), or a substituted or unsubstituted heterocyclic group having 5 to 50 ring atoms, or $R^{31}$ and $R^{32}$ form a substituted or unsubstituted ring structure, or $R^{33}$ forms a substituted or unsubstituted ring structure with at least one selected from adjacent $R^1$ to $R^{11}$ and Ar.

The present invention also provides, as still another embodiment thereof, a material for an organic EL device, containing the compound (1).

The present invention also provides, as still further another embodiment thereof, an organic EL device including an anode, a cathode, and an organic layer provided therebetween, the organic layer including a light emitting layer, at least one layer of the organic layer including the compound (1).

The present invention also provides, as still further another embodiment thereof, an electronic device including the organic EL device.

Advantageous Effects of Invention

The compound of the present invention can be used as a material for an organic EL device, and thereby can enhance the light emission efficiency of the organic EL device. Accordingly, an organic EL device including the compound of the present invention is useful for an electronic device.

DESCRIPTION OF EMBODIMENTS

Figure 1:
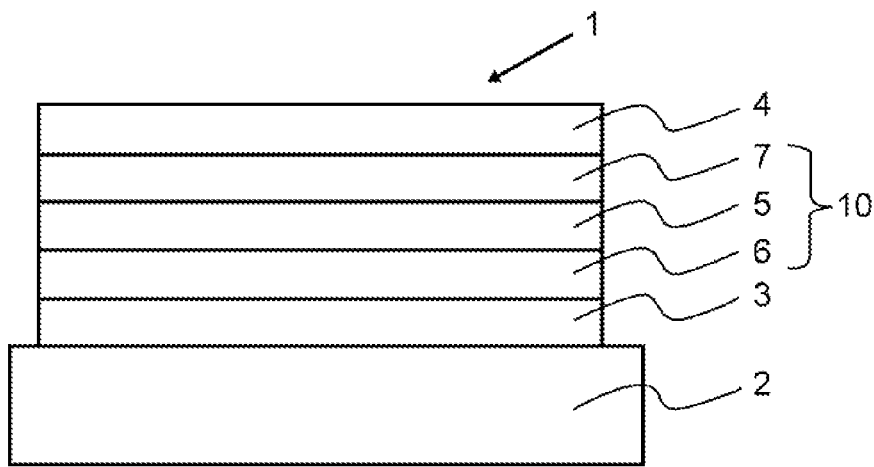
FIG. 1 is a schematic cross sectional view showing a layer structure of an organic EL device according to one embodiment of the present invention.

In the description herein, the "XX to YY carbon atoms" in the "substituted or unsubstituted ZZ group having XX to YY carbon atoms" means the number of carbon atoms of the unsubstituted ZZ group and does not include the number of carbon atoms of the substituent.

The "XX to YY atoms" in the "substituted or unsubstituted ZZ group having XX to YY atoms" means the number of atoms of the unsubstituted ZZ group and does not include the number of atoms of the substituent and the substituted atom.

The "unsubstituted ZZ group" in the "substituted or unsubstituted ZZ group" means that the hydrogen atom of the ZZ group is not substituted by a substituent or a substituted atom.

In the description herein, the "number of ring carbon atoms" means, in a compound having a structure including atoms bonded to form a ring (for example, a monocyclic compound, a condensed ring compound, a bridged compound, a carbocyclic compound, and a heterocyclic compound), the number of carbon atoms that form the ring itself. In the case where the ring has a substituent, the carbon atom contained in the substituent is not included in the number of ring carbon atoms unless otherwise indicated. For example, the number of ring carbon atoms of a benzene ring is 6, the number of ring carbon atoms of a naphthalene ring is 10, the number of ring carbon atoms of a pyridine ring is 5, and the number of ring carbon atoms of a furan ring is 4. In the case where a benzene ring or a naphthalene ring has, for example, an alkyl substituent, the carbon atom of the alkyl substituent is not included in the number of ring carbon atoms. In the case where a fluorene ring has a fluorene substituent (including a spirofluorene ring), the carbon atom of the fluorene substituent is not included in the number of ring carbon atoms.

In the description herein, the "number of ring atoms" means, in a compound including atoms bonded to form a ring (for example, a monocyclic compound, a condensed ring compound, a bridged compound, a carbocyclic compound, and a heterocyclic compound), the number of atoms that form the ring itself. The hydrogen atom bonded to the atom forming the ring, and in the case where the ring has a substituent, the atom constituting the substituent are not included in the number of ring atoms unless otherwise indicated. For example, the number of ring atoms of a pyridine ring is 6, the number of ring atoms of a quinazoline ring is 10, and the number of ring atoms of a furan ring is 5. The hydrogen atom and the atom constituting the substituent bonded to the ring carbon atom of a pyridine ring or a quinazoline ring are not included in the number of ring atoms. In the case where a fluorene ring has a fluorene substituent (including a spirofluorene ring), the atom constituting the fluorene substituent is not included in the number of ring atoms.

The atoms, the groups, and the ring structures represented by the symbols in the formulae shown in the description herein will be explained below.

(Hydrogen Atom: Specific Example Group G1)

The hydrogen atom includes isotopes having different neutron numbers, i.e., protium, deuterium, and tritium.

(Halogen Atom: Specific Example Group G2)

The halogen atom is a fluorine atom, a chlorine atom, a bromine atom, or an iodine atom, and preferably a fluorine atom.

(Alkyl Group: Specific Example Group G3)

The number of carbon atoms of the alkyl group is 1 to 20, preferably 1 to 10, and more preferably 1 to 6, unless otherwise indicated. The number of carbon atoms thereof may be, for example, 1 to 5, and also may be 1 to 4.

Specific examples of the alkyl group include a methyl group, an ethyl group, a n-propyl group, an isopropyl group, a n-butyl group, a s-butyl group, an isobutyl group, a t-butyl group, pentyl groups (including isomers), hexyl groups (including isomers), heptyl groups (including isomers), octyl groups (including isomers), nonyl groups (including isomers), decyl groups (including isomers), undecyl groups (including isomers), and dodecyl groups (including isomers). Specific examples of the substituted alkyl group include a fluoromethyl group, a 1-fluoroethyl group, a 2-fluoroethyl group, a 2-fluoroisobutyl group, a 1,2-difluoroethyl group, a 1,3-difluoroisopropyl group, a 2,3-difluoro-t-butyl group, a 1,2,3-trifluoropropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, and a 1,2,3-triiodopropyl group (Specific Example Group G3).

Among these, unless otherwise indicated, the alkyl group is preferably a methyl group, an ethyl group, a n-propyl group, an isopropyl group, a n-butyl group, an isobutyl group, a s-butyl group, a t-butyl group, or pentyl groups (including isomers), more preferably a methyl group, an ethyl group, a n-propyl group, an isopropyl group, a n-butyl group, an isobutyl group, a s-butyl group, or a t-butyl group, and more preferably a methyl group, an ethyl group, an isopropyl group, or a t-butyl group.

(Alkenyl Group: Specific Example Group G4)

The number of carbon atoms of the alkenyl group is 1 to 20, preferably 1 to 10, and more preferably 1 to 6, unless otherwise indicated.

Specific examples of the alkenyl group include a vinyl group, a 2-propenyl group, a 2-butenyl group, a 3-butenyl group, a 4-pentenyl group, a 2-methyl-2-propenyl group, a 2-methyl-2-butenyl group, and a 3-methyl-2-butenyl group. (Specific Example Group G4).

(Alkynyl Group: Specific Example Group G5)

The number of carbon atoms of the alkynyl group is 1 to 20, preferably 1 to 10, and more preferably 1 to 6, unless otherwise indicated.

Specific examples of the alkynyl group include a 2-propynyl group, a 2-butynyl group, a 3-butynyl group, a 4-pentynyl group, a 5-hexynyl group, a 1-methyl-2-propynyl group, a 1-methyl-2-butynyl group, and a 1,1-dimethyl-2-propynyl group (Specific Example Group G5).

(Cycloalkyl Group: Specific Example Group G6)

The number of ring carbon atoms of the cycloalkyl group is 3 to 20, preferably 3 to 6, and more preferably 5 or 6, unless otherwise indicated.

Specific examples of the cycloalkyl group include a cyclopropyl group, a cyclobutyl group, a cyclopentyl group, a cyclohexyl group, a 4-methylcyclohexyl group, a cycloheptyl group, a cyclooctyl group, an adamantyl group, and a norbornyl group (Specific Example Group G6).

Among these, a cyclopentyl group and a cyclohexyl group are preferred unless otherwise indicated.

(Alkoxy Group: Specific Example Group G7)

The number of carbon atoms of the alkoxy group is 1 to 20, preferably 1 to 10, and more preferably 1 to 6, unless otherwise indicated.

The alkoxy group is a group represented by —$OR^4$, in which $R^4$ represents an alkyl group or a cycloalkyl group, and is a group selected, for example, from the specific examples of the alkyl group (Specific Example Group G3) and the specific examples of the cycloalkyl group (Specific Example Group G6) (Specific Example Group G7).

Among these, unless otherwise indicated, the alkoxy group is preferably a methoxy group, an ethoxy group, a n-propoxy group, an isopropoxy group, or a t-butoxy group.

(Alkylthio Group: Specific Example Group G8)

The number of carbon atoms of the alkylthio group is 1 to 20, preferably 1 to 10, and more preferably 1 to 6, unless otherwise indicated.

The alkylthio group is a group represented by —$SR^A$ ($R^A$ has the same definition as above) (Specific Example Group G8).

Among these, unless otherwise indicated, the alkylthio group is preferably a methylthio group, an ethylthio group, a n-propylthio group, an isopropylthio group, or a t-butylthio group.

(Aryl Group: Specific Example Group G9)

The number of ring carbon atoms of the aryl group is 6 to 50, preferably 6 to 30, and more preferably 6 to 24, unless otherwise indicated.

Specific examples of the aryl group include a phenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, a 1-naphthyl group, a 2-naphthyl group, an acenaphthylenyl group, a 1-anthryl group, a 2-anthryl group, a 9-anthryl group, a benzanthryl group, an aceanthryl group, a 1-phenanthryl group, a 2-phenanthryl group, a 3-phenanthryl group, a 4-phenanthryl group, a 9-phenanthryl group, a 1-napthacenyl group, a 2-naphthacenyl group, a 9-naphthacenyl group, a benzo[c]phenanthryl group, a phenalenyl group, a fluorenyl group, a picenyl group, a pentaphenyl group, a 1-pyrenyl group, a 2-pyrenyl group, a 4-pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group. Examples of the substituted aryl group include an o-tolyl group, a m-tolyl group, a p-tolyl group, a 2,6-dimethylphenyl group, a p-isopropylphenyl group, a m-isopropylphenyl group, an o-isopropylphenyl group, a p-t-butylphenyl group, a m-t-butylphenyl group, an o-t-butylphenyl group, a (2-phenylpropyl)phenyl group, 3,4,5-trimethylphenyl group, a 4-methoxyphenyl group, a 4-phenoxyphenyl group, a 3,4-dimethoxyphenyl group, a 3,4,5-trimethoxyphenyl group, a 4'-methylbiphenylyl group, a 4"-t-butyl-p-terphenyl-4-yl group, a 3-methyl-2-naphthyl group, a 4-methyl-1-naphthyl group, a 4-methyl-1-anthryl group, a 9,9-dimethylfluorenyl group, a 9,9-di(4-methylphenyl)fluorenyl group, a 9,9-di(4-isopropylphenyl)fluorenyl group, a 9,9-di(4-t-butylphenyl)fluorenyl group, a 9,9-diphenylfluorenyl group, a 9,9'-spirobifluorenyl group, a 4-(methylsulfanyl)phenyl group, a 4-(phenylsulfanyl)phenyl group, and an N',N'-dimethyl-N-phenyl group (Specific Example Group G9).

Among these, unless otherwise indicated, the aryl group is preferably a phenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, a 1-naphthyl group, a 2-naphthyl group, a 1-anthryl group, a 2-anthryl group, a 9-anthryl group, a 1-pyrenyl group, a 2-pyrenyl group, a 4-pyrenyl group, or a fluoranthenyl group, more preferably a phenyl group, a 2-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, or a m-terphenyl-2-yl group, and further preferably a phenyl group.

(Aralkyl Group: Specific Example Group G10)

The number of ring carbon atoms of the aralkyl group is 6 to 50, preferably 6 to 30, and more preferably 6 to 24, unless otherwise indicated. The number of carbon atoms of the aralkyl group is 7 to 51, preferably 7 to 30, and more preferably 7 to 20, unless otherwise indicated.

The aralkyl group is a group represented by —$R^B Ar^C$. $R^B$ represents an alkylene group, and for example, is an alkylene group obtained by removing one hydrogen atom from $R^A$, and $Ar^C$ represents an aryl group, and for example, is a group selected from the specific examples of the aryl group (Specific Example Group G9) (Specific Example Group G10).

Among these, unless otherwise indicated, the aralkyl group is preferably a benzyl group, a phenethyl group, or a phenylpropyl group, and more preferably a benzyl group.

(Aryloxy Group: Specific Example Group G11)

The number of ring carbon atoms of the aryloxy group is 6 to 50, preferably 6 to 25, and more preferably 6 to 18, unless otherwise indicated.

The aryloxy group is a group represented by —$SAr^C$ (in which $Ar^C$ has the same definition as above) (Specific Example Group G11).

Among these, unless otherwise indicated, the aryloxy group is preferably a phenoxy group, a biphenyloxy group, or a terphenyloxy group, more preferably a phenoxy group or a biphenyloxy group, and further preferably a phenoxy group.

(Arylthio Group: Specific Example Group G12)

The number of ring carbon atoms of the arylthio group is 6 to 50, preferably 6 to 25, and more preferably 6 to 18, unless otherwise indicated.

The arylthio group is a group represented by —$SAr^C$ (in which $Ar^C$ has the same definition as above) (Specific Example Group G12).

Among these, unless otherwise indicated, the arylthio group is preferably a phenylthio group, a biphenylthio group, or a terphenylthio group, more preferably a phenylthio group or a biphenylthio group, and further preferably a phenylthio group.

(Group Represented by —$Si(R^{101})(R^{102})(R^{103})$: Specific Example Group G13)

$R^{101}$ to $R^{103}$ in the group represented by —$Si(R^{101})(R^{102})(R^{103})$ each independently represent a hydrogen atom, a substituted or unsubstituted alkyl group having 1 to 20 (preferably 1 to 10, and more preferably 1 to 6) carbon atoms, a substituted or unsubstituted cycloalkyl group having 3 to 20 (preferably 3 to 6, and more preferably 5 or 6) ring carbon atoms, a substituted or unsubstituted aryl group having 6 to 50 (preferably 6 to 25, and more preferably 6 to 18) ring carbon atoms, or a substituted or unsubstituted heterocyclic group having 5 to 50 (preferably 5 to 24, and more preferably 5 to 13) ring atoms.

Specific examples of the group represented by —$Si(R^{101})(R^{102})(R^{103})$ include a group, in which $R^{101}$ to $R^{103}$ each independently represent a group represented by the specific examples of the alkyl group (Specific Example Group G3), the specific examples of the aryl group (Specific Example Group G9), or the specific examples of the heterocyclic group (Specific Example Group G15) described later (Specific Example Group G13).

Preferred examples of the group represented by —$Si(R^{101})(R^{102})(R^{103})$ include a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, and a tritolylsilyl group.

(Group Represented by —$N(R^{104})(R^{105})$: Specific Example Group G14)

$R^{104}$ and $R^{105}$ in the group represented by —$N(R^{104})(R^{105})$ have the same definitions as $R^{101}$ to $R^{103}$ described above.

Specific examples of the group represented by —$N(R^{104})(R^{105})$ include a group, in which $R^{104}$ and $R^{105}$ each independently represent a group represented by the specific examples of the alkyl group (Specific Example Group G3), the specific examples of the aryl group (Specific Example Group G9), or the specific examples of the heterocyclic group (Specific Example Group G15) described later (Specific Example Group G14).

Preferred examples of the group represented by —$N(R^{104})(R^{105})$ include a dimethylamino group, a diethylamino group, a diisopropylamino group, a diphenylamino group, and a dinaphthylamino group.

(Heterocyclic Group: Specific Example Group G15)

The number of ring atoms of the heterocyclic group is 3 to 50, preferably 5 to 24, and more preferably 5 to 13, unless otherwise indicated.

The heterocyclic group contains one atom or two or more atoms selected, for example, from a nitrogen atom, an oxygen atom, and a sulfur atom. The free valence of the heterocyclic group exists on the ring carbon atom or the ring hetero atom.

The heterocyclic group includes an aliphatic heterocyclic group and an aromatic heterocyclic group. Specific examples of the aliphatic heterocyclic group include an epoxy group, an oxetanyl group, a tetrahydrofuranyl group, a pyrrolopyridyl group, a piperidinyl group, and a morpholinyl group, and specific examples of the aromatic heterocyclic group include a pyrrolyl group, an imidazolyl group, a pyrazolyl group, a triazolyl group, a furyl group, a thienyl group, an oxazolyl group, an isoxazolyl group, an oxadiazolyl group, a thiazolyl group, an isothiazolyl group, a thiadiazolyl group, a pyridyl group, a pyridazinyl group, a pyrimidinyl group, a pyrazinyl group, a triazinyl group, an indolyl group, an isoindolyl group, an indolizinyl group, a quinolizinyl group, a quinolyl group, an isoquinolyl group, a cinnolinyl group, a phthalazinyl group, a quinazolinyl group, a quinoxalinyl group, a benzoimidazolyl group, an indazolyl group, a phenanthrolinyl group, a phenanthridinyl group, an acridinyl group, a phenazinyl group, a carbazolyl group, a benzocarbazolyl group, a xanthenyl group, a benzofuranyl group, an isobenzofuranyl group, a dibenzofuranyl group, a naphthobenzofuranyl group, a benzothiophenyl group (benzothienyl group), a dibenzothiophenyl group (dibenzothienyl group), and a naphthobenzothiophenyl group (naphthobenzothienyl group) (Specific Example Group G15).

Among these, unless otherwise indicated, the heterocyclic group is preferably a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, a naphthobenzofuranyl group, a dibenzothiophenyl group, a naphthobenzothiophenyl group, a carbazolyl group, or a benzocarbazolyl group.

(Ring Structure)

The ring stricture includes a condensed or non-condensed aromatic or aliphatic ring. Specific examples thereof include a substituted or unsubstituted aromatic hydrocarbon ring, a substituted or unsubstituted aliphatic hydrocarbon ring, a substituted or substituted aromatic heterocyclic ring, and a substituted or unsubstituted aliphatic heterocyclic ring.

The ring structure also includes a condensed or non-condensed ring including a combination of a substituted or unsubstituted aromatic hydrocarbon ring, a substituted or unsubstituted aliphatic hydrocarbon ring, a substituted or substituted aromatic heterocyclic ring, and a substituted or unsubstituted aliphatic heterocyclic ring.

<Aromatic Hydrocarbon Ring>

The number of ring carbon atoms of the aromatic hydrocarbon ring is 6 to preferably 6 to 25, and more preferably 6 to 18, unless otherwise indicated.

Specific examples of the aromatic hydrocarbon ring include a benzene ring, a biphenylene ring, a naphthalene ring, an anthracene ring, a benzanthracene ring, a phenanthrene ring, a benzphenanthrene ring, a phenalene ring, a pyrene ring, a chrysene ring, and a triphenylene ring.

Among these, a benzene ring and a naphthalene ring are preferred.

<Aliphatic Hydrocarbon Ring>

The number of ring carbon atoms of the aliphatic hydrocarbon ring is 5 to preferably 6 to 25, and more preferably 6 to 18, unless otherwise indicated.

Specific examples of the aliphatic hydrocarbon ring include a cyclopentene ring, a cyclopentadiene ring, a cyclohexene ring, a cyclohexadiene ring, and an aliphatic hydrocarbon ring obtained by partially hydrogenating the aromatic hydrocarbon ring.

<Aromatic Heterocyclic Ring>

The number of ring atoms of the aromatic heterocyclic ring is 5 to 30, preferably 6 to 25, and more preferably 6 to 18, unless otherwise indicated.

Specific examples of the aromatic heterocyclic ring include a pyrrole ring, a furan ring, a thiophene ring, a pyridine ring, an imidazole ring, a pyrazole ring, an indole ring, an isoindole ring, a benzofuran ring, an isobenzofuran ring, a benzothiophene ring, a benzoimidazole ring, an indazole ring, a dibenzofuran ring, a naphthobenzofuran ring, a dibenzothiophene ring, a naphthobenzothiophene ring, a carbazole ring, and a benzocarbazole ring.

<Aliphatic Heterocyclic Ring>

The number of ring atoms of the aliphatic heterocyclic ring is 5 to 30, preferably 6 to 25, and more preferably 6 to 18, unless otherwise indicated.

Specific examples of the aliphatic heterocyclic ring include an aliphatic heterocyclic ring obtained by partially hydrogenating the aromatic heterocyclic ring.

In the description herein, unless otherwise indicated, the arbitrary substituted atom or substituent in the expression "substituted or unsubstituted" is selected from the group consisting of a halogen atom, a cyano group, an alkyl group, an alkenyl group, an alkynyl group, a cycloalkyl group, an alkoxy group, an alkylthio group, an aryl group, an aralkyl group, an aryloxy group, an arylthio group, a group represented by —Si($R^{101}$)($R^{102}$)($R^{103}$), a group represented by —N($R^{104}$)($R^{105}$), a heterocyclic group, a nitro group, a hydroxy group, a carboxy group, a vinyl group, a carbonyl group having a group selected from an alkyl group and an aryl group, a sulfonyl group having a group selected from an alkyl group and an aryl group, a disubstituted phosphoryl group having a group selected from an alkyl group and an aryl group, an alkylcarbonyloxy group, an arylcarbonyloxy group, an alkylsulfonyloxy group, an arylsulfonyloxy group, and a (meth)acryloyl group, or arbitrary adjacent substituents form a substituted or unsubstituted ring structure. The details of the halogen atom, the alkyl group, the alkenyl group, the alkynyl group, the cycloalkyl group, the alkoxy group, the alkylthio group, the aryl group, the aralkyl group, the aryloxy group, the arylthio group, $R^{101}$ to $R^{105}$, and the heterocyclic group are as described above.

Among these, unless otherwise indicated, a halogen atom, a cyano group, an alkyl group, a cycloalkyl group, an aryl group, and a heterocyclic group are preferred.

[Compound]

The compound according to one embodiment of the present invention (i.e., the compound (1)) is represented by the formula (1).

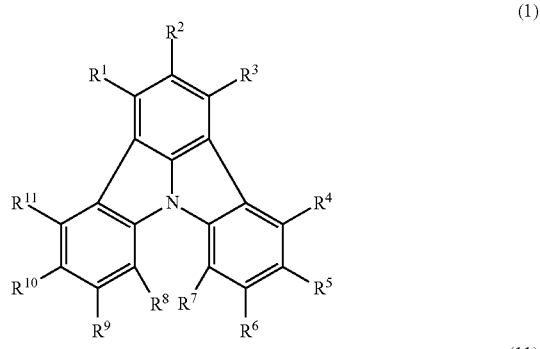

(1)

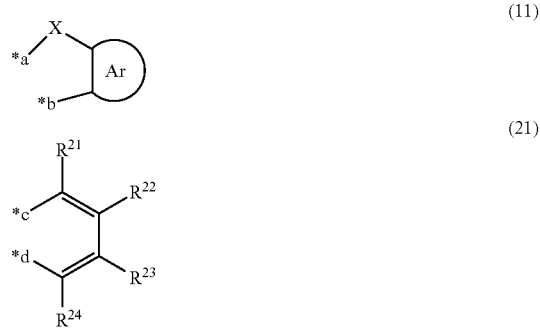

(11)

(21)

In the formula (1), in any one pair selected from $R^4$ and $R^5$, $R^5$ and $R^6$, and $R^6$ and $R^7$, and preferably in any one pair selected from $R^4$ and $R^5$, and $R^5$ and $R^6$, one member of the pair represents a single bond bonded to *a of a group represented by the formula (11), and the other member represents a single bond bonded to *b of the group represented by the formula (11).

In any one pair selected from $R^1$ and $R^2$, $R^2$ and $R^3$, $R^8$ and $R^9$, $R^9$ and $R^{10}$, and $R^{10}$ and $R^{11}$, one member of the pair represents a single bond bonded to *a of a group represented by the formula (11), and the other member represents a single bond bonded to *b of the group represented by the formula (11), or one member of the pair represents a single bond bonded to *c of a group represented by the formula (21), and the other member represents a single bond bonded to *d of the group represented by the formula (21).

In one embodiment of the compound (1), it is preferred that $R^1$ to $R^3$ each are not any of the single bonds, and only in any one pair selected from $R^8$ and $R^9$, $R^9$ and $R^{10}$, and $R^{10}$ and $R^{11}$, one member of the pair represents a single bond bonded to *a of a group represented by the formula (11), and the other member represents a single bond bonded to *b of the group represented by the formula (11). It is more preferred that $R^1$ to $R^3$ each are not any of the single bonds, and only in any one pair selected from $R^9$ and $R^{10}$, and $R^{10}$ and $R^{11}$, one member of the pair represents a single bond bonded to *a of a group represented by the formula (11), and the other member represents a single bond bonded to *b of the group represented by the formula (11).

In one embodiment of the compound (1), it is also preferred that $R^1$ to $R^3$ each are not any of the single bonds, and only in any one pair selected from $R^8$ and $R^9$, $R^9$ and $R^{10}$, and $R^{10}$ and $R^{11}$, one member of the pair represents a single bond bonded to *c of a group represented by the formula (21), and the other member represents a single bond bonded to *d of the group represented by the formula (21).

In the case where two or more groups represented by the formula (11) exist in the formula (1), the two groups may be the same as or different from each other.

A preferred embodiment of the compound (1) is represented by any of the following formulae (1-1) to (1-3). In the formulae (1-1) to (1-3), $R^1$ to $R^3$, $R^6$ to $R^9$, X, and Ar have the same definitions as above, provided that $R^1$ to $R^3$, $R^8$, and $R^9$ are not any of the single bonds.

One embodiment of the compound (1) is more preferably represented by the formula (1-1), and is also preferably represented by the formula (1-2). Accordingly, the compound (1) preferably has an axisymmetric structural formula represented by the formula (1-1) or (1-2) with the line connecting the nitrogen atom of the indolo[3,2,1-jk]carbazole skeleton and $R^2$ as the axis.

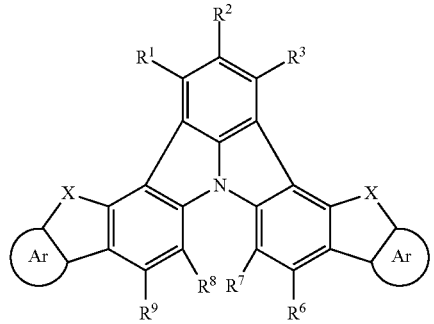

(1-1)

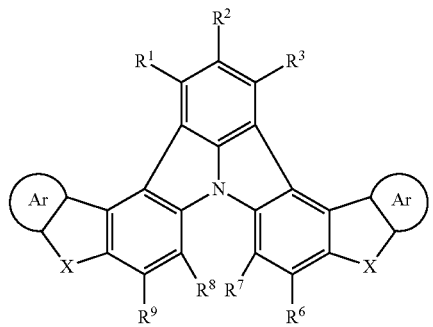

(1-2)

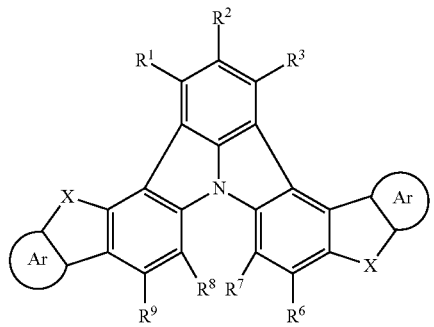

(1-3)

Another preferred embodiment of the compound (1) is represented by any of the following formulae (2-1) to (2-3). In the formulae (2-1) to (2-3), $R^1$ to $R^4$, $R^7$, $R^8$, $R^{11}$, X, and Ar have the same definitions as above, provided that $R^1$ to $R^3$ are not any of the single bonds.

One embodiment of the compound (1) is more preferably represented by the formula (2-1), and is also preferably represented by the formula (2-2). Accordingly, the compound (1) preferably has an axisymmetric structural formula represented by the formula (2-1) or (2-2) with the line connecting the nitrogen atom of the indolo[3,2,1-jk]carbazole skeleton and $R^2$ as the axis.

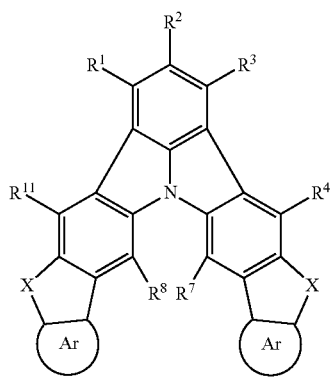

(2-1)

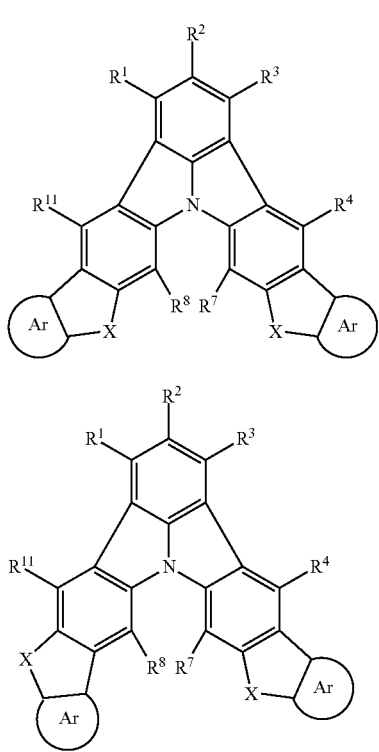

R¹ to R¹¹ except for the single bonds each independently represent a hydrogen atom, a halogen atom, a cyano group, a substituted or unsubstituted alkyl group having 1 to 20 carbon atoms, a substituted or unsubstituted alkenyl group having 1 to 20 carbon atoms, a substituted or unsubstituted alkynyl group having from 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted alkylthio group having 1 to 20 carbon atoms, a substituted or unsubstituted aryl group having 6 to 50 ring carbon atoms, a substituted or unsubstituted aralkyl group having 7 to 51 carbon atoms, a substituted or unsubstituted aryloxy group having 6 to 50 ring carbon atoms, a substituted or unsubstituted arylthio group having 6 to 50 ring carbon atoms, a group represented by $-Si(R^{101})(R^{102})(R^{103})$, a group represented by $-N(R^{104})(R^{105})$ or a substituted or unsubstituted heterocyclic group having 5 to 50 ring atoms.

R¹ to R¹¹ except for the single bonds each are preferably a hydrogen atom, a cyano group, a substituted or unsubstituted alkyl group having 1 to 20 carbon atoms, a substituted or unsubstituted aryl group having 6 to 50 ring carbon atoms, or a substituted or unsubstituted heterocyclic group having 5 to 50 ring atoms. In one preferred embodiment of the compound (1), R¹ to R¹¹ except for the single bonds are all hydrogen atoms.

In the formula (11), X represents an oxygen atom (—O—), a sulfur atom (—S—), a group represented by $-C(R^{31})(R^{32})-$, or a group represented by $-NR^{33}-$, and preferably an oxygen atom or a group represented by $-C(R^{31})(R^{32})-$.

R³¹ to R³³ have the same definitions as R¹ to R¹¹ except for the single bonds, or R³¹ and R³² form a substituted or unsubstituted ring structure. R³¹ and R³² each preferably independently represent a hydrogen atom, a substituted or unsubstituted alkyl group having 1 to 20 carbon atoms, or a substituted or unsubstituted aryl group having 6 to 50 ring carbon atoms. In one preferred embodiment, R³¹ and R³² are hydrogen atoms. R³³ preferably represents a hydrogen atom or a substituted or unsubstituted aryl group having 6 to 50 ring carbon atoms.

The ring structure formed by R³¹ and R³² becomes a spiro ring with the carbon atom bonded to R³¹ and R³² as the spiro atom. In the spiro ring, the ring atoms of the ring containing R³¹ and R³² are selected from arbitrary two or more atoms selected from a carbon atom, a nitrogen atom, an oxygen atom, and a sulfur atom. The number of ring atoms is preferably 3 to 15, more preferably 3 to 12, and further preferably 3 to 5. For example, in the case where the ring structure is formed with the carbon atom bonded to R³¹ and R³² and five carbon atoms, a cyclohexane ring can be formed as shown by the following formula (11-5). The formula (11-5) shows that all the five carbon atoms forming the cyclohexane ring each have two hydrogen atoms bonded thereto, and have no substituent, but the five carbon atoms each may have a substituent.

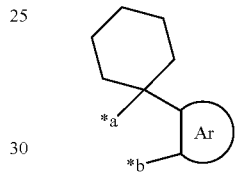

(11-5)

R³³ may form a substituted or unsubstituted ring structure with at least one selected from adjacent R¹ to R¹¹ and Ar. The number of ring atoms and the number thereof in the ring structure are the same as in the ring structure formed by R³¹ and R³².

In the formula (11), Ar represents a substituted or unsubstituted aromatic hydrocarbon ring having 6 to 18 ring carbon atoms or a substituted or unsubstituted aromatic heterocyclic group having 5 to 18 ring atoms. Ar preferably represents a substituted or unsubstituted benzene ring or a substituted or unsubstituted naphthalene ring. Accordingly, the group represented by the formula (11) is preferably represented by any of the following formulae (11-1) to (11-4), and more preferably represented by the formula (11-1), and is also preferably represented by the formula (11-3). In the formulae (11-1) to (11-4), R⁴¹ to R⁶² have the same definitions as R¹ to R¹¹ except for the single bonds.

In one preferred embodiment of each of the formulae (11-1) to (11-4), R⁴¹ to R⁴⁴, R⁴⁵ to R⁵⁰, R⁵¹ to R⁵⁶, and R⁵⁷ to R⁶² are all hydrogen atoms.

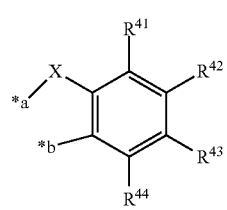

(11-1)

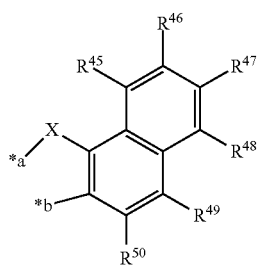

(11-2)

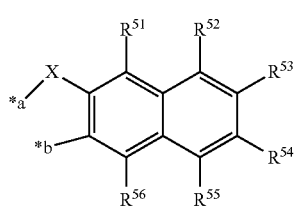

(11-3)

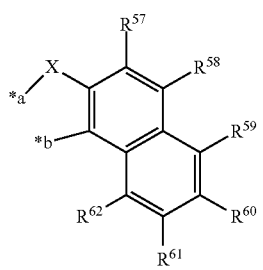

(11-4)

In one embodiment, the compound (1) is preferably a compound represented by any of the following formulae (1-11), (1-13), (1-21), (1-23), (2-11), (2-13), (2-21), and (2-23). In the formulae, $R^1$ to $R^4$, $R^6$ to $R^9$, $R^{41}$ to $R^{44}$, $R^{51}$ to $R^{56}$, and X have the same definitions as above. The groups represented by R with the same superscript number and the two groups represented by X each may represent the same atom or group or different atoms or groups (which is hereinafter the same).

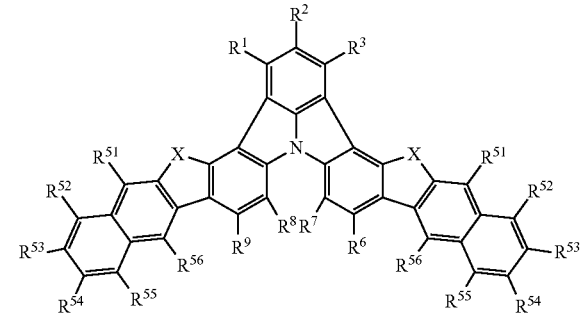

(2-13)
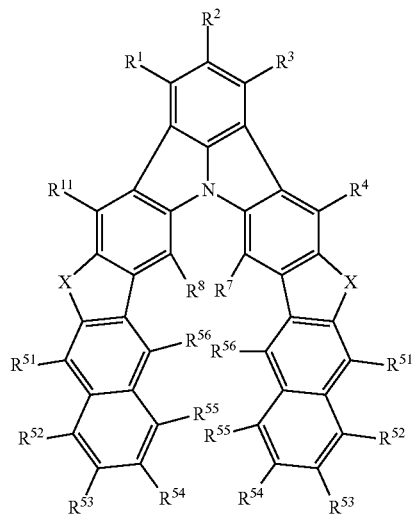
(1-11A)
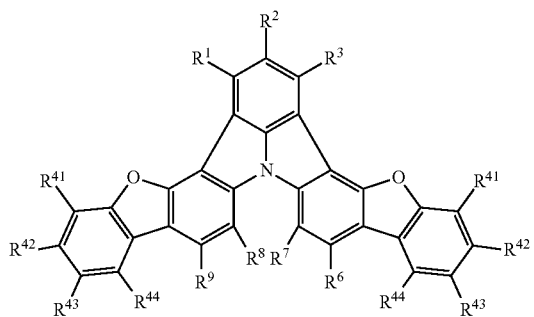
(2-21)
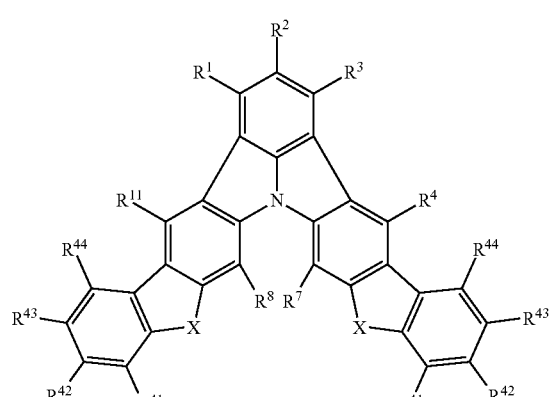
(1-13A)
(1-21A)
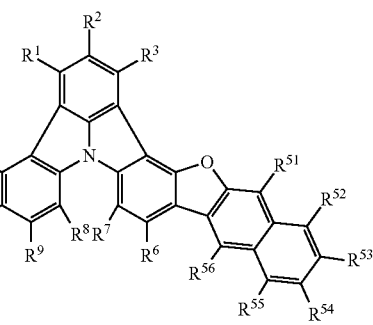
(2-23)
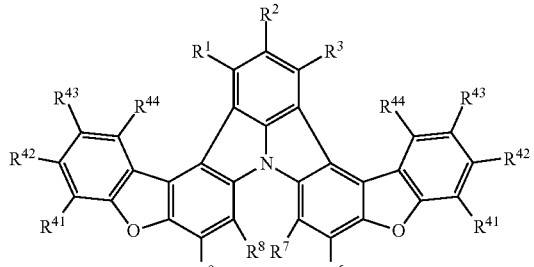
In one embodiment of the compound (1), two atoms represented by X are preferably oxygen atoms. Accordingly, in one embodiment, the compound (1) is preferably a compound represented by any of the following formulae (1-11A), (1-13A), (1-21A), (1-23A), (2-11A), (2-13A), (2-21A), and (2-23A). In the formulae, $R^1$ to $R^4$, $R^6$ to $R^9$, $R^{41}$ to $R^{44}$, and $R^{51}$ to $R^{56}$ have the same definitions as above.
(1-23A)
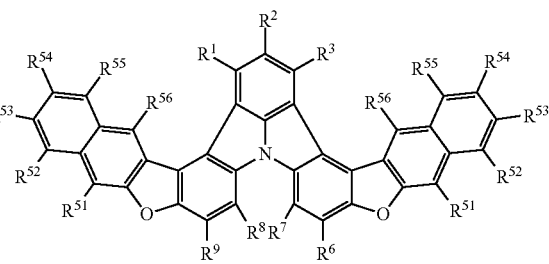

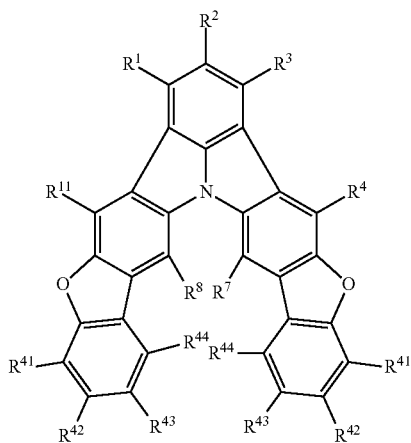

(2-11A)

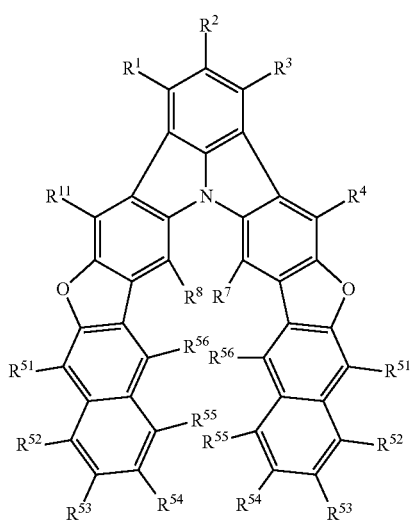

(2-13A)

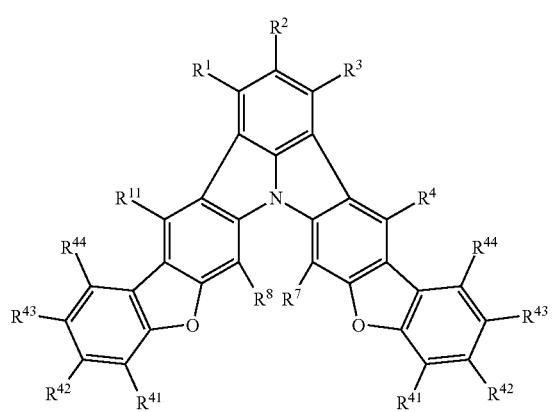

(2-21A)

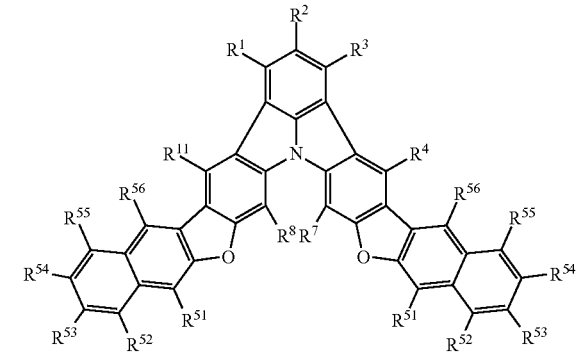

(2-23A)

In the formula (21), $R^{21}$ to $R^{24}$ have the same definitions as $R^1$ to $R^{11}$ except for the single bonds, or adjacent two groups selected from $R^{21}$ to $R^{24}$ form a substituted or unsubstituted ring structure. $R^{21}$ to $R^{24}$ each preferably independently represent a hydrogen atom, a substituted or unsubstituted alkyl group having 1 to 20 carbon atoms, or a substituted or unsubstituted aryl group having 6 to 50 ring carbon atoms. In one preferred embodiment, $R^{21}$ to $R^{24}$ are all hydrogen atoms.

The adjacent two groups in the ring structure formed by adjacent two groups selected from $R^{21}$ to $R^{24}$ mean pairs of $R^{21}$ and $R^{22}$, $R^{22}$ and $R^{23}$, and $R^{23}$ and $R^{24}$. The ring atoms and the number thereof in the ring structure are the same as in the ring structure formed by $R^{31}$ and $R^{32}$. For example, in the case where the ring structure is formed with the carbon atom bonded to $R^{21}$, the carbon atom bonded to $R^{22}$, and four carbon atoms, a benzene ring can be formed as shown by the following formula (21-1). In in the case where the ring structure is formed with the carbon atom bonded to $R^{22}$, the carbon atom bonded to $R^{23}$, and four carbon atoms, a benzene ring can be formed as shown by the following formula (21-2). The formulae (21-1) and (21-2) show that all four carbon atoms forming the benzene ring each have one hydrogen atom bonded thereto, and have no substituent, but the four carbon atoms each may have a substituent.

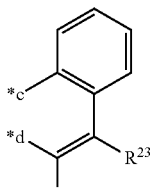

(21-1)

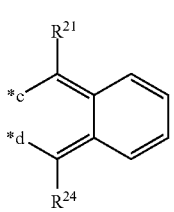

(21-2)

Specific examples of the compound (1) are shown below, but the compound of the present invention is not limited thereto.

-continued
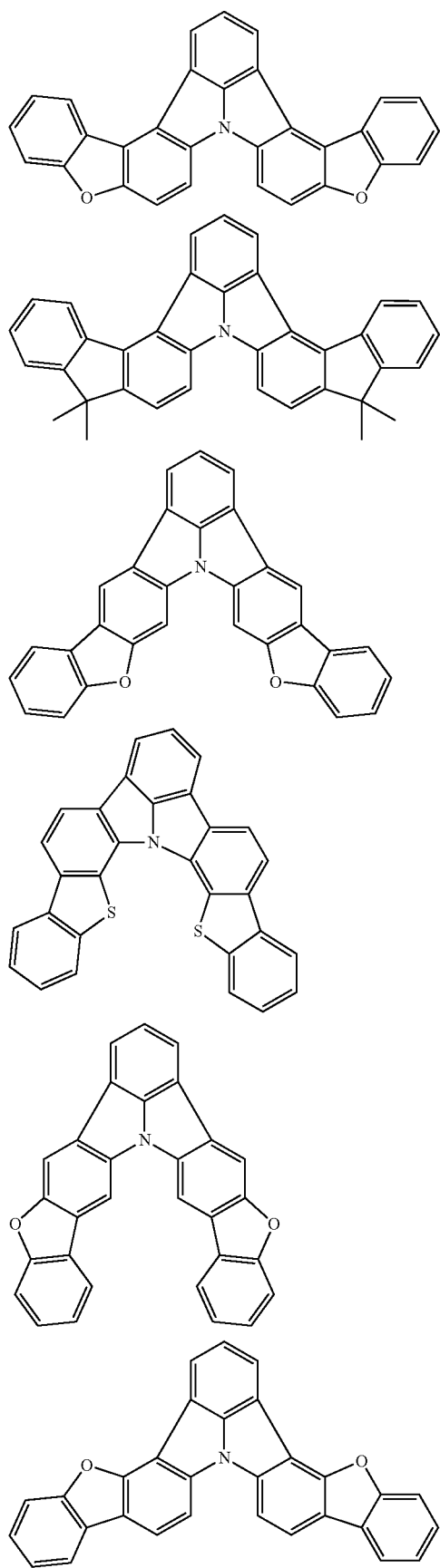
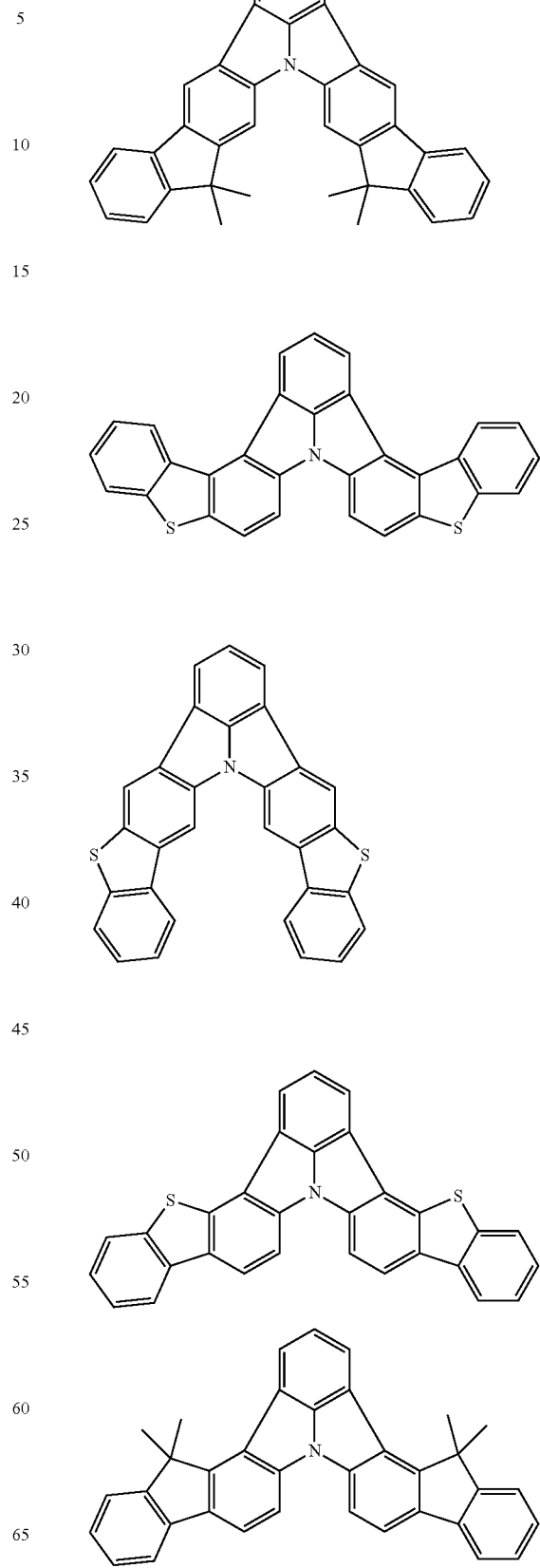

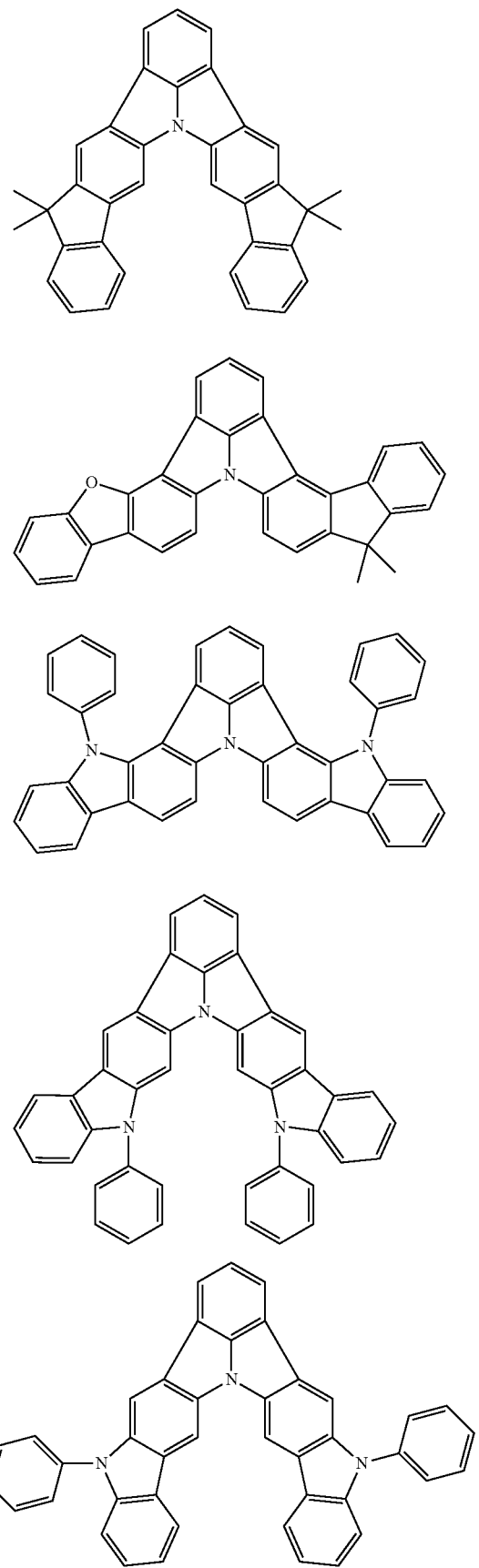
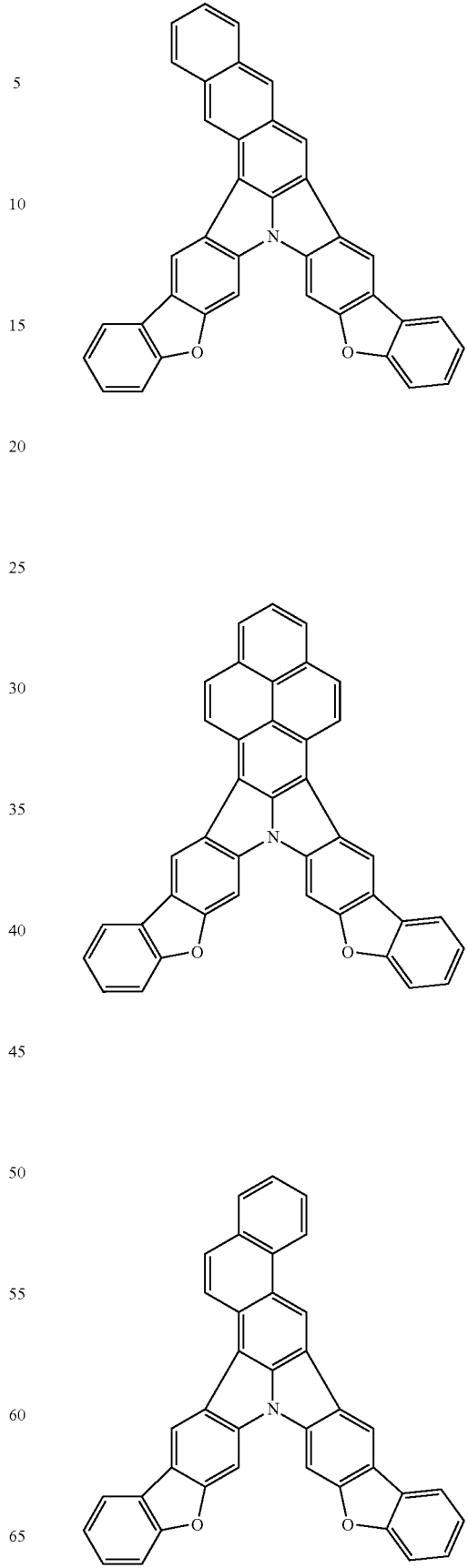

27
-continued
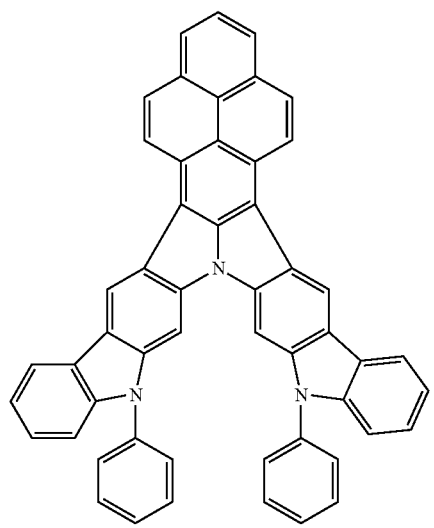
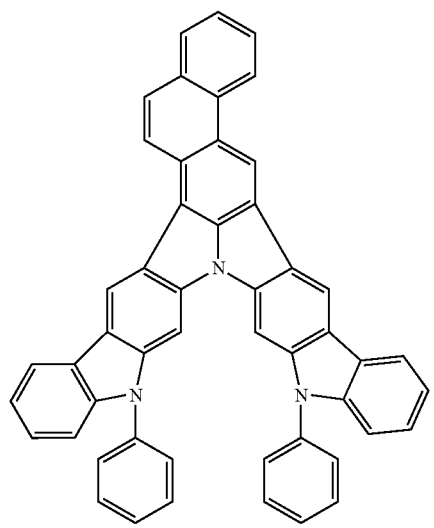
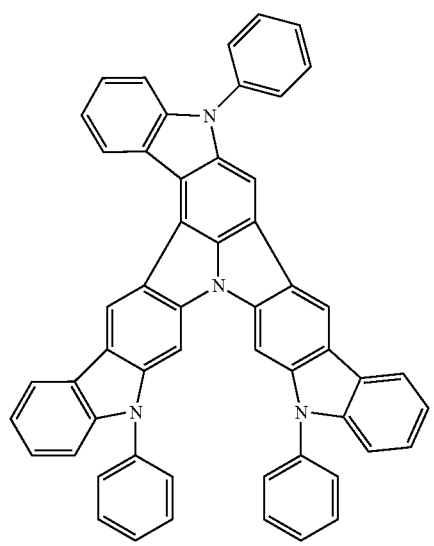
28
-continued
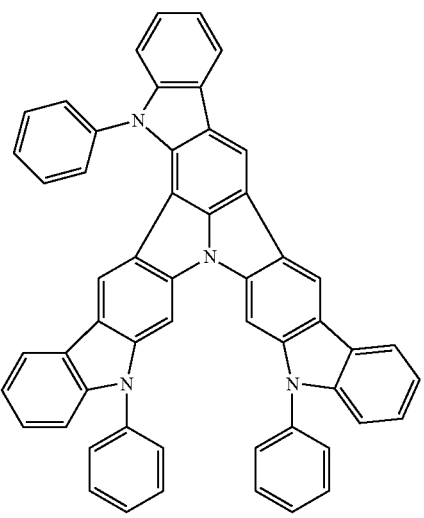
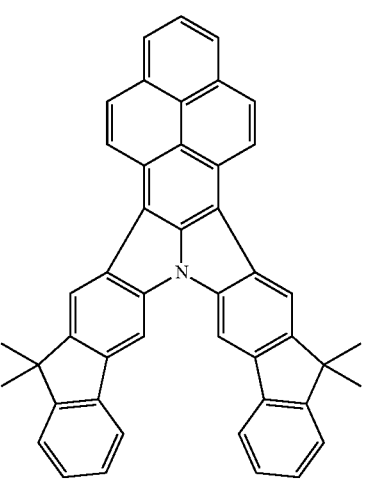
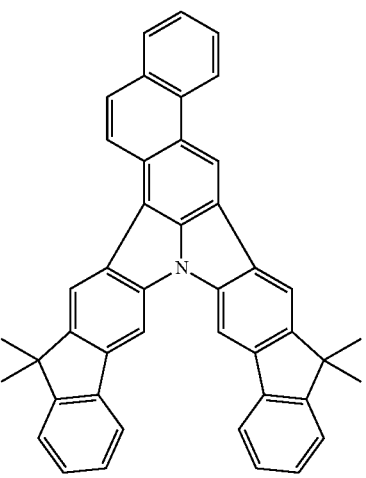

29
-continued
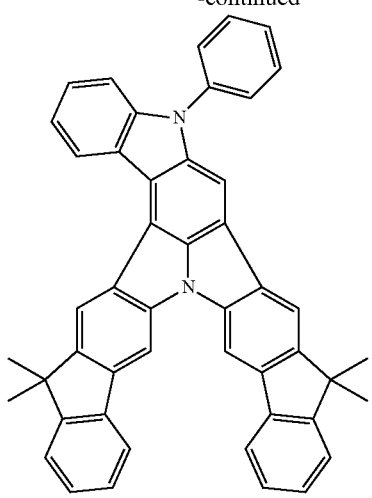
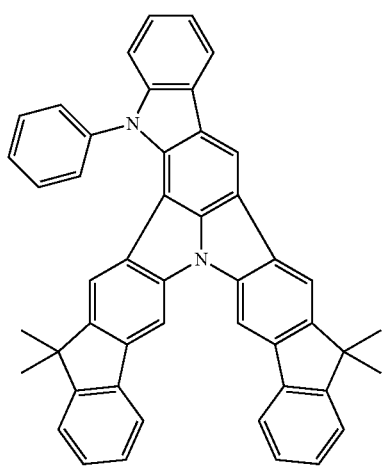
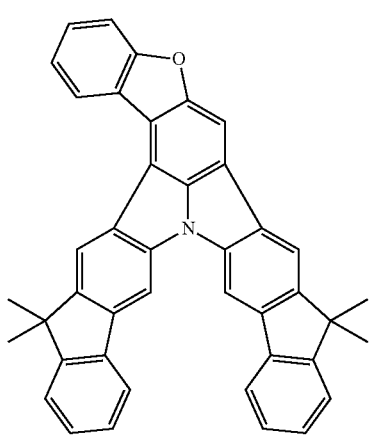
30
-continued
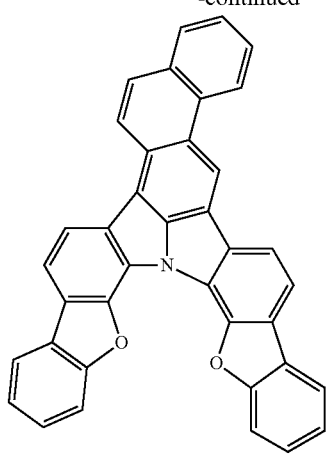
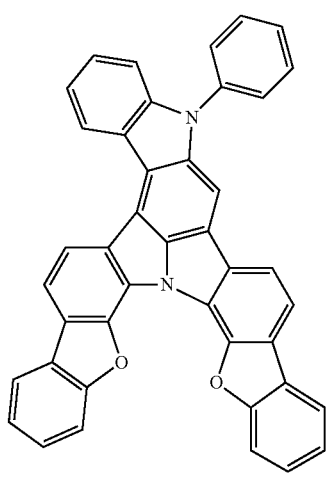
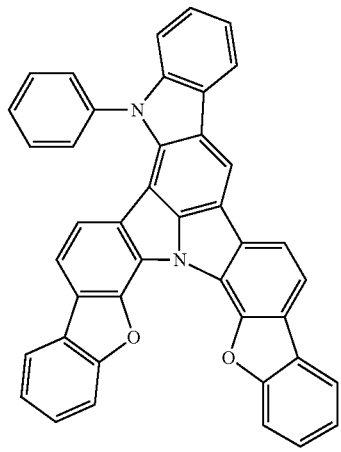

31
-continued
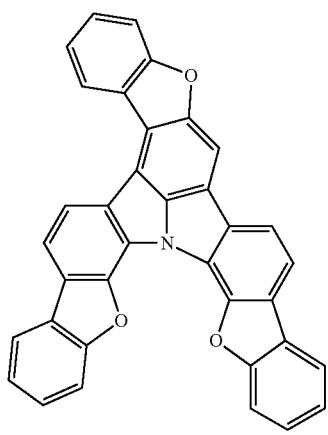
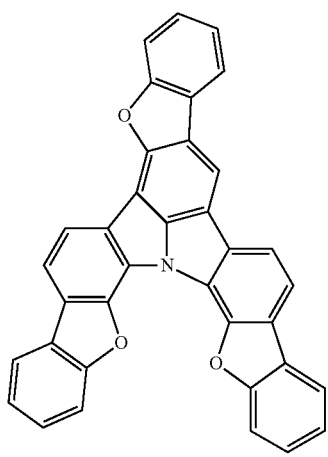
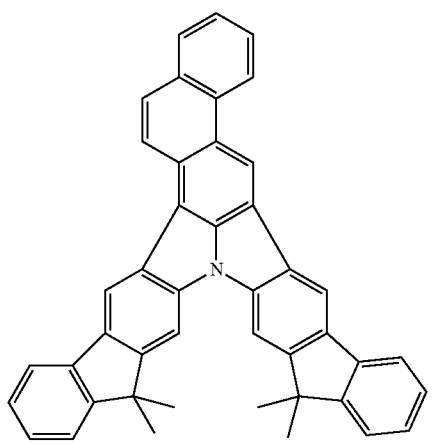
32
-continued
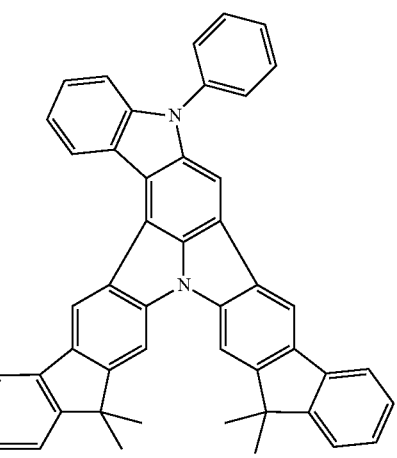
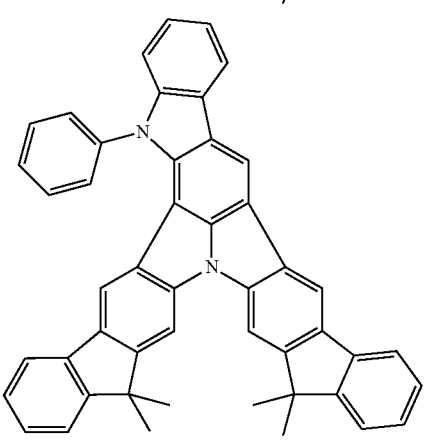
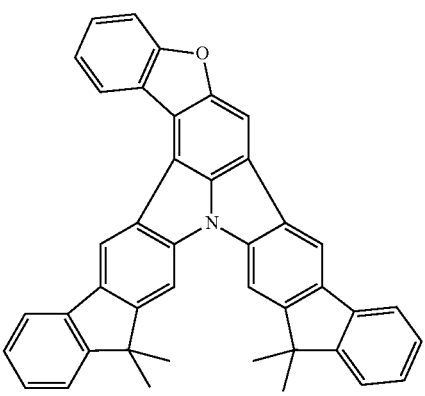
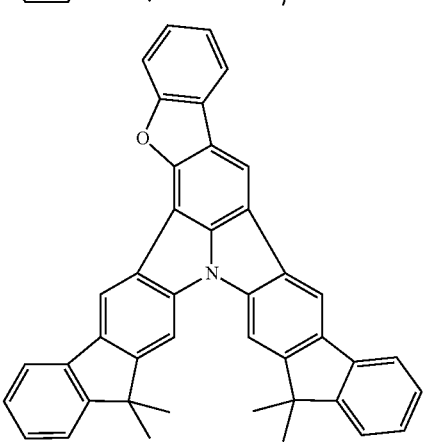

33
-continued
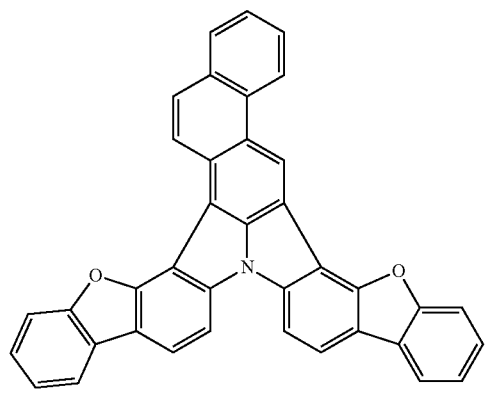
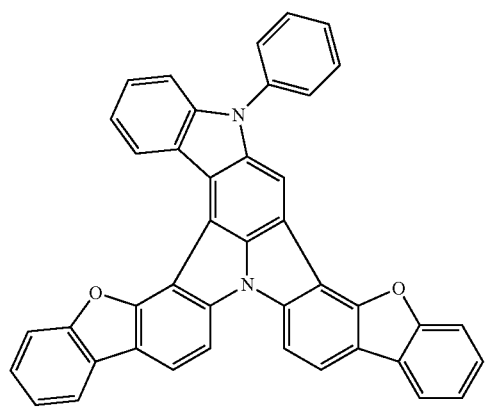
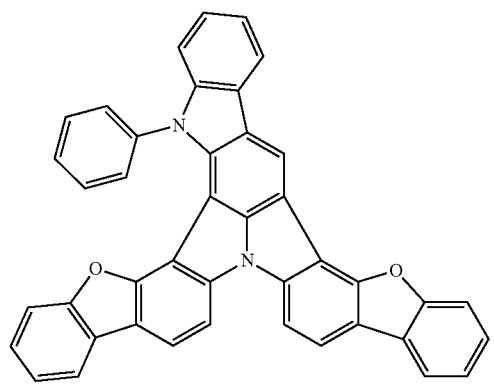
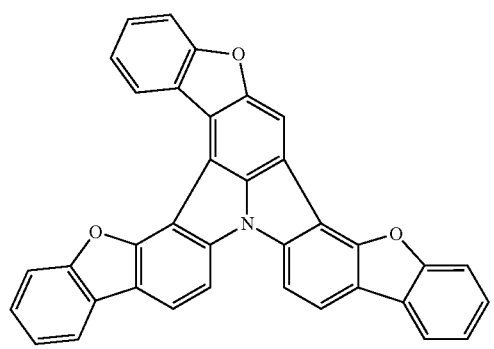
34
-continued
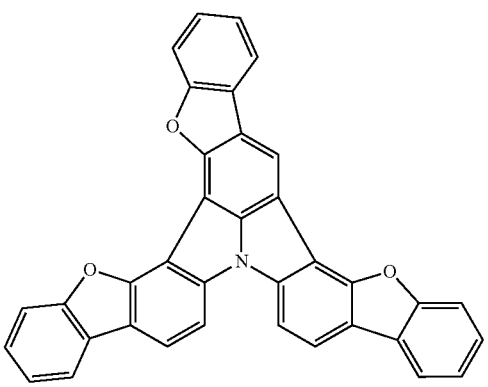
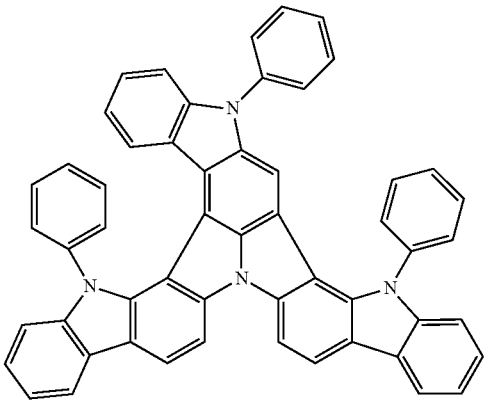
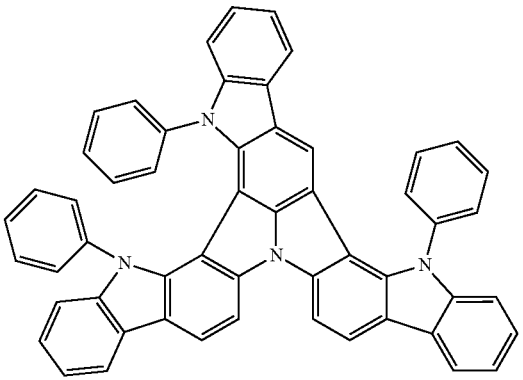
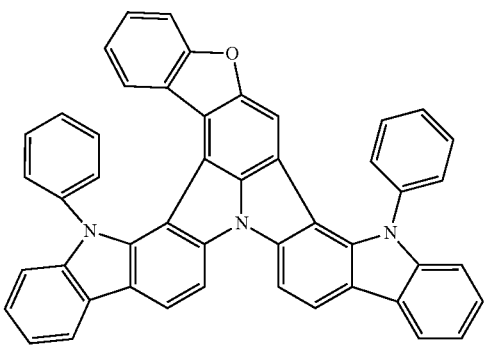

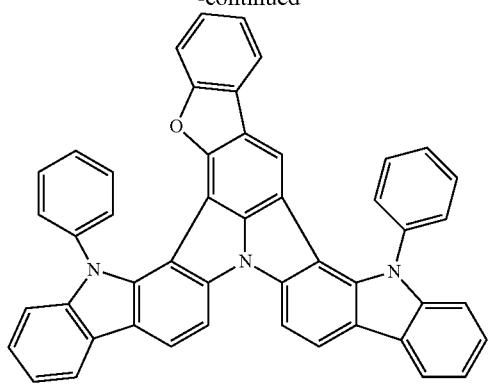
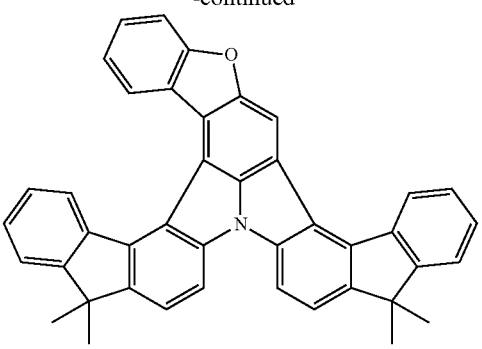
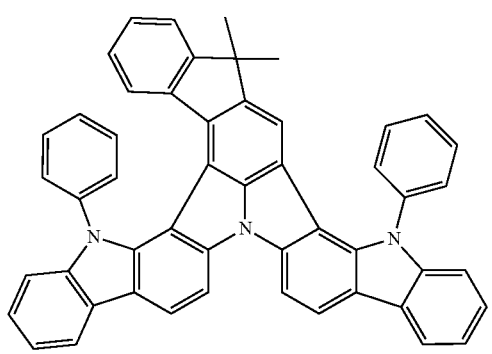
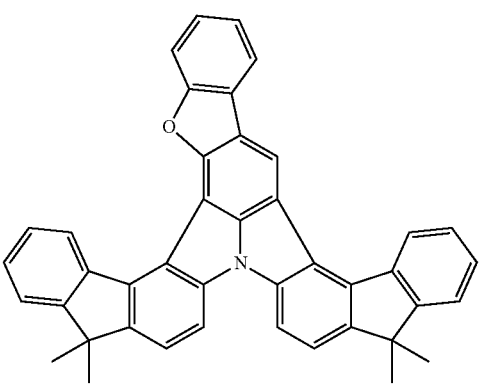
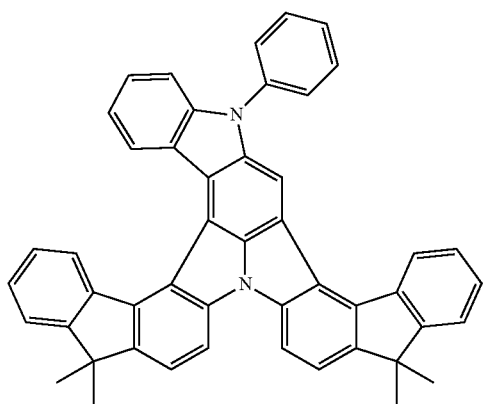
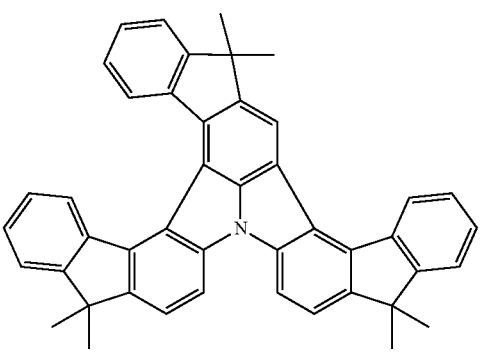
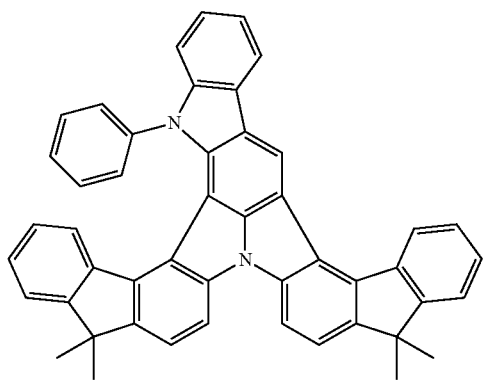
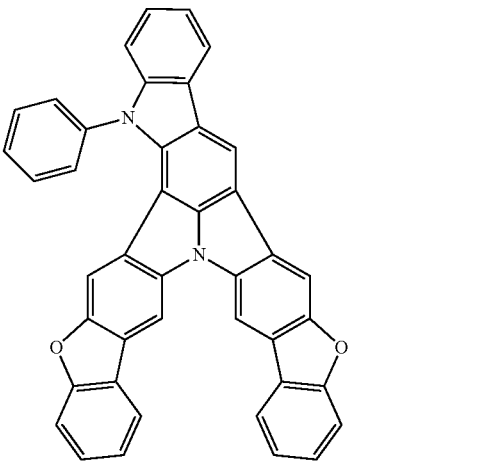

-continued
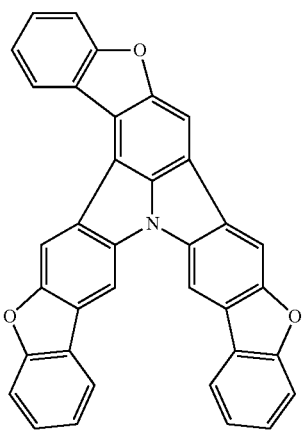
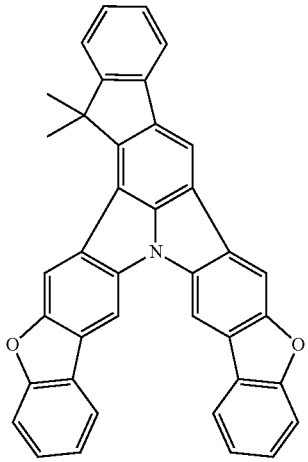
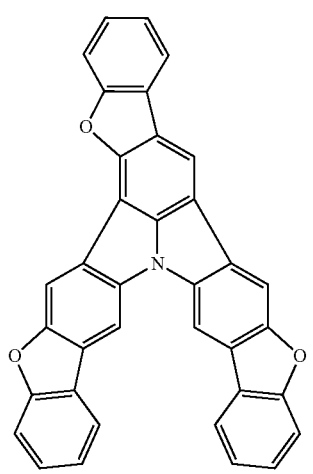
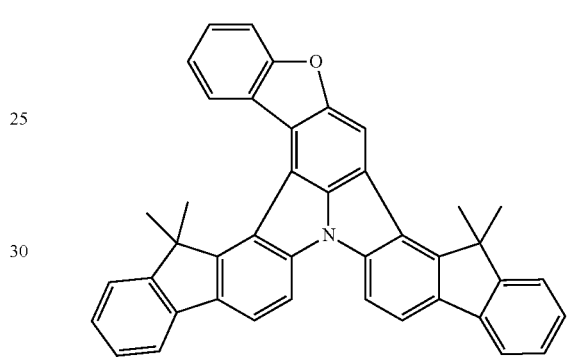
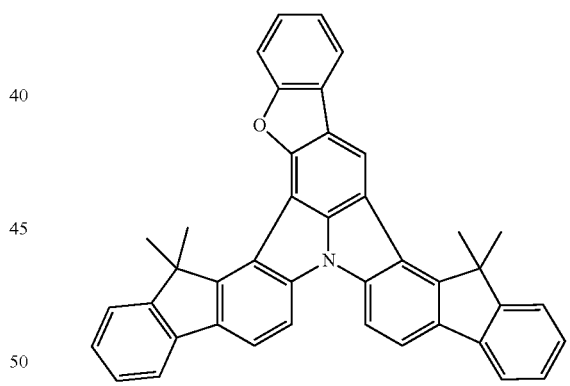
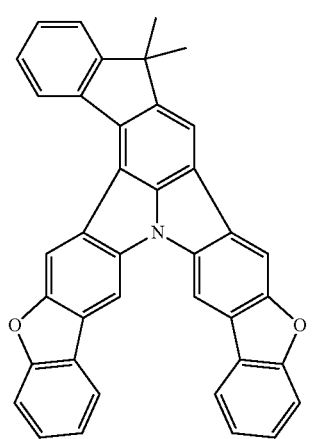
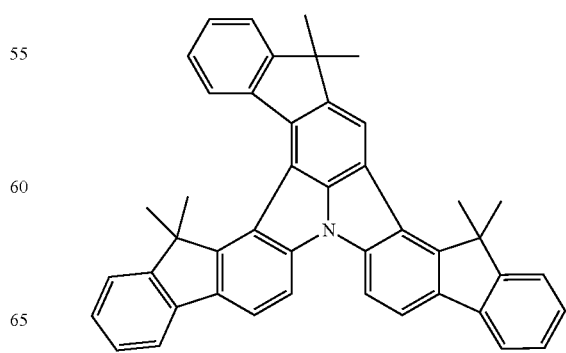

-continued
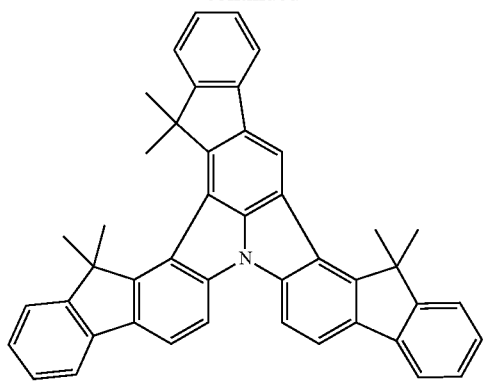
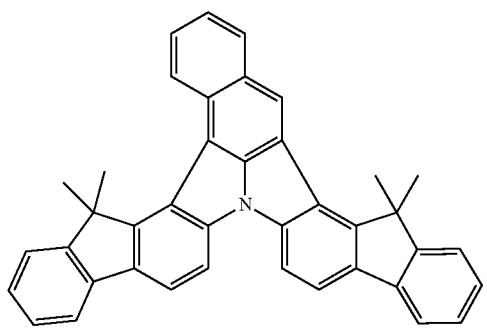
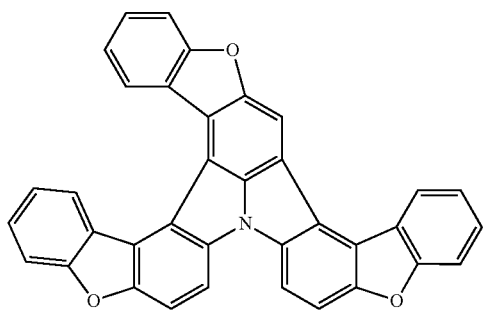
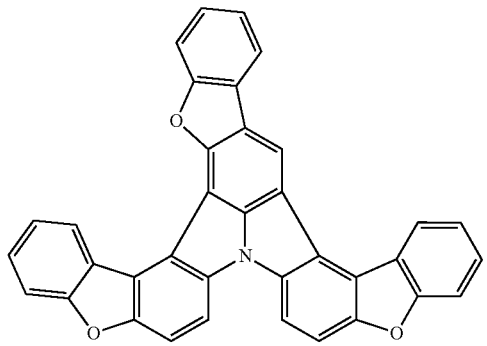
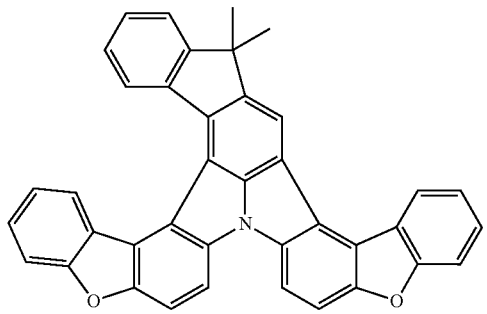
-continued
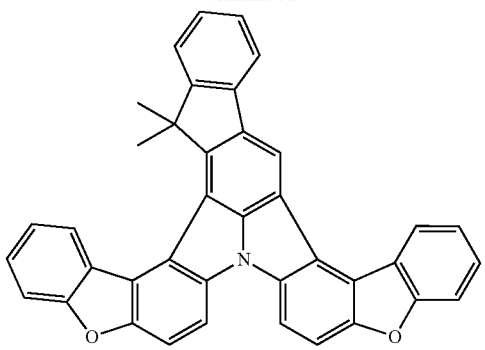
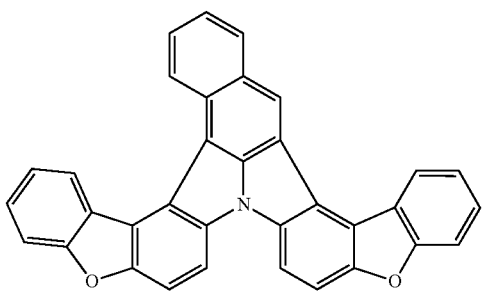
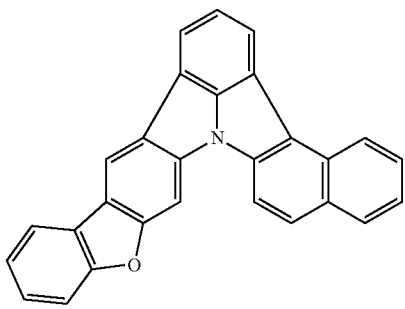
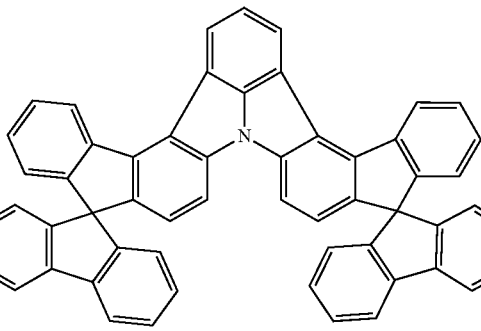
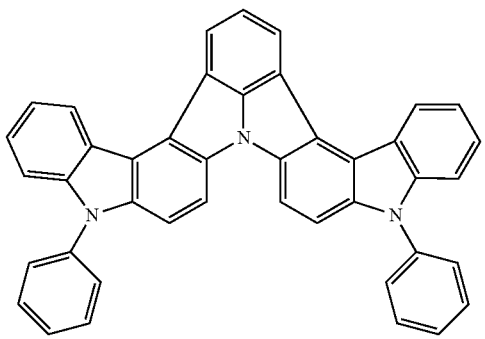

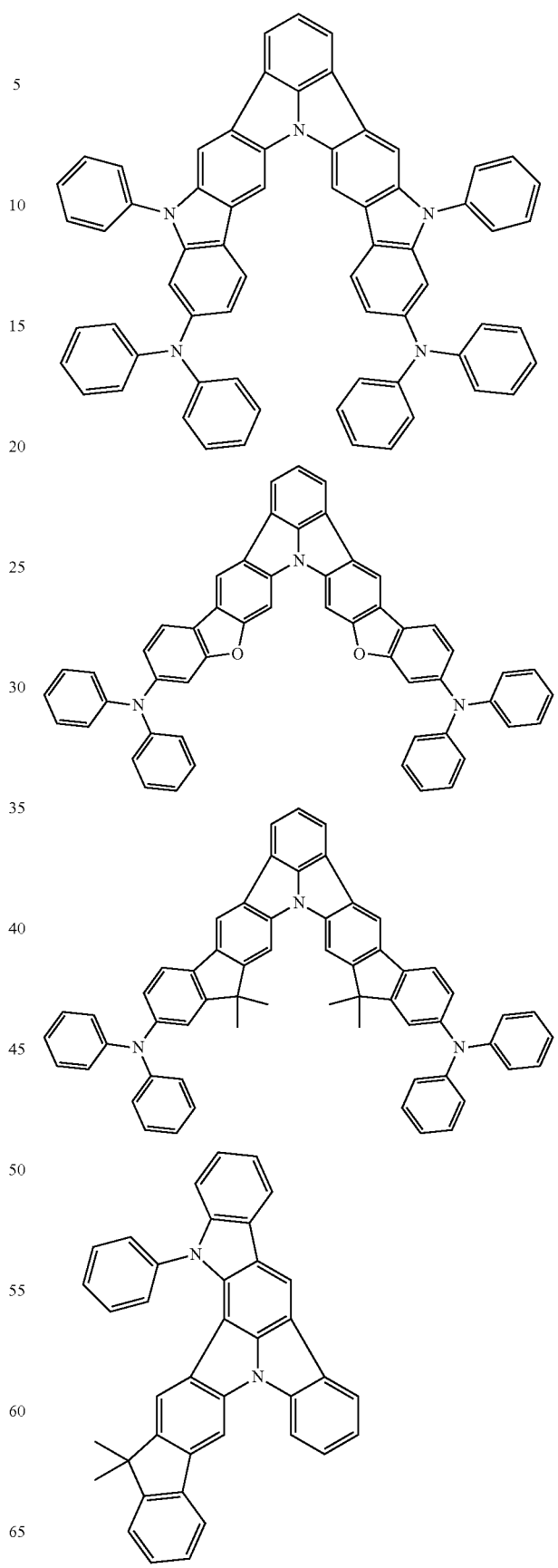

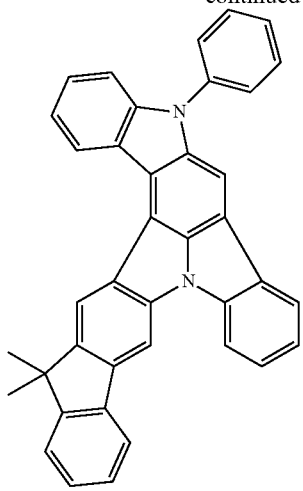
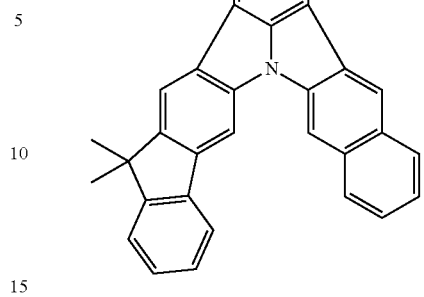
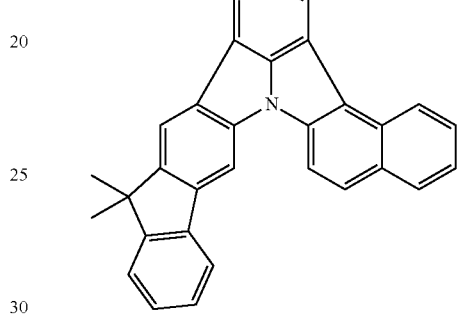
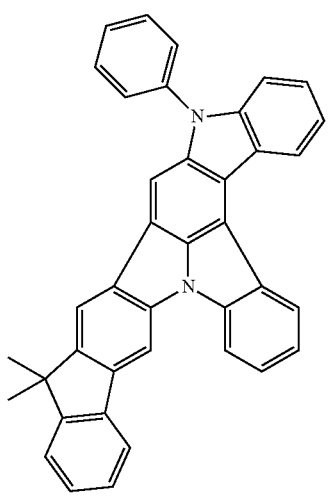
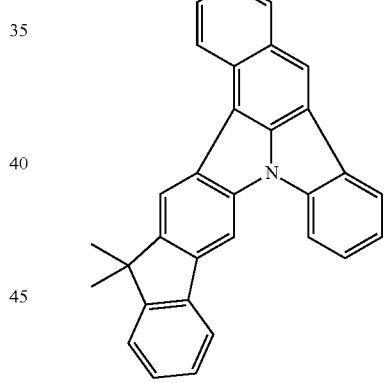
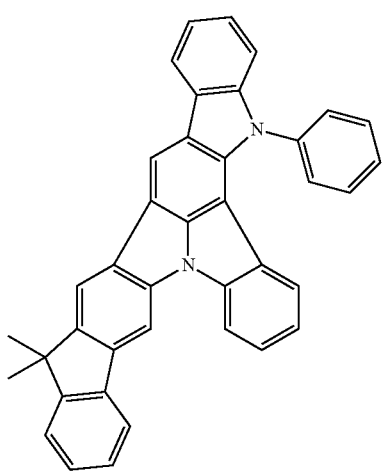
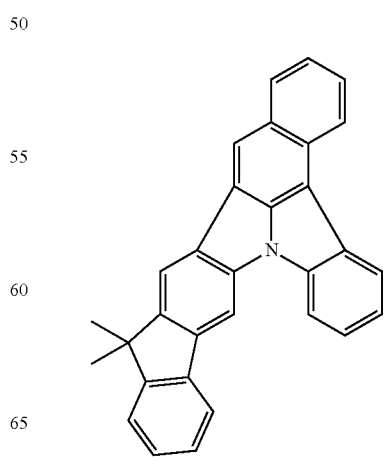

45
-continued
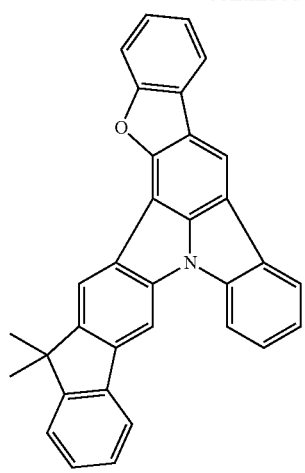
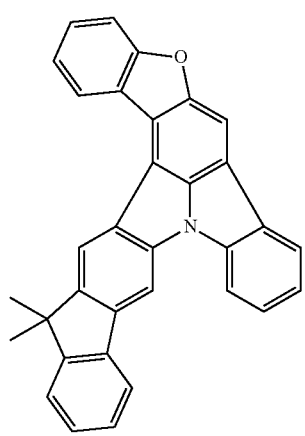
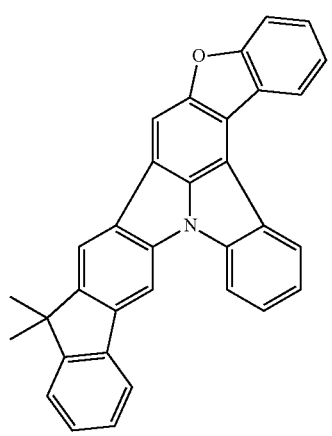
46
-continued
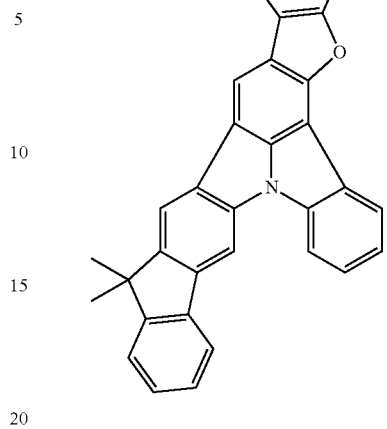
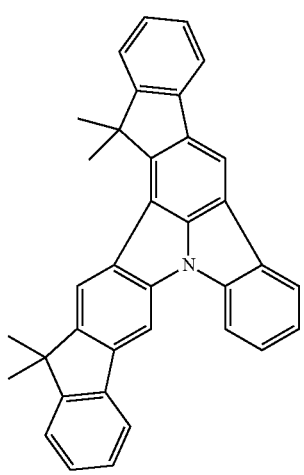
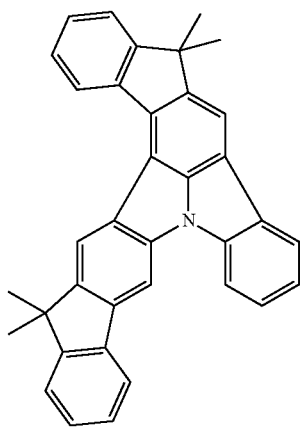

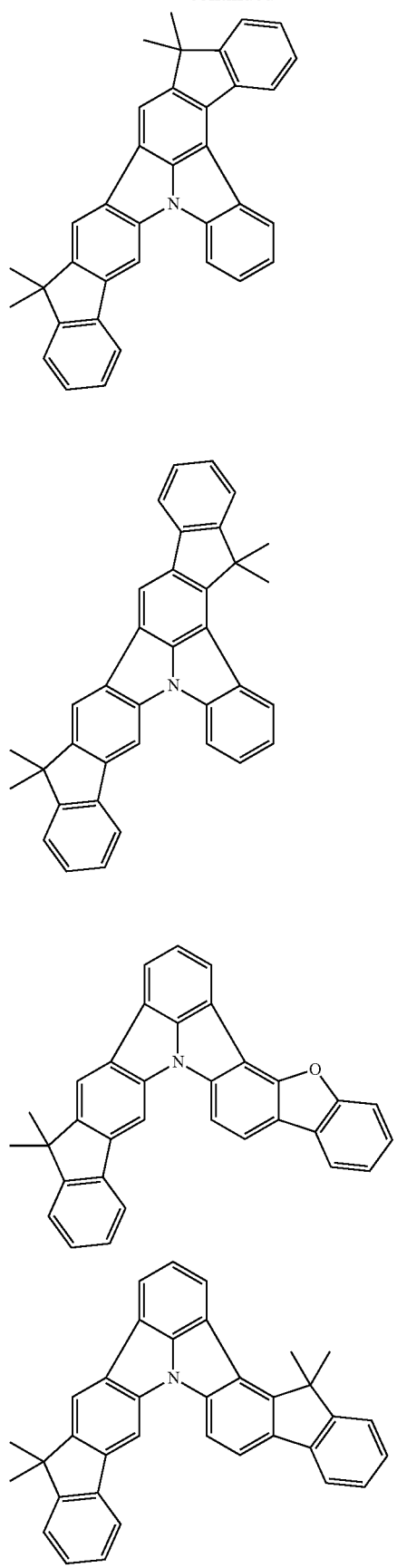
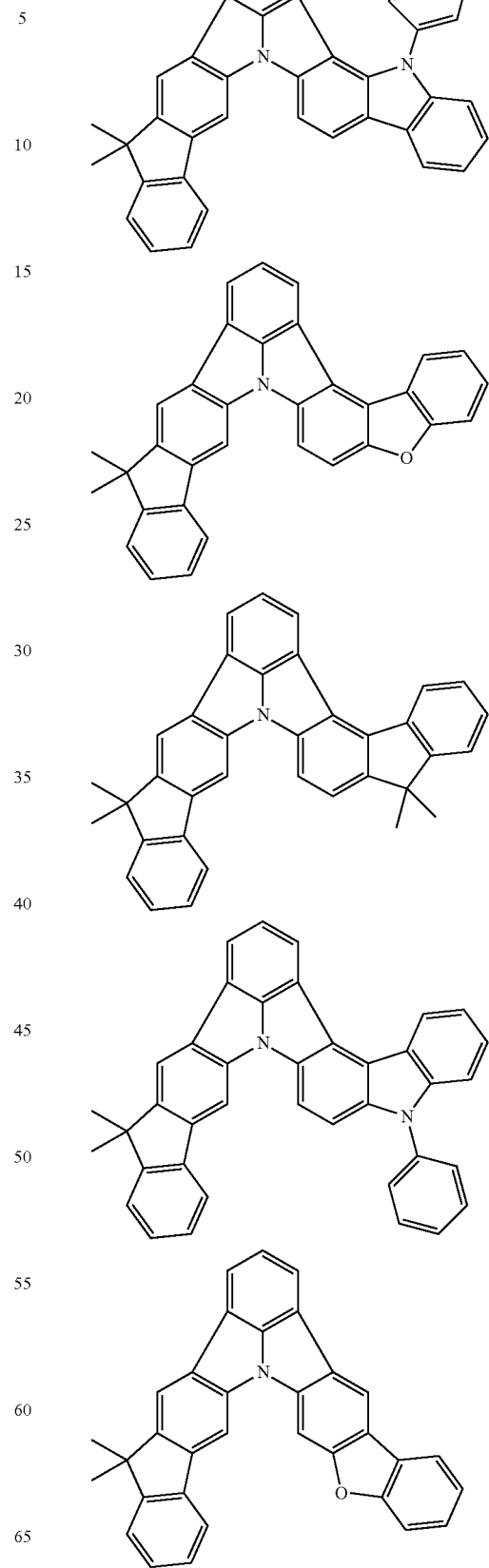

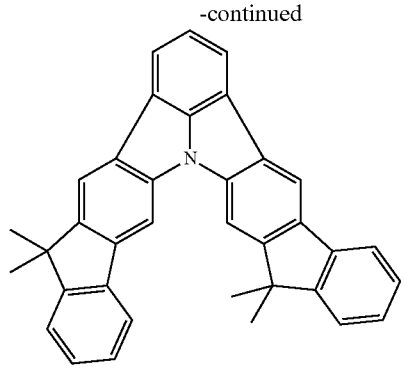
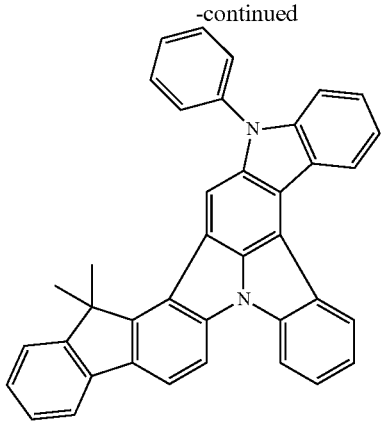
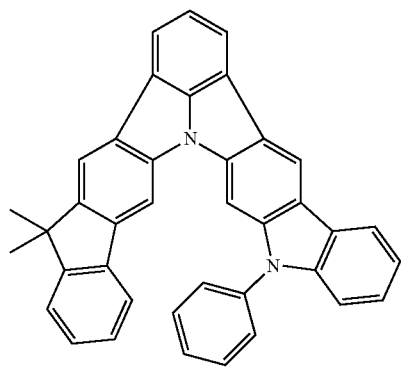
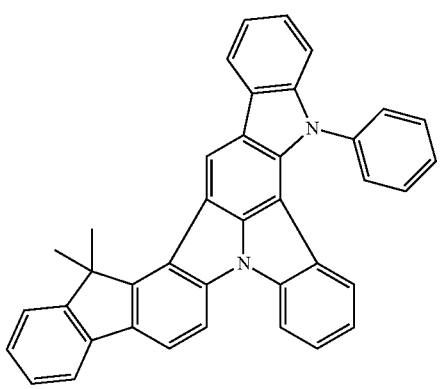
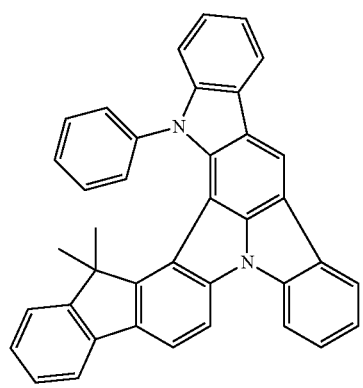
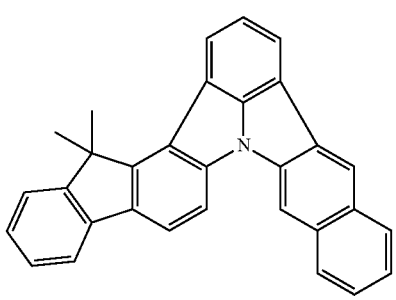
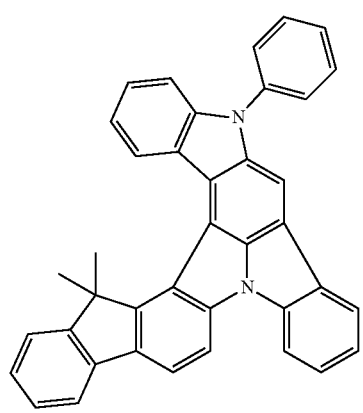
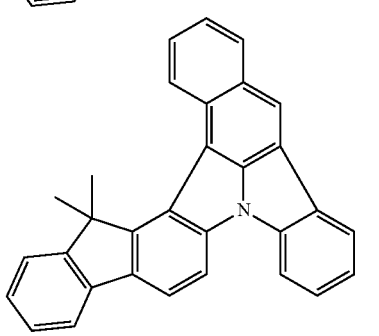

51
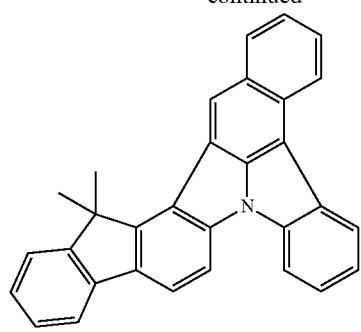
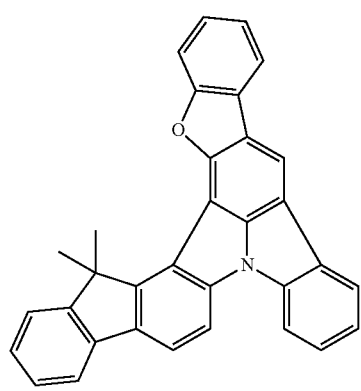
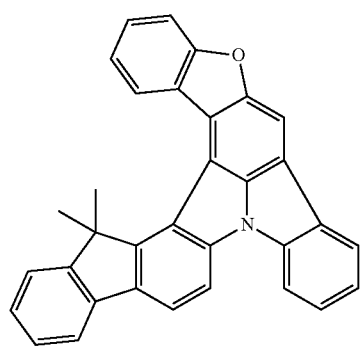
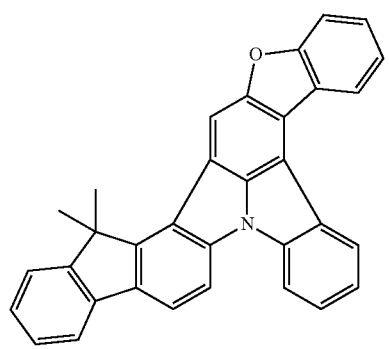
52
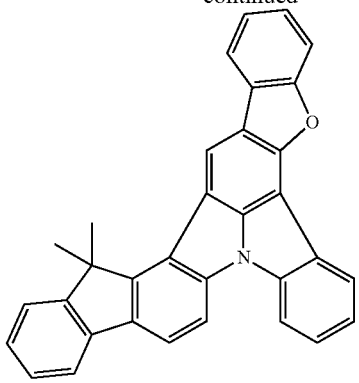
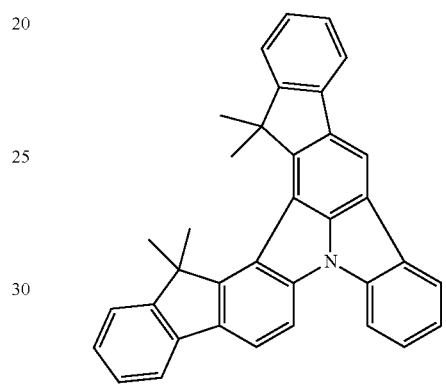
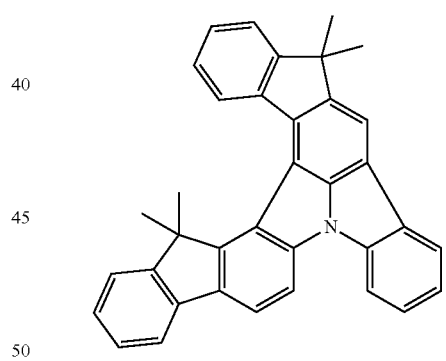
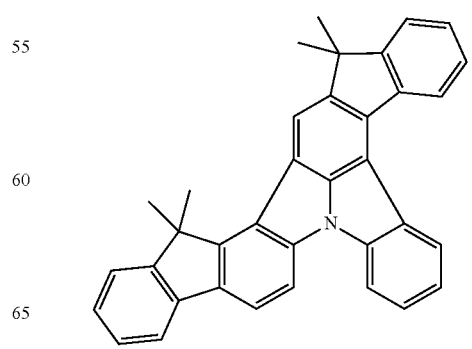

-continued
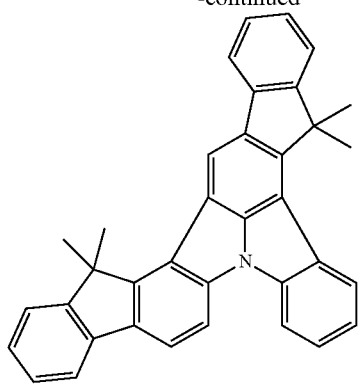
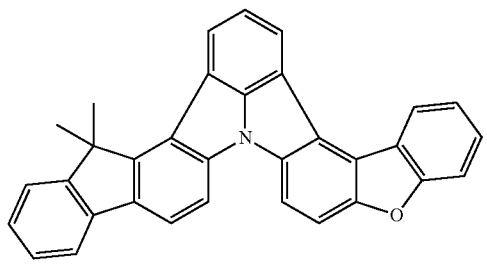
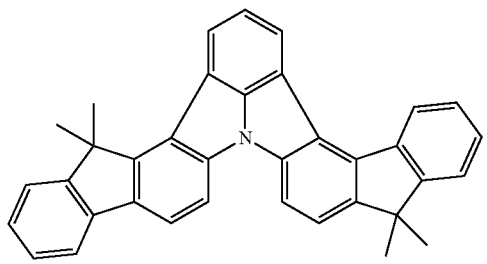
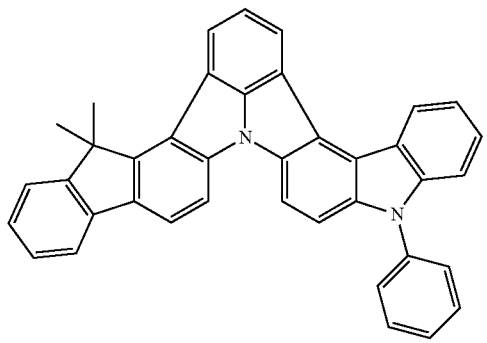
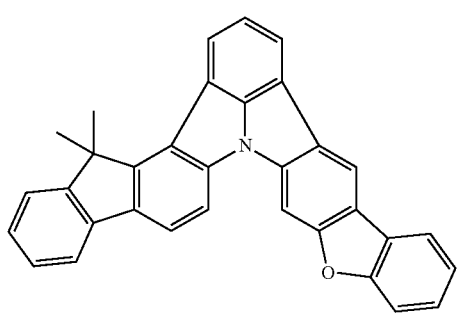
-continued
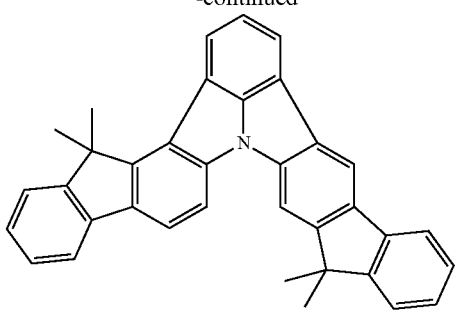
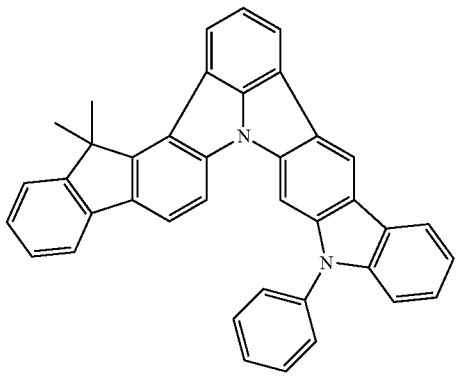
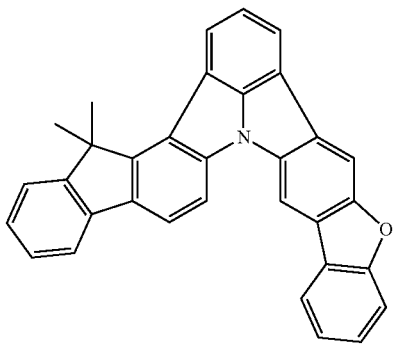
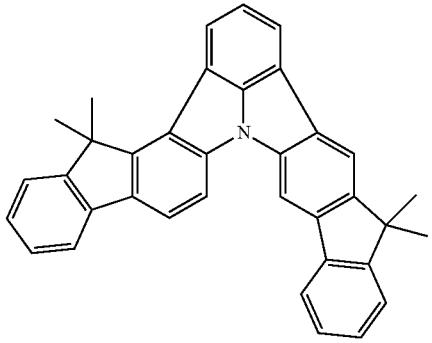
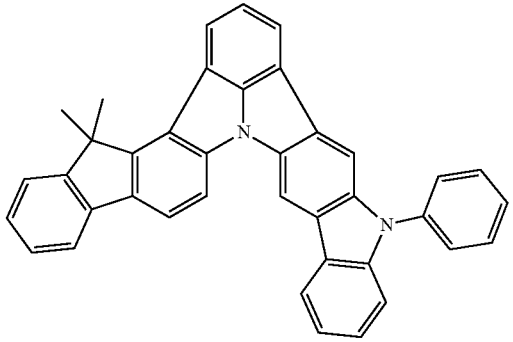

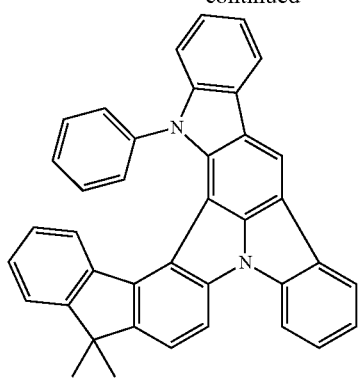
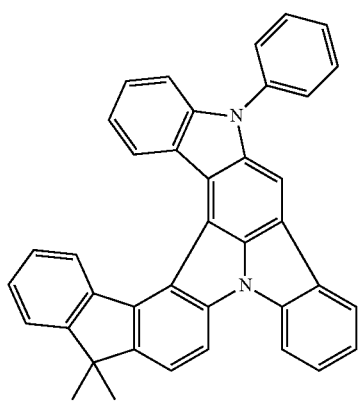
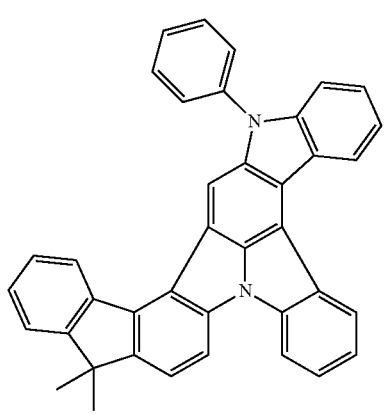
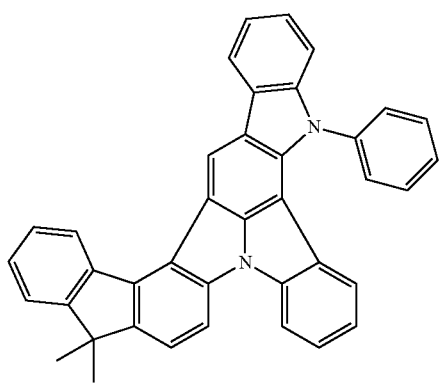
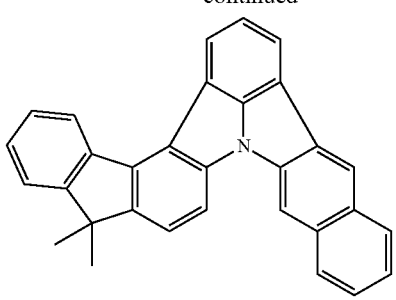
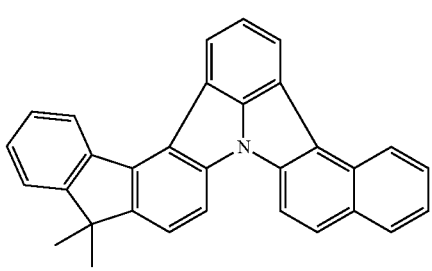
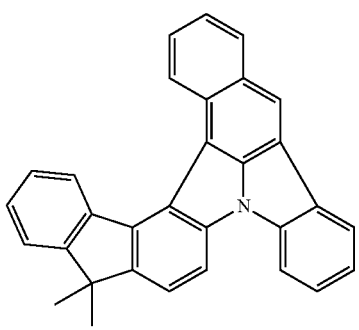
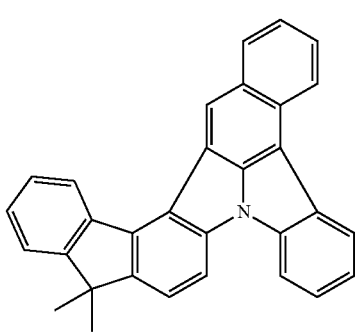
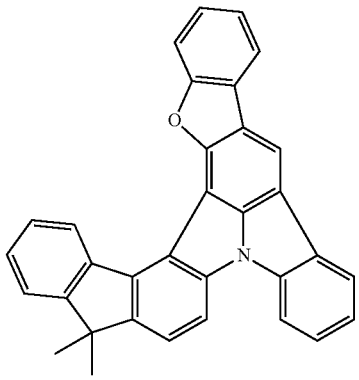

57
-continued
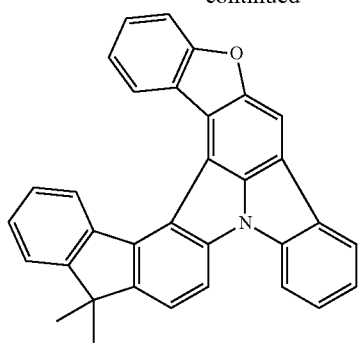
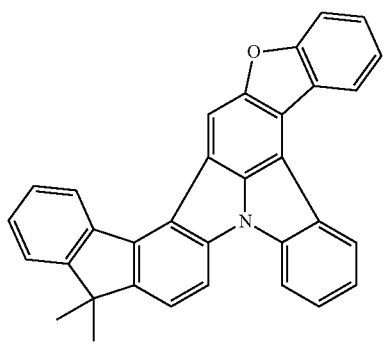
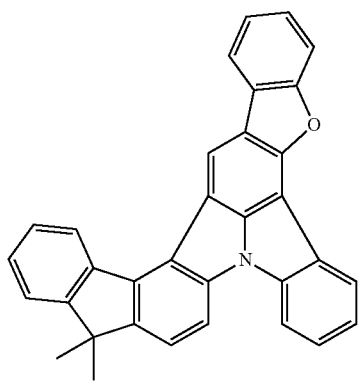
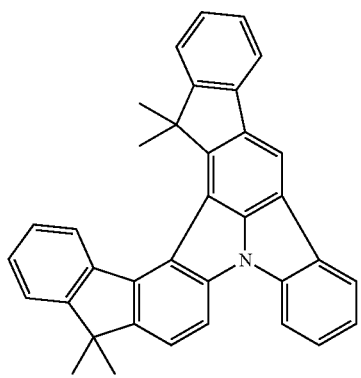
58
-continued
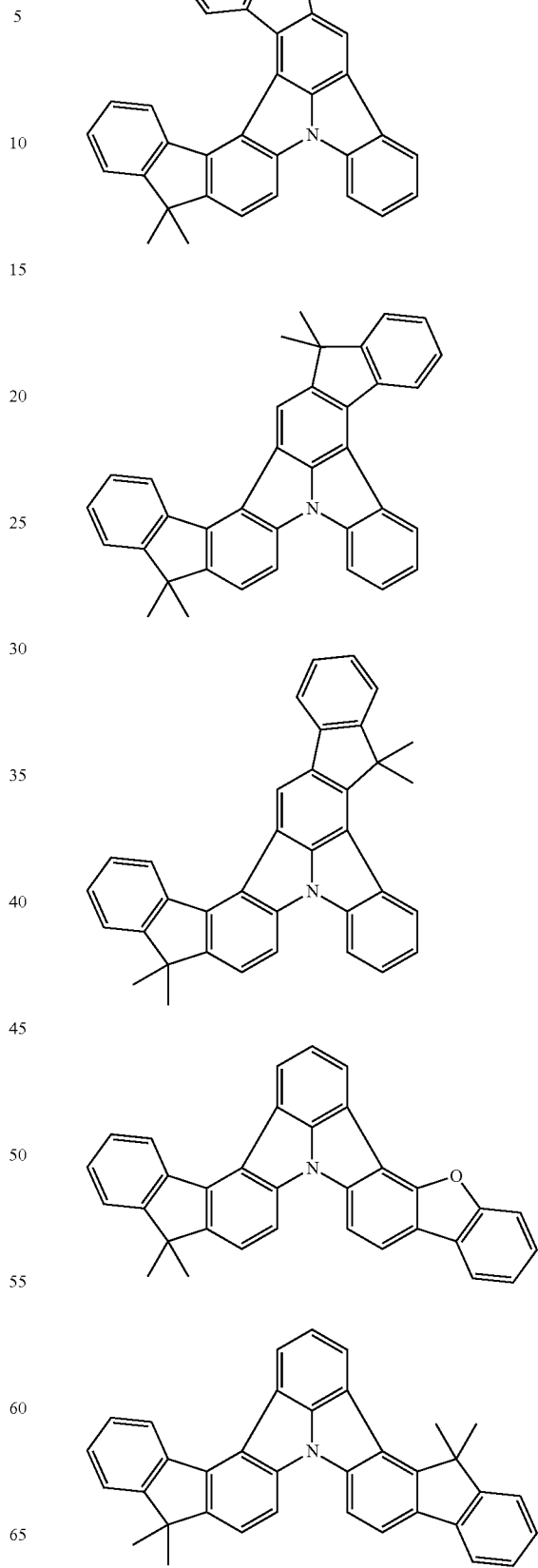

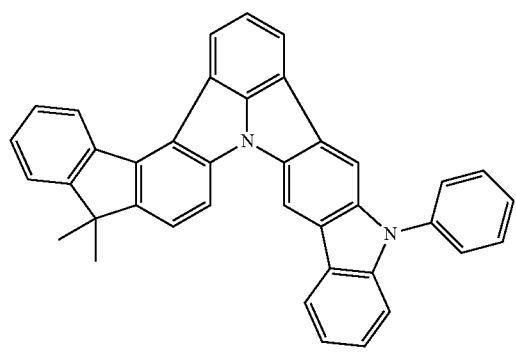
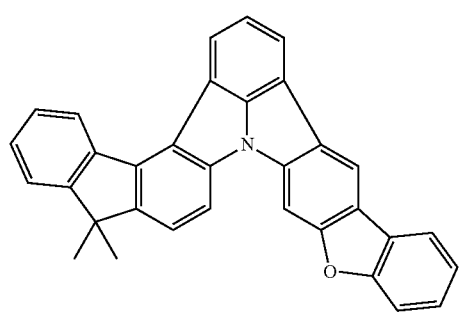
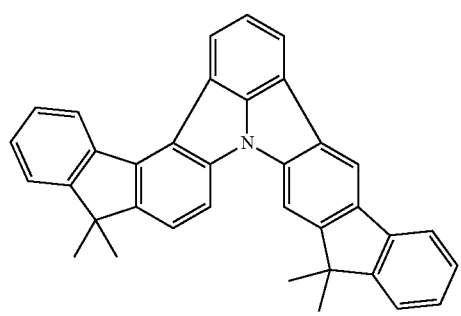
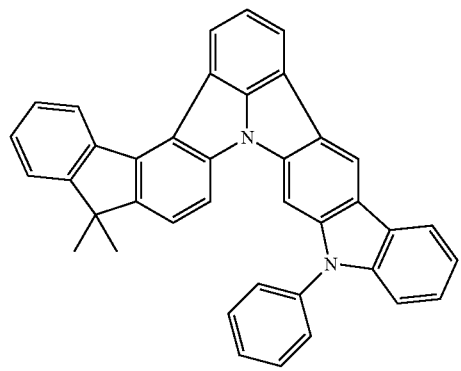
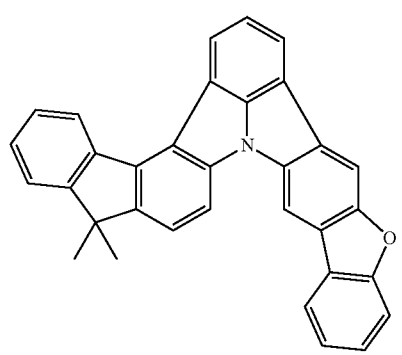
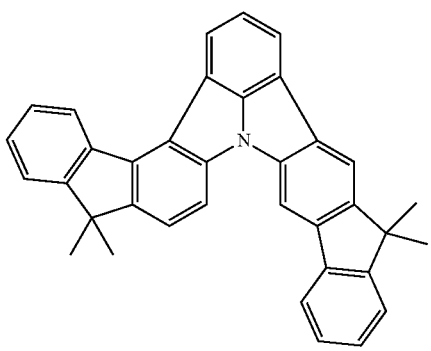
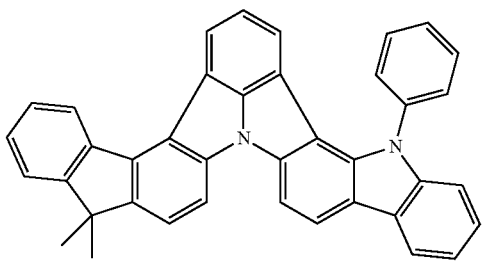
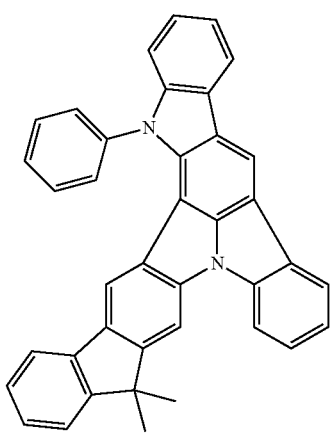
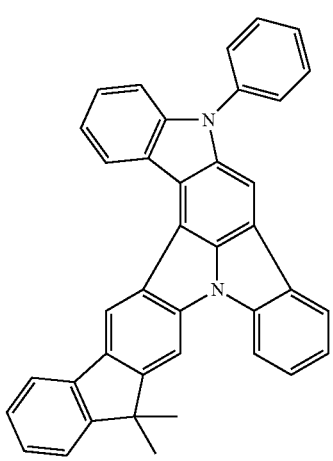

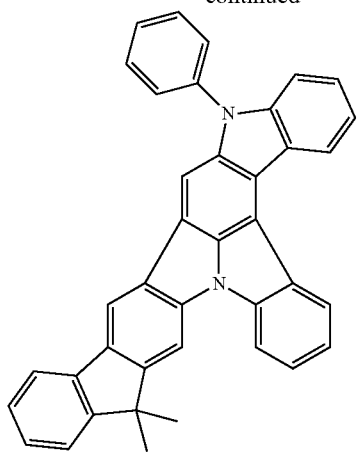
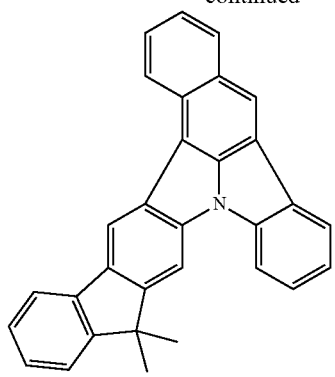
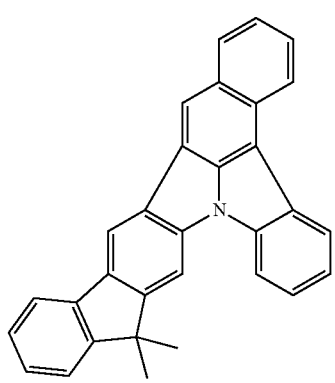
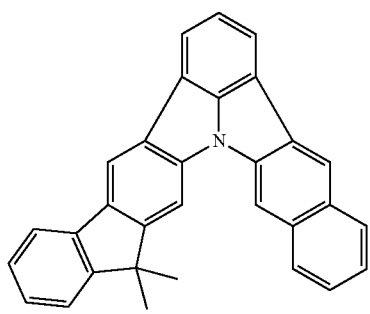
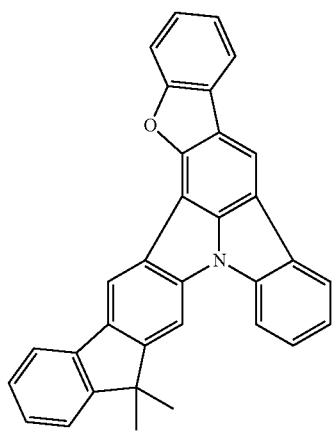
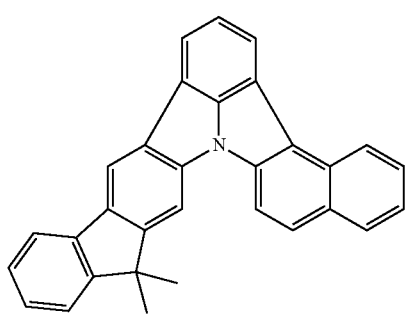
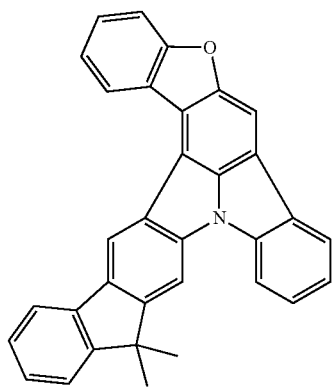

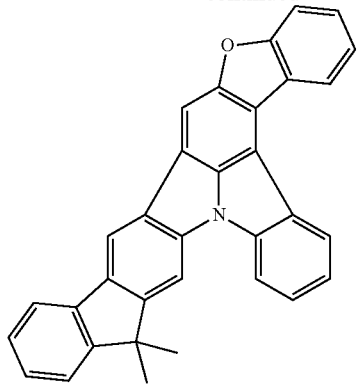
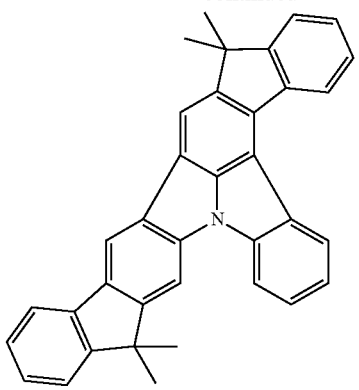
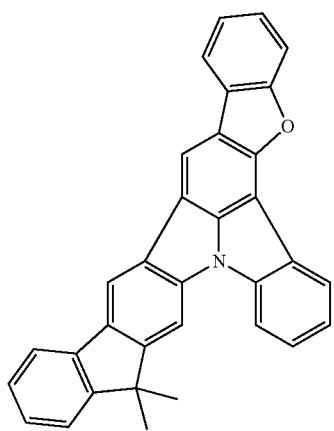
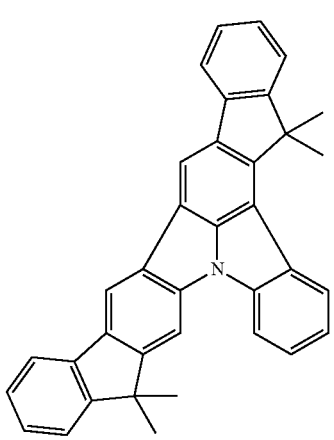
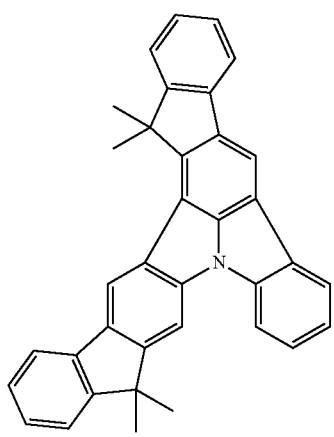
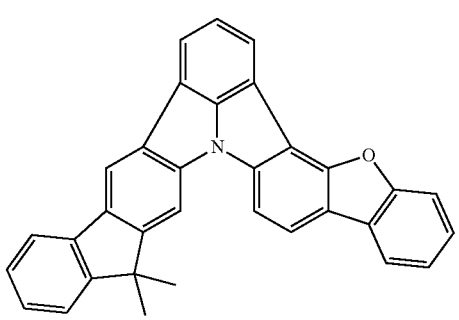
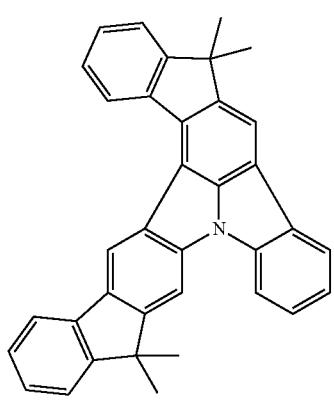
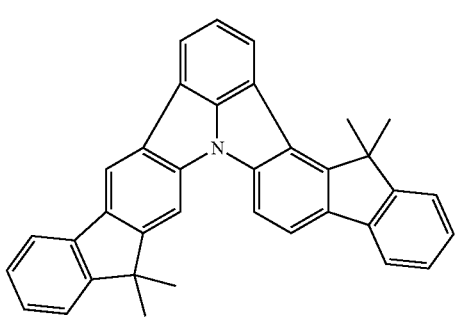

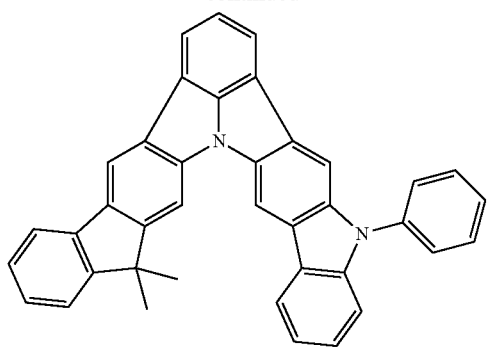
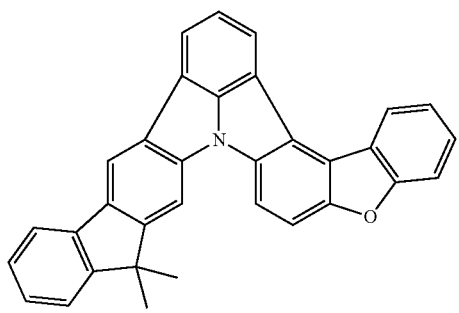
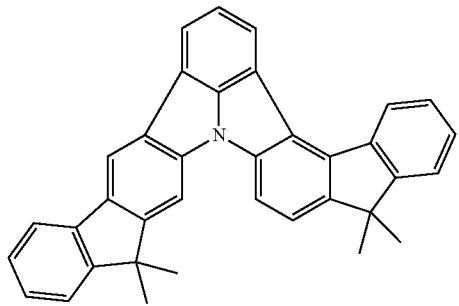
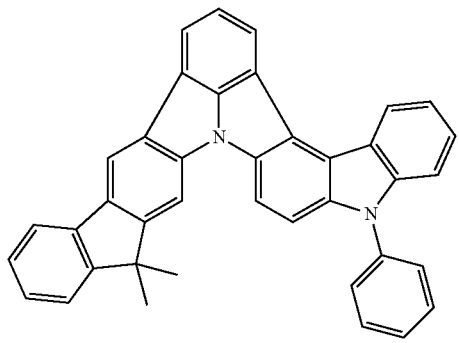
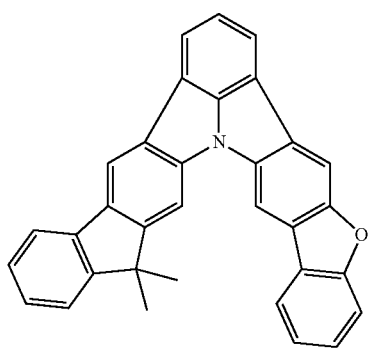
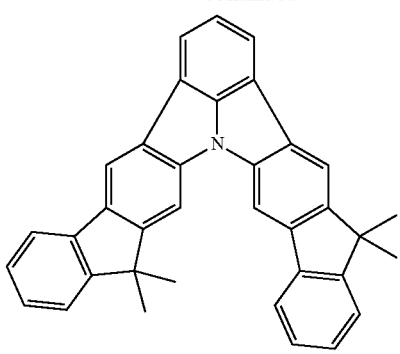
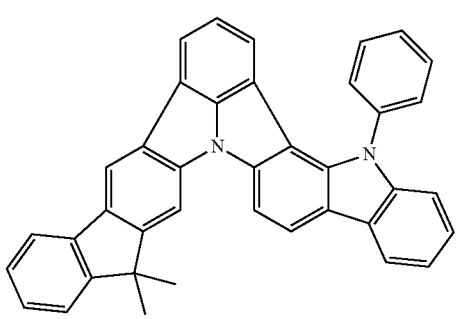
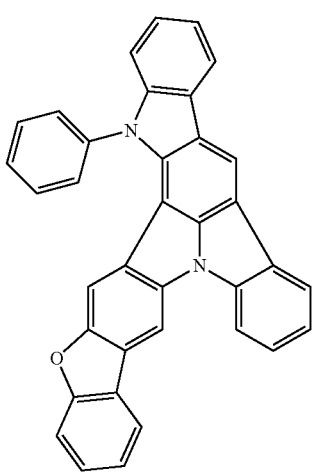
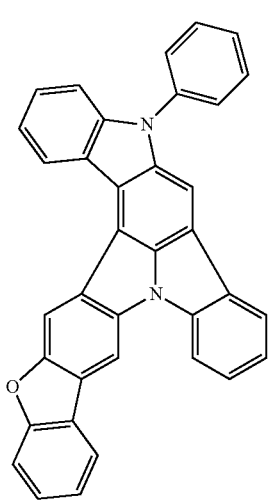

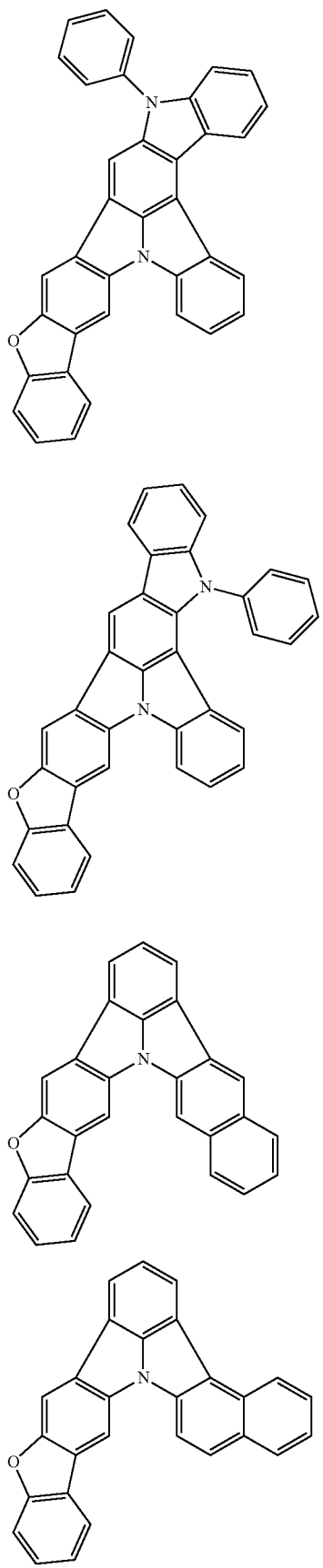
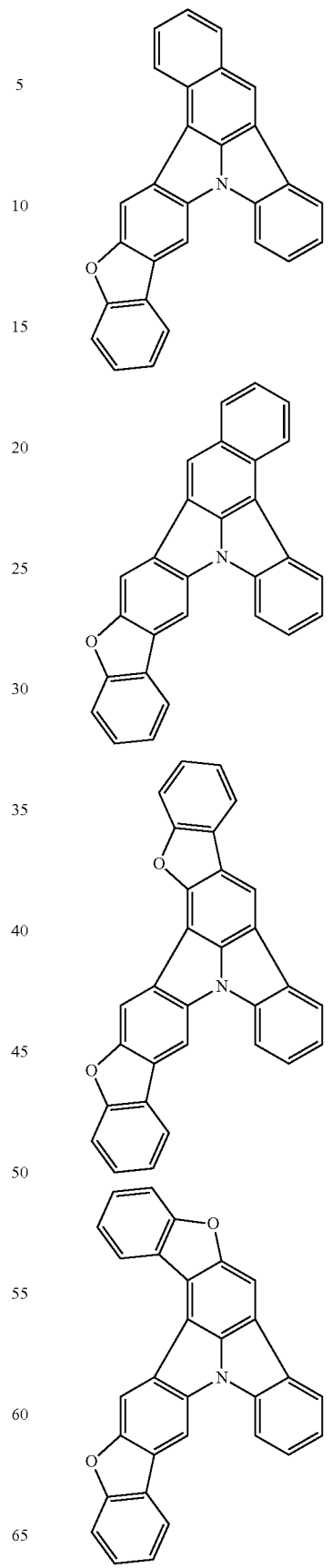

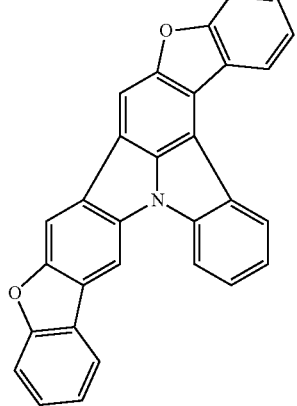
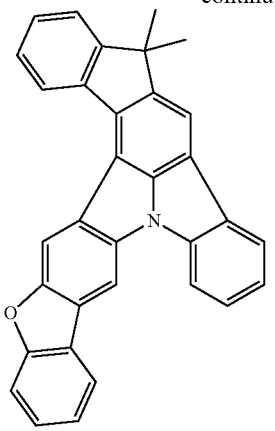
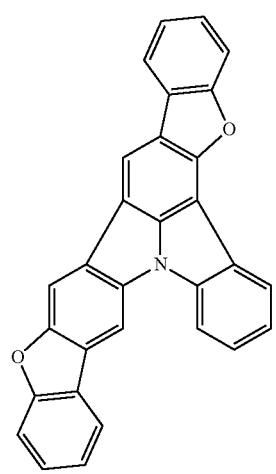
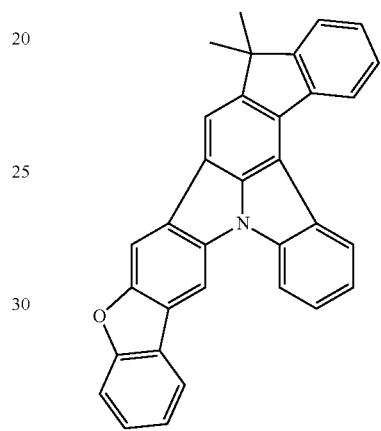
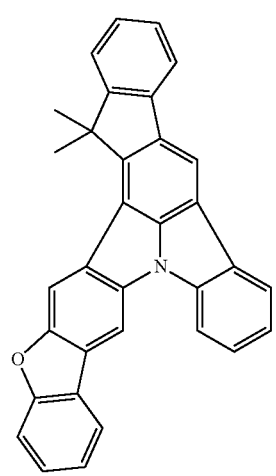
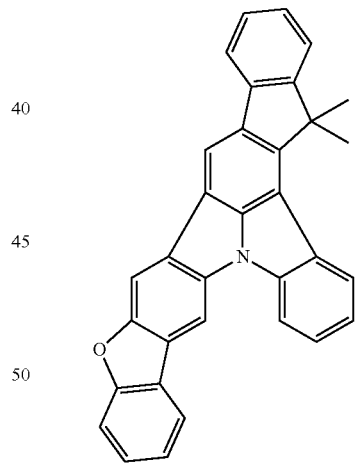
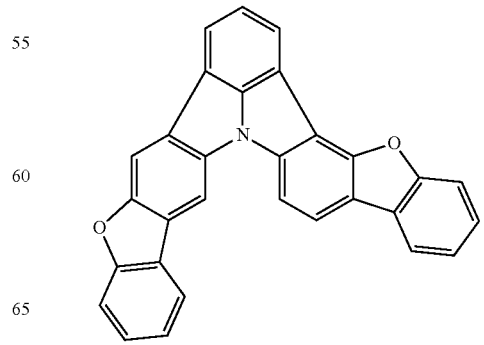

71
-continued
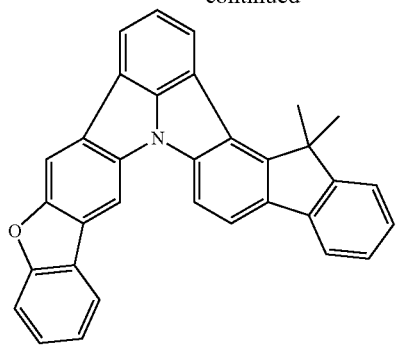
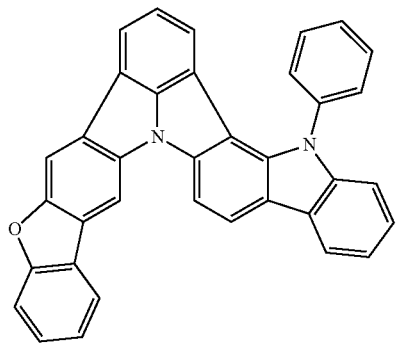
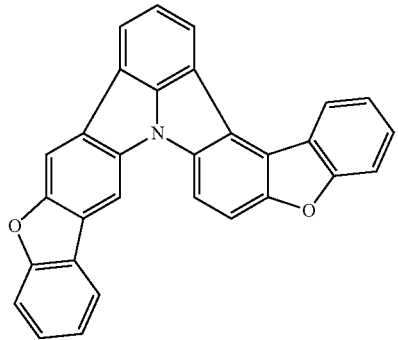
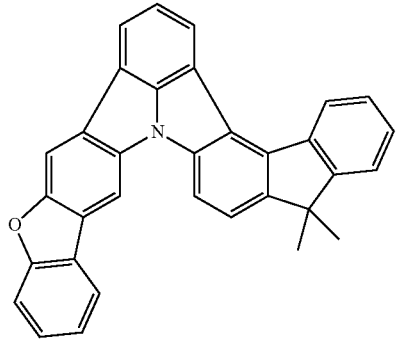
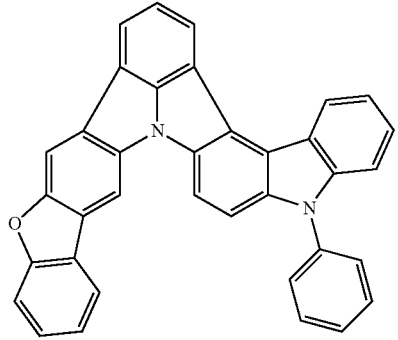
72
-continued
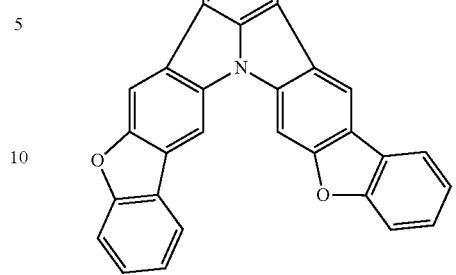
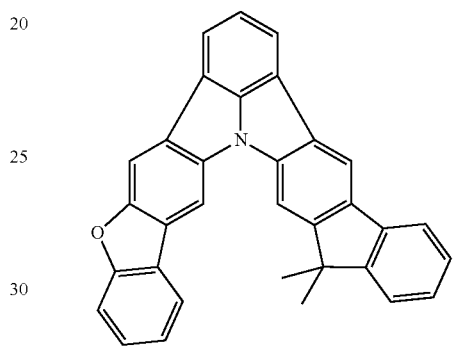
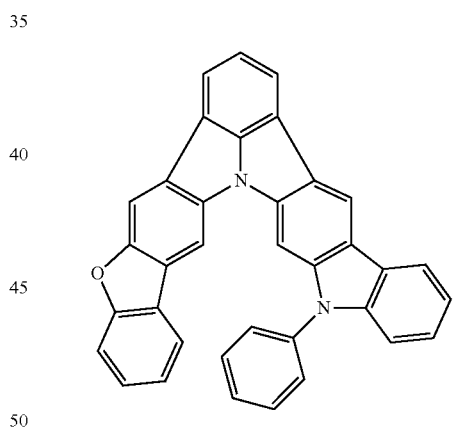
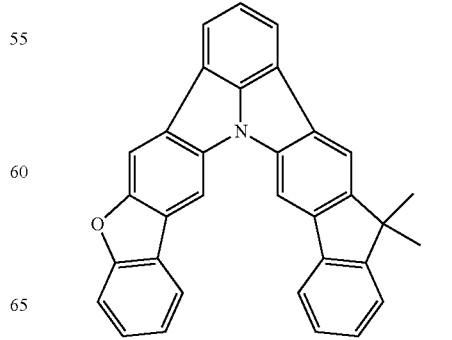

73
-continued
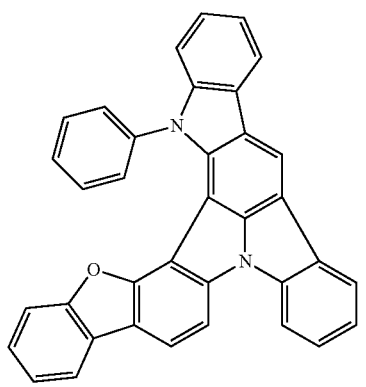
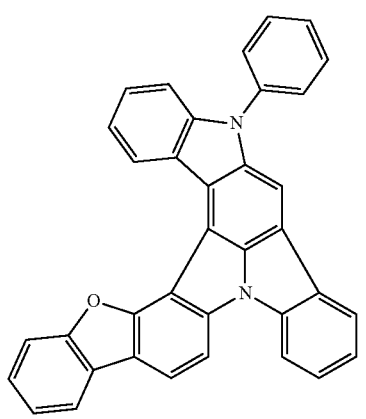
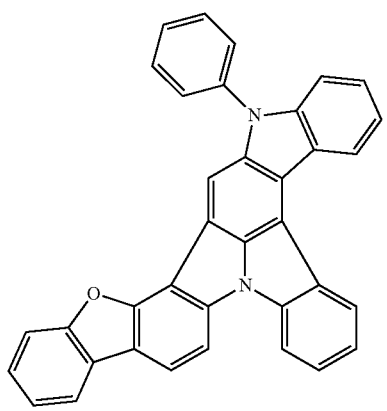
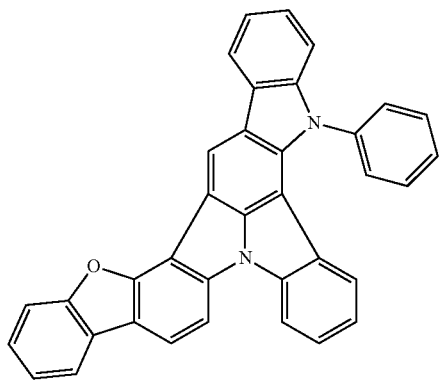
74
-continued
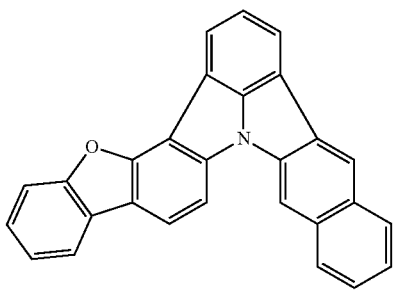
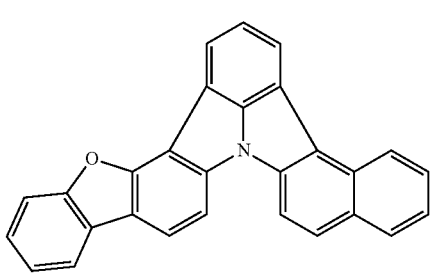
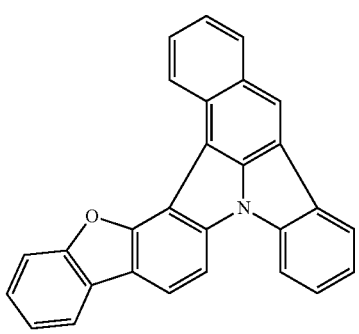
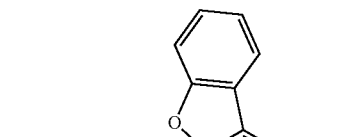
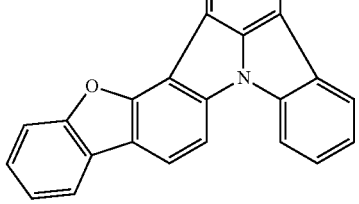

75
-continued
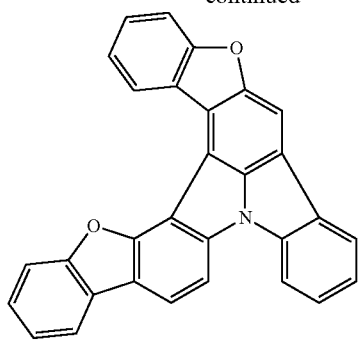
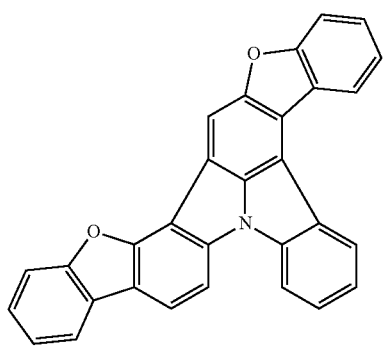
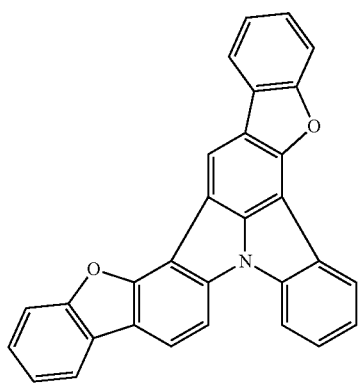
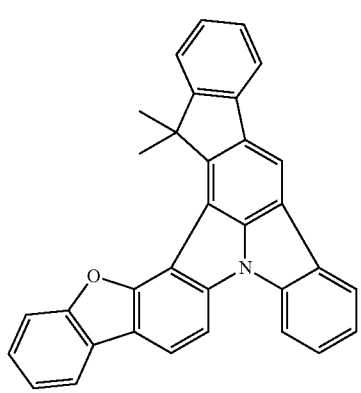
76
-continued
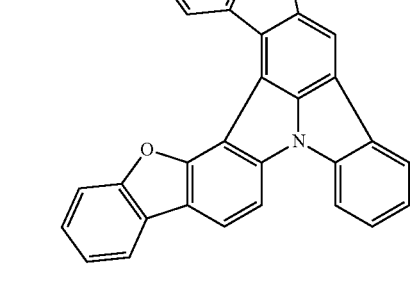
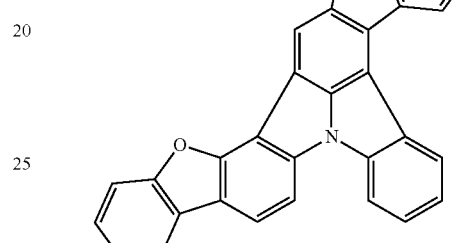
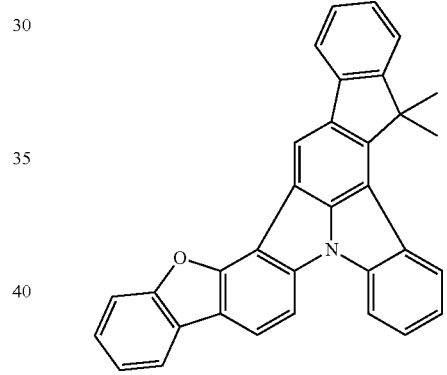
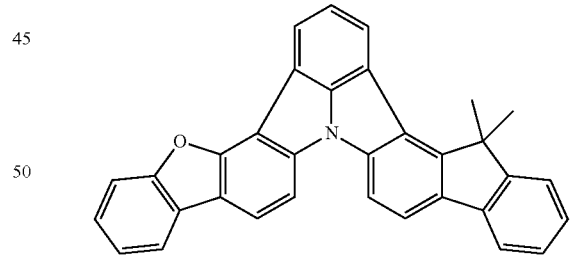
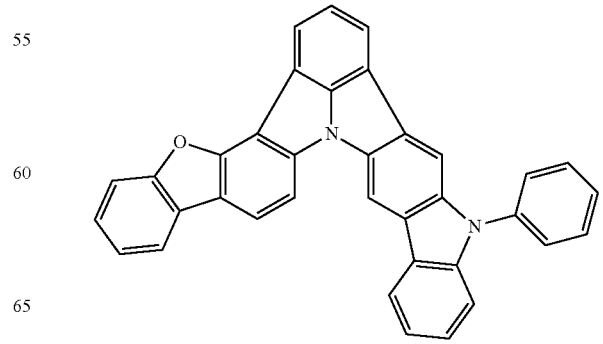

-continued
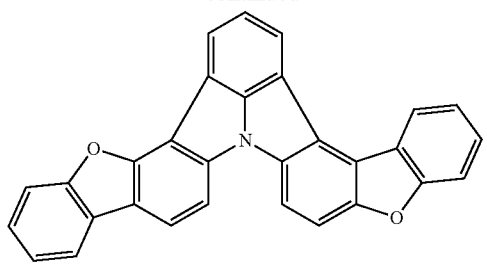
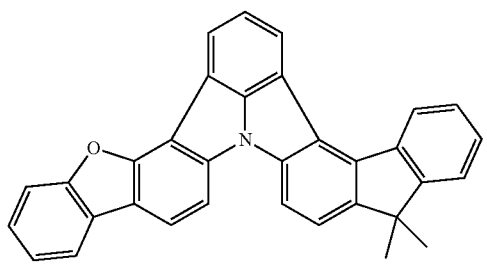
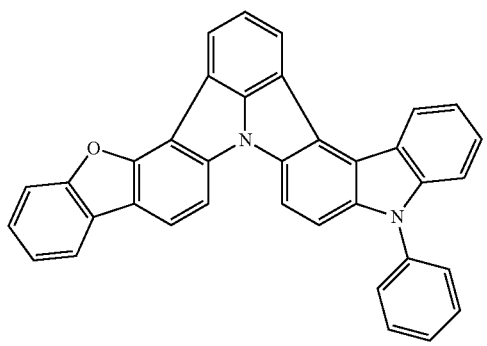
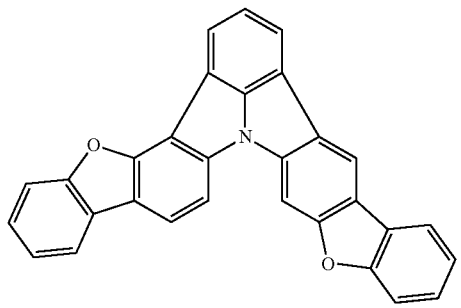
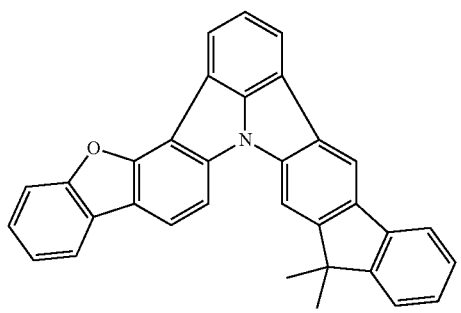
-continued
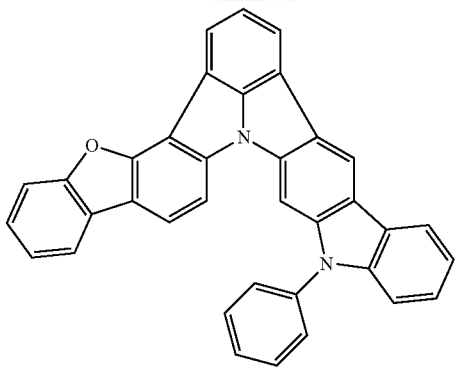
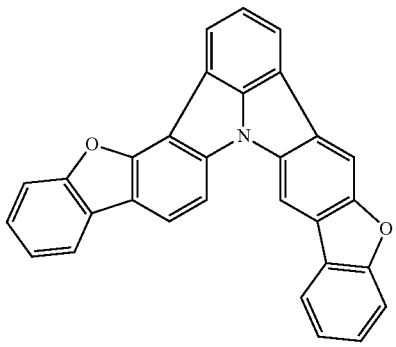
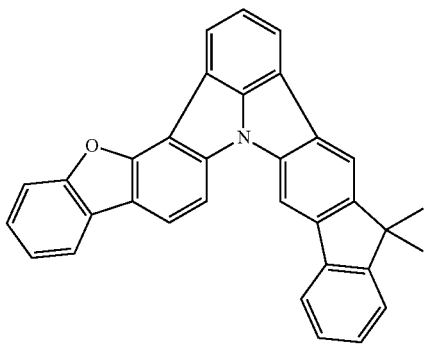
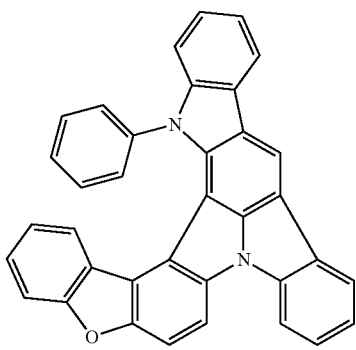

-continued
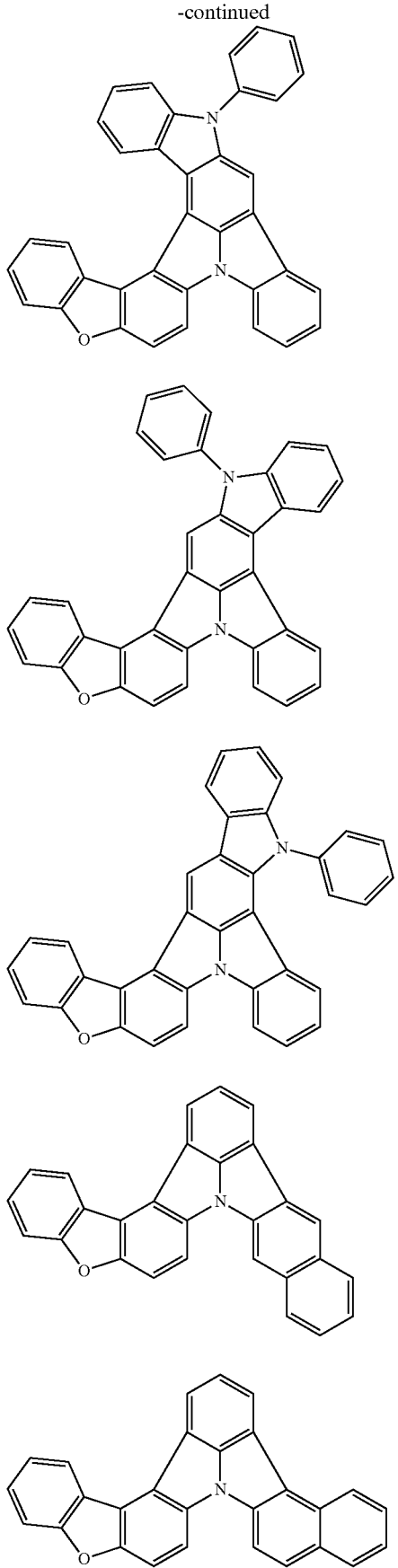
-continued
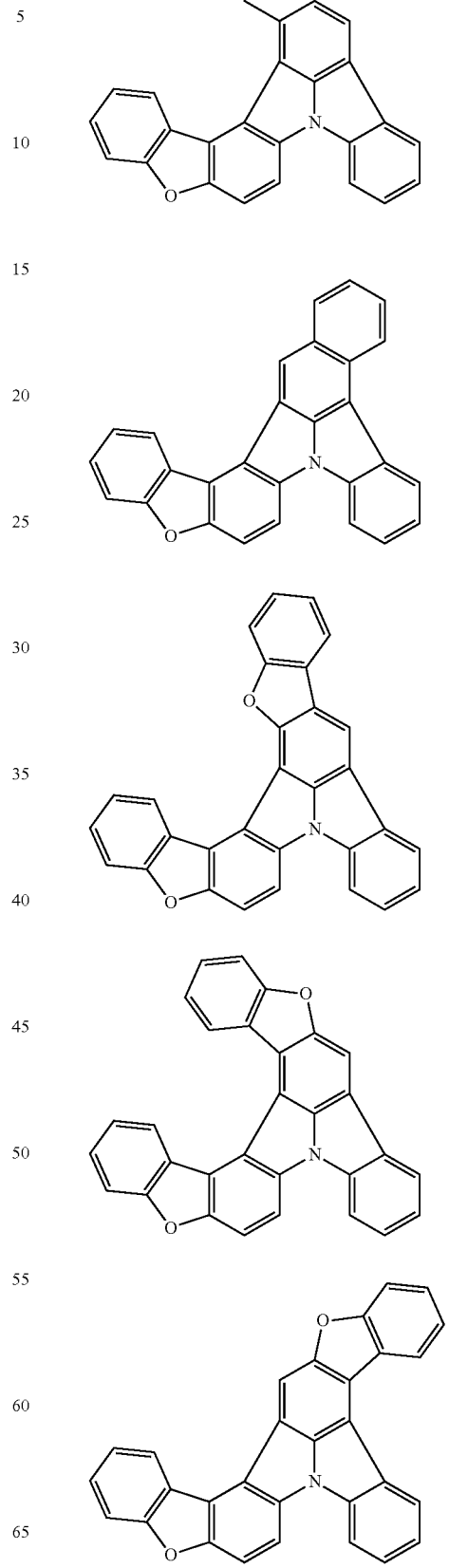

81
-continued
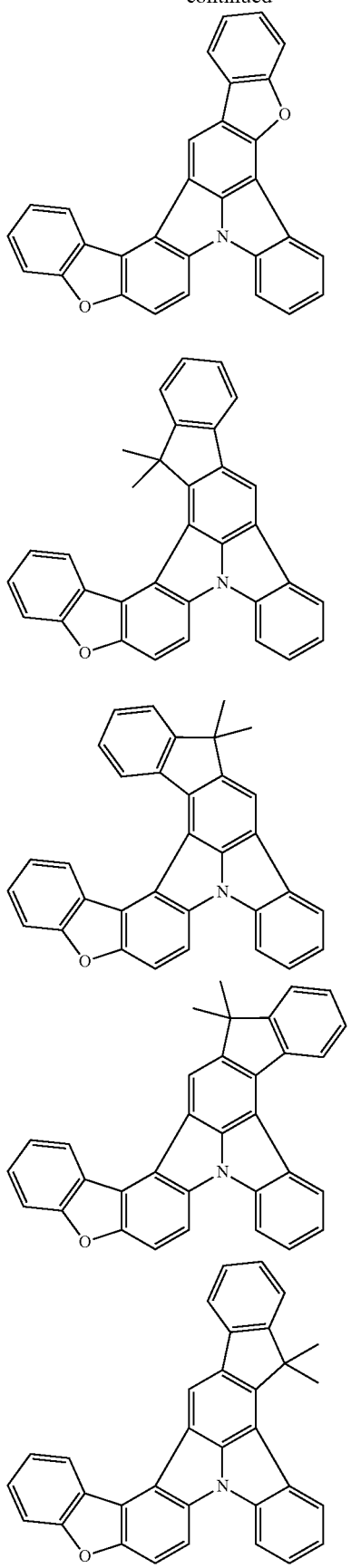
82
-continued
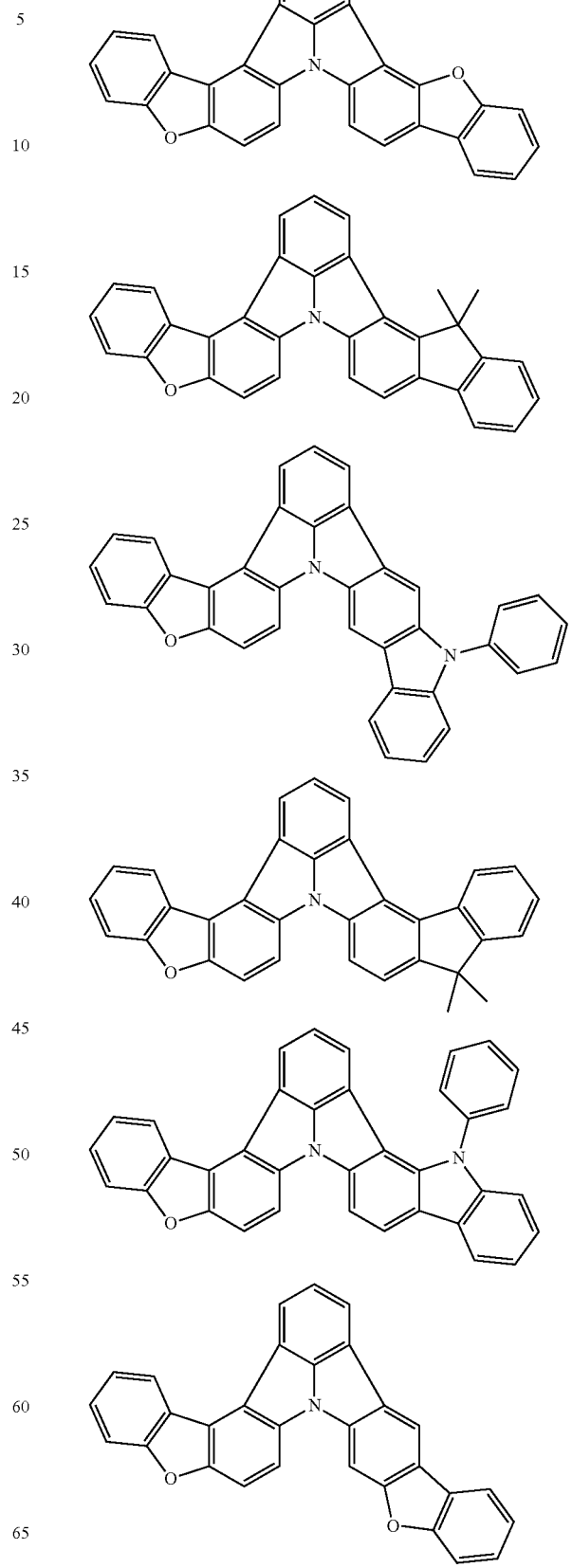

-continued
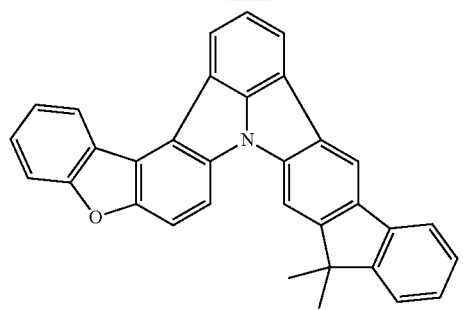
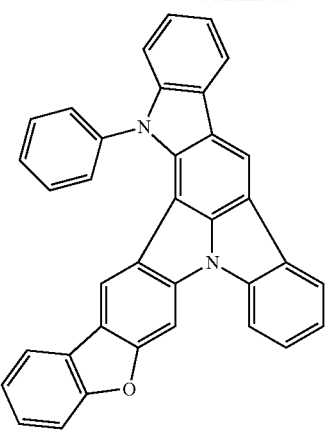
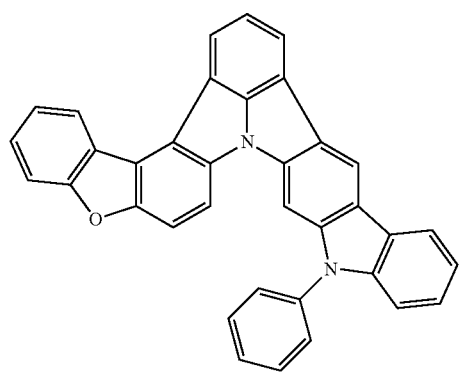
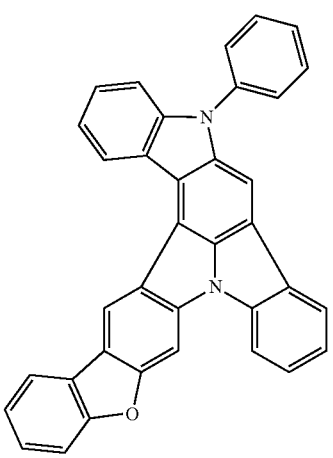
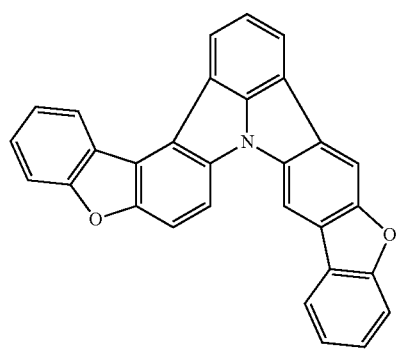
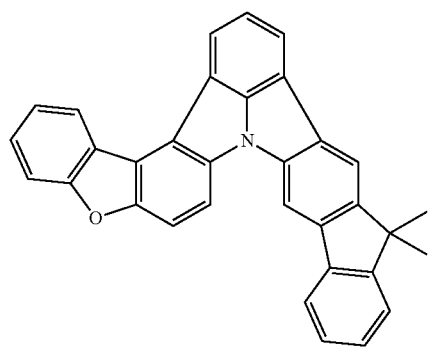

-continued
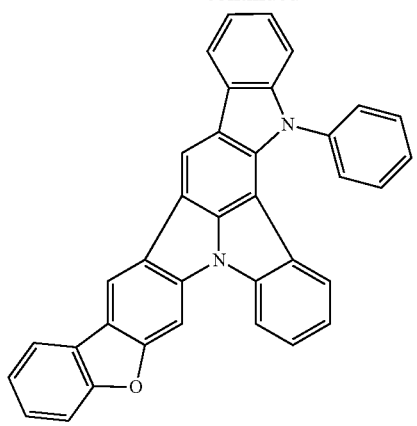
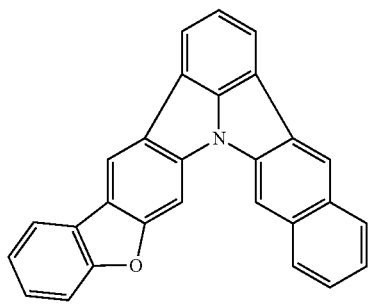
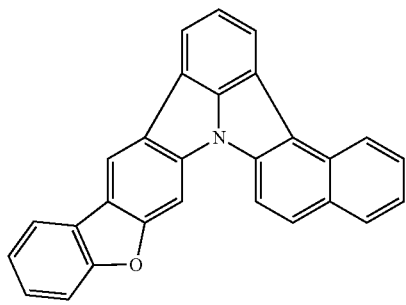
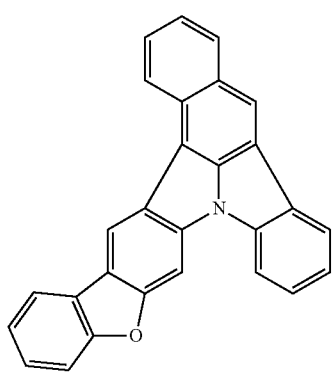
-continued
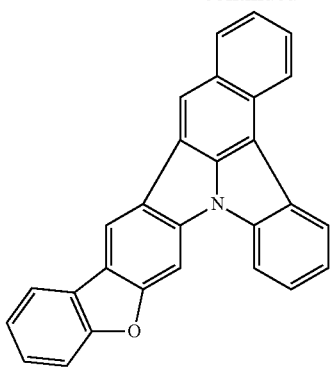
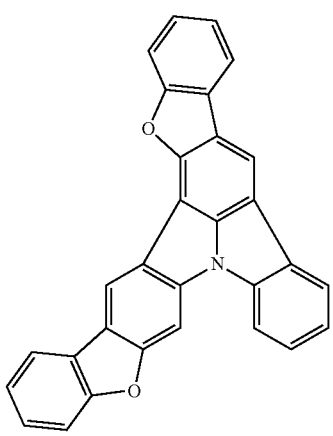
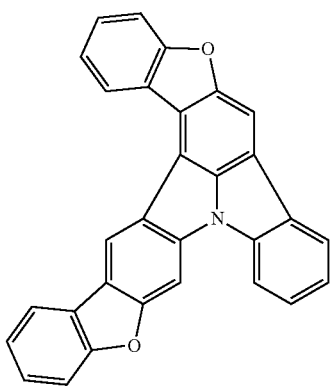
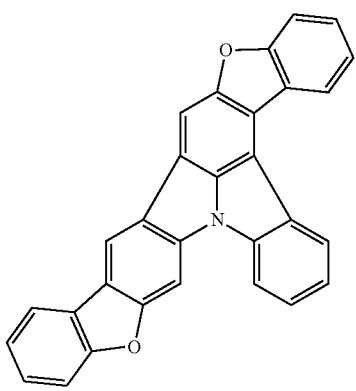

87
-continued
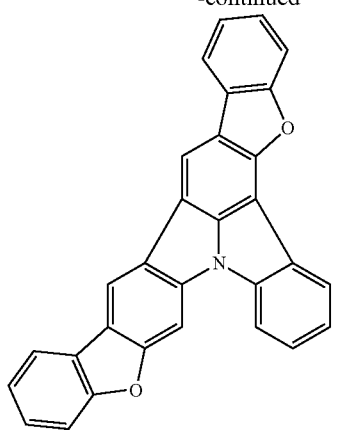
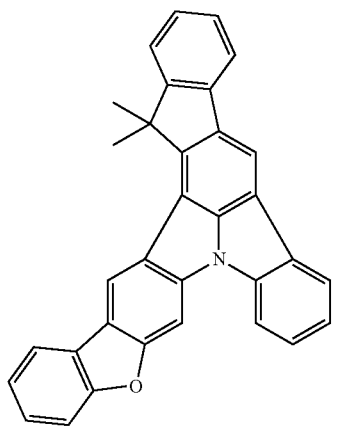
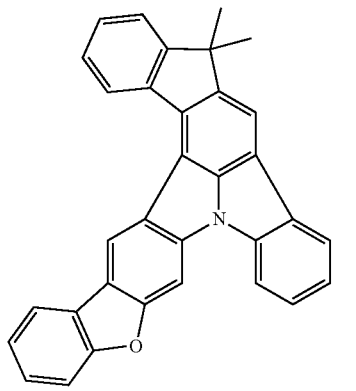
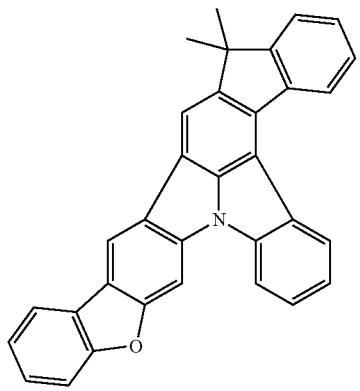
88
-continued
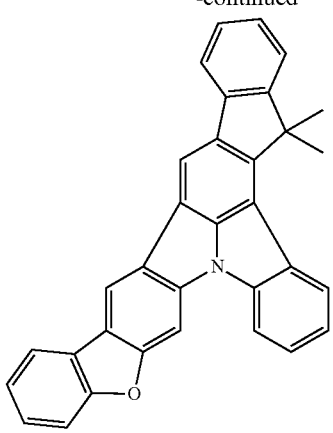
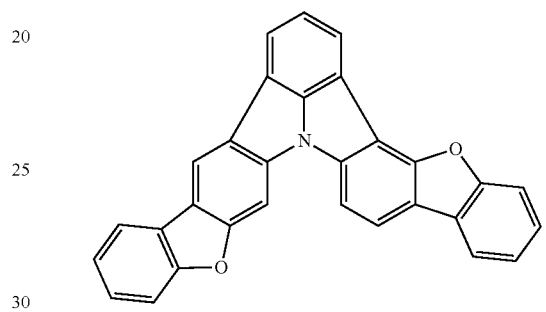
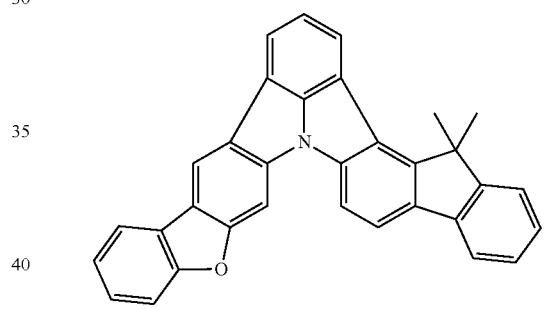
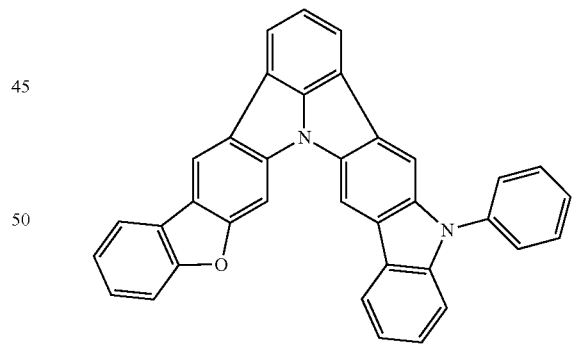
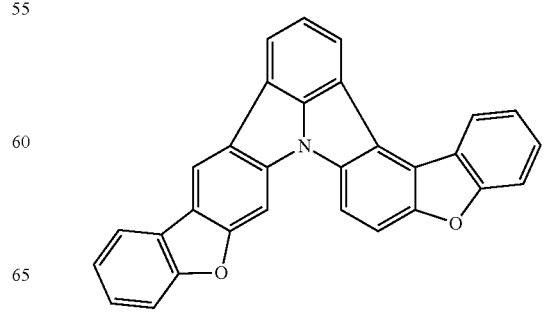

-continued
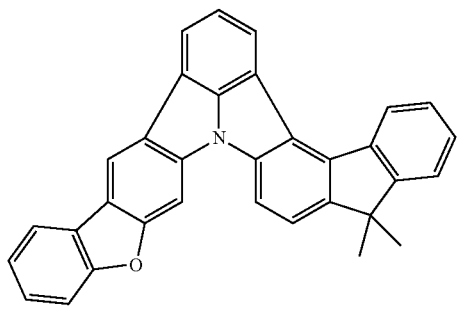
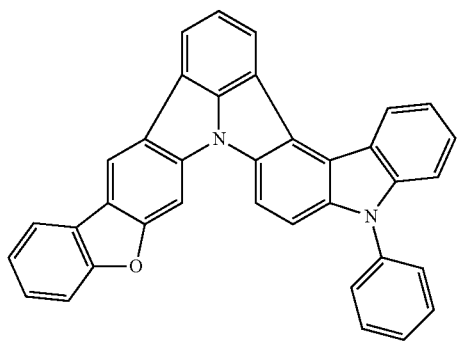
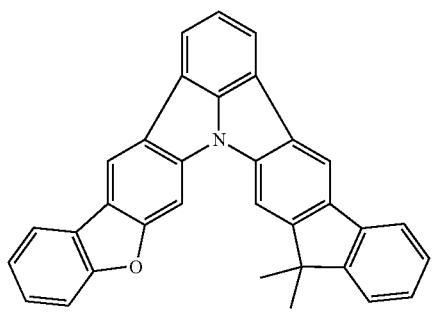
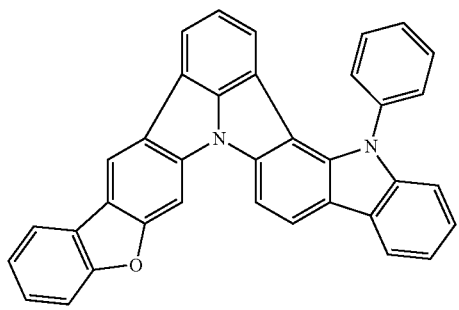
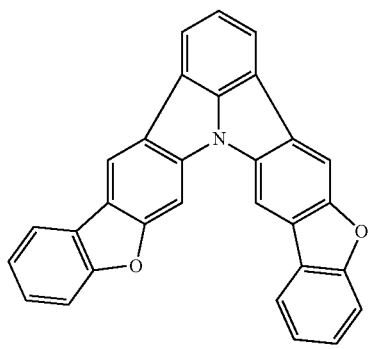
-continued
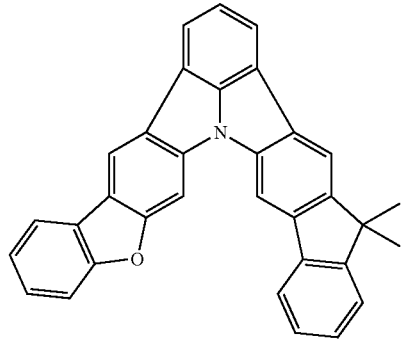
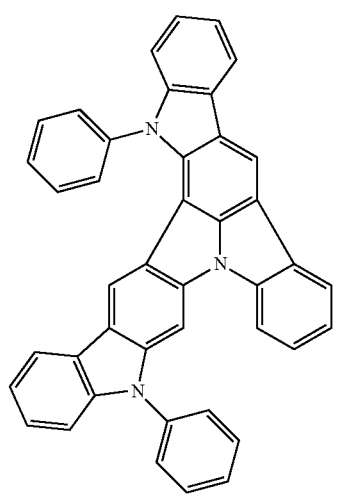
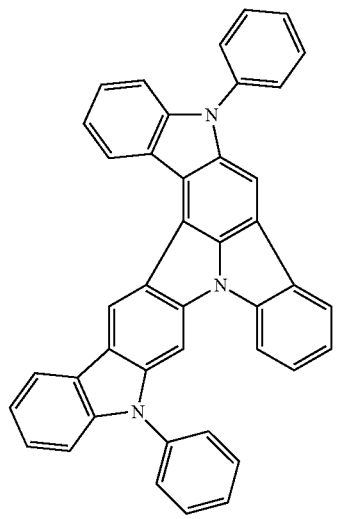

91
-continued
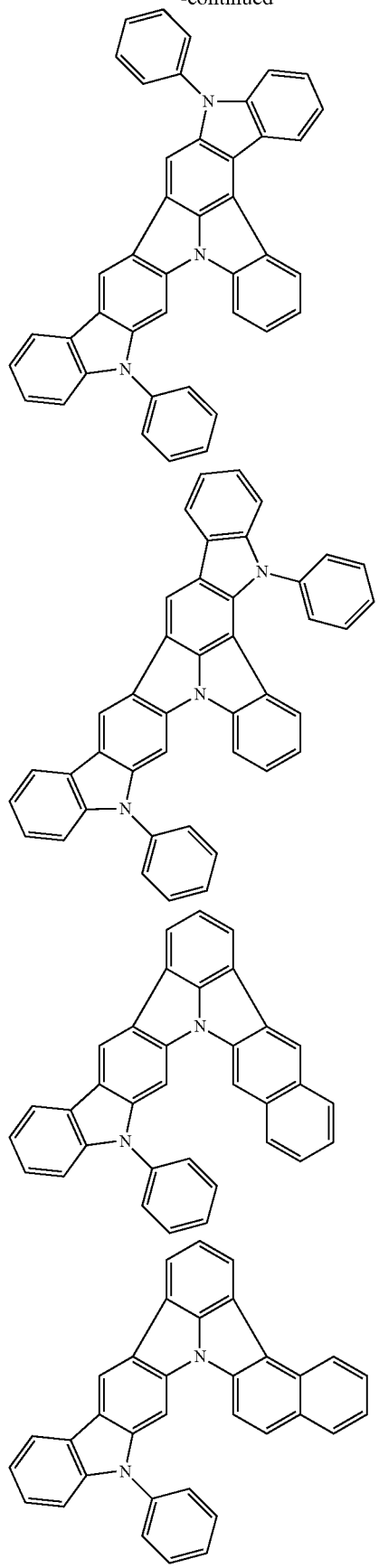
92
-continued
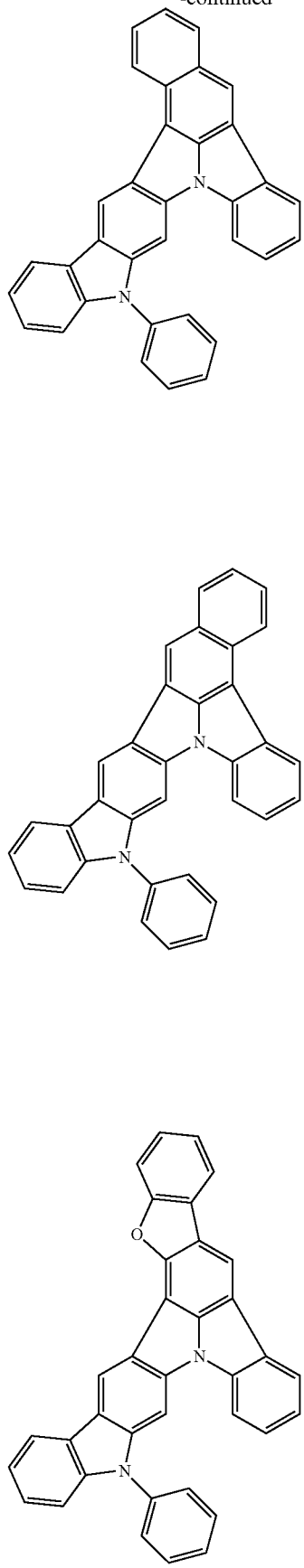

93
-continued
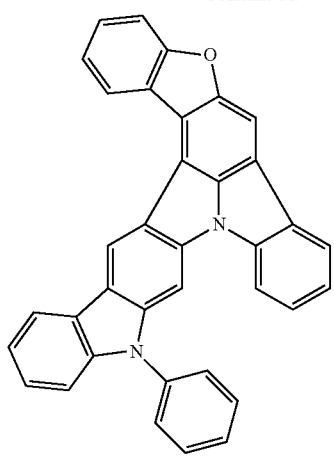
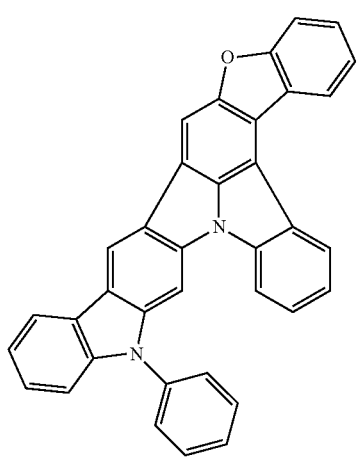
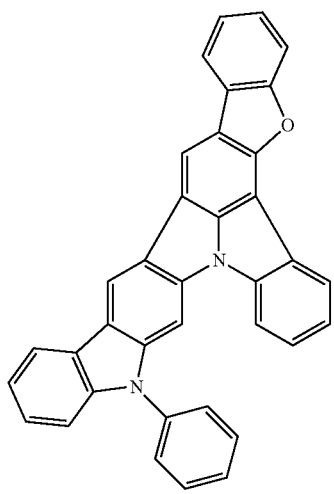
94
-continued
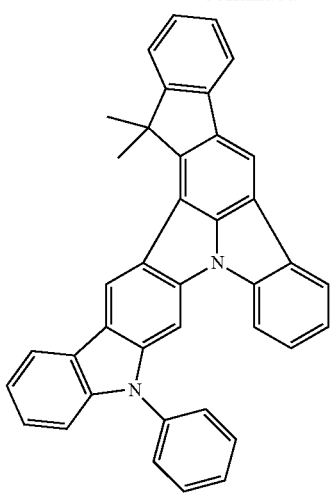
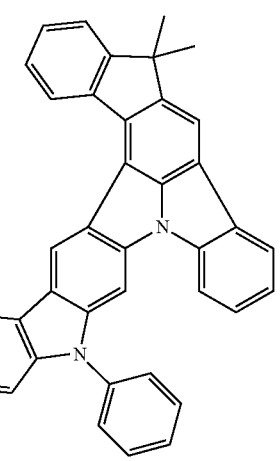
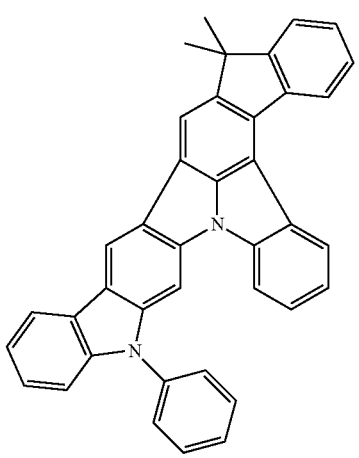

-continued
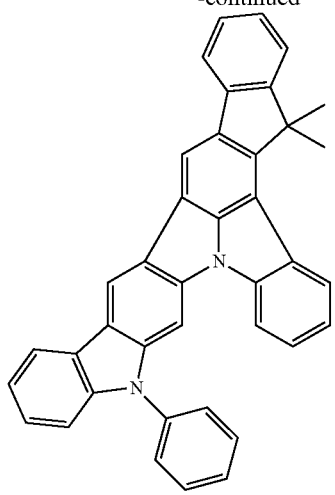
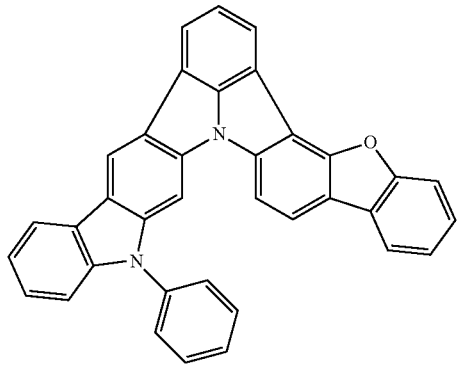
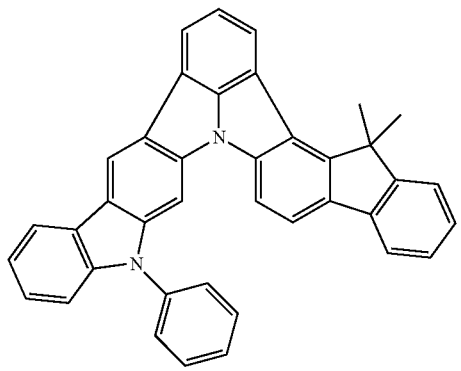
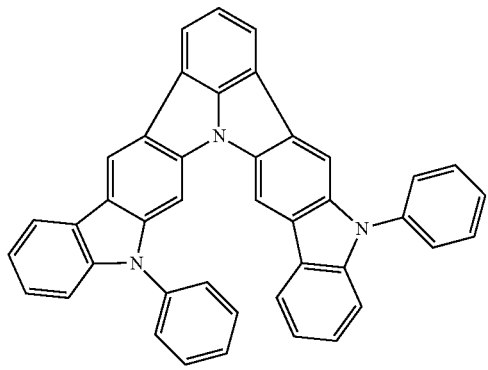
-continued
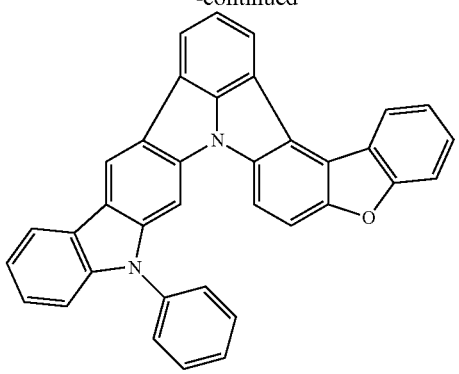
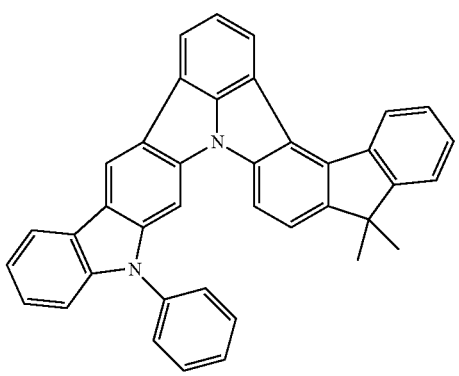
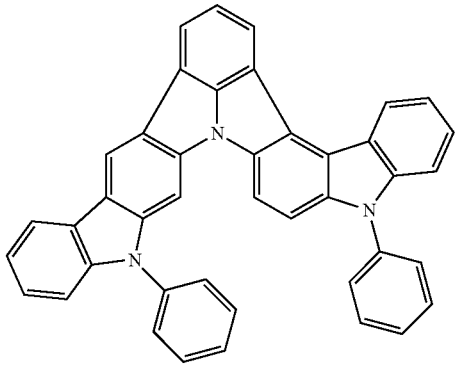
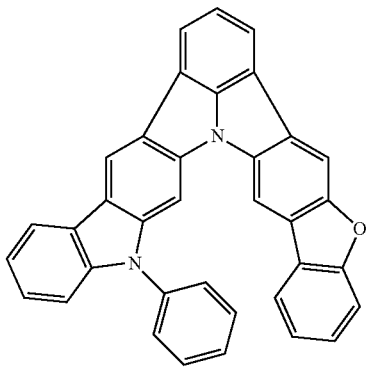

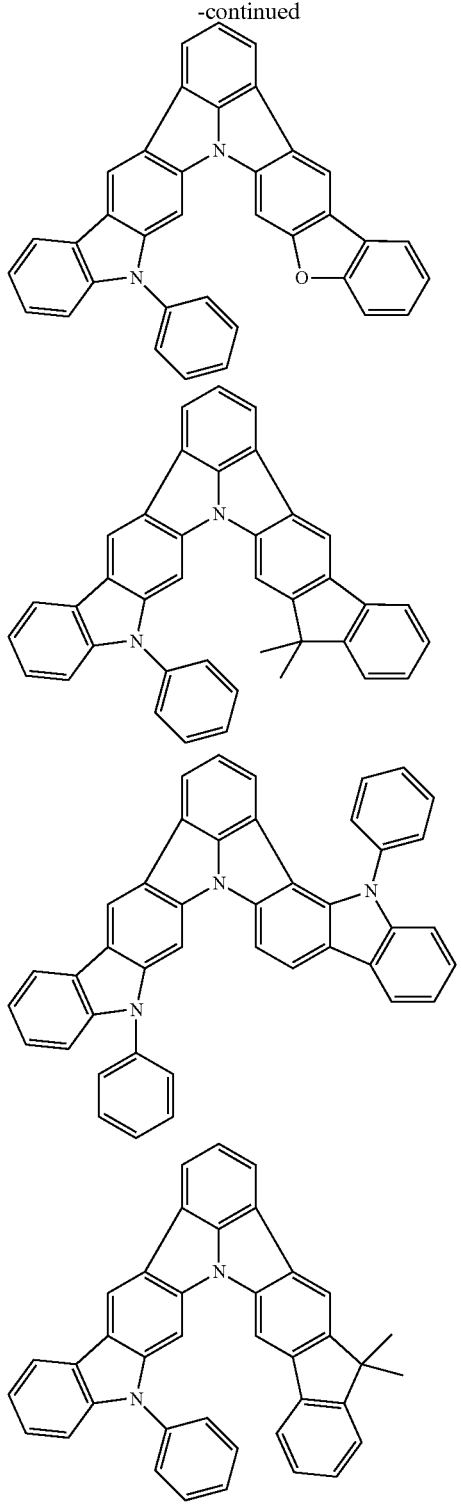

The compounds shown in the description herein are not limited in the production method thereof, and can be produced by appropriately utilizing and modifying the known synthesis reactions with reference to the examples and the like in the description herein depending on necessity.

[Material for Organic EL Device]

A material for an organic EL device according to one embodiment of the present invention contains the compound (1). The content of the compound (1) in the material for an organic EL device is not particularly limited, and for example, may be 1 to 100% by mass, preferably 10 to 100 by mass, more preferably 50 to 100% by mass, further preferably 80 to 100% by mass, and still further preferably to 100% by mass.

The material for an organic EL device is useful for the production of an organic EL device.

[Organic EL Device]

An organic EL device according to one embodiment of the present invention includes an anode, a cathode, and an organic layer provided therebetween, the organic layer includes a light emitting layer, and at least one layer of the organic layer includes the compound (1).

The layer structure of the organic EL device according to one embodiment of the present invention will be explained below.

The organic EL device according to one embodiment of the present invention has an organic layer between one pair of electrode including a cathode and an anode. The organic layer includes at least one layer of a layer constituted by an organic compound. In alternative, the organic layer includes plural layers each constituted by an organic compound, laminated on each other. The organic layer may further contain an inorganic compound in addition to the organic compound.

At least one layer of the organic layer is a light emitting layer.

The organic layer may be constituted, for example, as one layer of a light emitting layer, and may include other layers that can be used in the layer structure of an organic EL device. The layers that can be used in the layer structure of an organic EL device are not particularly limited, and examples thereof include a hole transport band provided between an anode and a light emitting layer (such as a hole transport layer, a hole injection layer, an electron block layer, and an exciton block layer), a light emitting layer, a space layer, and an electron transport band provided between a cathode and a light emitting layer (such as an electron transport layer, an electron injection layer, and a hole block layer).

The organic EL device according to one embodiment of the present invention may be, for example, a fluorescent or phosphorescent monochromatic light emitting device or a fluorescent-phosphorescent hybrid type white light emitting device. The organic EL device may also be a simple type having a single light emitting unit or a tandem type having plural light emitting units.

The "light emitting unit" shown in the description herein means the minimum unit that includes an organic layer, in which at least one layer of the organic layer is a light emitting layer, and emits light through recombination of a hole and an electron injected thereto.

The "light emitting layer" shown in the description herein means an organic layer that has a light emitting function. The light emitting layer is, for example, a phosphorescent light emitting layer, a fluorescent light emitting layer, or the like, and may be a single layer or plural layers.

The light emitting unit may be a laminated type having plural layers including a phosphorescent light emitting layer and a fluorescent light emitting layer, and in this case, may have, between the light emitting layers, a space layer for preventing an exciton formed in the phosphorescent light emitting layer from being diffused to the fluorescent light emitting layer.

Examples of the simple type organic EL device include a device structure of anode/light emitting unit/cathode.

Representative layer structures of the light emitting unit are shown below. The layers in parentheses are optional layers.
- (a) (hole injection layer/) hole transport layer/fluorescent light emitting layer (/electron transport layer/electron injection layer)
- (b) (hole injection layer/) hole transport layer/phosphorescent light emitting layer (/electron transport layer/electron injection layer)
- (c) (hole injection layer/) hole transport layer/first fluorescent light emitting layer/second fluorescent light emitting layer (/electron transport layer/electron injection layer)
- (d) (hole injection layer/) hole transport layer/first phosphorescent light emitting layer/second phosphorescent light emitting layer (/electron transport layer/electron injection layer)
- (e) (hole injection layer/) hole transport layer/phosphorescent light emitting layer/space layer/fluorescent light emitting layer (/electron transport layer/electron injection layer)
- (f) (hole injection layer/) hole transport layer/first phosphorescent light emitting layer/second phosphorescent light emitting layer/space layer/fluorescent light emitting layer (/electron transport layer/electron injection layer)
- (g) (hole injection layer/) hole transport layer/first phosphorescent light emitting layer/space layer/second phosphorescent light emitting layer/space layer/fluorescent light emitting layer (/electron transport layer/electron injection layer)
- (h) (hole injection layer/) hole transport layer/phosphorescent light emitting layer/space layer/first fluorescent light emitting layer/second fluorescent light emitting layer (/electron transport layer/electron injection layer)
- (i) (hole injection layer/) hole transport layer/electron block layer/fluorescent light emitting layer (/electron transport layer/electron injection layer)
- (j) (hole injection layer/) hole transport layer/electron block layer/phosphorescent light emitting layer (/electron transport layer/electron injection layer)
- (k) (hole injection layer/) hole transport layer/exciton block layer/fluorescent light emitting layer (/electron transport layer/electron injection layer)
- (l) (hole injection layer/) hole transport layer/exciton block layer/phosphorescent light emitting layer (/electron transport layer/electron injection layer)
- (m) (hole injection layer/) first hole transport layer/second hole transport layer/fluorescent light emitting layer (/electron transport layer/electron injection layer)
- (n) (hole injection layer/) first hole transport layer/second hole transport layer/fluorescent light emitting layer (/first electron transport layer/second electron transport layer/electron injection layer)
- (o) (hole injection layer/) first hole transport layer/second hole transport layer/phosphorescent light emitting layer (/electron transport layer/electron injection layer)
- (p) (hole injection layer/) first hole transport layer/second hole transport layer/phosphorescent light emitting layer (/first electron transport layer/second electron transport layer/electron injection layer)
- (q) (hole injection layer/) hole transport layer/fluorescent light emitting layer/hole block layer (/electron transport layer/electron injection layer/electron injection layer)
- (r) (hole injection layer/) hole transport layer/phosphorescent light emitting layer/hole block layer (/electron transport layer/electron injection layer)
- (s) (hole injection layer/) hole transport layer/fluorescent light emitting layer/exciton block layer (/electron transport layer/electron injection layer)
- (t) (hole injection layer/) hole transport layer/phosphorescent light emitting layer/exciton block layer (/electron transport layer/electron injection layer)

The layer structure of the organic EL device according to one embodiment of the present invention is not limited to the above. For example, in the case where the organic EL device has a hole injection layer and a hole transport layer, the hole injection layer is preferably provided between the hole transport layer and the anode. In the case where the organic EL device has an electron injection layer and an electron transport layer, the electron injection layer is preferably provided between the electron transport layer and the cathode. The hole injection layer, the hole transport layer, the electron transport layer, and the electron injection layer each may be constituted by one layer or may be constituted by plural layers.

The plural phosphorescent light emitting layers, and the phosphorescent light emitting layer and the fluorescent light emitting layer may be light emitting layers that are different from each other in emission color. For example, the light emitting unit (f) may be hole transport layer/first phosphorescent light emitting layer (red light emission)/second phosphorescent light emitting layer (green light emission)/space layer/fluorescent light emitting layer (blue light emission)/electron transport layer.

An electron block layer may be provided between each of the light emitting layers and the hole transport layer or the space layer. A hole block layer may be provided between each of the light emitting layers and the electron transport layer. The electron block layer and the hole block layer provided can confine electrons or holes inside the light emitting layer to enhance the recombination probability of charges in the light emitting layer, and thereby the light emission efficiency can be enhanced.

Examples of the representative device structure of the tandem type organic EL device include a device structure of anode/first light emitting unit/intermediate layer/second light emitting unit/cathode.

The first light emitting unit and the second light emitting unit each may be independently selected, for example, from the aforementioned light emitting units.

The intermediate layer may also be generally referred to as an intermediate electrode, an intermediate conductive layer, a charge generating layer, an electron withdrawing layer, a connecting layer, or an intermediate insulating layer. The intermediate layer is a layer that supplies electrons to the first light emitting unit and holes to the second light emitting unit, and may be formed with known materials.

FIG. 1 schematically shows one example of the layer structure of the organic EL device. The organic EL device 1 has a substrate 2, an anode 3, a cathode 4, and a light emitting unit (organic layer) 10 disposed between the anode 3 and the cathode 4. The light emitting unit 10 has at least one light emitting layer 5.

A hole transport band (such as a hole injection layer and a hole transport layer) 6 may be formed between the light emitting layer 5 and the anode 3, and an electron transport band (such as an electron injection layer and an electron transport layer) 7 may be formed between the light emitting layer 5 and the cathode 4. An electron block layer (which is not shown in the figure) may be provided on the light emitting layer 5 on the side of the anode 3, and a hole block layer (which is not shown in the figure) may be provided on the light emitting layer 5 on the side of the cathode 4. The structure can confine electrons and holes inside the light emitting layer 5, and thereby the generation efficiency of excitons in the light emitting layer 5 can be further enhanced.

Figure 2:
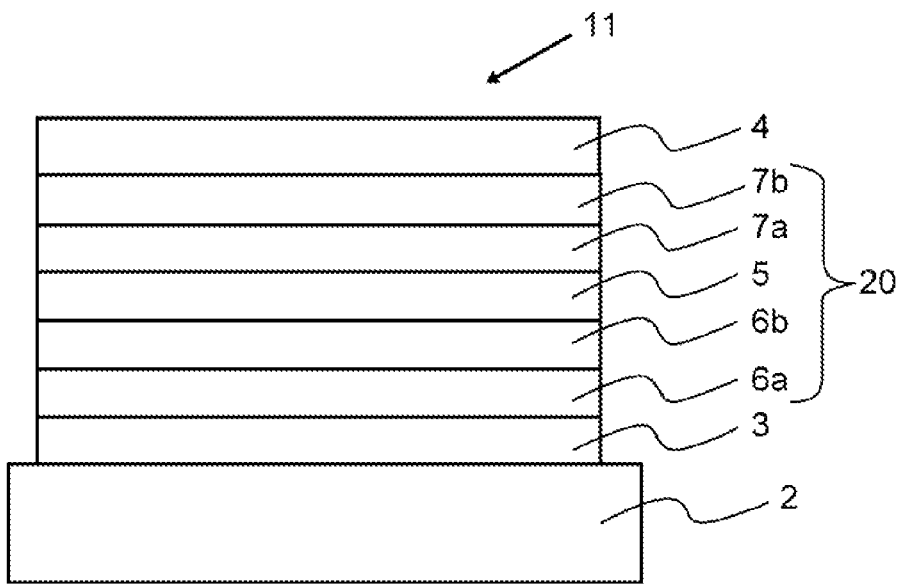
FIG. 2 is a schematic cross sectional view showing a layer structure of an organic EL device according to another embodiment of the present invention.

FIG. 2 schematically shows another example of the layer structure of the organic EL device. In the light emitting unit 20 of the organic EL device 11 shown in FIG. 2, the hole transport layer of the hole transport band 6 and the electron transport layer of the electron transport band 7 of the light emitting unit 10 of the organic EL device 1 in FIG. 1 each have a two-layer structure. The hole transport band 6 has a first hole transport layer 6a on the side of the anode and a second hole transport layer 6b on the side of the cathode. The electron transport band 7 has a first electron transport layer 7a on the side of the anode and a second electron transport layer 7b on the side of the cathode. The other symbols herein are the same as in FIG. 1, and the descriptions therefor are omitted.

The functions, the materials, and the like of the layers of the organic EL device shown in the description herein will be described below.

(Substrate)

The substrate is used as a support of the organic EL device. The substrate preferably has a transmittance for light in the visible region with a wavelength of 400 to 700 nm of 50% or more, and a flat and smooth substrate is preferred. Examples of the material of the substrate include soda-lime glass, aluminosilicate glass, quartz glass, and plastics. A flexible substrate may also be used as the substrate. The flexible substrate means a foldable substrate, and examples thereof include a plastic substrate. Specific examples of the material for forming the plastic substrate include polycarbonate, polyarylate, polyether sulfone, polypropylene, polyester, polyvinyl fluoride, polyvinyl chloride, polyimide, and polyethylene naphthalate. An inorganic vapor-deposited film may also be used.

(Anode)

The anode used is preferably, for example, a metal, an alloy, a conductive compound, or a mixture thereof, having a large work function (which may be specifically 4.0 eV or more). Specific examples of the material of the anode include indium tin oxide (ITO), indium tin oxide containing silicon or silicon oxide, indium zinc oxide, indium oxide containing tungsten oxide or zinc oxide, and graphene. Examples thereof also include gold, silver, platinum, nickel, tungsten, chromium, molybdenum, iron, cobalt, copper, palladium, titanium, and nitrides of these metals (such as titanium nitride).

The anode is generally formed by forming a film of the material by a sputtering method. For example, indium zinc oxide may be formed by a sputtering method with indium oxide having 1 to 10% by mass of zinc oxide added thereto as the target. For example, furthermore, indium oxide containing tungsten oxide or zinc oxide may be formed by a sputtering method with indium oxide having 0.5 to 5% by mass of tungsten oxide or 0.1 to 1% by mass of zinc oxide added thereto as the target.

Examples of the other methods for forming the anode include a vacuum deposition method, a coating method, an ink-jet method, and a spin coating method. For example, in the case where a silver paste or the like is used, a coating method, an ink-jet method, or the like may be used.

The hole injection layer formed in contact with the anode is formed with a material capable of readily injecting holes, irrespective of the work function of the anode. Therefore, the anode can be formed with the ordinary electrode material, such as a metal, an alloy, a conductive compound, and a mixture thereof. Specifically, a material having a small work function may also be used. Examples thereof include an alkali metal, such as lithium and cesium; an alkaline earth metal, such as magnesium, calcium, and strontium; an alloy containing these metals (such as magnesium-silver and aluminum-lithium); a rare earth metal, such as europium and ytterbium; and an alloy containing a rare earth metal.

(Hole Injection Layer)

The hole injection layer is a layer containing a substance having a high hole injection capability, and has a function injecting holes from the anode to the organic layer. Examples of the substance having a high hole injection capability include a molybdenum oxide, a titanium oxide, a vanadium oxide, a rhenium oxide, a ruthenium oxide, a chromium oxide, a zirconium oxide, a hafnium oxide, a tantalum oxide, a silver oxide, a tungsten oxide, a manganese oxide, an aromatic amine compound, an electron attracting (acceptive) compound, and a high-molecular weight compound (such as an oligomer, a dendrimer, and a polymer). Among these, an aromatic amine compound and an acceptive compound are preferred, and an acceptive compound is more preferred.

Specific examples of the aromatic amine compound include 4,4',4''-tris[N,N-diphenylamino]triphenylamine (abbr: TDATA), 4,4',4''-tris(N-(3-methylphenyl)-N-phenylamino)triphenylamine (abbr: MTDATA), 4,4'-bis(N-[4-diphenylaminophenyl]-N-phenylamino)biphenyl (abbr: DPAB), 4,4'-bis(N-{4-[N'-(3-methylphenyl)-N'-phenylamino]}N-phenylamino)biphenyl (abbr: DNTPD), 1,3,5-tris[N-(4-diphenylaminophenyl)-N-phenylamino]benzene (abbr: DPA3B), 3-[N-(9-phenylcarbazol-3-yl)-N-phenylamino]-9-phenylcarbazole (abbr: PCzPCA1), 3,6-bis[N-(9-phenylcarbazol-3-yl)-N-phenylamino]-9-phenylcarbazole (abbr: PCzPCA2), and 3-[N-(1-naphthyl)-N-(9-phenylcarbazol-3-yl)amino]-9-phenylcarbazole (abbr: PCzPCN1).

The acceptive compound is preferably, for example, a heterocyclic derivative having an electron attracting group, a quinone derivative having an electron attracting group, an arylborane derivative, and a heteroarylborane derivative, and specific examples thereof include hexacyanohexaazatriphenylene, 2,3,5,6-tetrafluoro-7,7,8,8-tetracyanoquinodimethane (abbr: F4TCNQ), and 1,2,3-tris[(cyano)(4-cyano-2,3,5,6-tetrafluorophenyl)methylene]cyclopropane.

In the case where the acceptive compound is used, the hole injection layer preferably further contains a matrix material. The matrix material used may be a known material as a material for an organic EL device, and for example, an electron donating (donative) compound is preferably used, and the aforementioned aromatic amine compound is more preferably used.

(Hole Transport Layer)

The hole transport layer is a layer containing a substance having a high hole transport capability, and has a function transporting holes from the anode to the organic layer.

The hole transport layer preferably contains the compound (1) alone, or another substance having a high hole transport capability in combination.

The substance having a high hole transport capability other than the compound (1) is preferably a substance having a hole mobility of $10^{-6}$ $cm^2/(V \cdot s)$ or more, and examples thereof include an aromatic amine compound, a carbazole derivative, an anthracene derivative, and a high-molecular weight compound.

Specific examples of the aromatic amine compound include 4,4'-bis[N-(1-naphthyl)-N-phenylamino]biphenyl (abbr: NPB), N,N'-bis(3-methylphenyl)-N,N'-diphenyl-[1, 1'-biphenyl]-4,4'-diamine (abbr: TPD), 4-phenyl-4'-(9-phenylfluoren-9-yl)triphenylamine (abbr: BAFLP), 4,4'-bis[N-(9,9-dimethylfluoren-2-yl)-N-phenylamino]biphenyl (abbr: DFLDPBi), 4,4',4"-tris(N,N-diphenylamino)triphenylamine (abbr: TDATA), 4,4',4"-tris[N-(3-methylphenyl)-N-phenylamino]triphenylamine (abbr: MTDATA), and 4,4'-bis[N-(spiro-9,9'-bifluoren-2-yl)-N-phenylamino]biphenyl (abbr: BSPB).

Specific examples of the carbazole derivative include 4,4'-di(9-carbazolyl)biphenyl (abbr: CBP), 9-[4-(9-carbazolyl)phenyl]-10-phenylanthracene (abbr: CzPA), and 9-phenyl-3-[4-(10-phenyl-9-anthryl)phenyl]-9H-carbazole (abbr: PCzPA).

Specific examples of the anthracene derivative include 2-t-butyl-9,10-di(2-naphthyl)anthracene (abbr: t-BuDNA), 9,10-di(2-naphthyl)anthracene (abbr: DNA), and 9,10-diphenylanthracene (abbr: DPAnth).

Specific examples of the high-molecular weight compound include poly(N-vinylcarbazole) (abbr: PVK) and poly(4-vinyltriphenylamine) (abbr: PVTPA).

A substance other than the above may be used in the hole transport layer, as far as the substance has a higher hole transport capability than an electron transport capability.

The hole transport layer may be a single layer or may be two or more layers laminated. In this case, it is preferred that a substance that has a larger energy gap among the substances having a high hole transport capability is disposed on the side near the light emitting layer.

For example, as shown in FIG. 2, the structure may include the first hole transport layer 6a on the side of the anode and the second hole transport layer 6b on the side of the cathode. In this case, it is preferred that the compound (1) is contained in one of the first hole transport layer and the second hole transport layer, and it is more preferred that different compounds (1) are contained in both layers respectively.

(Light Emitting Layer)

The light emitting layer is a layer containing a substance having a high light emission capability (i.e., a dopant material). The dopant material used may be various materials, and examples thereof include a fluorescent light emitting compound (i.e., a fluorescent dopant) and a phosphorescent light emitting compound (i.e., a phosphorescent dopant). The fluorescent light emitting compound is a compound capable of emitting light from the singlet excited state, and the light emitting layer containing this compound is referred to as a fluorescent light emitting layer. The phosphorescent light emitting compound is a compound capable of emitting light from the triplet excited state, and the light emitting layer containing this compound is referred to as a phosphorescent light emitting layer.

The light emitting layer generally contains the dopant material and a host material for making the dopant material to emit light efficiently. The dopant material may also be referred to as a guest material, an emitter, or a light emitting material, depending on literatures. The host material may also be referred to as a matrix material depending on literatures.

Plural dopant materials and plural host materials may be contained in one light emitting layer. Plural light emitting layers may be used.

In the description herein, the host material combined with the fluorescent dopant is referred to as a "fluorescent host", and the host material combined with the phosphorescent dopant is referred to as a "phosphorescent host". The fluorescent host and the phosphorescent host are not distinguished from each other only by the molecular structures. The phosphorescent host is a material that forms the phosphorescent light emitting layer along with the phosphorescent dopant, but this does not mean that the material cannot be used as a material for forming the fluorescent light emitting layer. The same can be applied to the fluorescent host.

The compound (1) is preferably contained in the light emitting layer, and is more preferably contained as the dopant material. The compound (1) is preferably contained in the light emitting layer as the fluorescent dopant.

The content of the compound (1) as the dopant material in the light emitting layer is not particularly limited, and for example, is preferably 0.1 to 70% by mass, more preferably 0.1 to 30% by mass, further preferably 1 to 30% by mass, still further preferably 1 to 20% by mass, and particularly preferably 1 to 10% by mass, from the standpoint of the sufficient light emission and concentration quenching.

<Fluorescent Dopant>

Examples of the fluorescent dopant other than the compound (1) include a condensed polycyclic aromatic derivative, a styrylamine derivative, a condensed ring amine derivative, a boron-containing compound, a pyrrole derivative, an indole derivative, and a carbazole derivative. Among these, a condensed ring amine derivative and a boron-containing compound are preferred.

Examples of the condensed ring amine derivative include a diaminopyrene derivative, a diaminochrysene derivative, a diaminofluorene derivative, and a diaminofluorene derivative having one or more benzofuro skeleton condensed thereto.

Examples of the boron-containing compound include a pyrromethene derivative and triphenylborane derivative.

Examples of the blue color fluorescent dopant include a pyrene derivative, a styrylamine derivative, a chrysene derivative, a fluoranthene derivative, a fluorene derivative, a diamine derivative, and a triarylamine derivative. Specific examples thereof include N,N'-bis[4-(9H-carbazol-9-yl)phenyl]-N,N'-diphenylstilbene-4,4'-diamine (abbr: YGA2S), 4-(9H-carbazol-9-yl)-4'-(10-phenyl-9-anthryl)triphenylamine (abbr: YGAPA), and 4-(10-phenyl-9-anthryl)-4'-(9-phenyl-9H-carbazol-3-yl)triphenylamine (abbr: PCBAPA).

Examples of the green color fluorescent dopant include an aromatic amine derivative. Specific examples thereof include N-(9,10-diphenyl-2-anthryl)-N,9-diphenyl-9H-carbazole-3-amine (abbr: 2PCAPA), N-[9,10-bis(1,1'-biphenyl-2-yl)-2-anthryl]-N,9-diphenyl-9H-carbazole-3-amine (abbr: 2PCABPhA), N-(9,10-diphenyl-2-anthryl)-N,N',N'-triphenyl-1,4-phenylenediamine (abbr: 2D PAPA) N-[9,10-bis(1,1'-biphenyl-2-yl)-2-anthryl]-N,N',N'-triphenyl-1,4-phenylenediamine (abbr: 2DPABPhA), N-[9,10-bis(1,1'-biphenyl-2-yl)]-N-[4-(9H-carbazol-9-yl)phenyl]-N-phenylanthracene-2-amine (abbr: 2YGABPhA), and N,N,9-triphenylanthracene-9-amine (abbr: DPhAPhA).

Examples of the red color fluorescent dopant include a tetracene derivative and a diamine derivative. Specific examples thereof include N,N,N',N'-tetrakis(4-methylphenyl)tetracene-5,11-diamine (abbr: p-mPhTD) and 7,14-diphenyl-N,N,N',N'-tetrakis(4-methylphenyl)acenaphtho[1,2-a]fluoranthene-3,10-diamine (abbr: p-mPhAFD).

<Phosphorescent Dopant>

Examples of the phosphorescent dopant include a heavy metal complex having a phosphorescent light emission capability and a rare earth metal complex having a phosphorescent light emission capability.

Examples of the heavy metal complex include an iridium complex, an osmium complex, and a platinum complex. The heavy metal complex is preferably an ortho metalated complex of a metal selected from iridium, osmium, and platinum.

Examples of the rare earth metal complex include a terbium complex and a europium complex. Specific examples thereof include tris(acetylacetonato) (monophenanthroline) terbium(III), (abbr: Tb(acac)$_3$(Phen)), tris(1,3-diphenyl-1,3-propanedionato) (monophenanthroline) europium(III) (abbr: Eu(DBM)$_3$(Phen)), and tris[1-(2-thenoyl)-3,3,3-trifluoroacetonato] (monophenanthroline) europium(III) (abbr: Eu(TTA)$_3$(Phen)). These rare earth complexes are preferred as the phosphorescent dopant since the rare earth metal ion emits light through electron transition between different multiplicities.

Examples of the blue color phosphorescent dopant include an iridium complex, an osmium complex, and a platinum complex. Specific examples thereof include bis[2-(4',6'-difluorophenyl)pyridinato-N,C2'] iridium(III) tetrakis(1-pyrazolyl)borate (abbr: FIr6), bis[2-(4',6'-difluorophenyl)pyridinato-N,C2'] iridium(III) picolinate (abbr: FIrpic), bis[2-(3',5'-bistrifluoromethylphenyl)pyridinato-N,C2'] iridium(III) picolinate (abbr: Ir(CF3ppy)$_2$(pic)), and bis[2-(4',6'-difluorophenyl)pyridinato-N,C2'] iridium(III) acetylacetonate (abbr: FIracac).

Examples of the green color phosphorescent dopant include an iridium complex. Specific examples thereof include tris(2-phenylpyridinato-N,C2') iridium(III) (abbr: Ir(ppy)$_3$), bis(2-phenylpyridinato-N,C2') iridium(III) acetylacetonate (abbr: Ir(ppy)$_2$(acac)), bis(1,2-diphenyl-1H-benzoimidazolato) iridium(III) acetylacetonate (abbr: Ir(pbi)$_2$(acac)), and bis(benzo[h]quinolinato) iridium(III) acetylacetonate (abbr: Ir(bzq)$_2$(acac)).

Examples of the red color phosphorescent dopant include an iridium complex, a platinum complex, a terbium complex, and a europium complex. Specific examples thereof include bis[2-(2'-benzo[4,5-α]thienyl)pyridinato-N,C3'] iridium(III) acetylacetonate (abbr: Ir(btp)$_2$(acac)), bis(1-phenylisoquinolinato-N,C2') iridium(III) acetylacetonate (abbr: Ir(piq)$_2$(acac)), (acetylacetonato) bis[2,3-bis(4-fluorophenyl)quinoxalinato] iridium(III) (abbr: Ir(Fdpq)$_2$(acac)), and 2,3,7,8,12,13,17,18-octaethyl-21H,23H-porphyrin platinum(II) (abbr: PtOEP).

<Host Material>

In the organic EL device according to one embodiment of the present invention, at least one layer of the organic layer preferably further contains a compound represented by the following formula (31) as a host material.

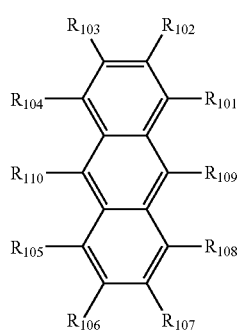

(31)

In the formula (31), at least one of $R_{101}$ to $R_{110}$ represents a group represented by the following formula (41). In the case where two or more groups represented by the following formula (41) exist, the two or more groups represented by the following formula (41) may be the same as or different from each other.

$-L_{101}-Ar_{101}$ (41)

In the formula (41), $L_{101}$ represents a single bond, a substituted or unsubstituted arylene group having 6 to 30 ring carbon atoms, or a substituted or unsubstituted divalent heterocyclic group having 5 to ring atoms.

$Ar_{101}$ represents a substituted or unsubstituted aryl group having 6 to 50 ring carbon atoms, or a substituted or unsubstituted monovalent heterocyclic group having 5 to ring atoms.

In $R_{101}$ to $R_{110}$ that do not represent a group represented by the formula (41), one or more combination of two or more adjacent groups forms a substituted or unsubstituted saturated or unsaturated ring or does not form the ring.

$R_{101}$ to $R_{110}$ that do not represent a group represented by the formula (41) and do not form the ring each independently represent a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a substituted or unsubstituted aryl group having 6 to 50 ring carbon atoms, or a substituted or unsubstituted monovalent heterocyclic group having 5 to ring atoms.

$R_{901}$ to $R_{907}$ each independently represent a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms. In the case where two or more groups represented by $R_{901}$ to $R_{907}$ exist, the two or more groups represented by $R_{901}$ to $R_{907}$ may be the same as or different from each other.

In one embodiment, the compound (31) is a compound represented by the following formula (31-1).

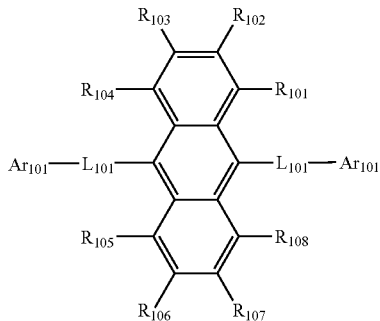

(31-1)

In the formula (31-1), $R_{101}$ to $R_{108}$, $L_{101}$, and $Ar_{101}$ have the same definitions as in the formula (31).

In one embodiment, the compound (31) is a compound represented by the following formula (31-2).

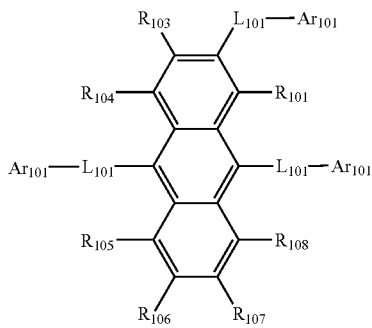

(31-2)

In the formula (31-2), $R_{101}$, $R_{103}$ to $R_{108}$, $L_{101}$, and $Ar_{101}$ have the same definitions as in the formula (31).

In one embodiment, the compound (31) is a compound represented by the following formula (31-3).

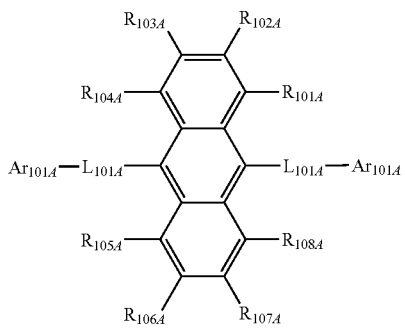

(31-3)

In the formula (31-3), $R_{101A}$ to $R_{108A}$ each independently represent a hydrogen atom or a substituted or unsubstituted aryl group having 6 to 50 ring carbon atoms.

$L_{101A}$ represents a single bond or a substituted or unsubstituted arylene group having 6 to 30 ring carbon atoms. The two groups represented by $L_{101A}$ may be the same as or different from each other.

$Ar_{101A}$ represents a substituted or unsubstituted aryl group having 6 to 50 ring carbon atoms. The two groups represented by $Ar_{101A}$ may be the same as or different from each other.

In one embodiment, the compound (31) is a compound represented by the following formula (31-4).

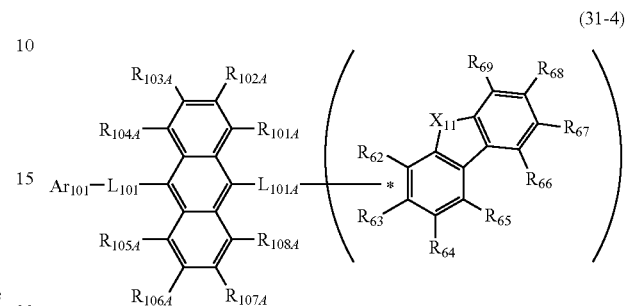

(31-4)

In the formula (31-4), $L_{101}$ and $Ar_{101}$ have the same definitions as in the formula (31).

$R_{101A}$ to $R_{108A}$ each independently represent a hydrogen atom or a substituted or unsubstituted aryl group having 6 to 50 ring carbon atoms.

$X_{11}$ represents an oxygen atom (—O—), a sulfur atom (—S—), —C($R_{91}$)($R_{92}$)—, or —$NR_{61}$—.

$R_{91}$ and $R_{92}$ have the same definition as $R^{31}$ and $R^{32}$, and specific examples and preferred groups thereof are also the same.

$R_{61}$ represents a hydrogen atom, a substituted or unsubstituted alkyl group having 1 to 50 carbon atoms, or a substituted or unsubstituted aryl group having 6 to 50 ring carbon atoms.

One of $R_{62}$ to $R_{69}$ represents a bond bonded to $L_{101}$.

In $R_{62}$ to $R_{69}$ that are not bonded to $L_{101}$, one or more combination of two or more adjacent groups forms a substituted or unsubstituted saturated or unsaturated ring or does not form the ring.

$R_{62}$ to $R_{69}$ that are not bonded to $L_{101}$ and do not form the ring each independently represent a hydrogen atom, a substituted or unsubstituted alkyl group having 1 to 50 carbon atoms, or a substituted or unsubstituted aryl group having 6 to 50 ring carbon atoms.

In one embodiment, the compound (31) is a compound represented by the following formula (31-4A).

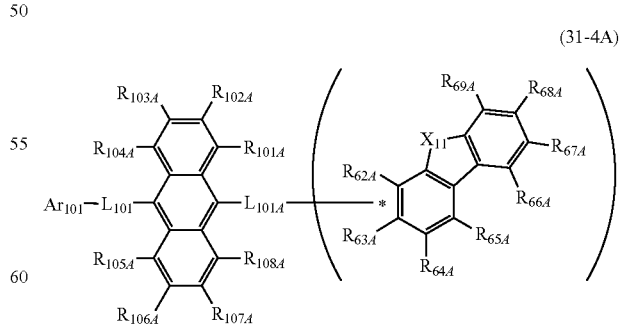

(31-4A)

In the formula (31-4A), $R_{101A}$ to $R_{108A}$ each independently represent a hydrogen atom or a substituted or unsubstituted aryl group having 6 to 50 ring carbon atoms.

$X_{11}$ represents an oxygen atom (—O—), a sulfur atom (—S—), —C($R_{91}$)($R_{92}$)—, or —N($R_{61}$)—.

$R_{91}$ and $R_{92}$ have the same definition as $R^{31}$ and $R^{32}$, and specific examples and preferred groups thereof are also the same.

$R_{61}$ represents a hydrogen atom, a substituted or unsubstituted alkyl group having 1 to 50 carbon atoms, or a substituted or unsubstituted aryl group having 6 to 50 ring carbon atoms.

In $R_{62A}$ to $R_{69A}$, any one combination of two adjacent groups forms a ring represented by the following formula (31-4A-1).

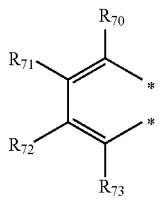

(31-4A-1)

In the formula (31-4A-1), two bonds * are bonded to adjacent two of $R_{62A}$ to $R_{69A}$ respectively.

One of $R_{70}$ to $R_{73}$ represents a bond bonded to $L_{101}$.

$R_{70}$ to $R_{73}$ that are not bonded to $L_{101}$ each independently represent a hydrogen atom, a substituted or unsubstituted alkyl group having 1 to 50 carbon atoms, or a substituted or unsubstituted aryl group having 6 to 50 ring carbon atoms.

In $R^{62A}$ to $R_{69A}$ that do not form the ring represented by the formula (31-4A-1), one or more combination of two or more adjacent groups forms a substituted or unsubstituted saturated or unsaturated ring or does not form the ring.

$R_{62A}$ to $R_{69A}$ that do not form the ring represented by the formula (31-4A-1) and do not form the substituted or unsubstituted saturated or unsaturated ring each independently represent a hydrogen atom, a substituted or unsubstituted alkyl group having 1 to 50 carbon atoms, or a substituted or unsubstituted aryl group having 6 to 50 ring carbon atoms.

In one embodiment, the compound (31) is a compound represented by the following formula (31-6).

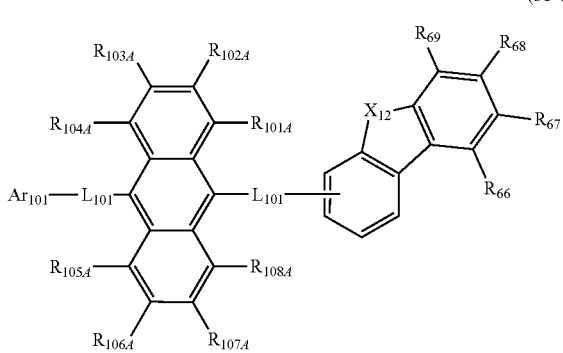

(31-6)

In the formula (31-6), $L_{101}$ and $Ar_{101}$ have the same definitions as in the formula (31).

$R_{101}$ to $R_{108A}$ have the same definitions as in the formula (31-4).

$R_{66}$ to $R_{69}$ have the same definitions as in the formula (31-4).

$X_{12}$ represents an oxygen atom (—O—), a sulfur atom (—S—), or —C($R_{91}$)($R_{92}$)—.

$R_{91}$ and $R_{92}$ have the same definition as $R^{31}$ and $R^{32}$, and specific examples and preferred groups thereof are also the same.

In one embodiment, the compound represented by the formula (31-6) is a compound represented by the following formula (31-6H).

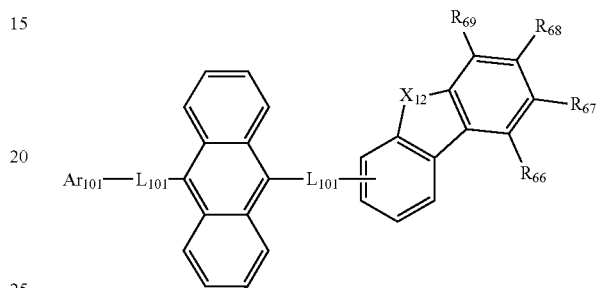

(31-6H)

In the formula (31-6H), $L_{101}$ and $Ar_{101}$ have the same definitions as in the formula (31).

$R_{66}$ to $R_{69}$ have the same definitions as in the formula (31-4).

$X_{12}$ represents an oxygen atom (—O—), a sulfur atom (—S—), or —C($R_{91}$)($R_{92}$)—.

$R_{91}$ and $R_{92}$ have the same definition as $R^{31}$ and $R^{32}$, and specific examples and preferred groups thereof are also the same.

In one embodiment, the compound represented by the formulae (31-6) and (31-6H) is a compound represented by the following formula (31-6Ha).

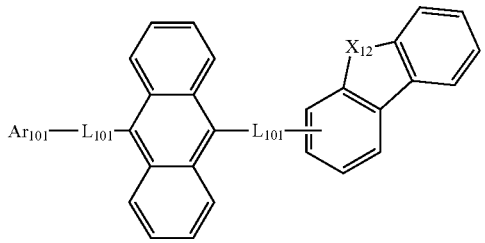

(31-6Ha)

In the formula (31-6Ha), $L_{101}$ and $Ar_{101}$ have the same definitions as in the formula (31).

$X_{12}$ represents an oxygen atom (—O—), a sulfur atom (—S—), or —C($R_{91}$)($R_{92}$)—.

$R_{91}$ and $R_{92}$ have the same definition as $R^{31}$ and $R^{32}$, and specific examples and preferred groups thereof are also the same.

In one embodiment, the compound represented by the formulae (31-6), (31-6H), and (31-6Ha) is a compound represented by the following formula (31-6Ha-1) or (31-6Ha-2).

(31-6Ha-1)

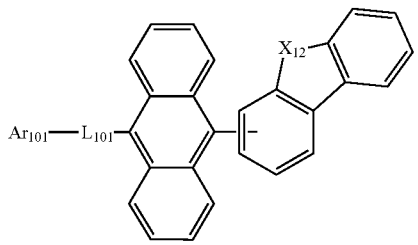

(31-6Ha-2)

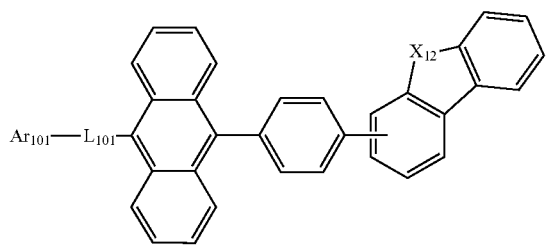

In the formulae (31-6Ha-1) and (31-6Ha-2), $L_{101}$ and $Ar_{101}$ have the same definitions as in the formula (31).

$X_{12}$ represents an oxygen atom (—O—), a sulfur atom (—S—), or —C($R_{91}$)($R_{92}$)—.

$R_{91}$ and $R_{92}$ have the same definition as $R^{31}$ and $R^{32}$, and specific examples and preferred groups thereof are also the same.

In one embodiment, the compound (31) is a compound represented by the following formula (31-7).

(31-7)

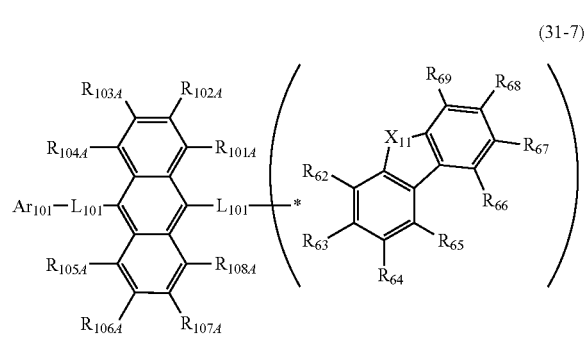

In the formula (31-7), $L_{101}$ and $Ar_{101}$ have the same definitions as in the formula (31).

$R_{101A}$ to $R_{108A}$ have the same definitions as in the formula (31-4).

$X_{11}$ has the same definition as in the formula (31-4).

$R_{62}$ to $R_{69}$ have the same definitions as in the formula (31-4), provided that any one of the combinations of $R_{66}$ and $R_{67}$, $R_{67}$ and $R_{68}$, and $R_{68}$ and $R_{69}$ forms a substituted or unsubstituted saturated or unsaturated ring through bonding the members thereof.

In one embodiment, the compound (31) is a compound represented by the following formula (31-7H).

(31-7H)

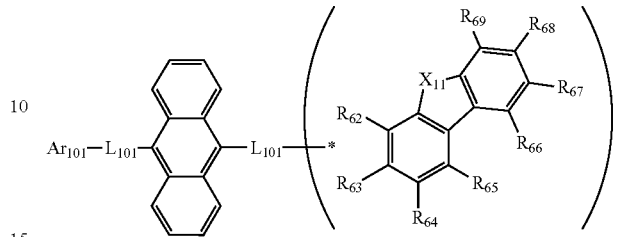

In the formula (31-7H), $L_{101}$ and $Ar_{101}$ have the same definitions as in the formula (31).

$X_{11}$ has the same definition as in the formula (31-4).

$R_{62}$ to $R_{69}$ have the same definitions as in the formula (31-4), provided that any one of the combinations of $R_{66}$ and $R_{67}$, $R_{67}$ and $R_{68}$, and $R_{68}$ and $R_{69}$ forms a substituted or unsubstituted saturated or unsaturated ring through bonding the members thereof.

In one embodiment, the compound (31) is a compound represented by the following formula (31-8).

(31-8)

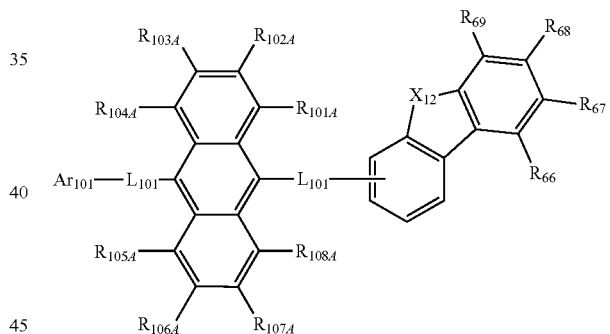

In the formula (31-8), $L_{201}$ and $Ar_{201}$ have the same definitions as in the formula (31).

$R_{201A}$ to $R_{208A}$ have the same definitions as in the formula (31-4).

$X_{12}$ represents an oxygen atom (—O—), a sulfur atom (—S—), or —C($R_{91}$)($R_{92}$)—.

$R_{91}$ and $R_{92}$ have the same definition as $R^{31}$ and $R^{32}$, and specific examples and preferred groups thereof are also the same.

$R_{76}$ to $R_{79}$ have the same definitions as in the formula (31-4), provided that any one of the combinations of $R_{76}$ and $R_{77}$, $R_{77}$ and $R_{78}$, and $R_{78}$ and $R_{79}$ forms a substituted or unsubstituted saturated or unsaturated ring through bonding the members thereof.

In one embodiment, the compound represented by the compound (31-8) is a compound represented by the following formula (31-8H).

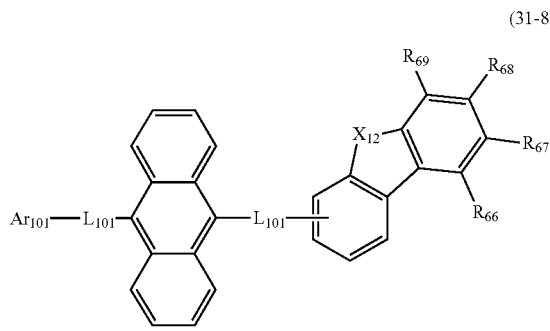

(31-8H)

In the formula (31-8H), $L_{101}$ and $Ar_{101}$ have the same definitions as in the formula (31).

$R_{66}$ to $R_{69}$ have the same definitions as in the formula (31-4), provided that any one of the combinations of $R_{66}$ and $R_{67}$, $R_{67}$ and $R_{68}$, and $R_{68}$ and $R_{69}$ forms a substituted or unsubstituted saturated or unsaturated ring through bonding the members thereof. The combination of $R_{66}$ and $R_{67}$, $R_{67}$ and $R_{68}$, or $R_{68}$ and $R_{69}$ preferably forms an unsubstituted benzene ring through bonding the members thereof.

$X_{12}$ represents an oxygen atom (—O—), a sulfur atom (—S—), or —C($R_{91}$)($R_{92}$)—.

$R_{91}$ and $R_{92}$ have the same definition as $R_{31}$ and $R_{32}$, and specific examples and preferred groups thereof are also the same.

In one embodiment, in the compound represented by the formula (31-7), (31-8), or (31-8H), any one of the combinations of $R_{66}$ and $R_{67}$, $R_{67}$ and $R_{68}$, and $R_{68}$ and $R_{69}$ forms a ring represented by the following formula (31-8-1) or (31-8-2) through bonding the members thereof, and $R_{66}$ to $R_{69}$ that do not form a ring represented by the following formula (31-8-1) or (31-8-2) do not form a substituted or unsubstituted saturated or unsaturated ring.

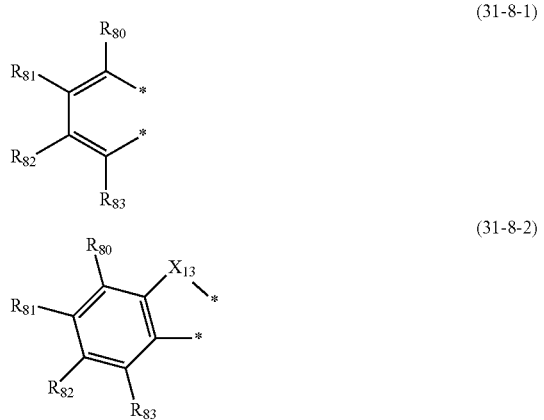

(31-8-1)

(31-8-2)

In the formulae (31-8-1) and (31-8-2), two bonds * are bonded to any one of the combinations of $R_{66}$ and $R_{67}$, $R_{67}$ and $R_{68}$, and $R_{68}$ and $R_{69}$.

$R_{80}$ to $R_{83}$ each independently represent a hydrogen atom, a substituted or unsubstituted alkyl group having 1 to 50 carbon atoms, or a substituted or unsubstituted aryl group having 6 to 50 ring carbon atoms.

$X_{13}$ represents O or S.

In one embodiment, the compound (31) is a compound represented by the following formula (31-9).

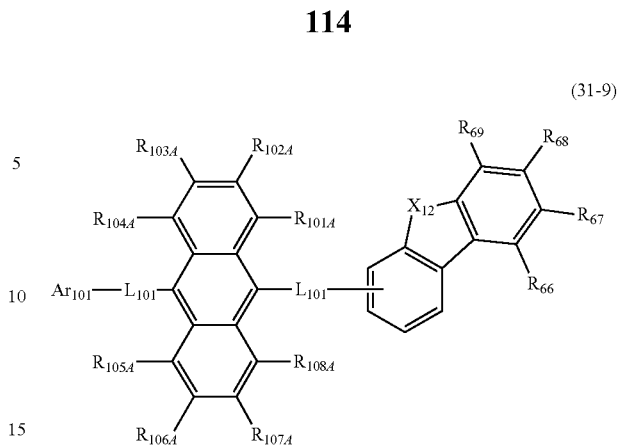

(31-9)

In the formula (31-9), $L_{101}$ and $Ar_{101}$ have the same definitions as in the formula (31).

$R_{101A}$ to $R_{108A}$ have the same definitions as in the formula (31-4).

$R_{66}$ to $R_{69}$ have the same definitions as in the formula (31-4), provided that $R_{66}$ and $R_{67}$, $R_{67}$ and $R_{68}$, and $R_{68}$ and $R_{67}$ each are not bonded to each other and do not form a substituted or unsubstituted saturated or unsaturated ring.

$X_{12}$ represents an oxygen atom (—O—), a sulfur atom (—S—), or —C($R_{91}$)($R_{92}$)—.

$R_{91}$ and $R_{92}$ have the same definition as $R^{31}$ and $R^{32}$, and specific examples and preferred groups thereof are also the same.

In one embodiment, the compound (31) is selected from the group consisting of compounds represented by the following formulae (31-10-1) to (31-10-4).

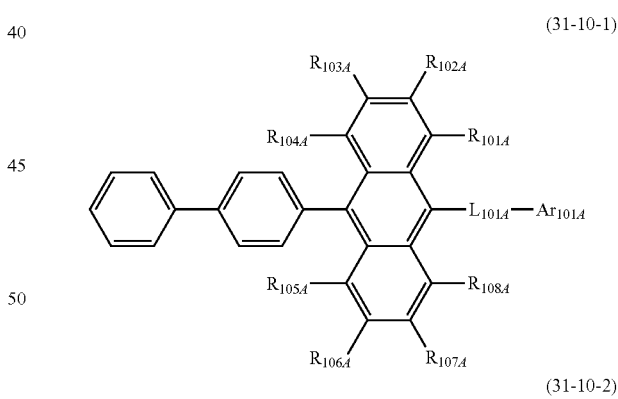

(31-10-1)

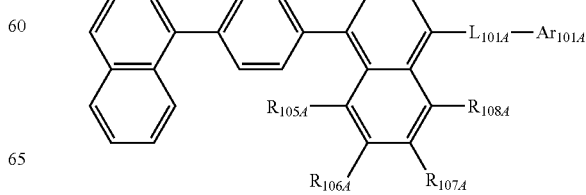

(31-10-2)

(31-10-3)

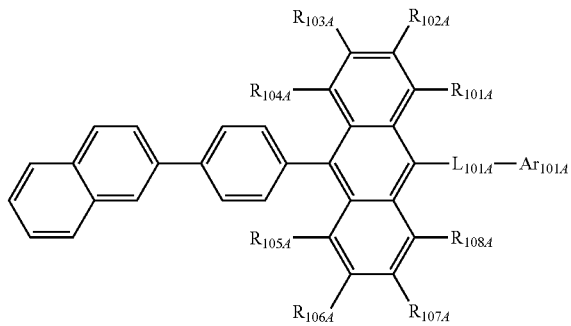

(31-10-2H)

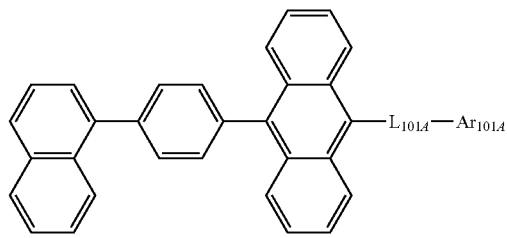

(31-10-3H)

(31-10-4)

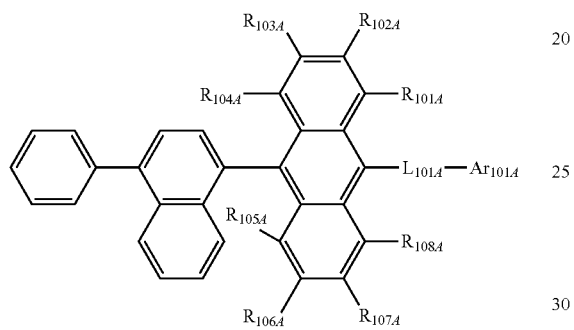

In the formulae (31-10-1) to (31-10-4), $L_{101}A$, $Ar_{101A}$, and $R_{101A}$ to $R_{108A}$ have the same definitions as in the formula (31-3).

In one embodiment, the compounds represented by the formulae (31-10-1) to (31-10-4) are selected from the group consisting of compounds represented by the following formulae (31-10-1H) to (31-10-4H).

(31-10-1H)

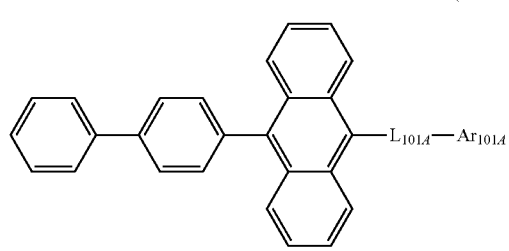

(31-10-4H)

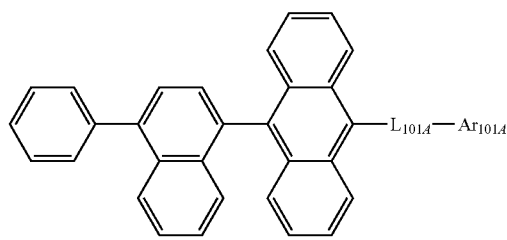

In the formulae (31-10-1H) to (31-10-4H), $L_{101A}$ and $Ar_{101A}$ have the same definitions as in the formula (31-3).

In the formulae (31), (31-1) to (31-4), (31-4-4A), (31-6), (31-6H), (31-6Ha), (31-6Ha-1), (31-6Ha-2), (31-7), (31-7H), (31-8), (31-8H), (31-9), (31-10-1) to (31-10-4), and (31-10-1H) to (31-10-4H), the details of the substituents and the details of the substituent in the expression "substituted or unsubstituted" have been described in the section "Definitions" in the description herein.

Specific examples of the compound represented by the formula (31) include the following compounds.

[Chem. 42]

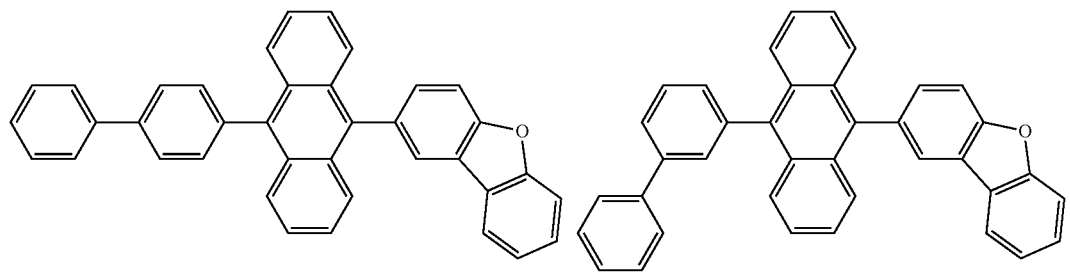

117 118
-continued
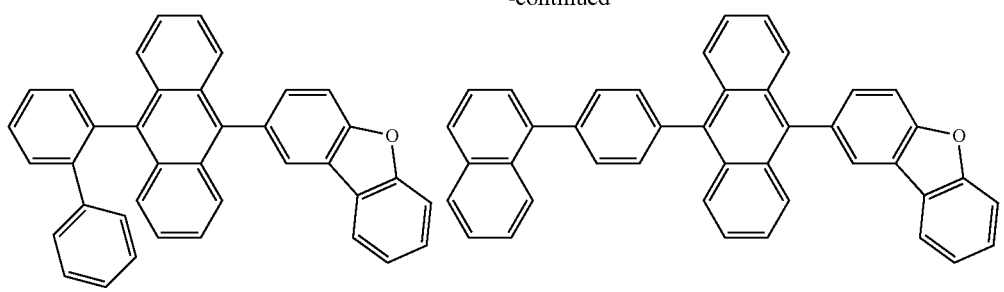
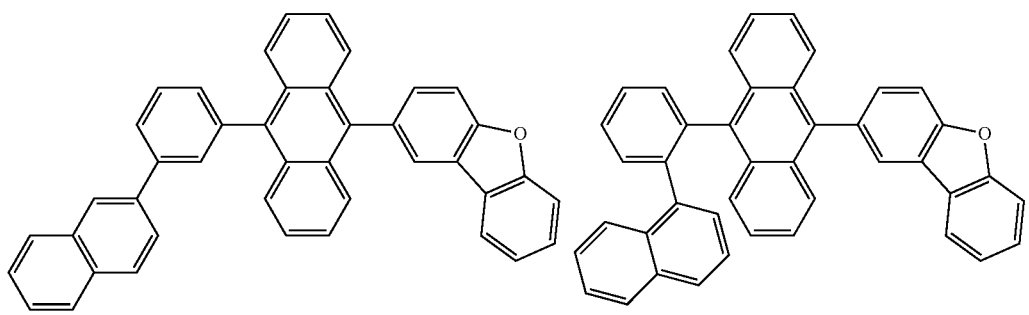
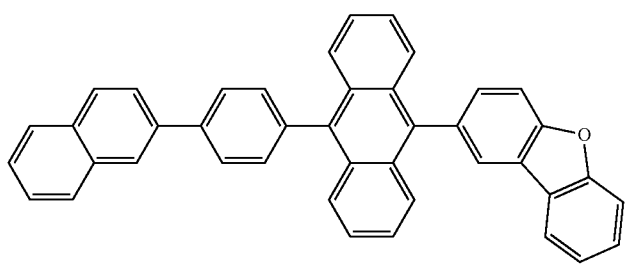
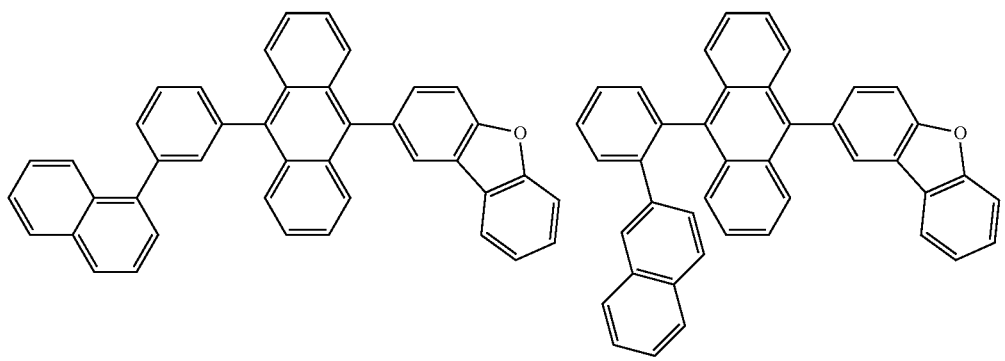
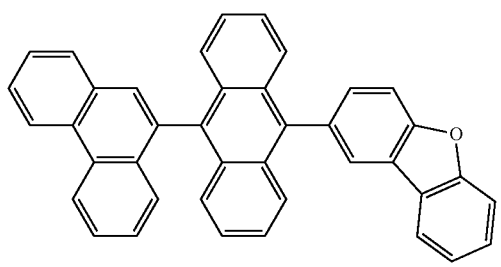

[Chem. 43]
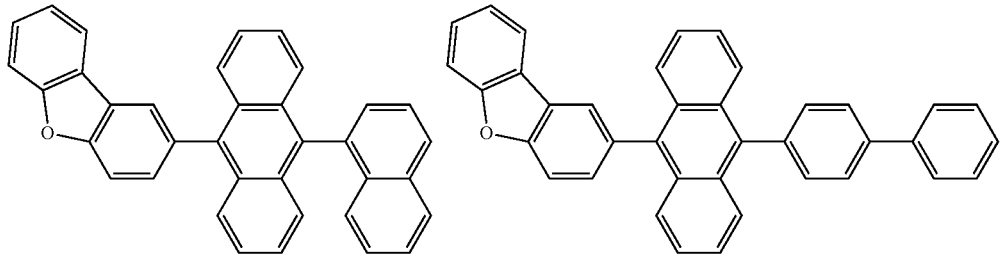

121 122
-continued
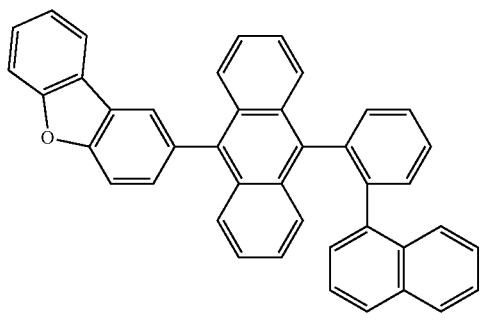
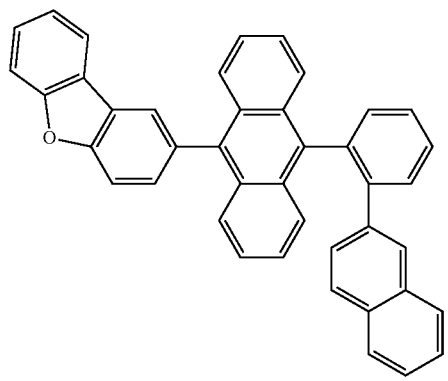
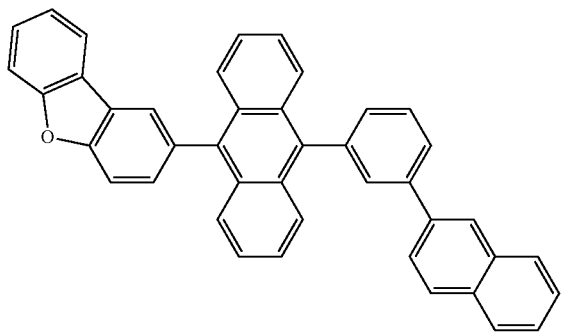
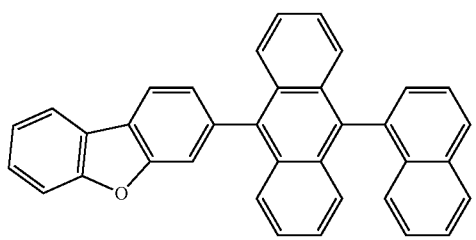
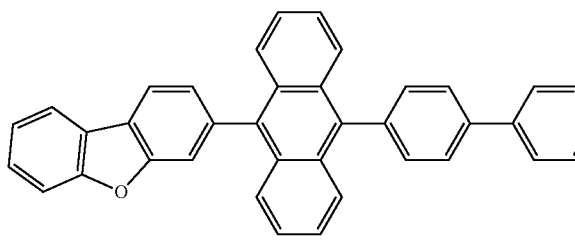
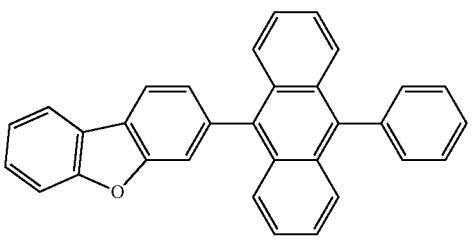
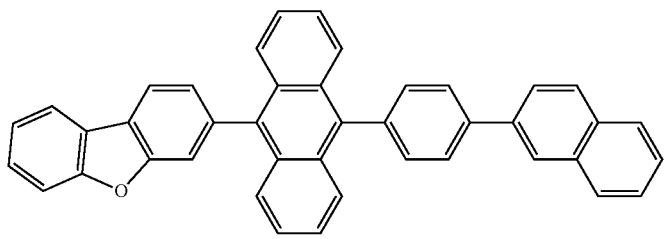
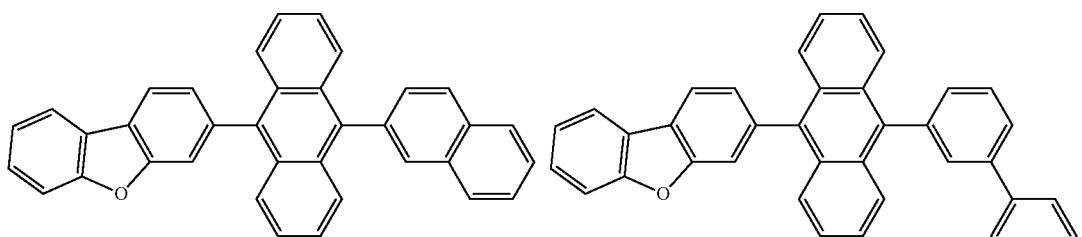
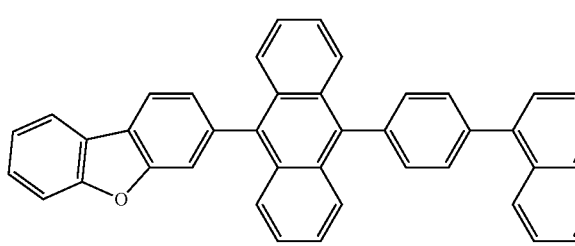
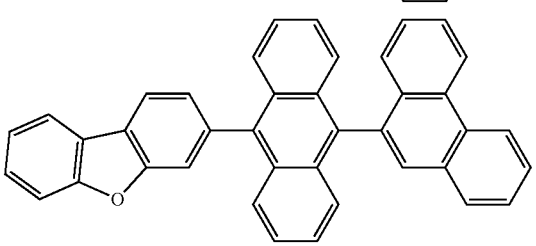

123 124
-continued
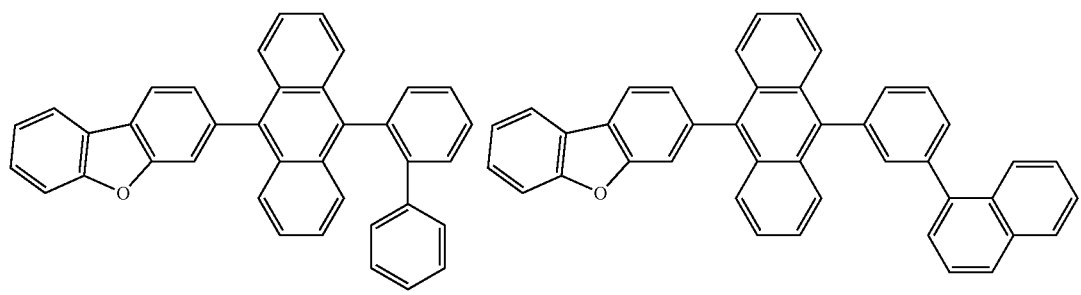
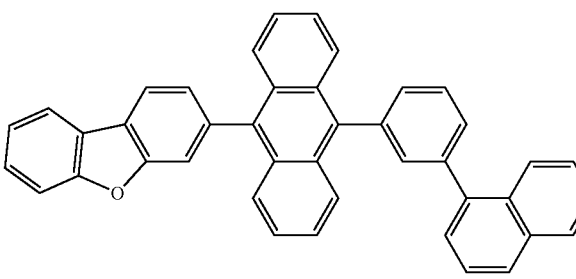
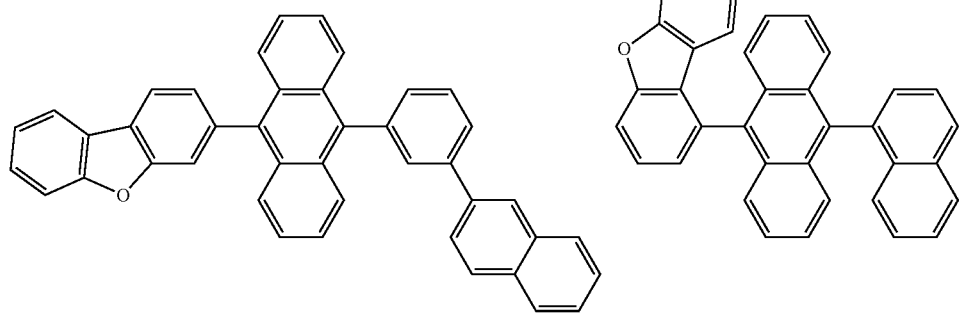
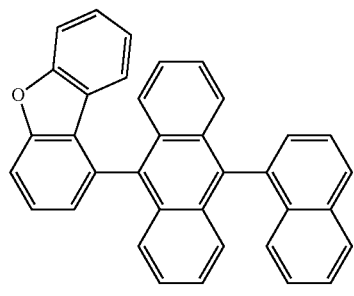
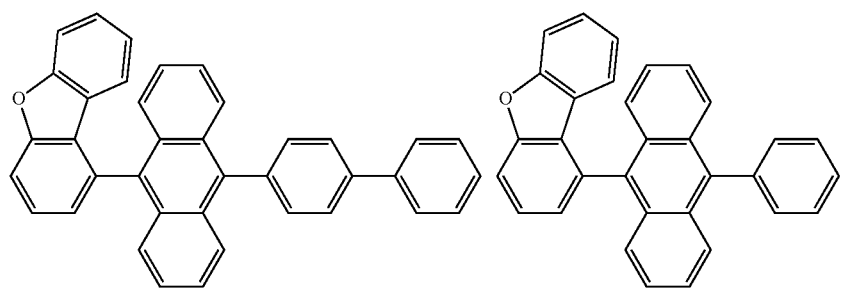
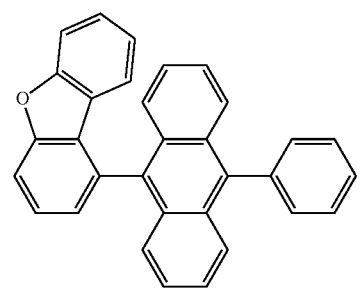
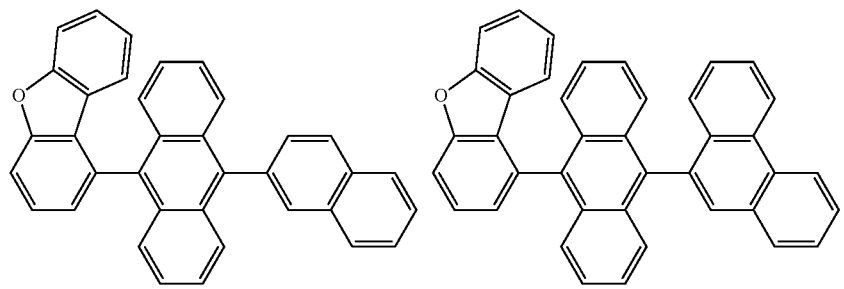
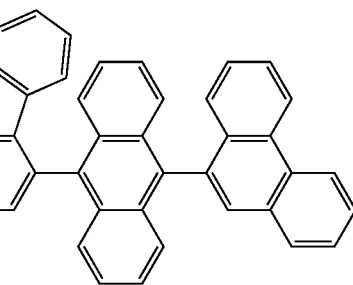
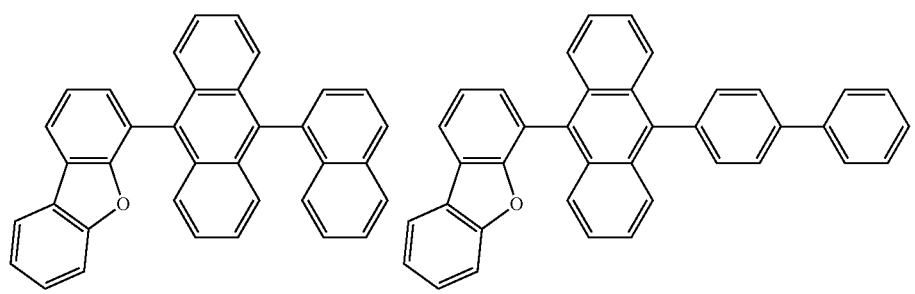
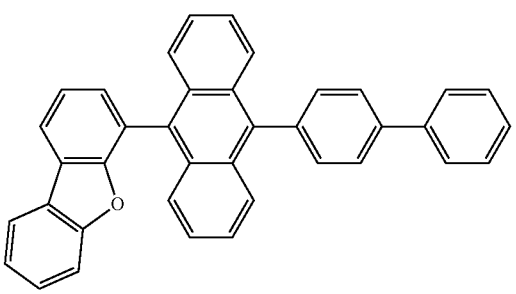

-continued
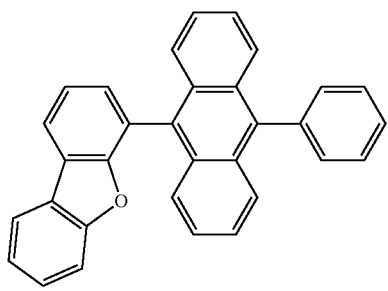
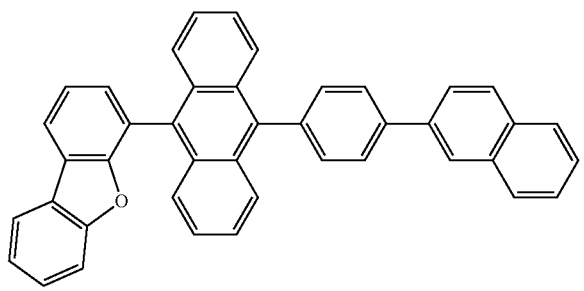
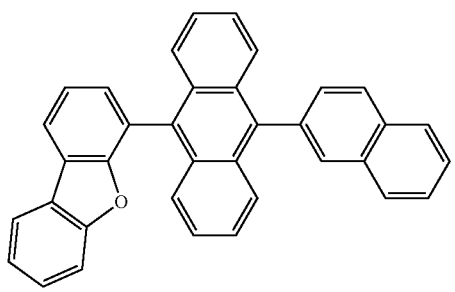
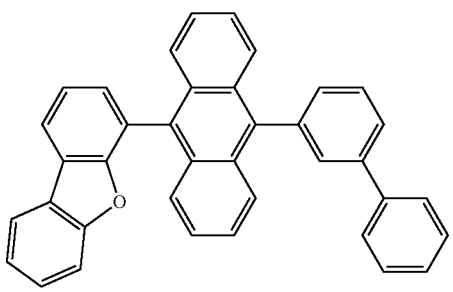
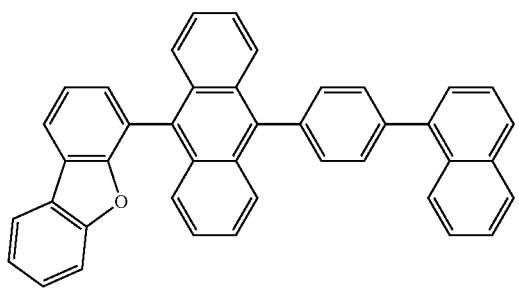
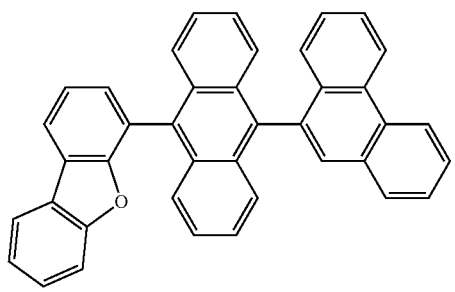
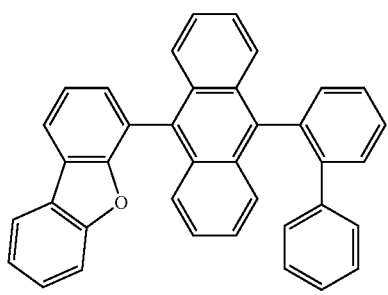
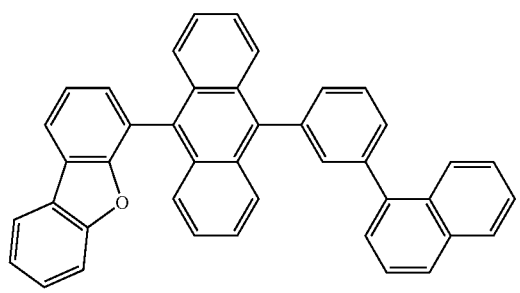
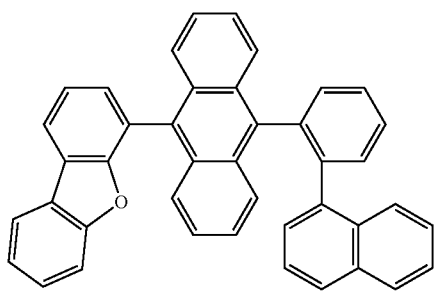
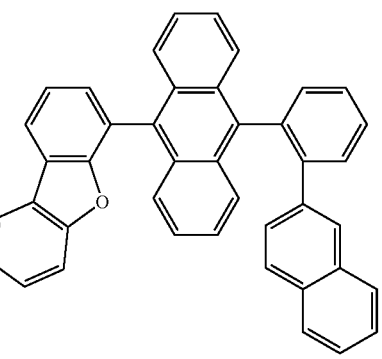

-continued
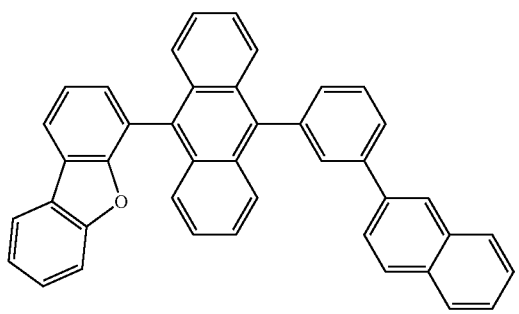
[Chem. 44]
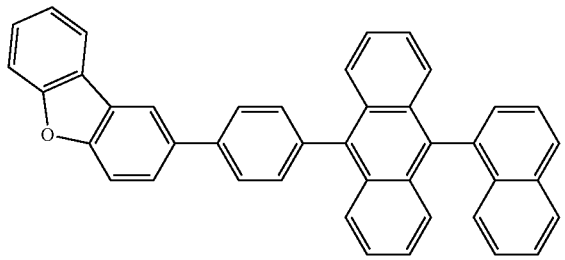
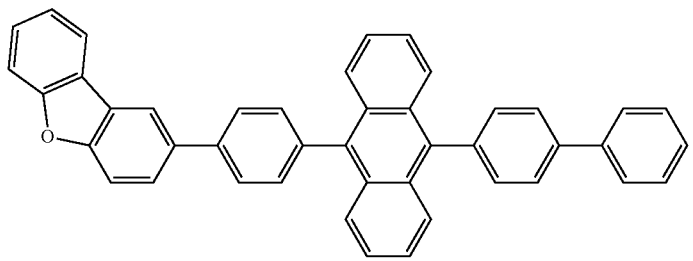
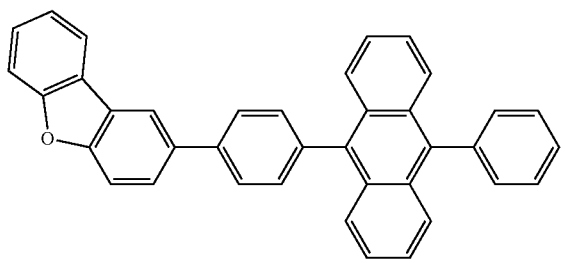
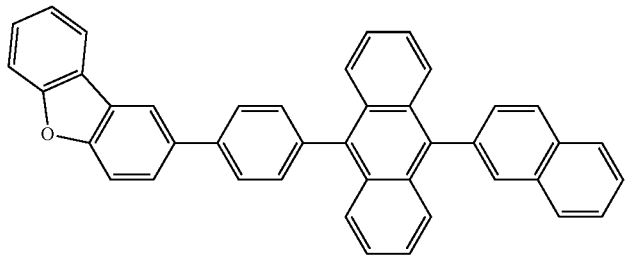
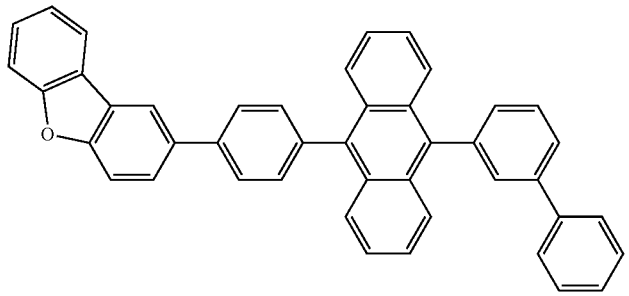

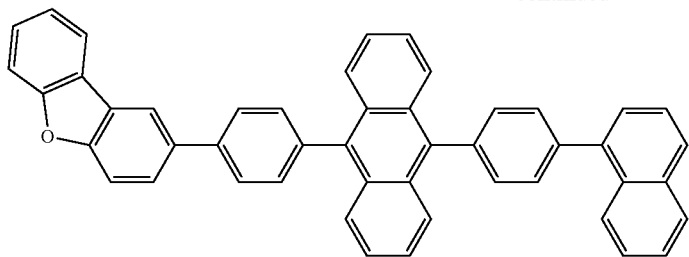
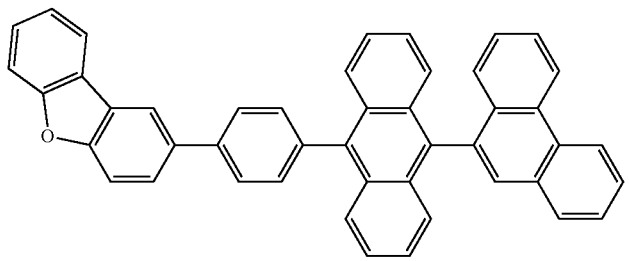
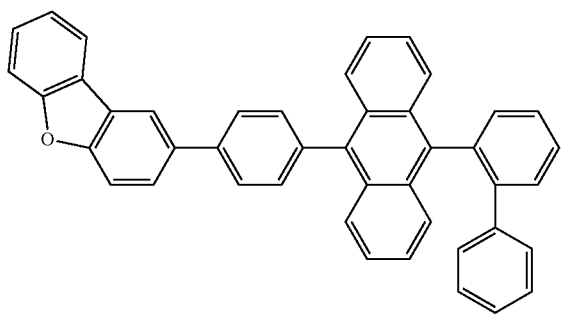
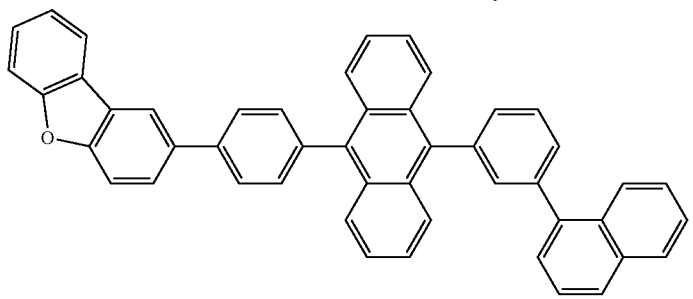
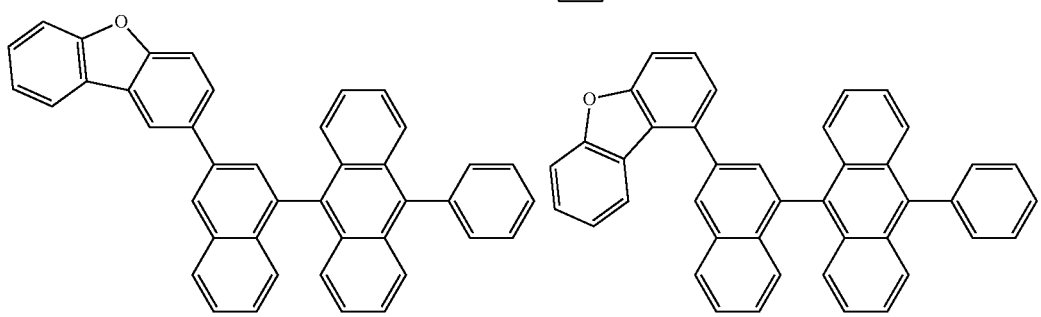
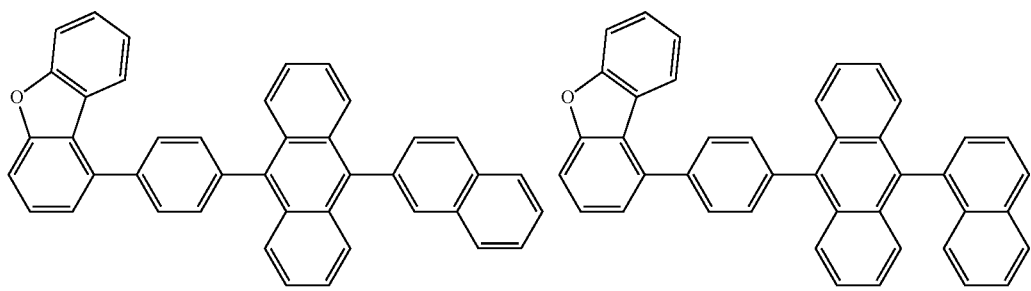

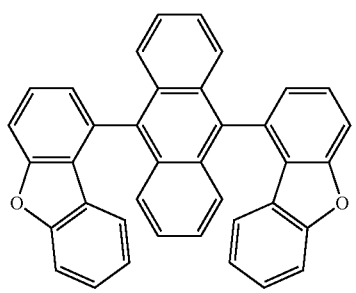
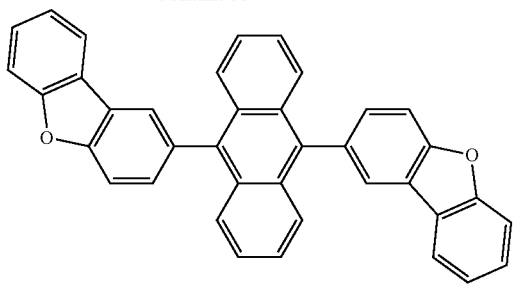
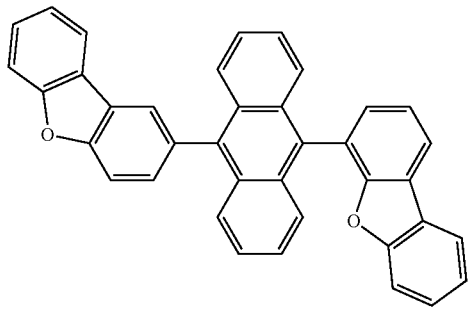
[Chem. 45]
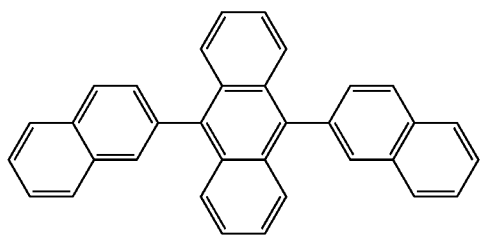
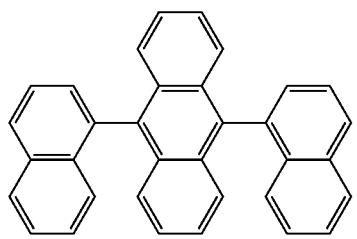
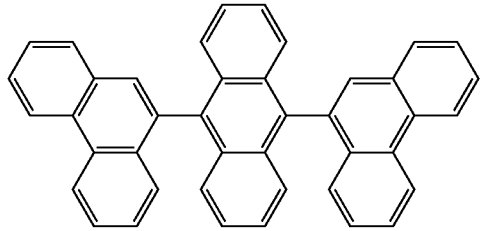
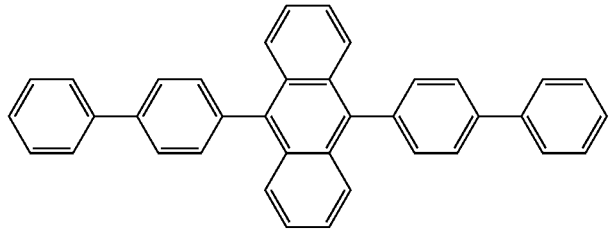
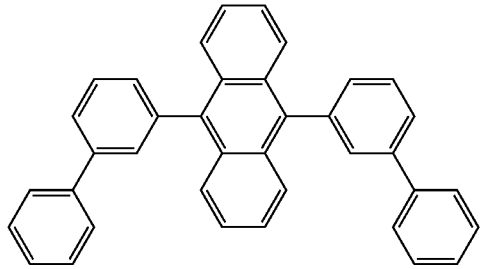
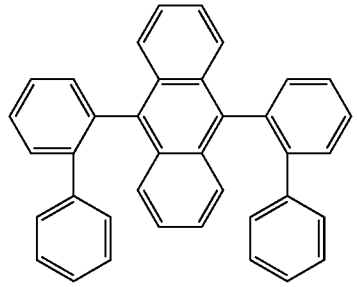
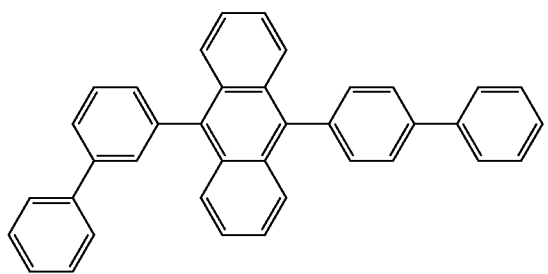

-continued
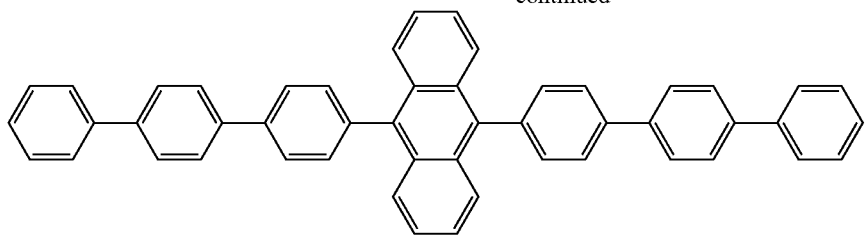
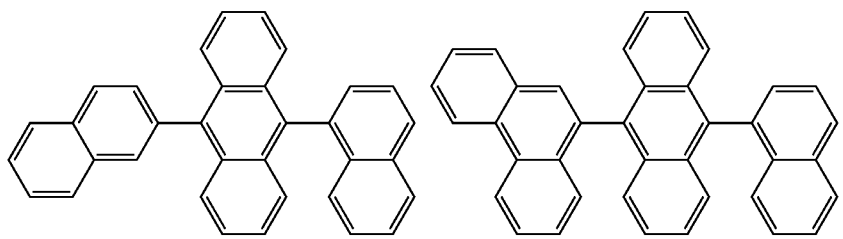
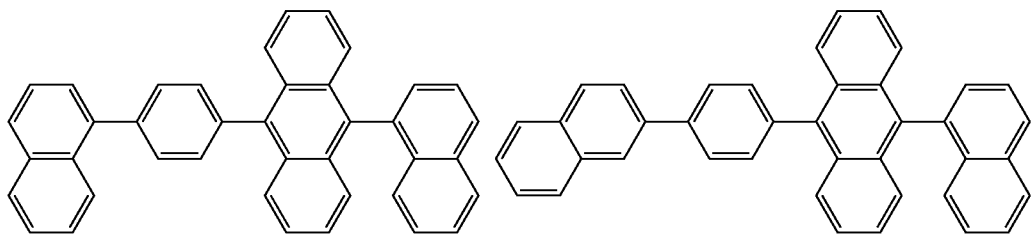
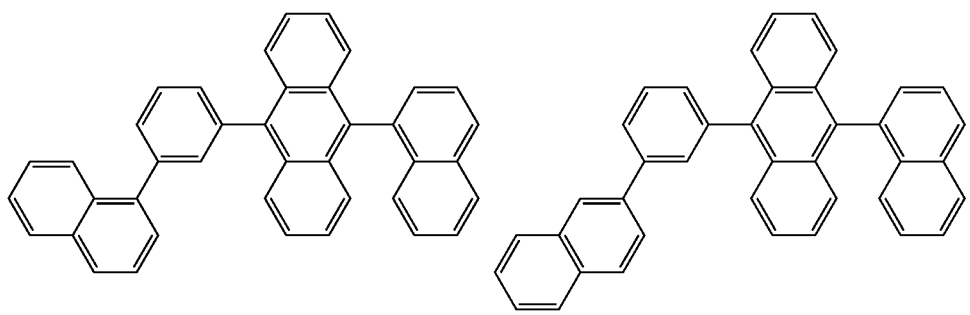
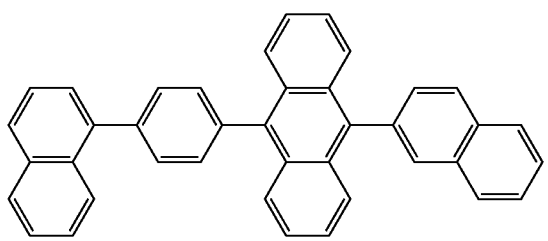
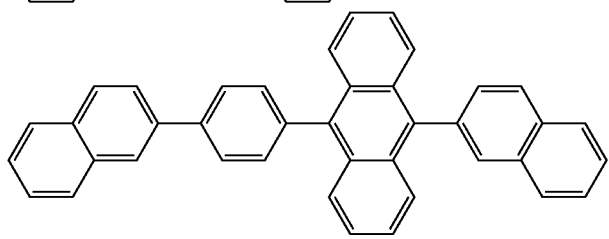

135 136
-continued
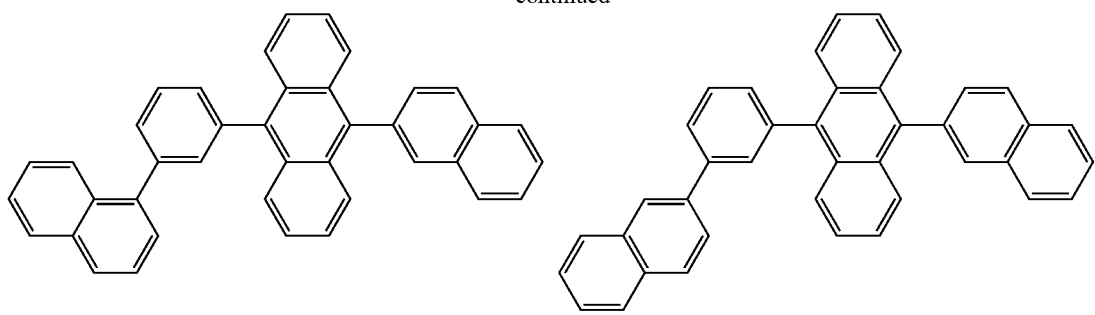
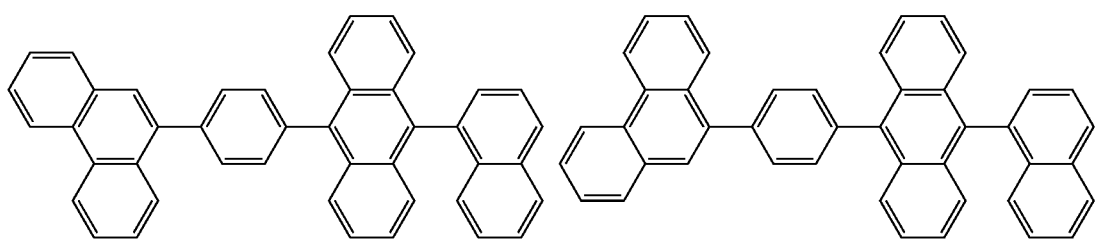
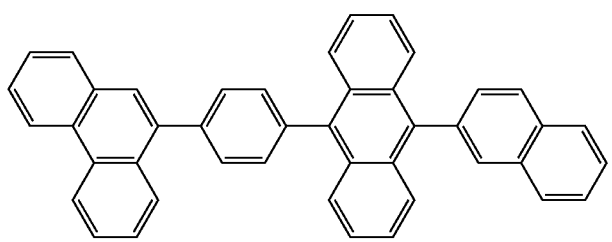
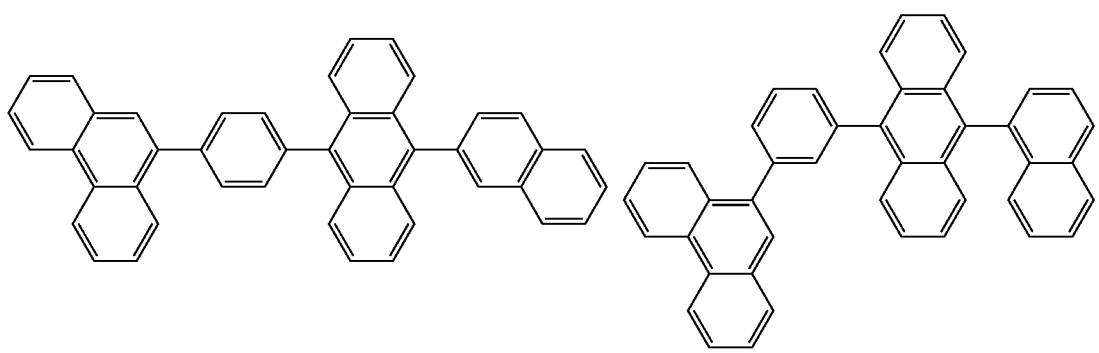
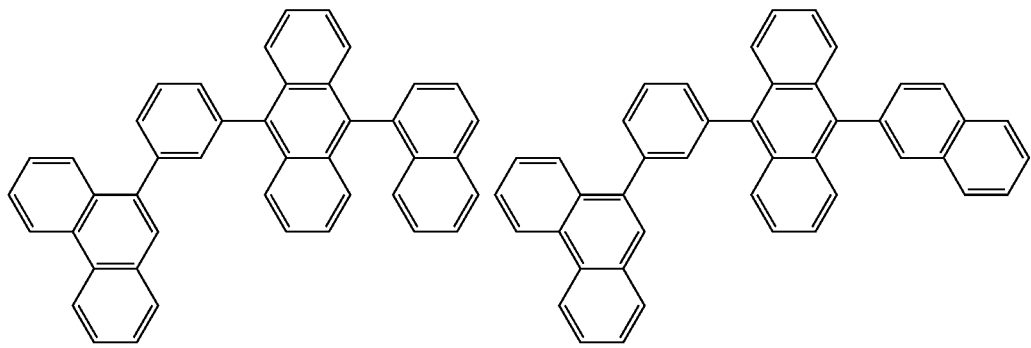

-continued
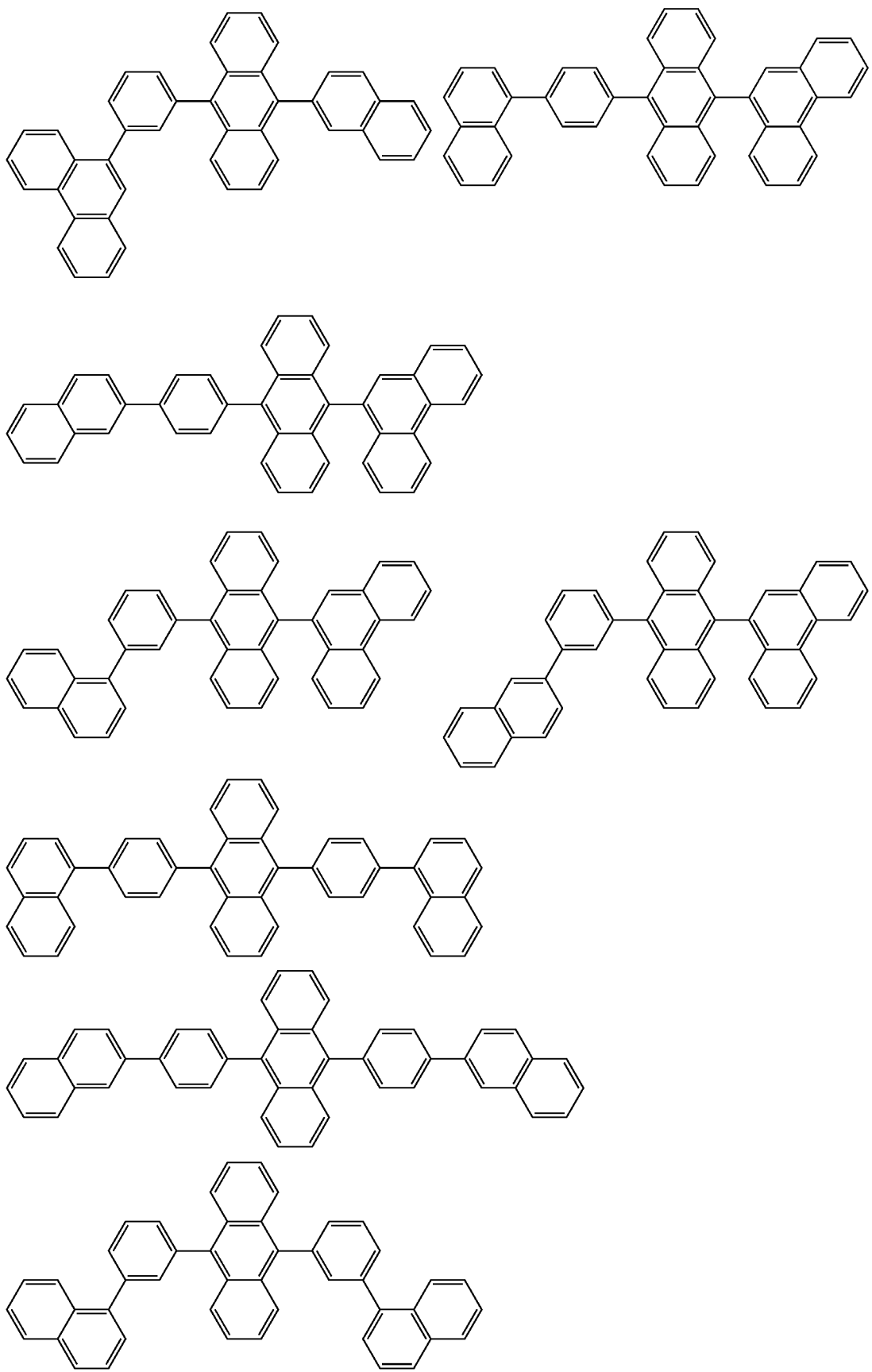

-continued
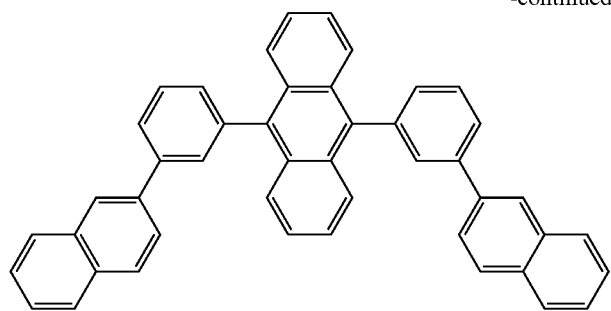
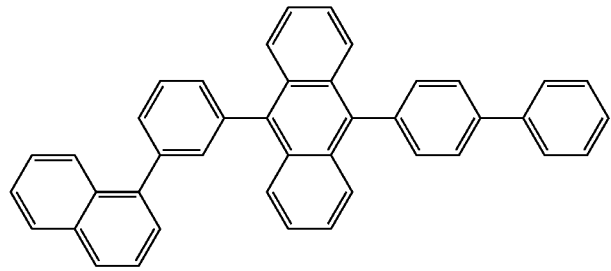
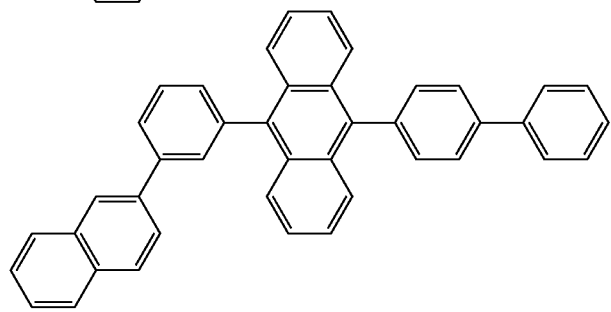
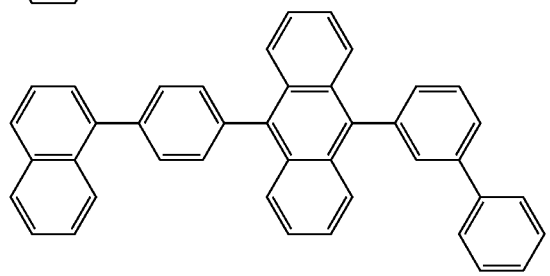
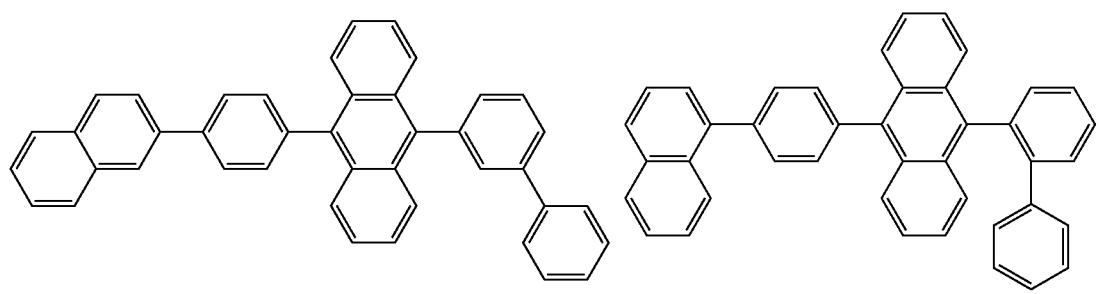
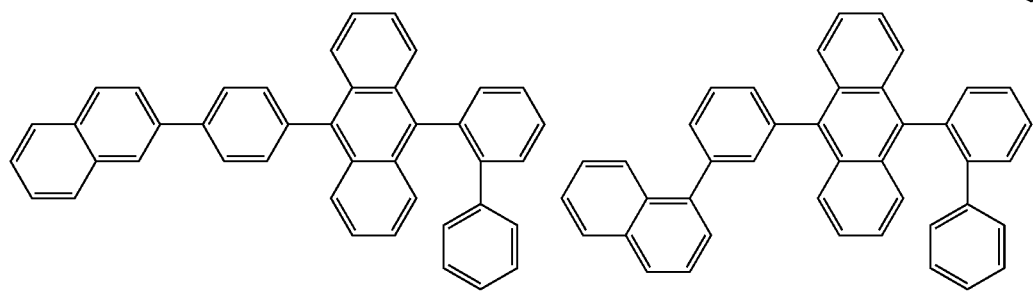

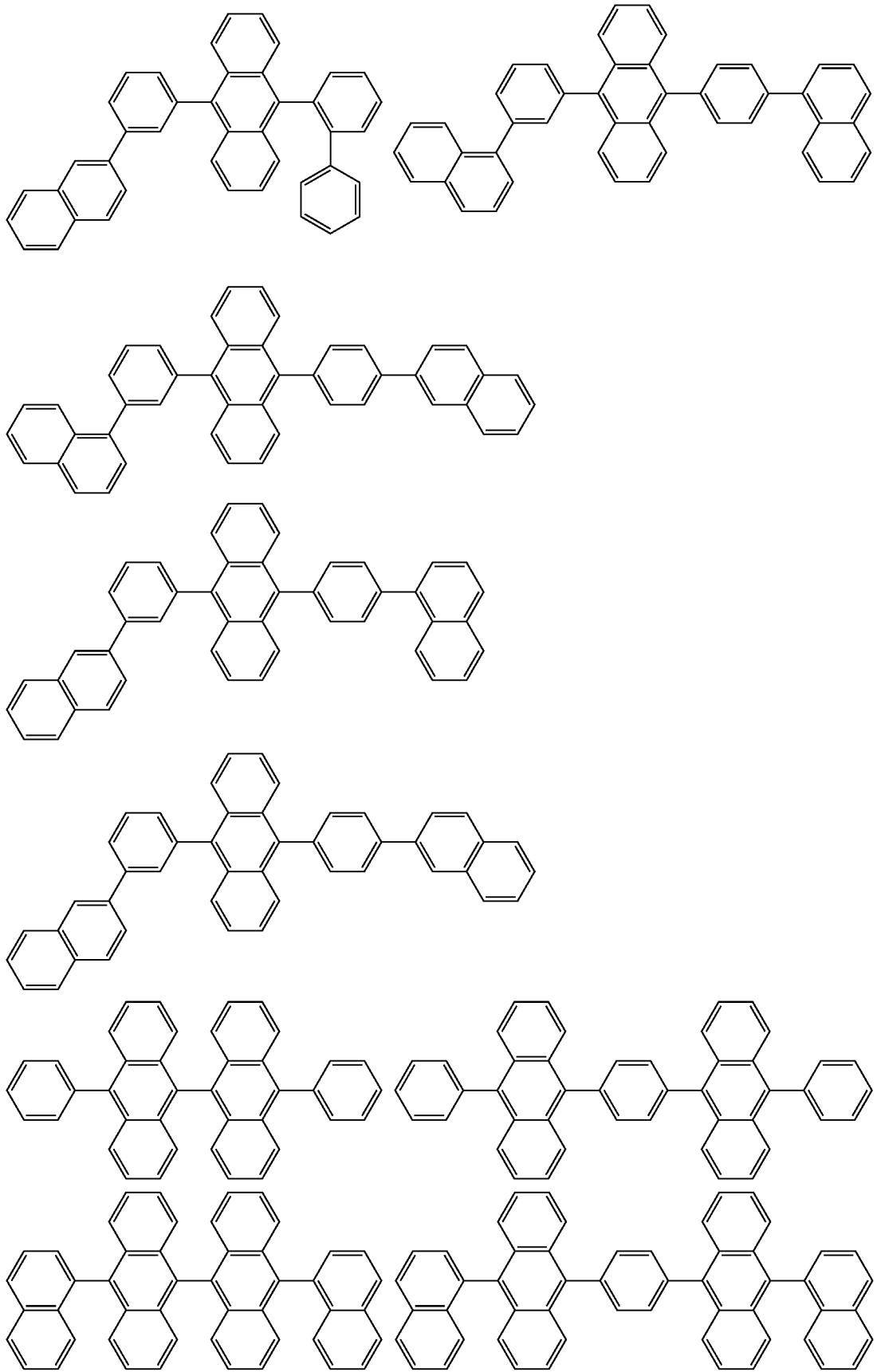

-continued
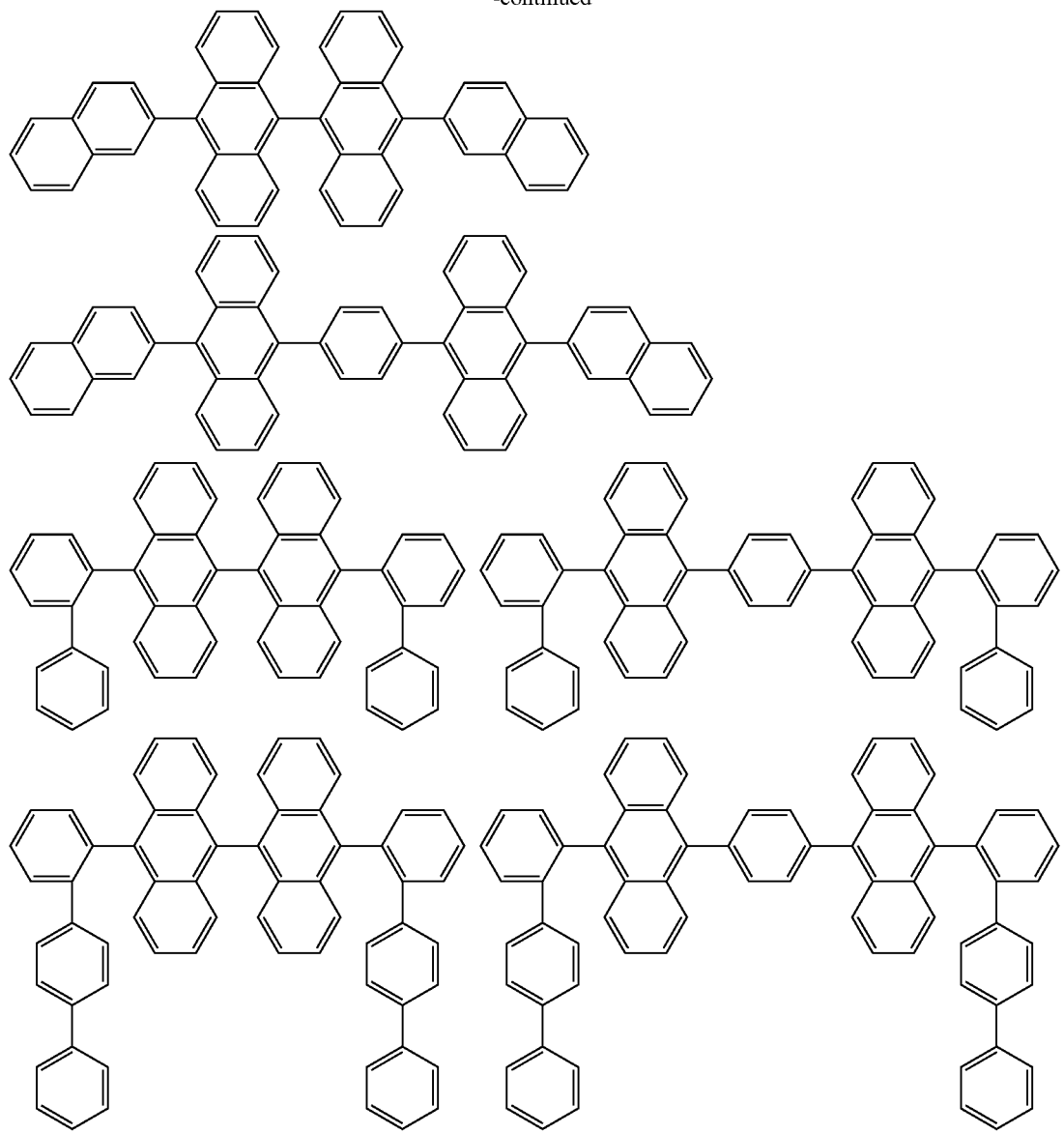
[Chem. 46]
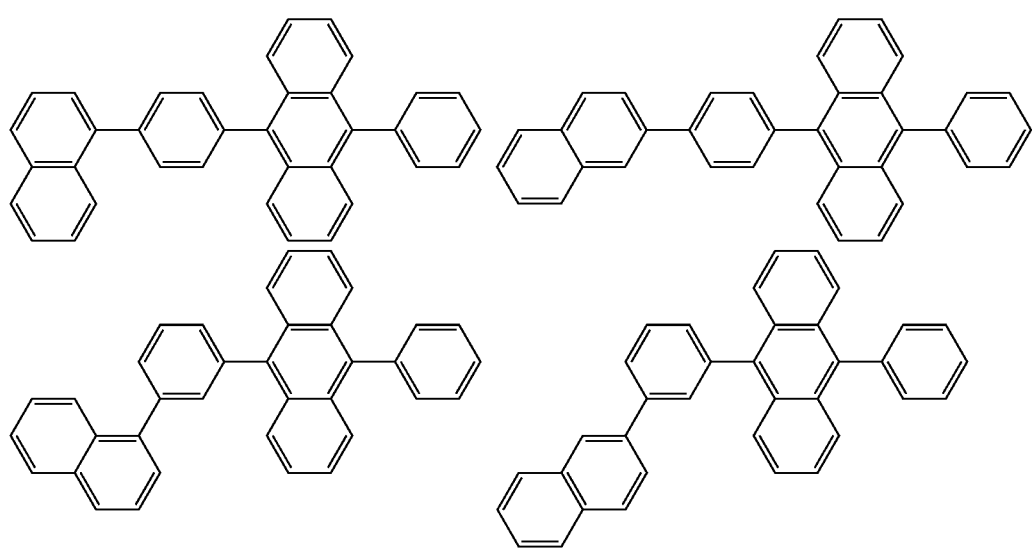

-continued
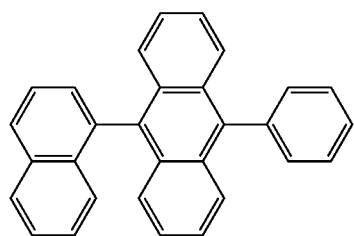 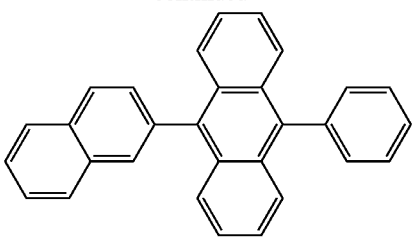
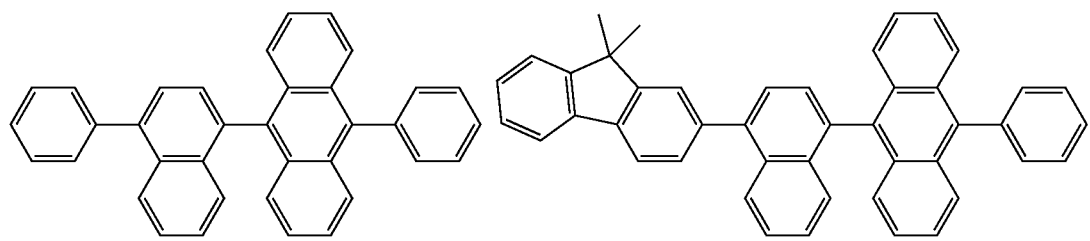
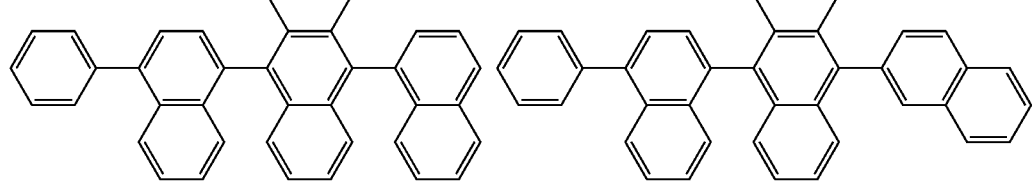
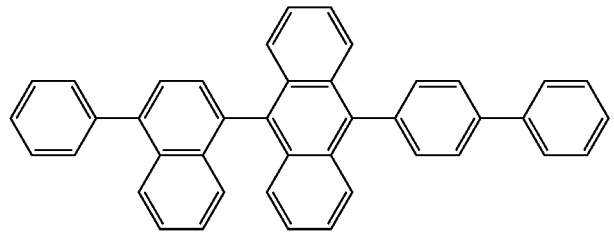
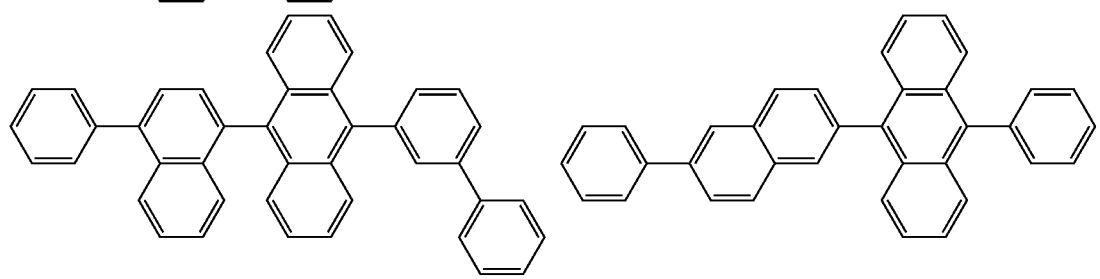
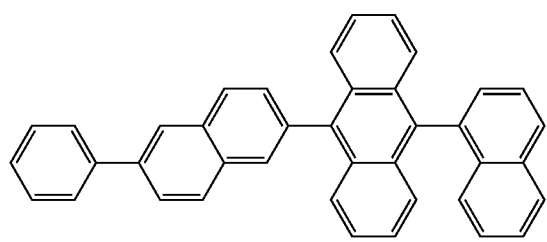
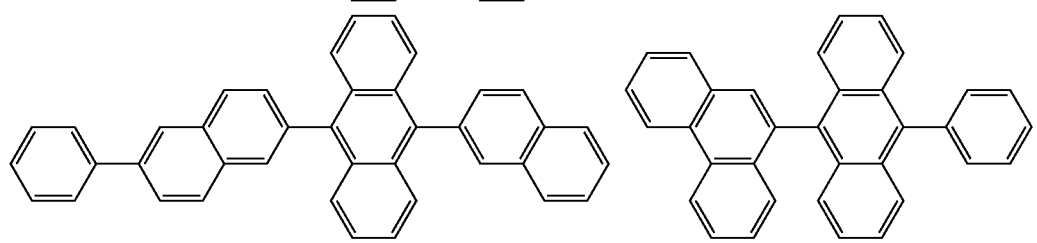

-continued
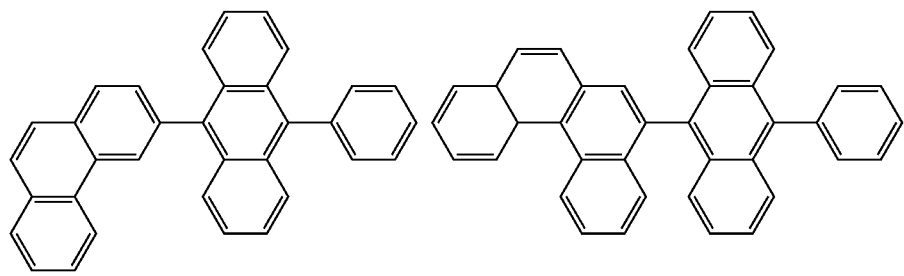
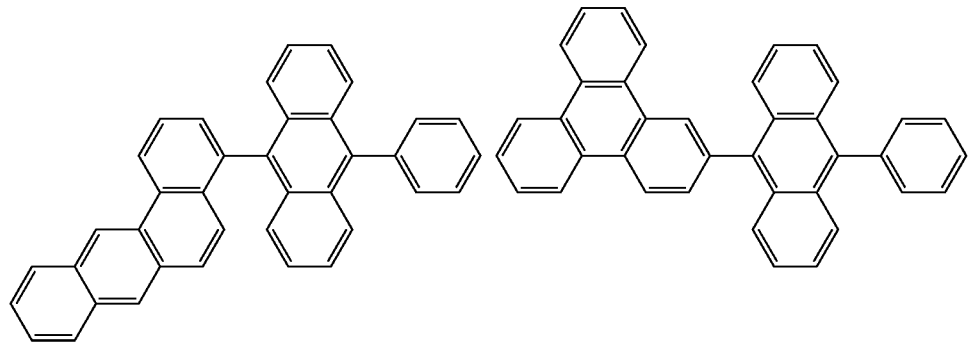
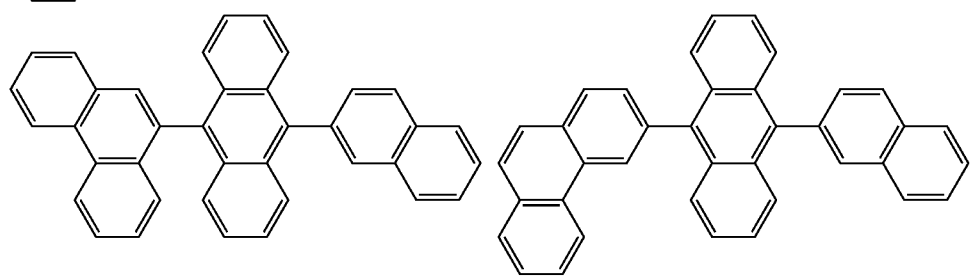
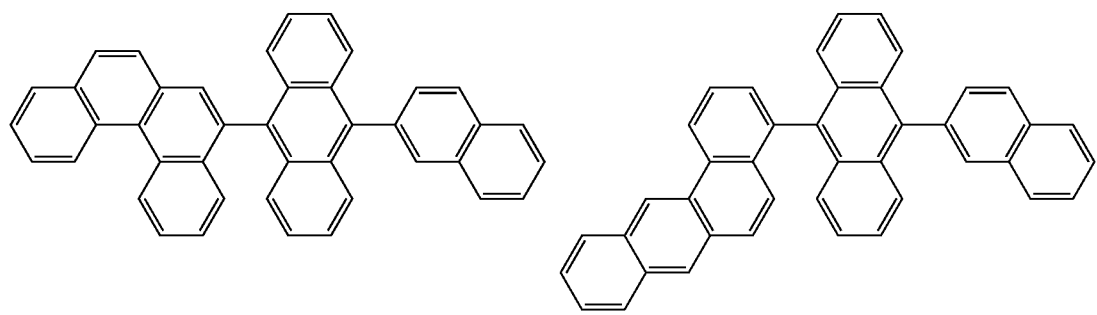
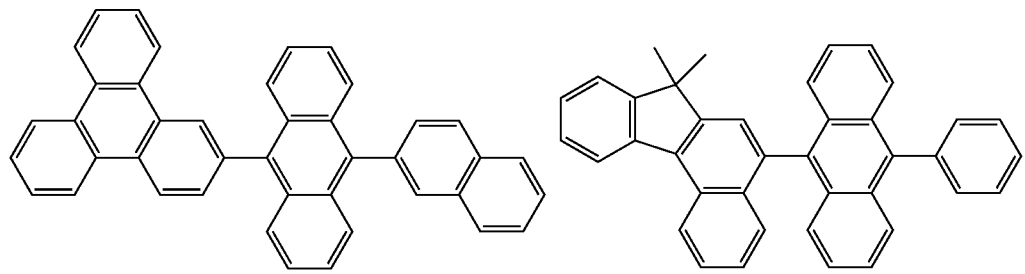
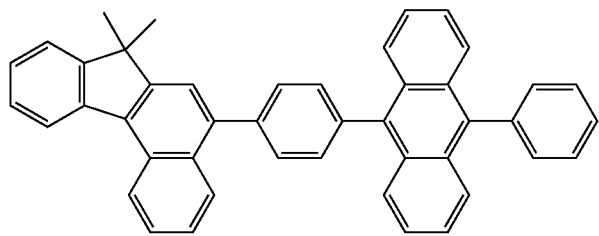

-continued
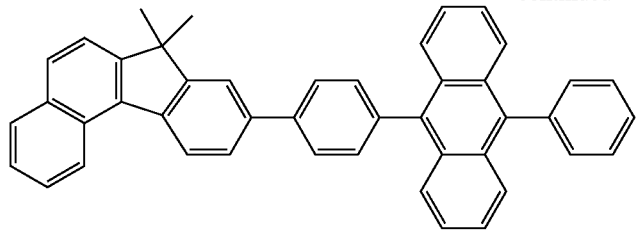
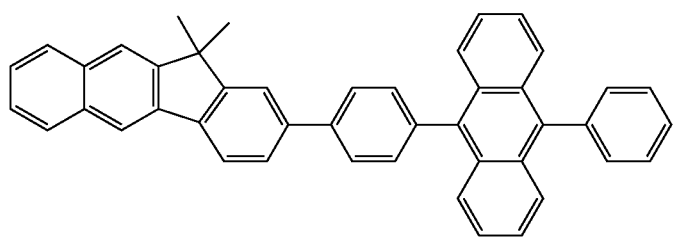
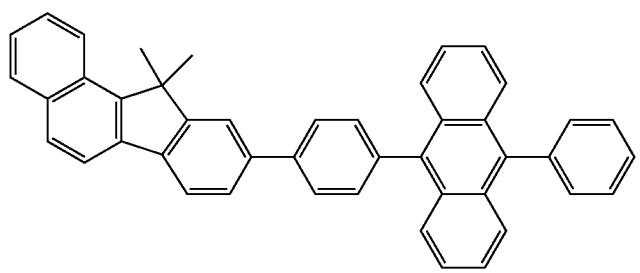
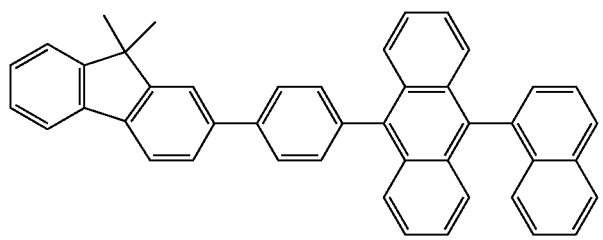
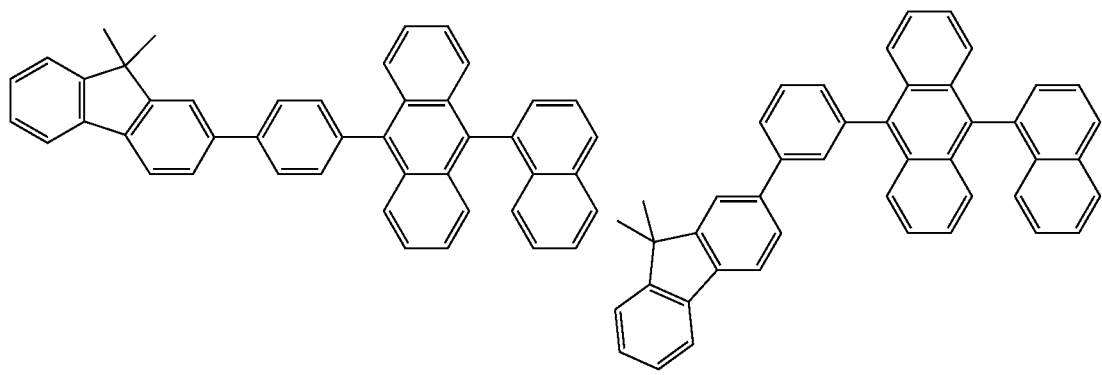
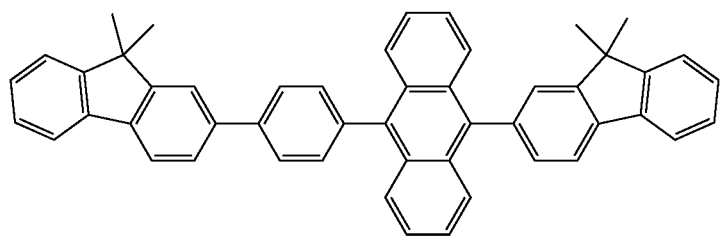

-continued
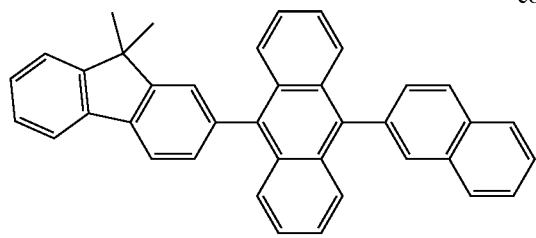
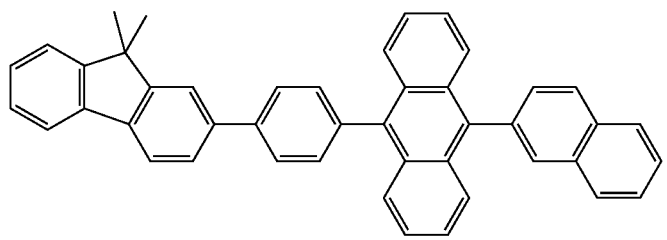
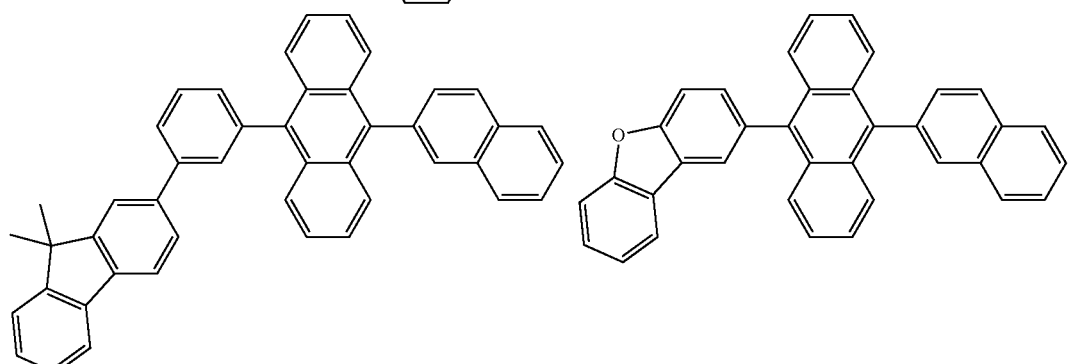
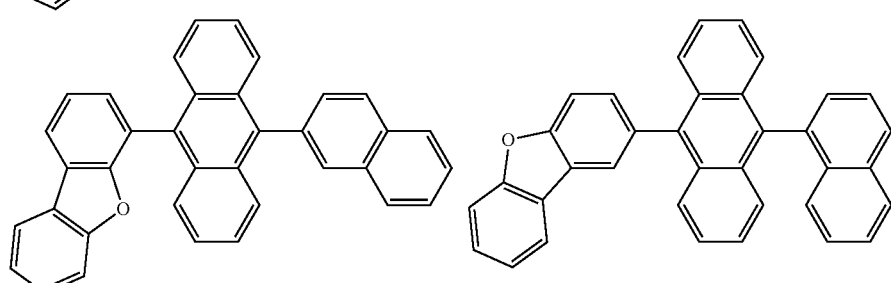
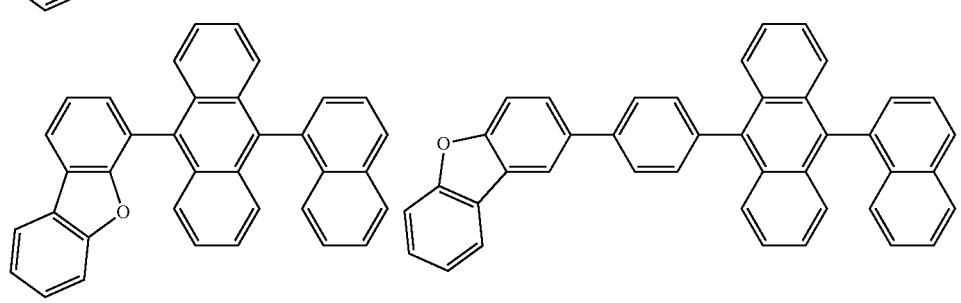
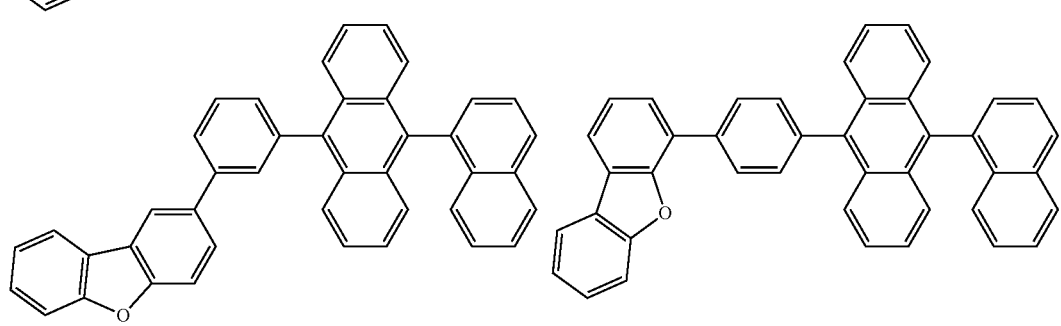

-continued
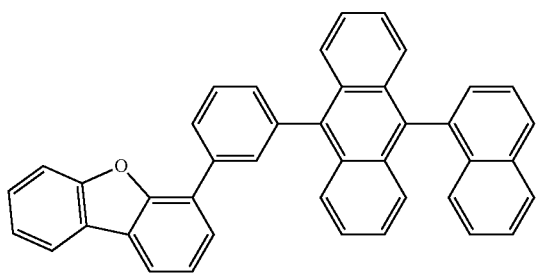
[Chem. 47]
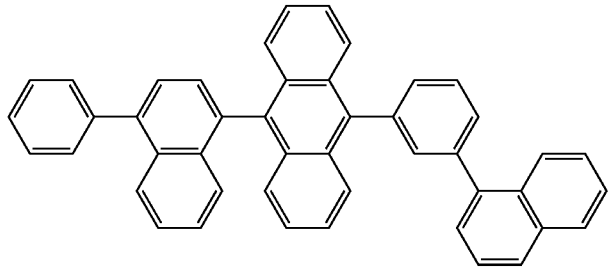
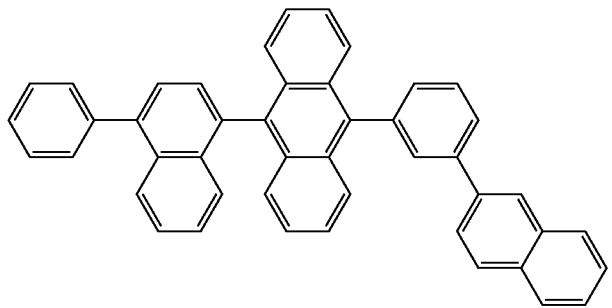
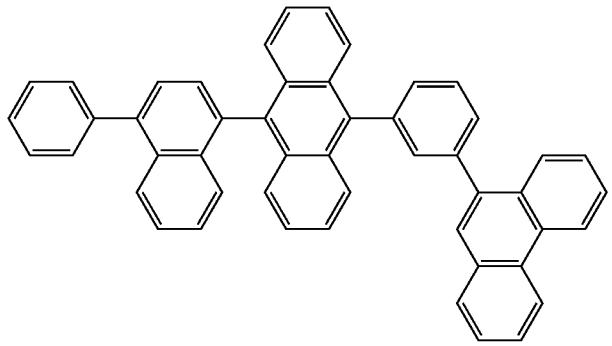
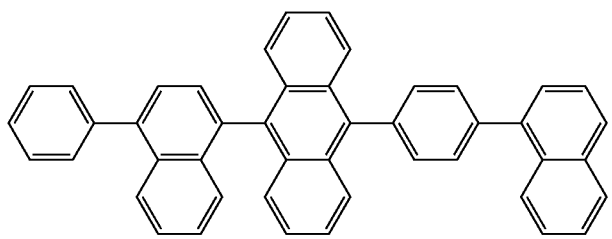
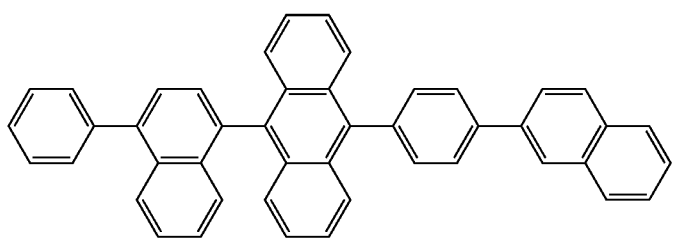

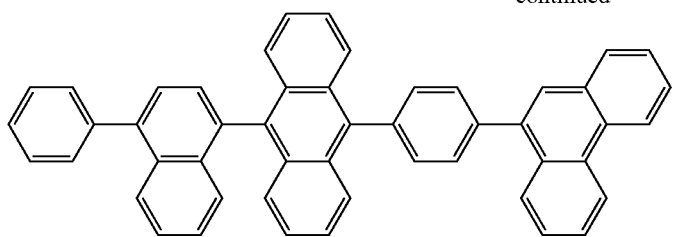
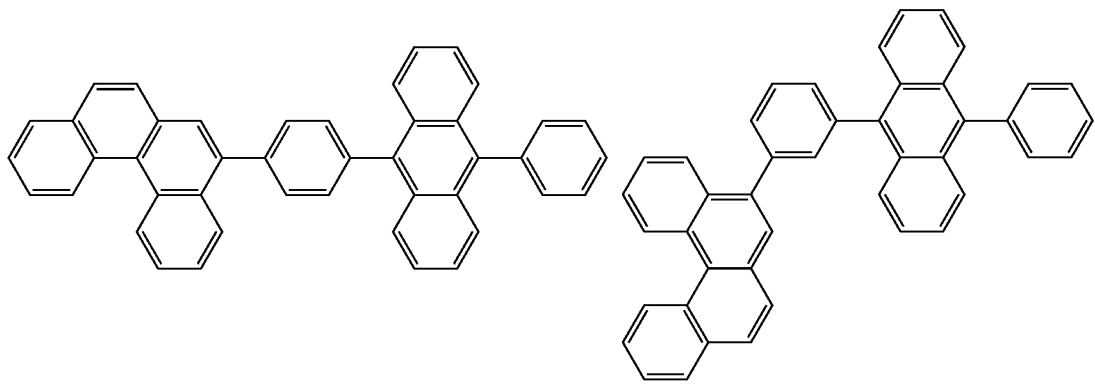
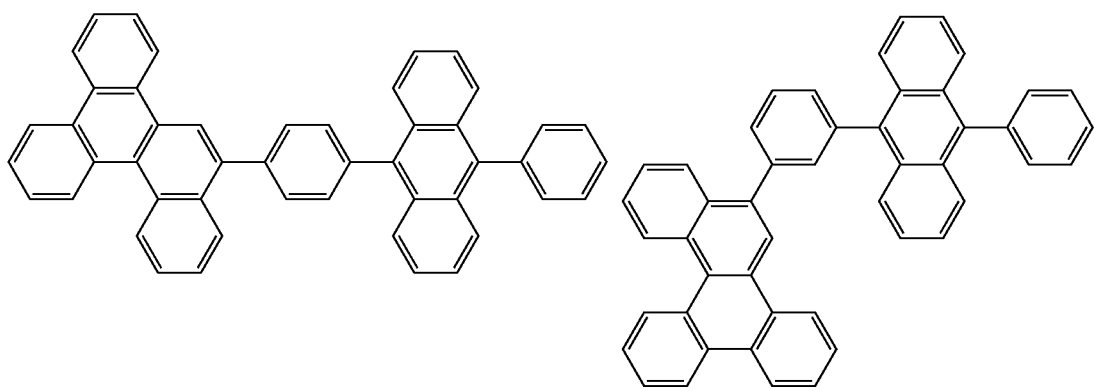
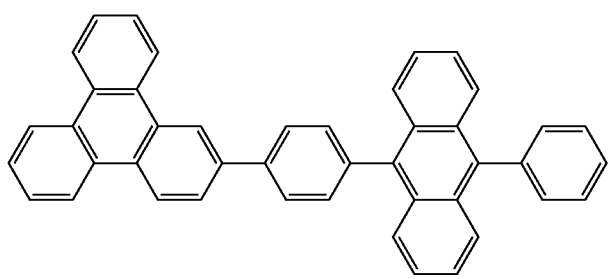
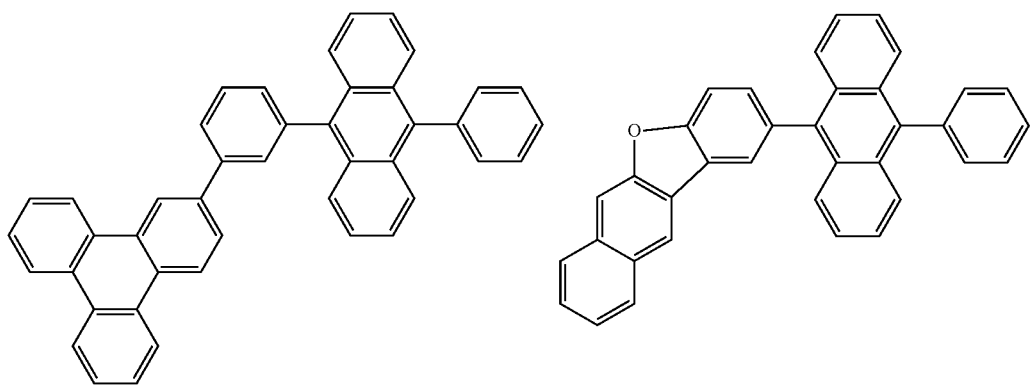

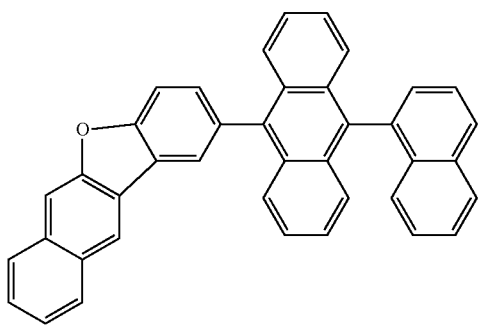
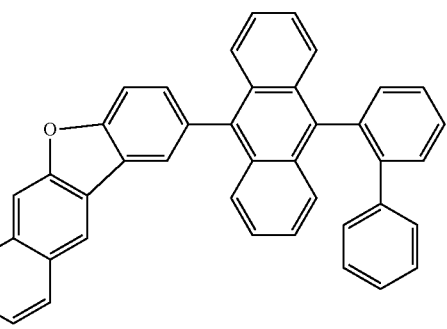
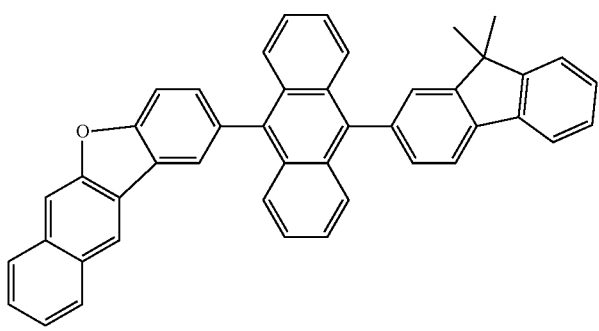
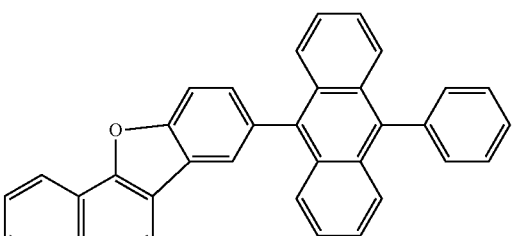
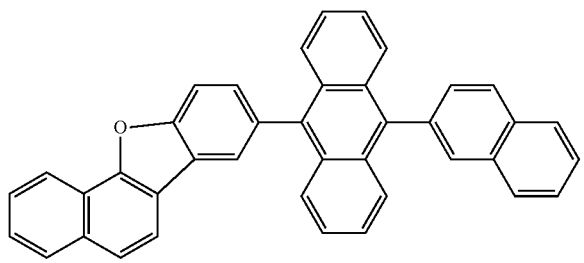
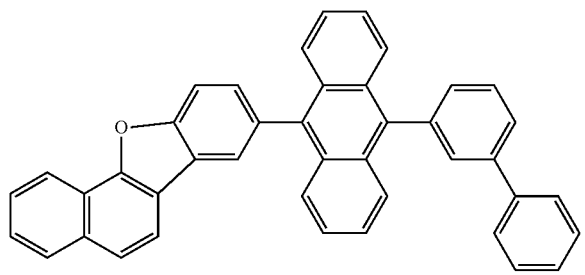
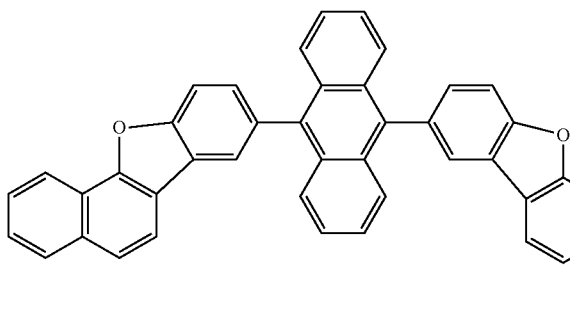
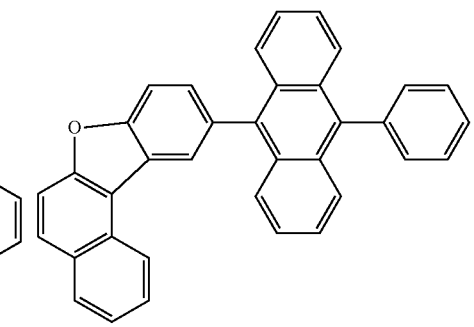
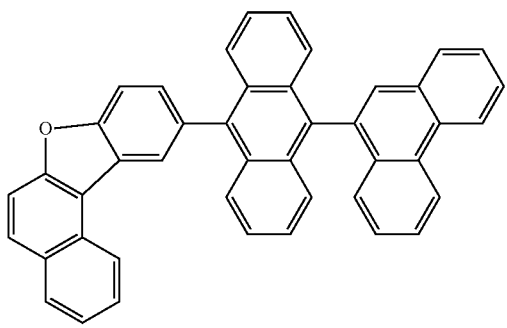
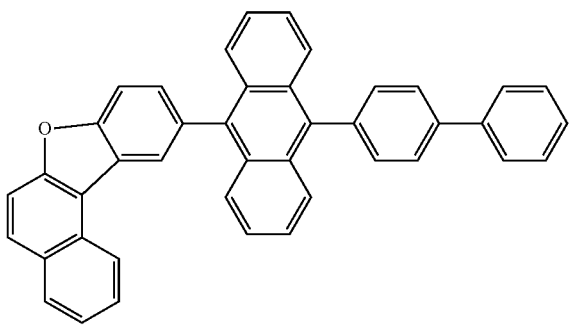

-continued
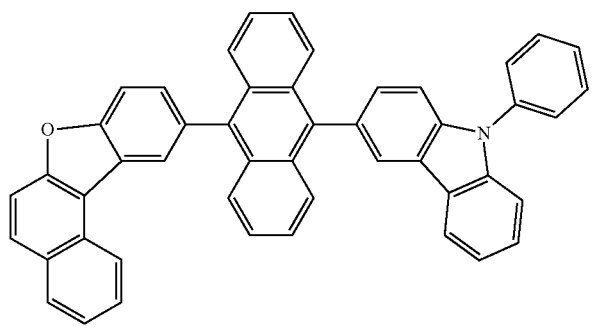
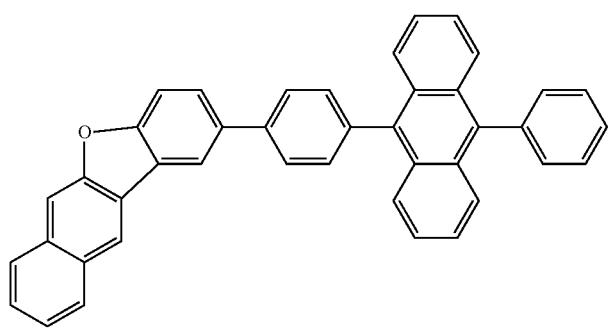
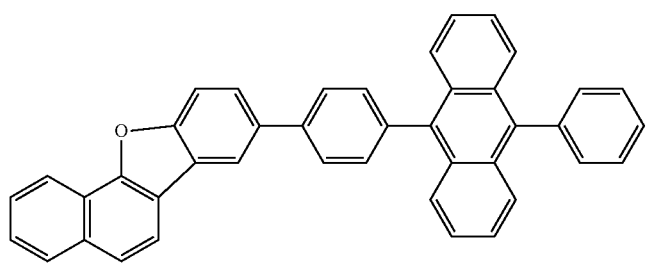
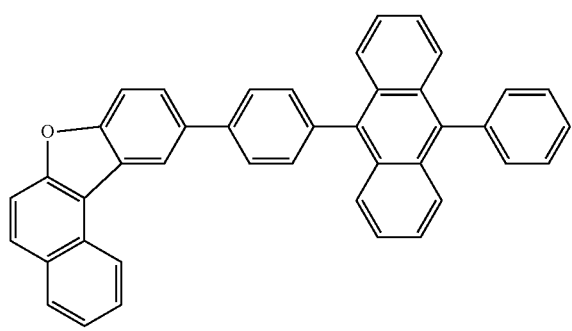
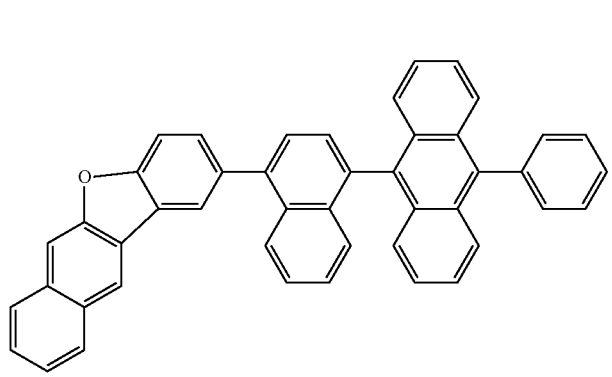
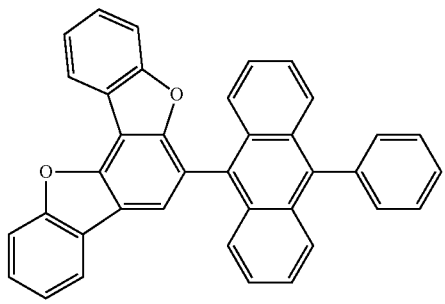

161
162
-continued
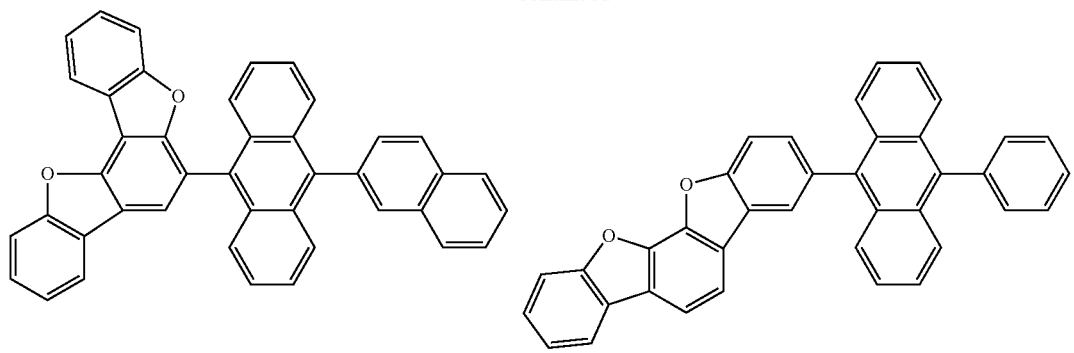
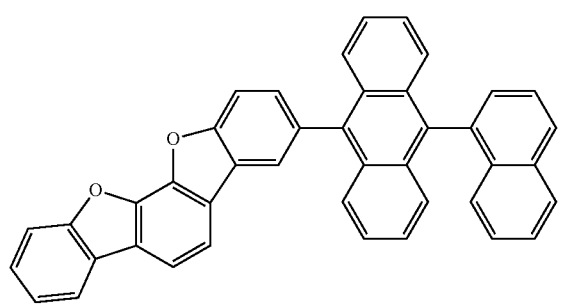
[Chem. 48]
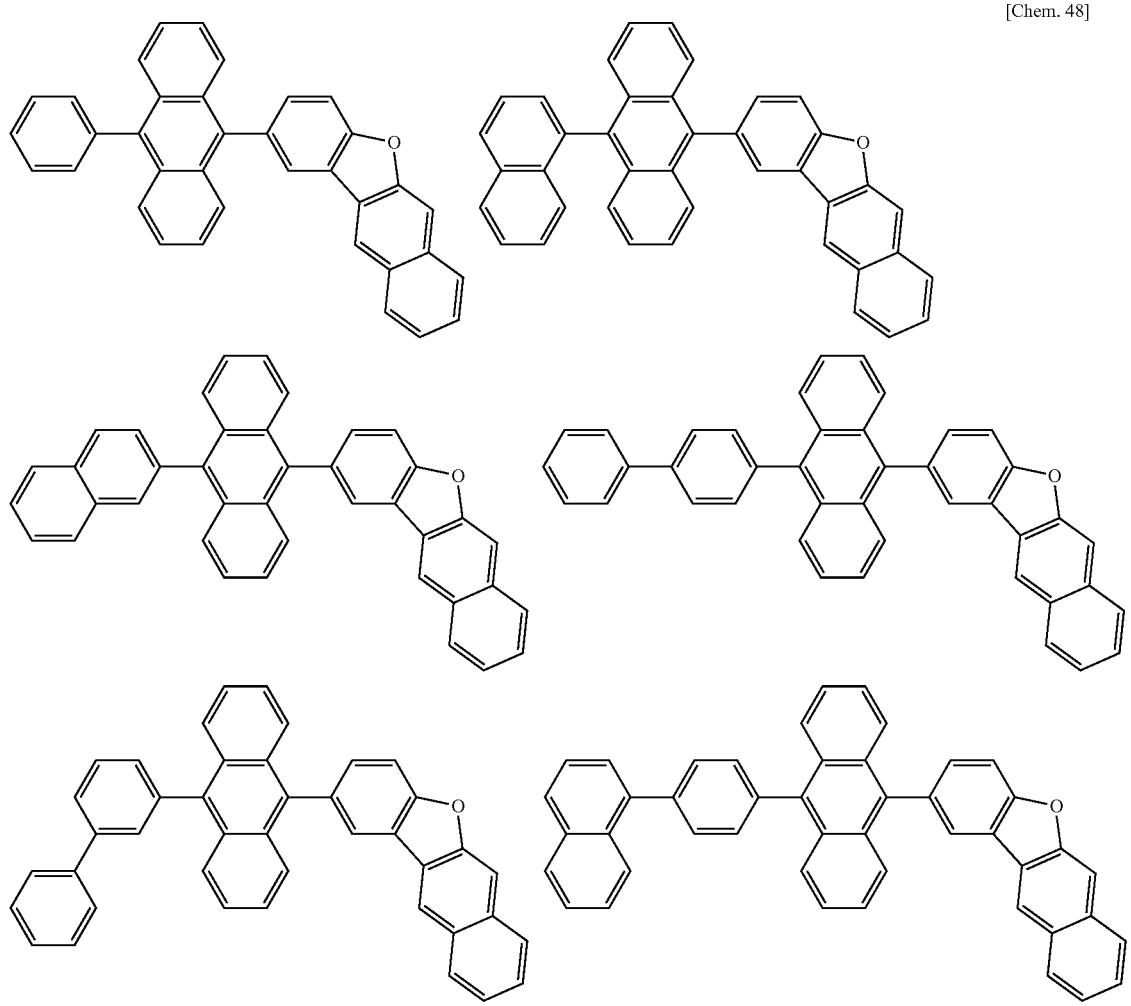

-continued
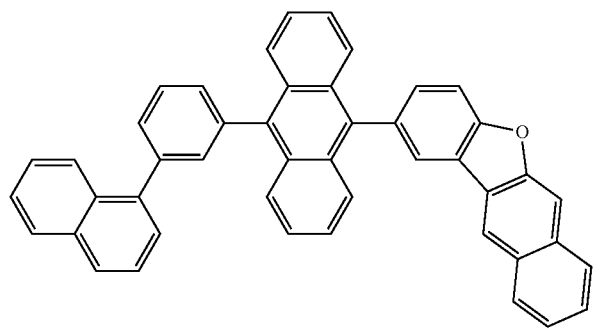
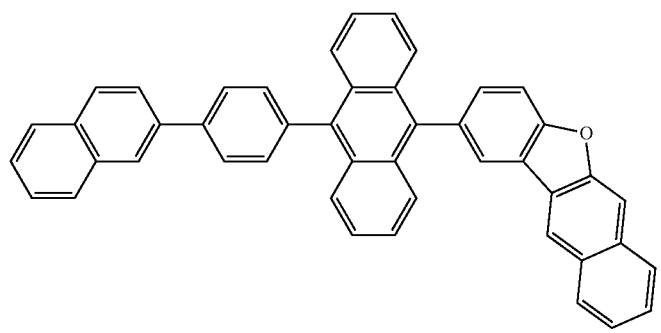
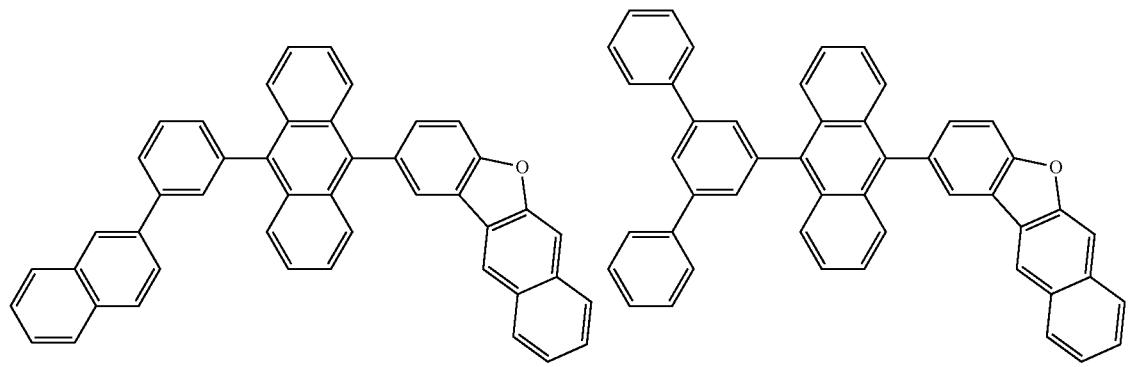
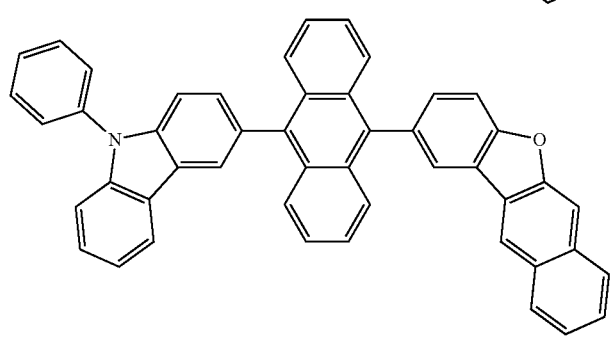
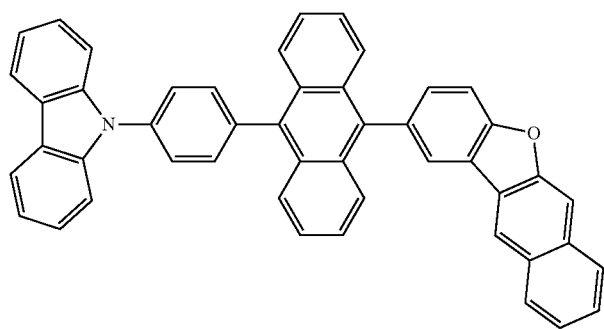

[Chem. 49]
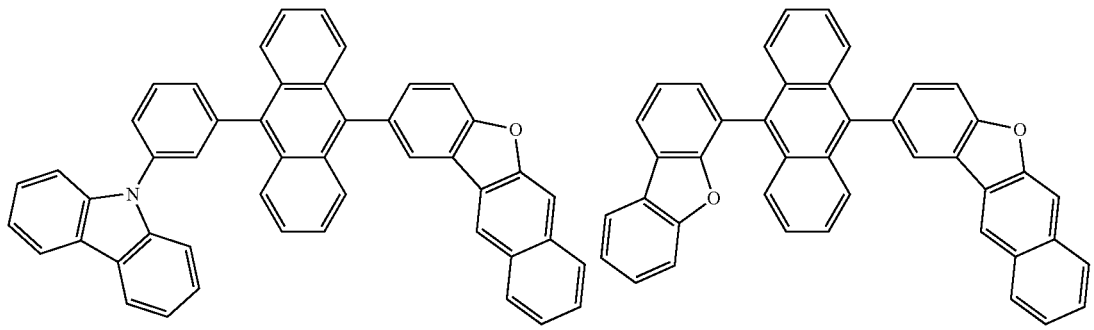
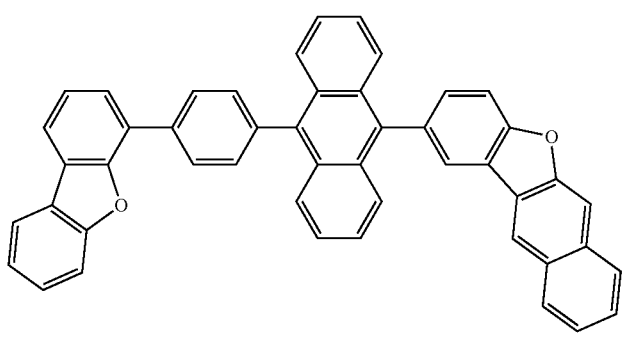
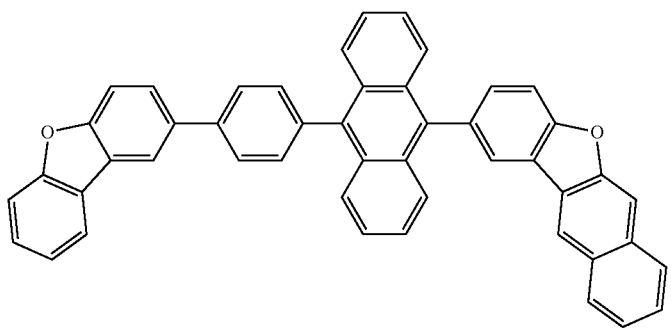
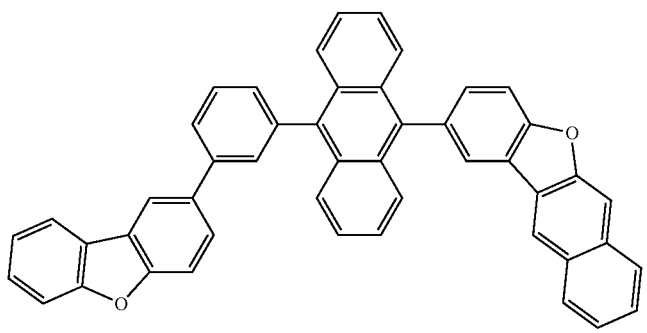
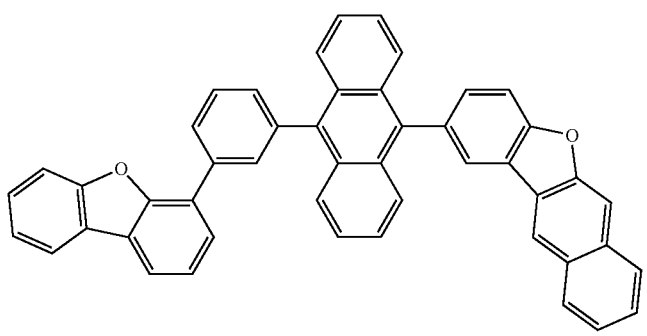

167     168
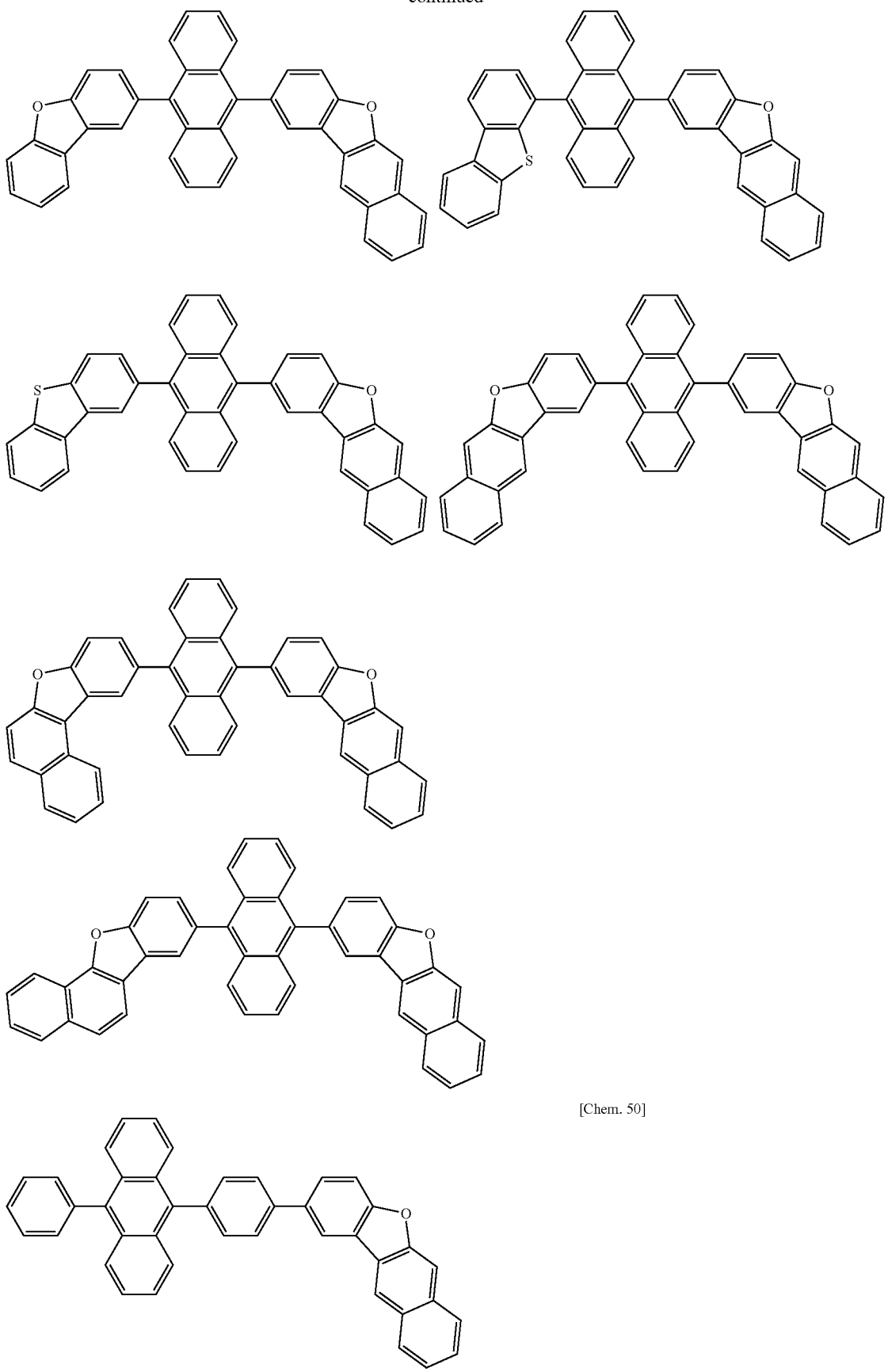
[Chem. 50]

-continued
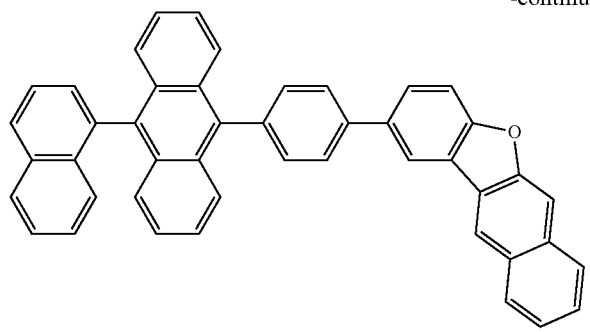
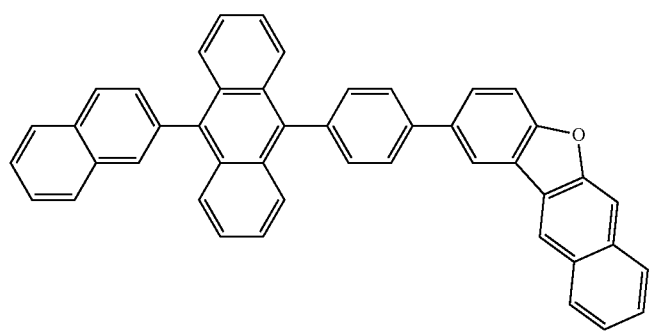
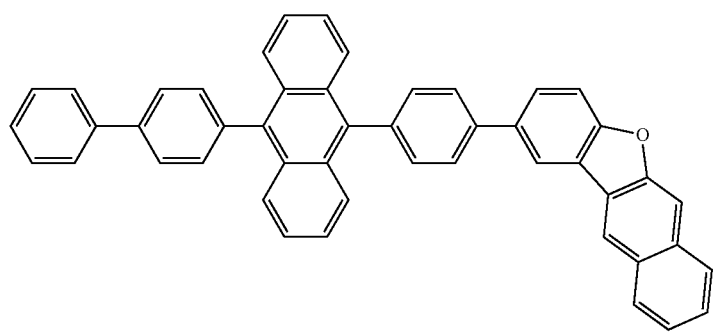
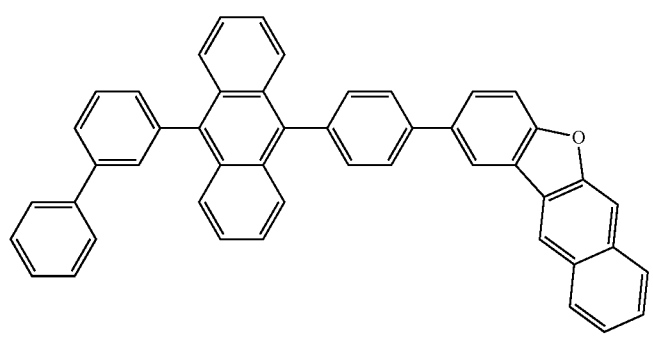
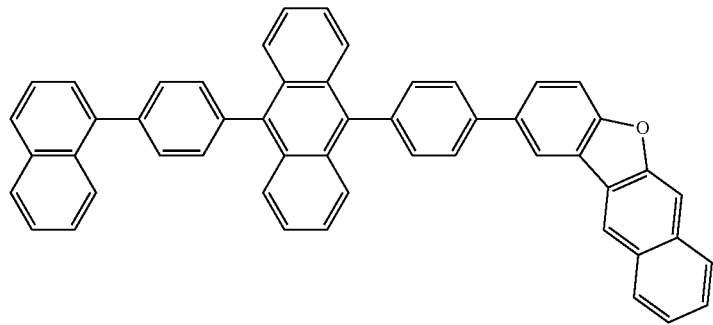

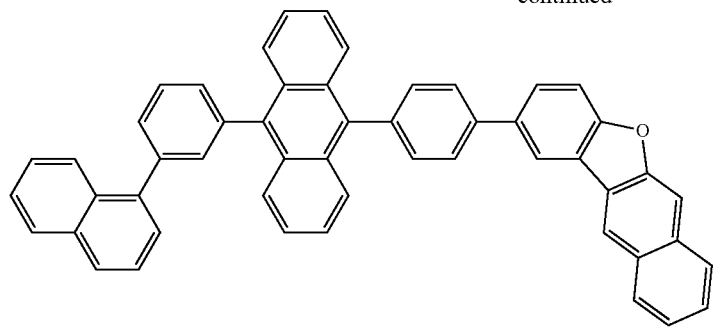
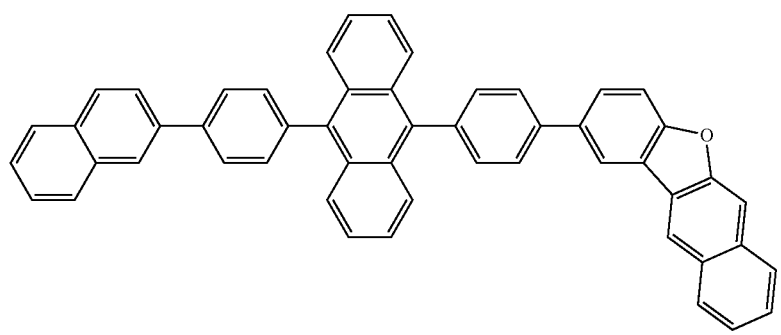
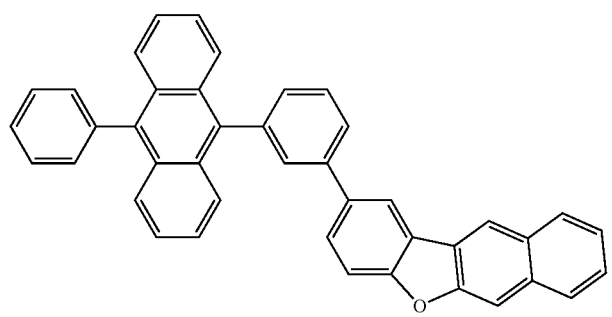
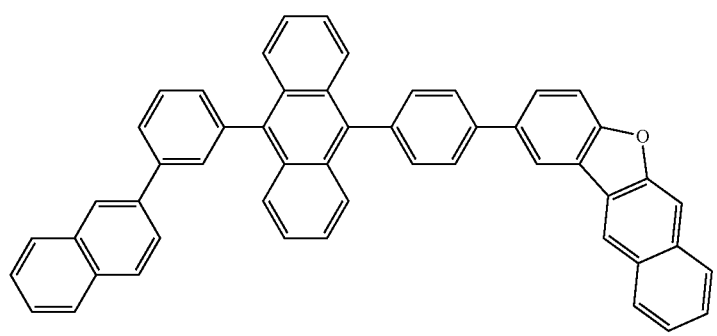
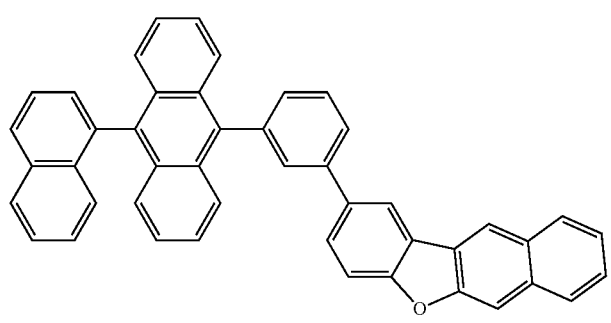

-continued
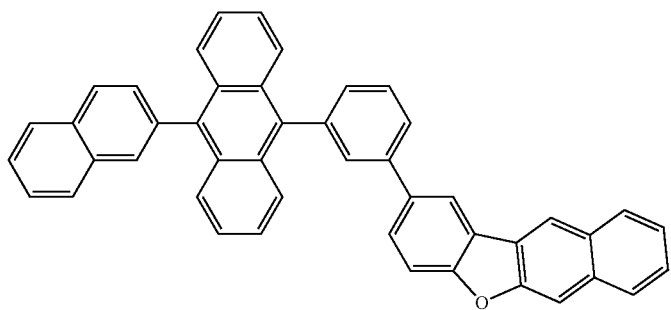
[Chem. 51]
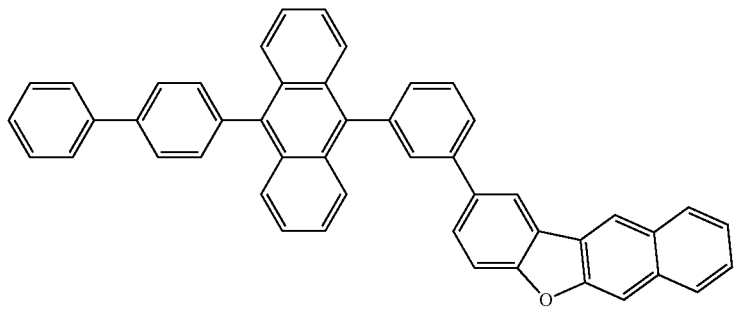
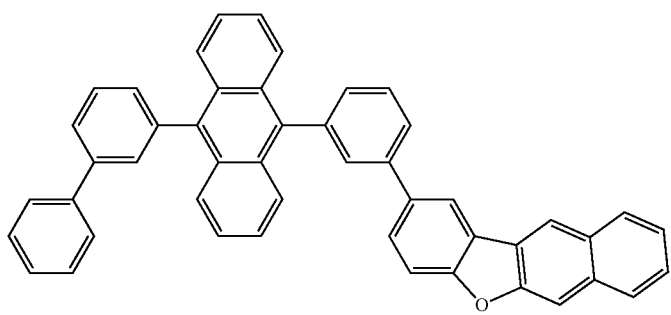
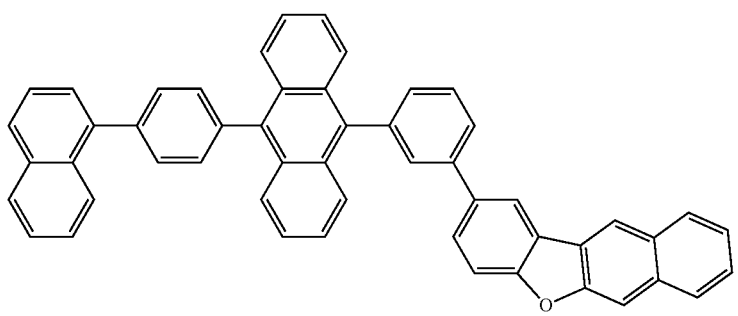
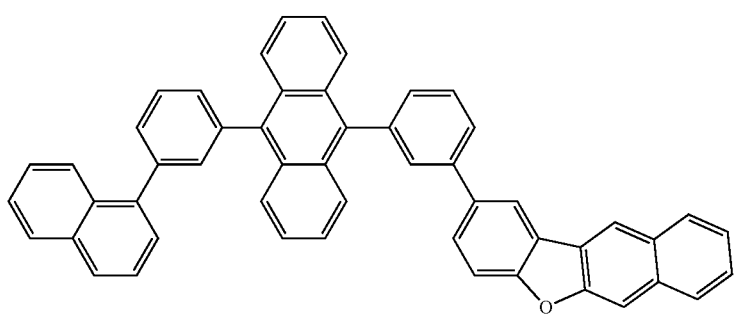

-continued
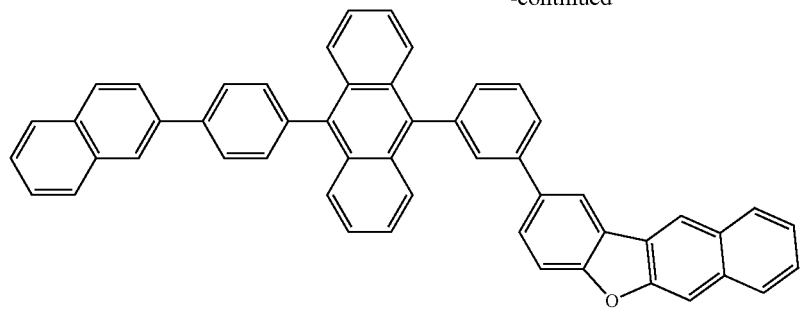
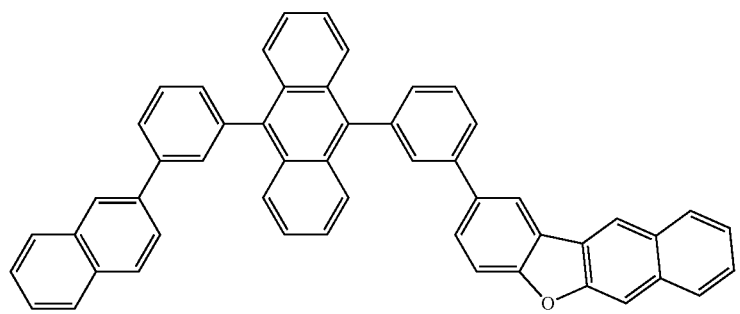
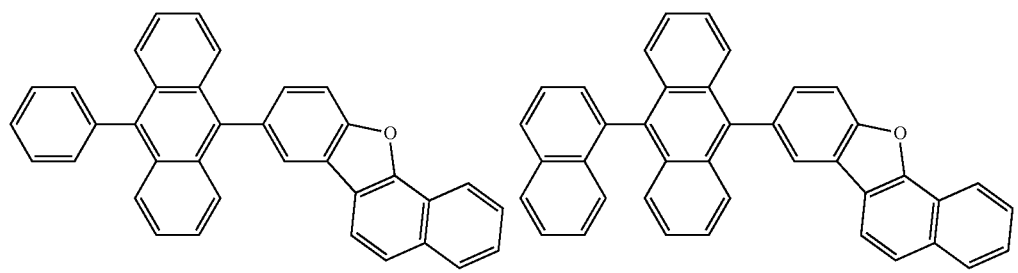
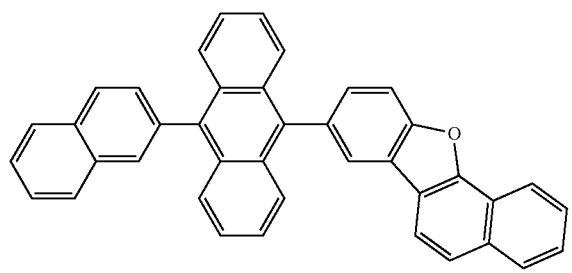
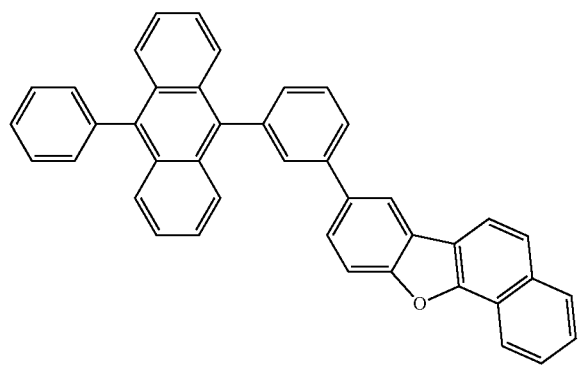

-continued
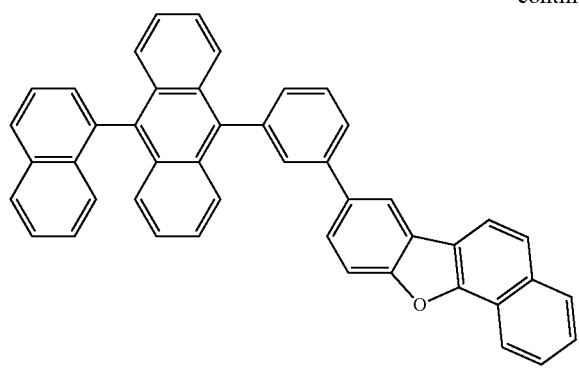
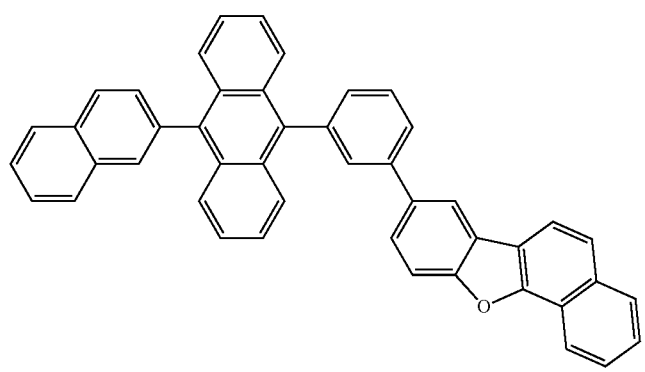
[Chem. 52]
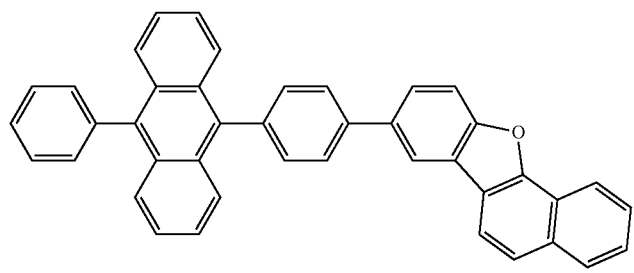
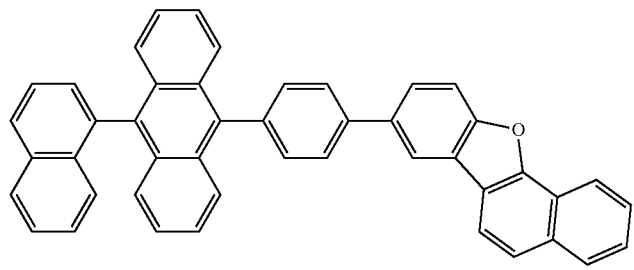
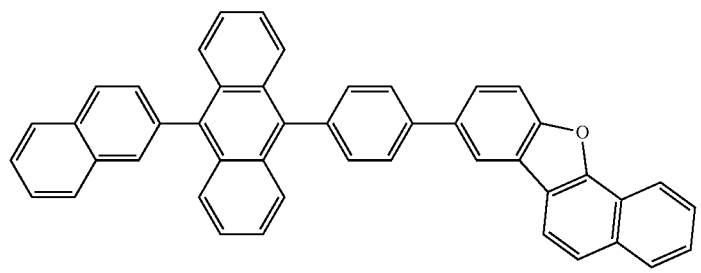

-continued
| 179 | 180 |
|---|---|
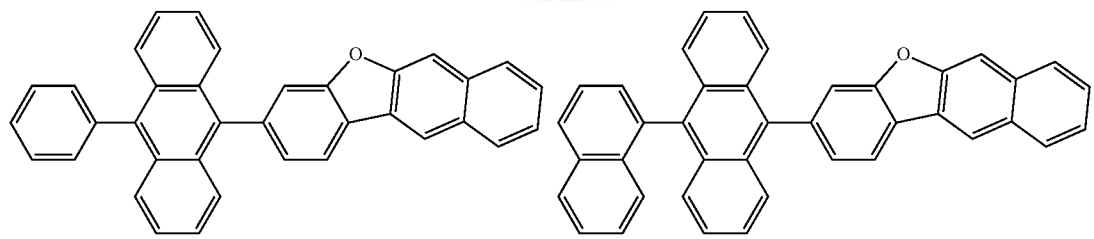
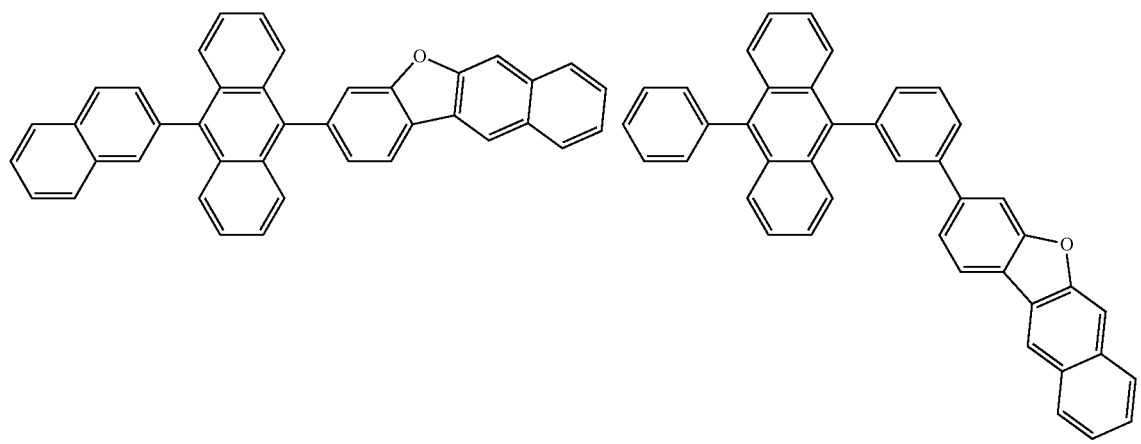
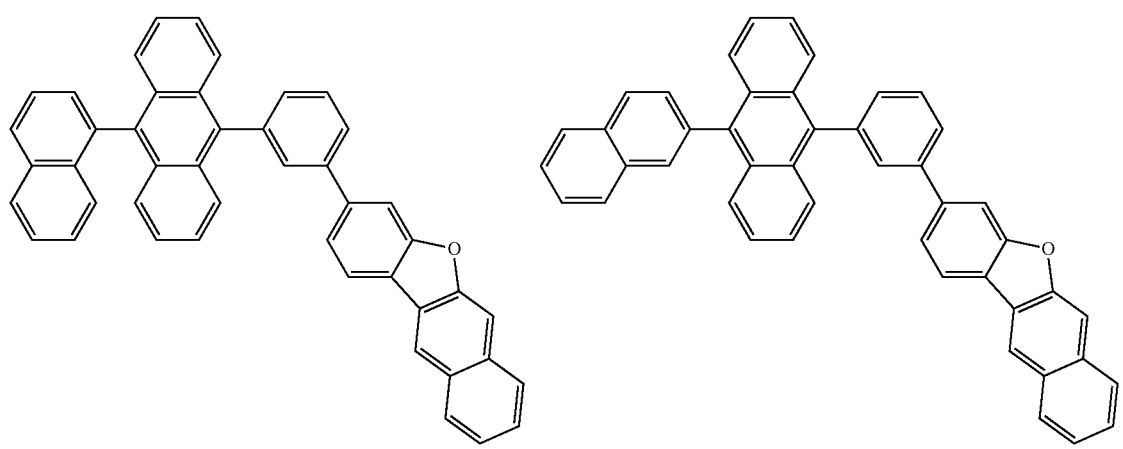
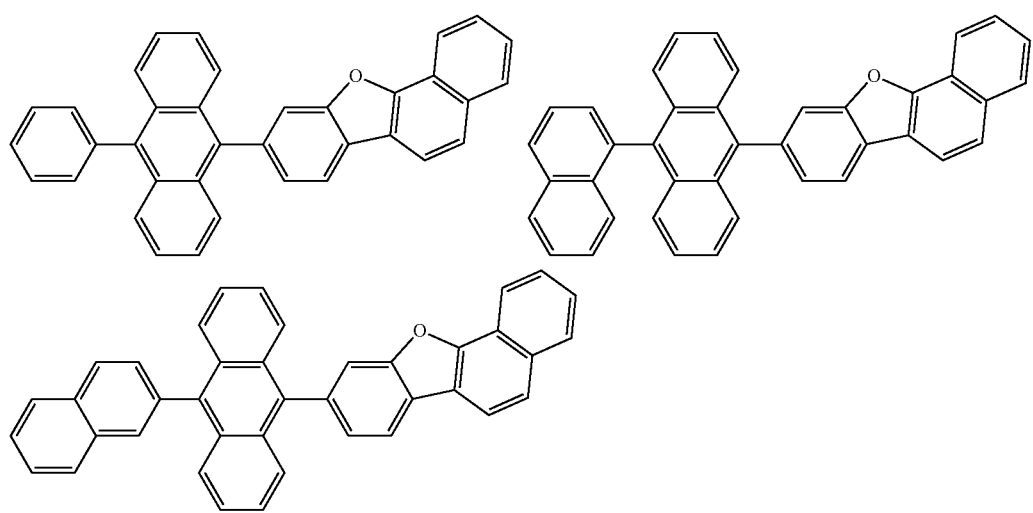

[Chem. 53]
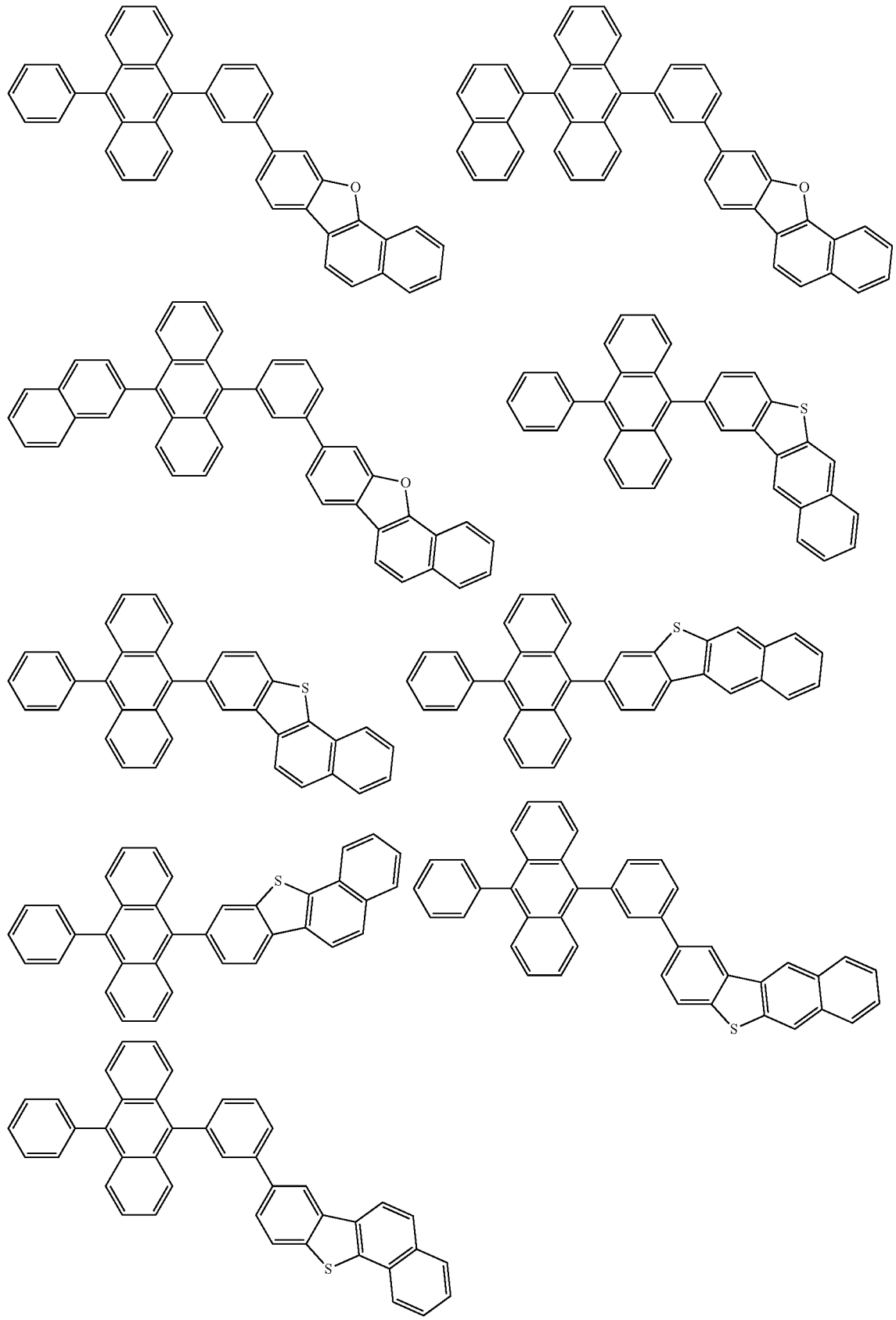

[Chem. 54]
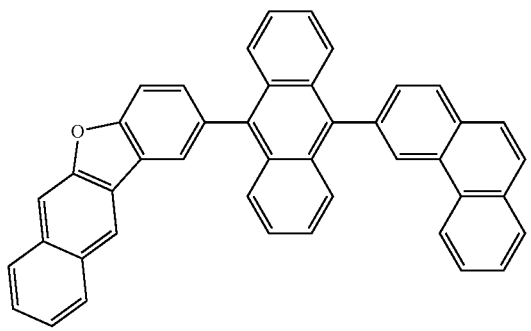
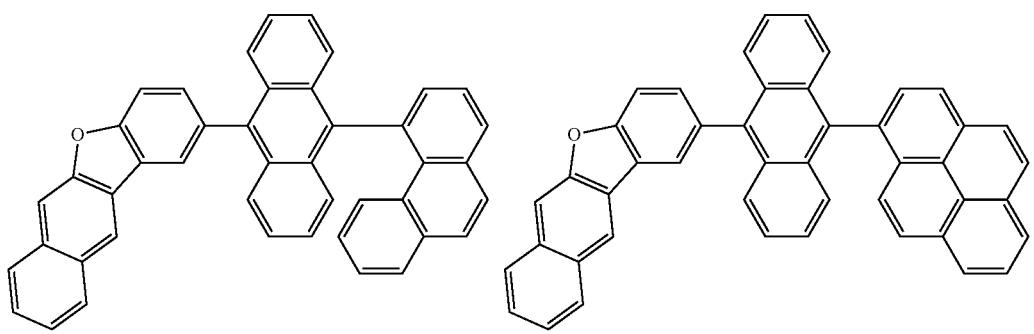
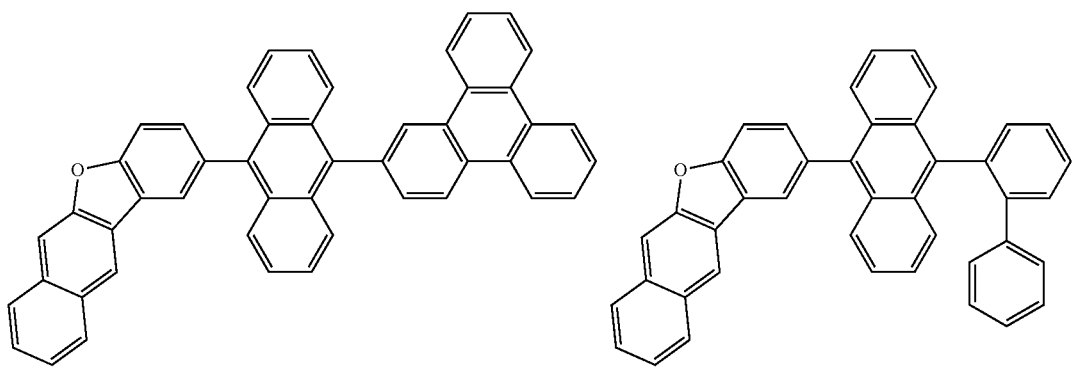
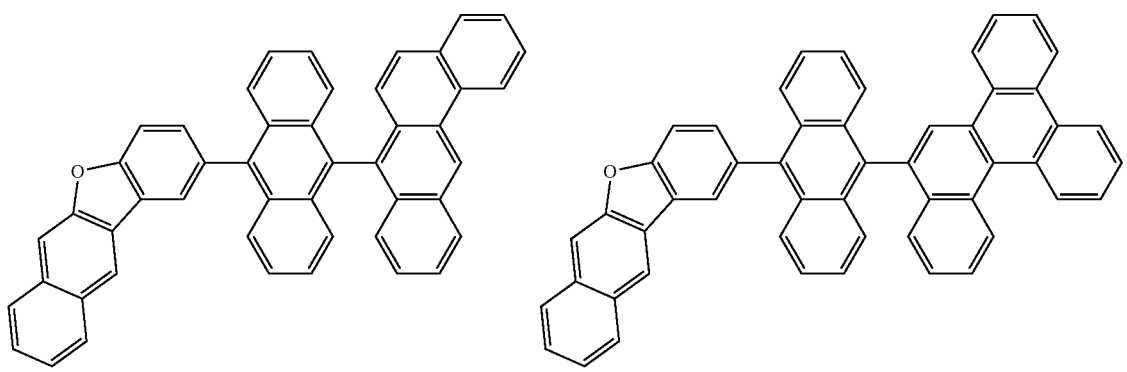

[Chem. 55]
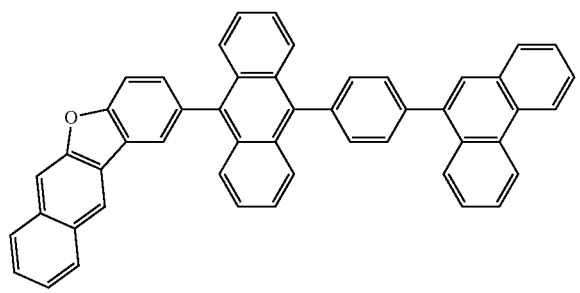
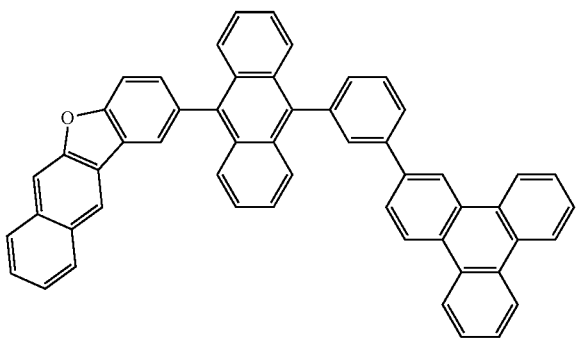
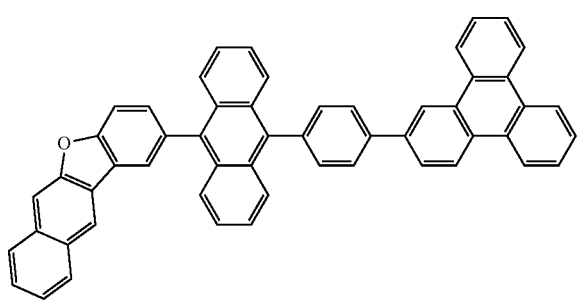
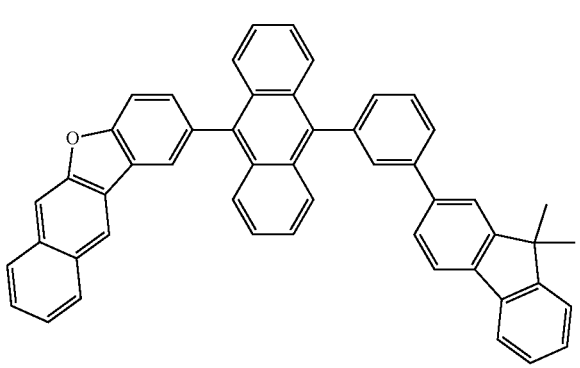
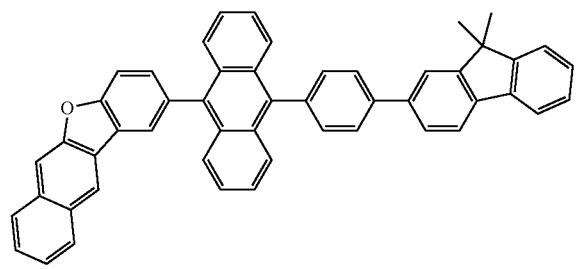
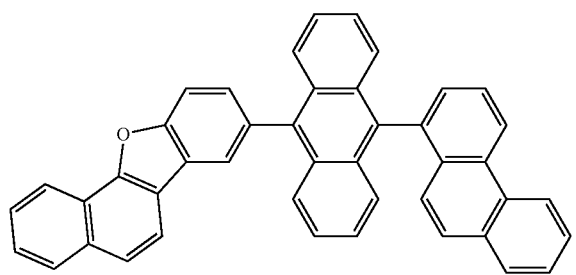
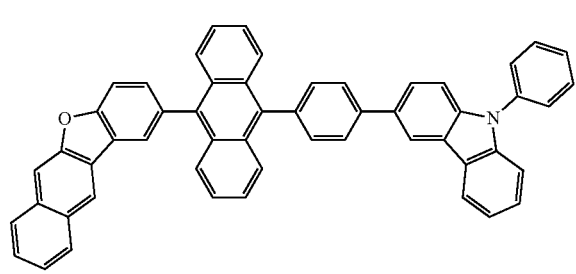
[Chem. 56]
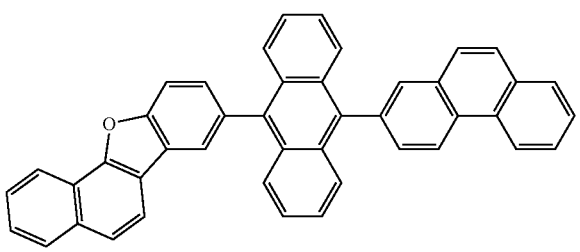
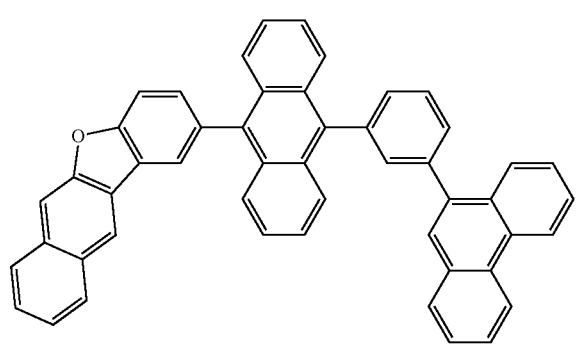
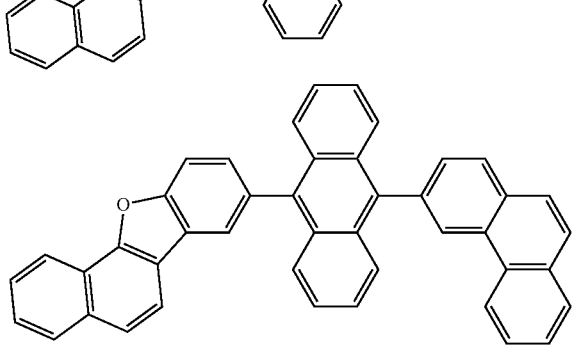

-continued
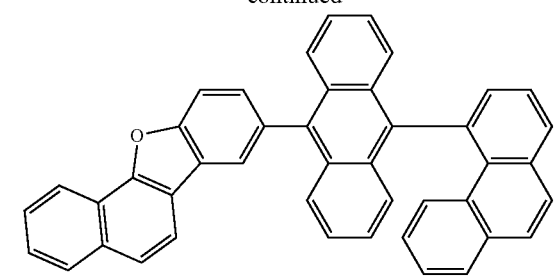
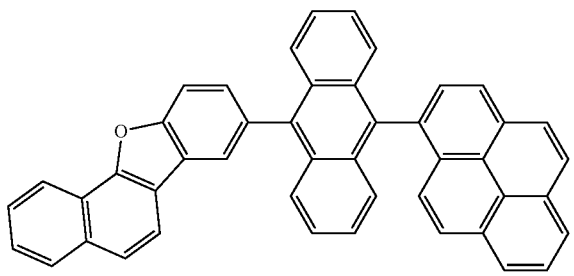
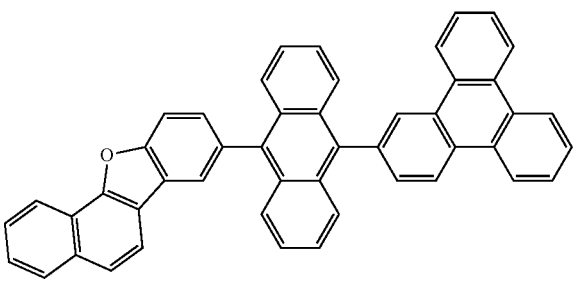
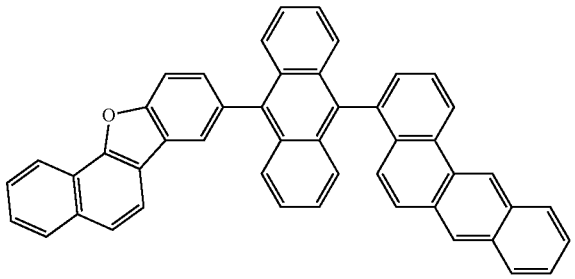
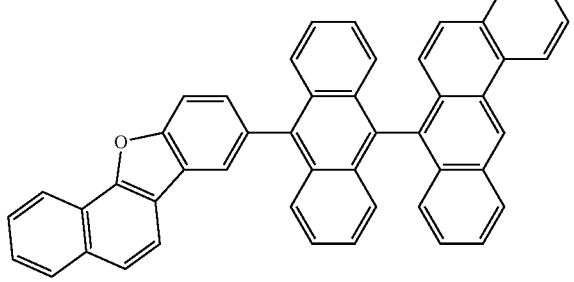
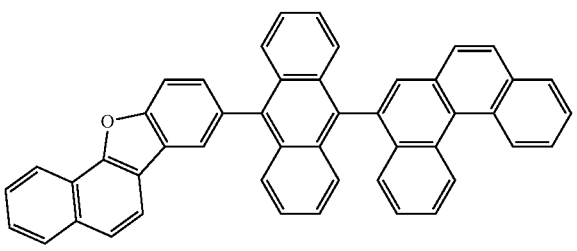
-continued
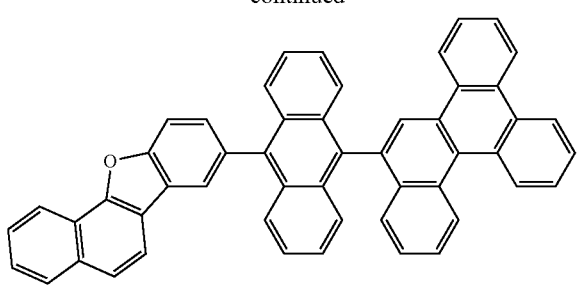
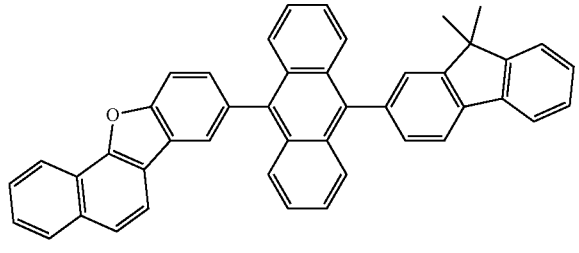
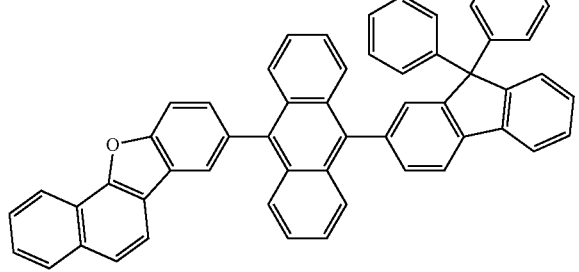
[Chem. 57]
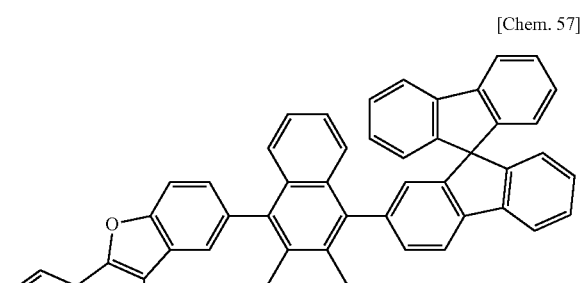
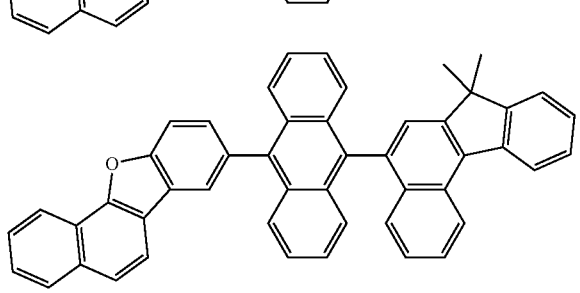
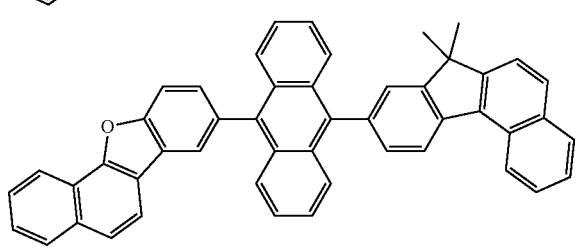

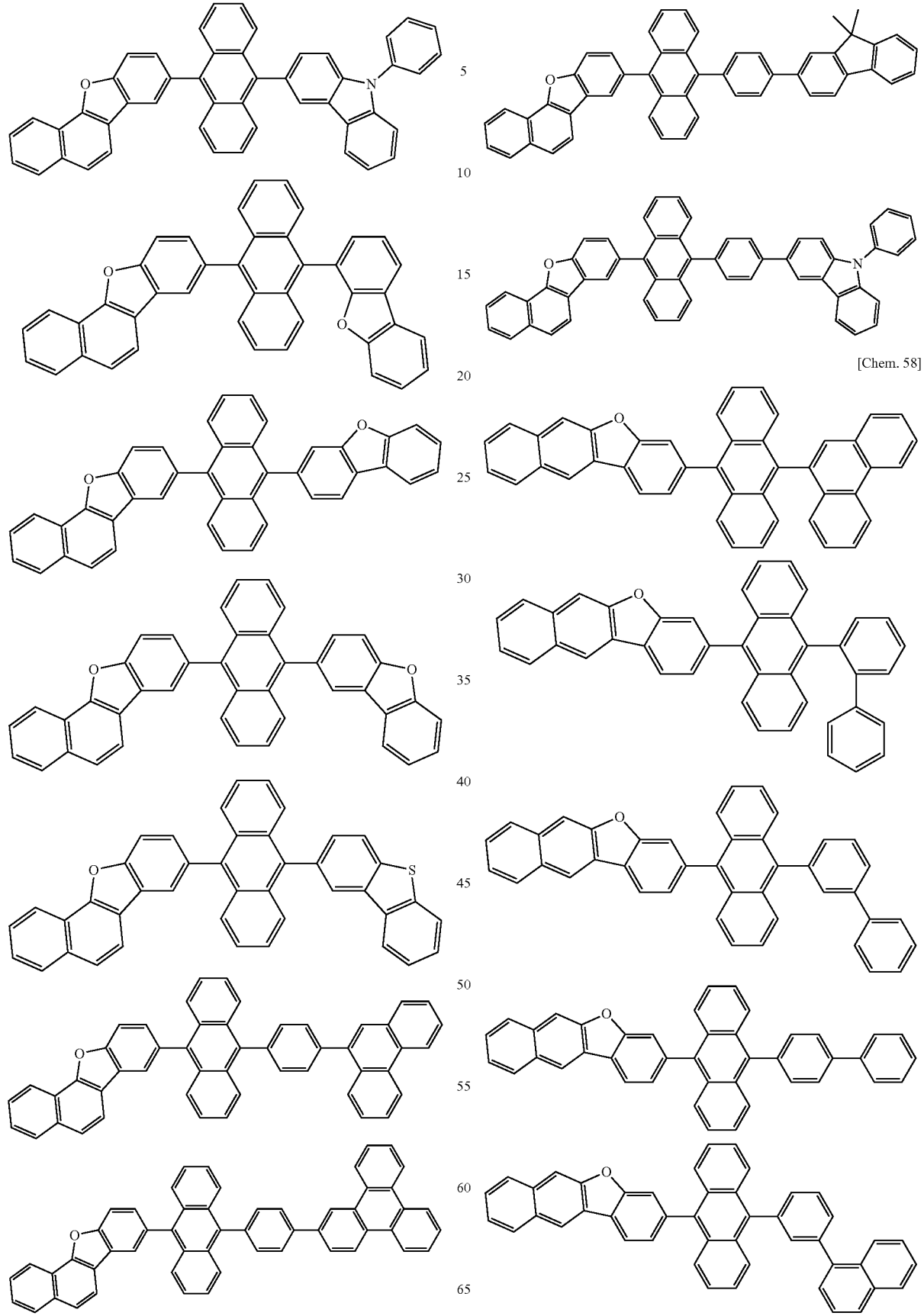

191
-continued
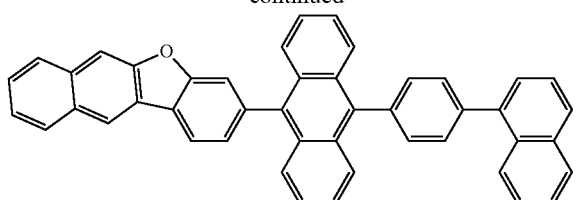
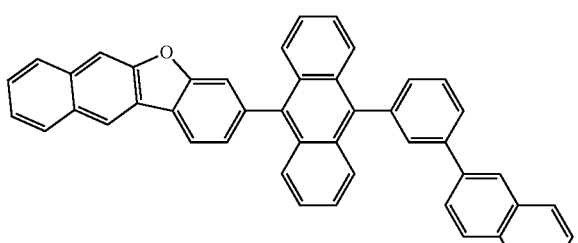
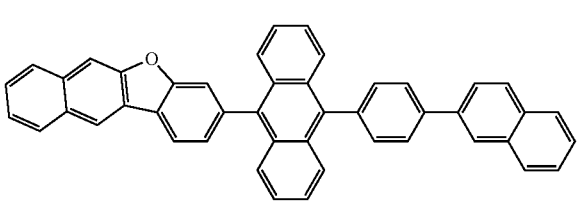
[Chem. 59]
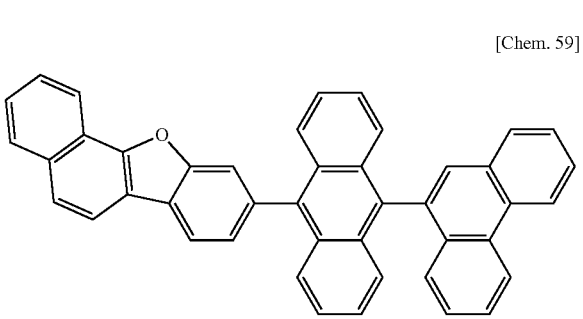
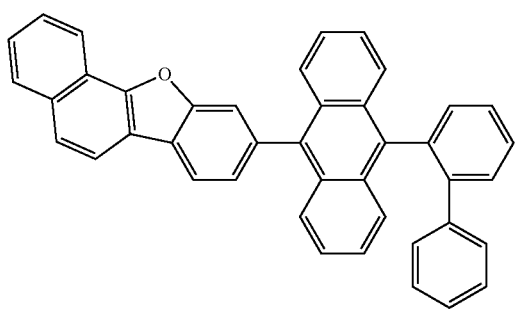
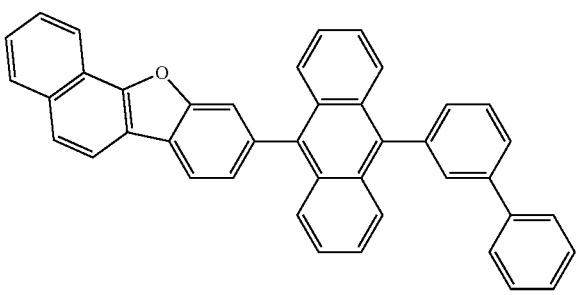
192
-continued
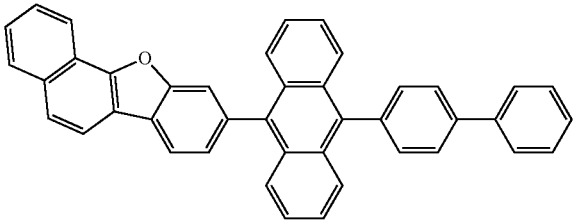
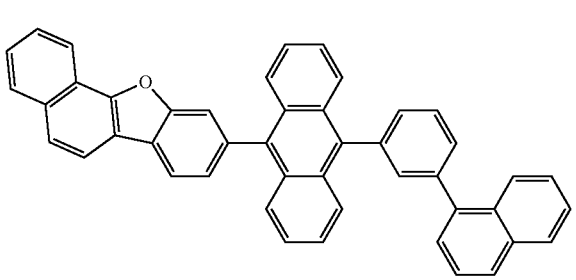
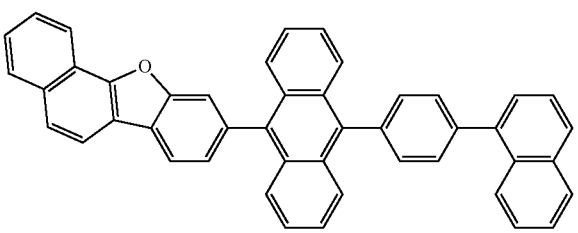
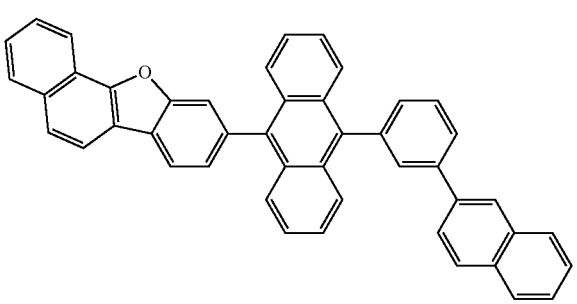
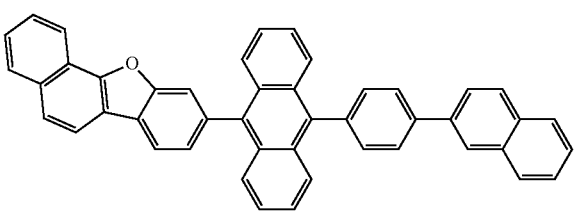

193
-continued
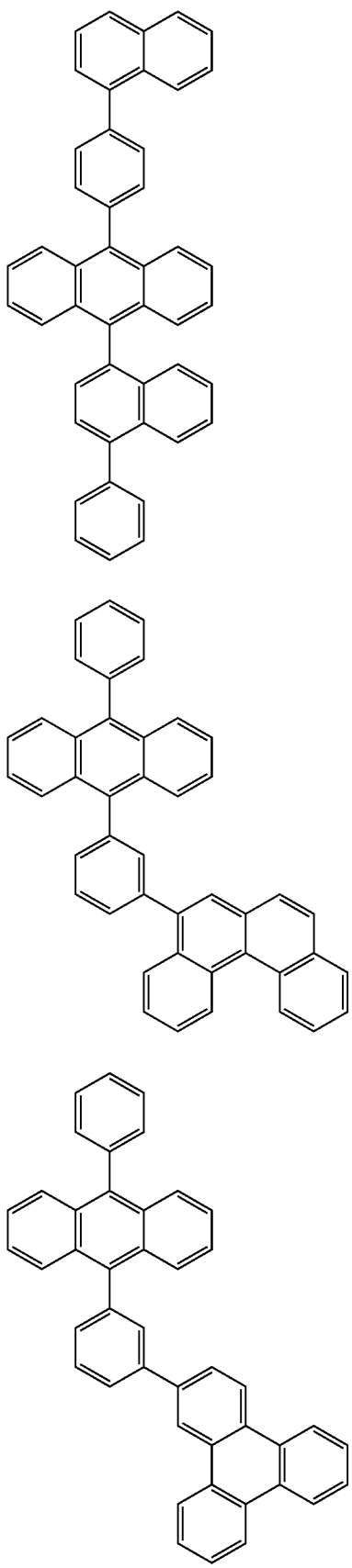
194
-continued
[Chem. 60]
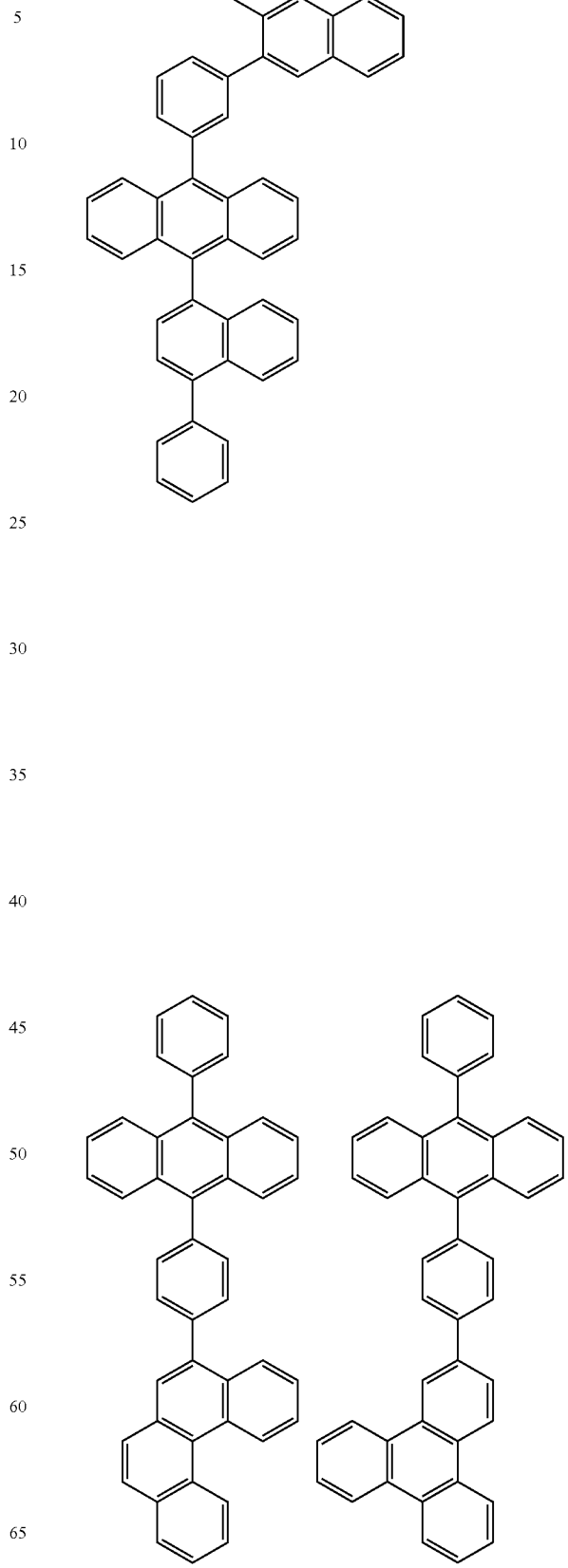

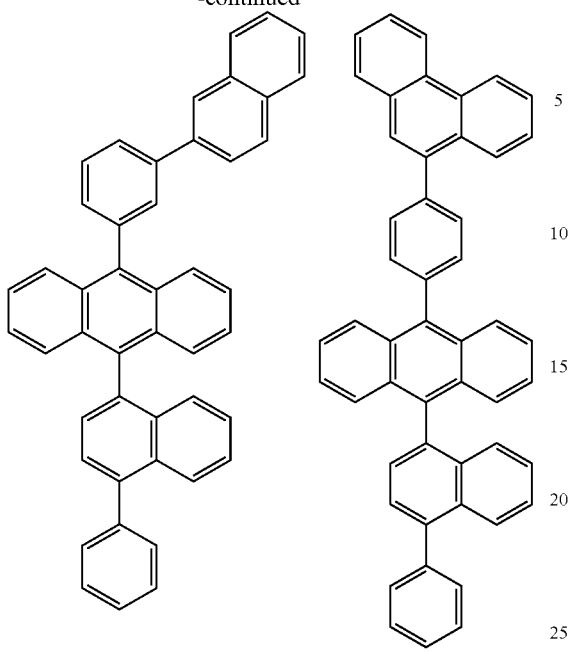
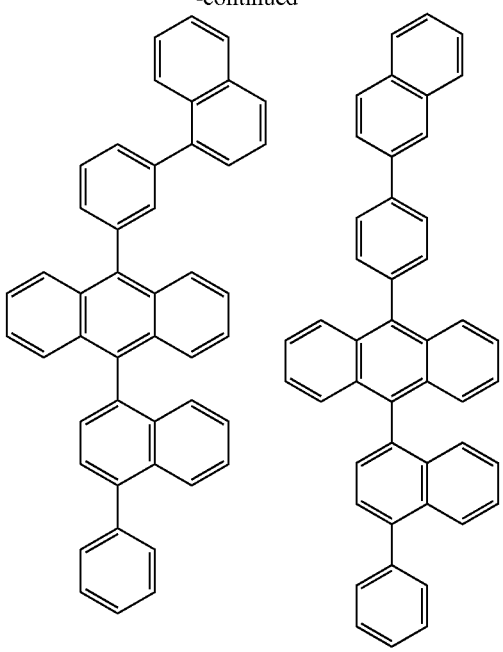
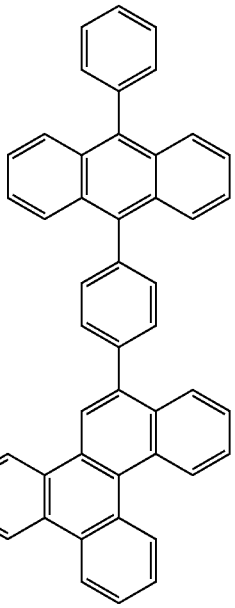
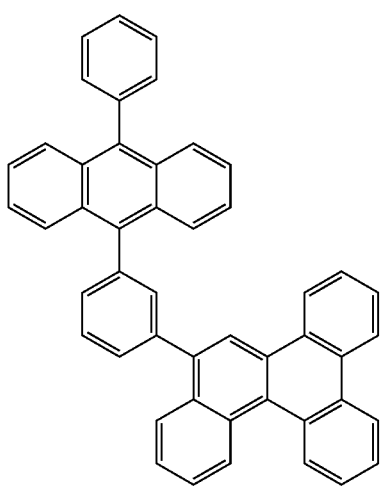
[Chem. 61]
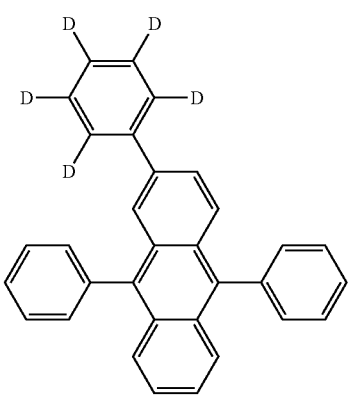

197
-continued
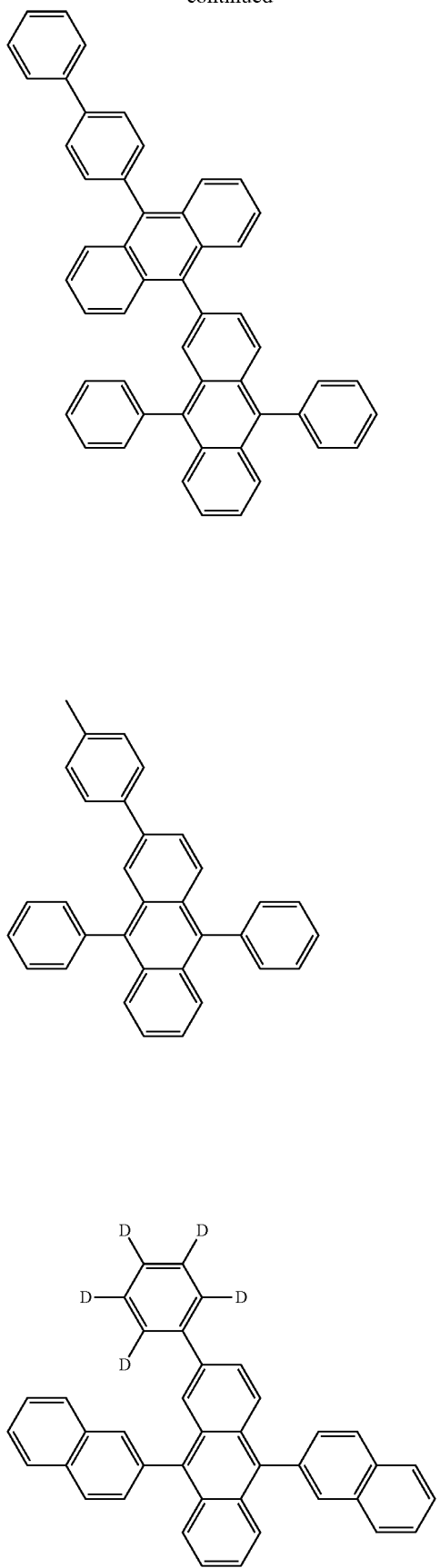
198
-continued
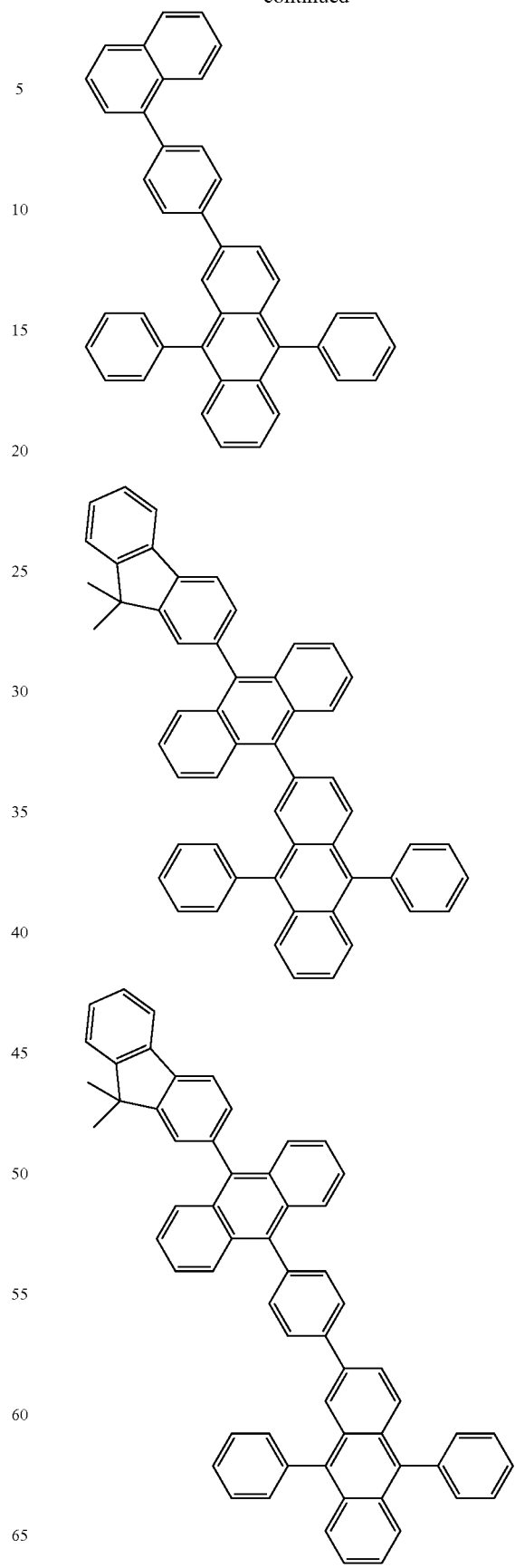

199 200
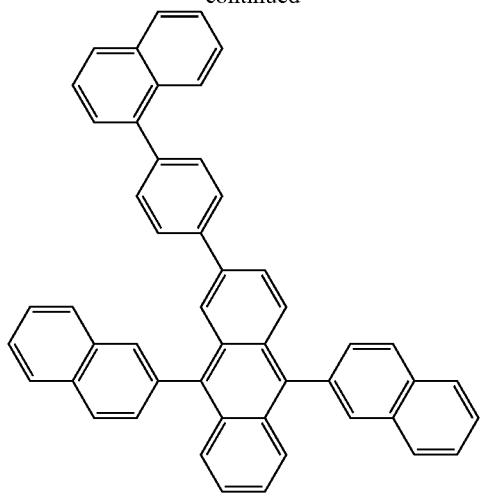
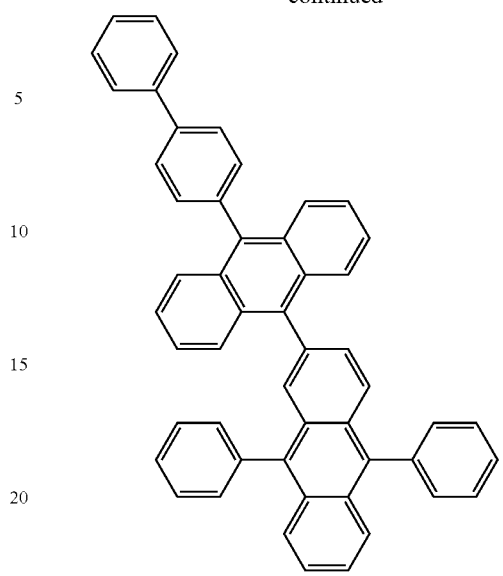
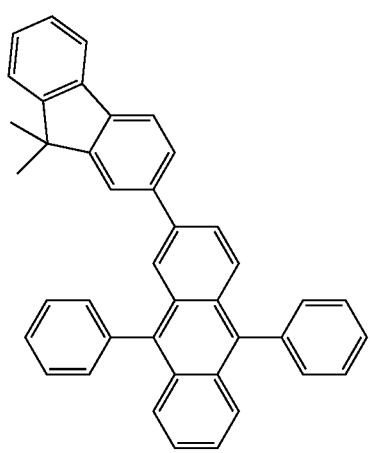
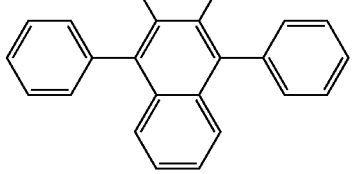
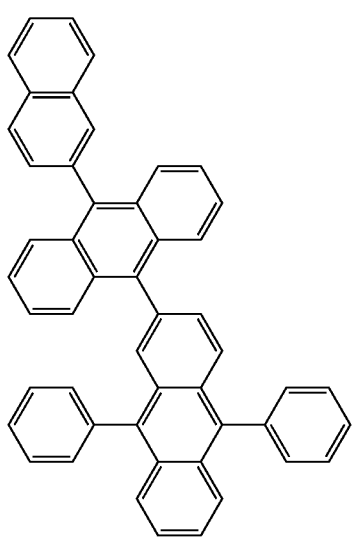

201
-continued
202
-continued
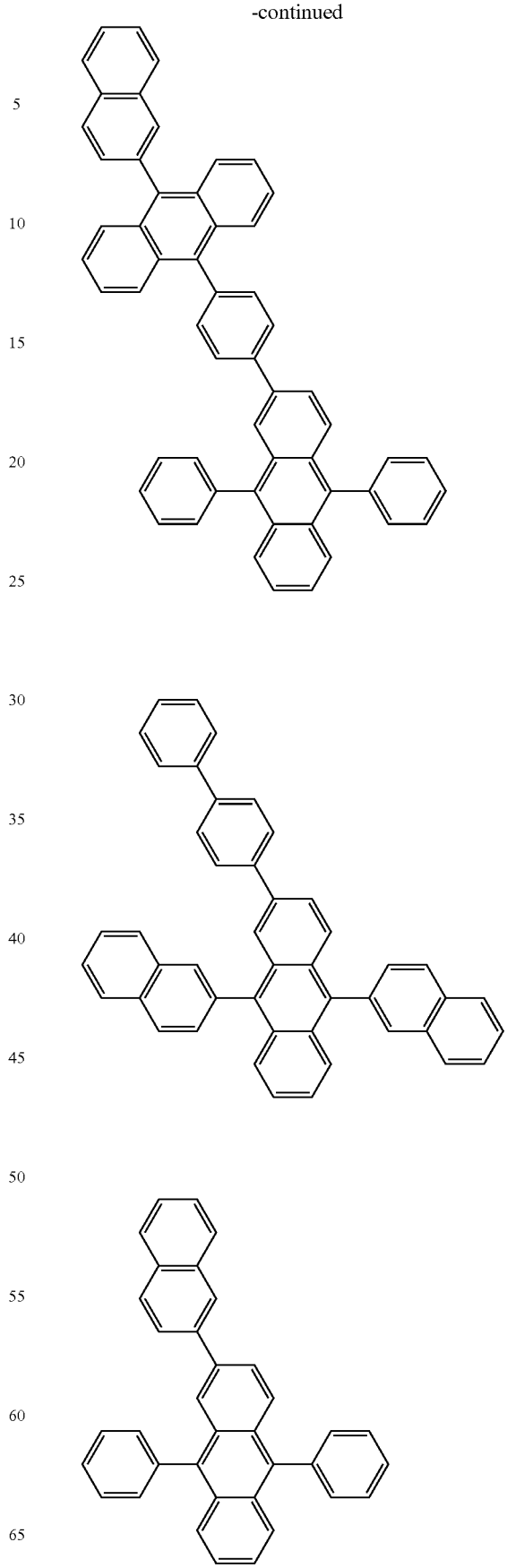

203
-continued
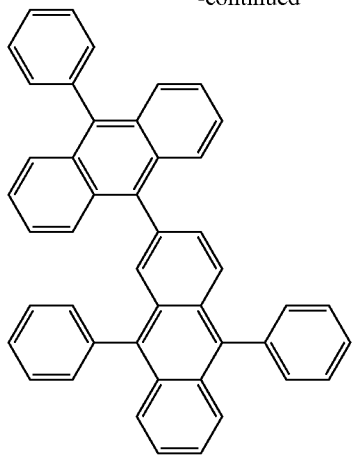
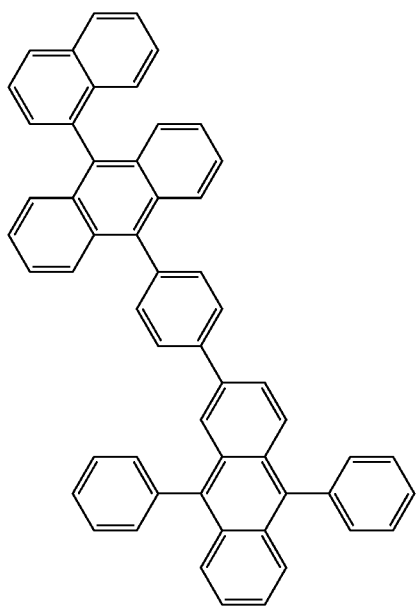
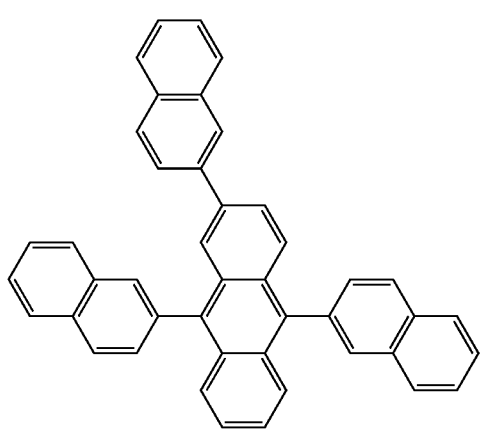
204
-continued
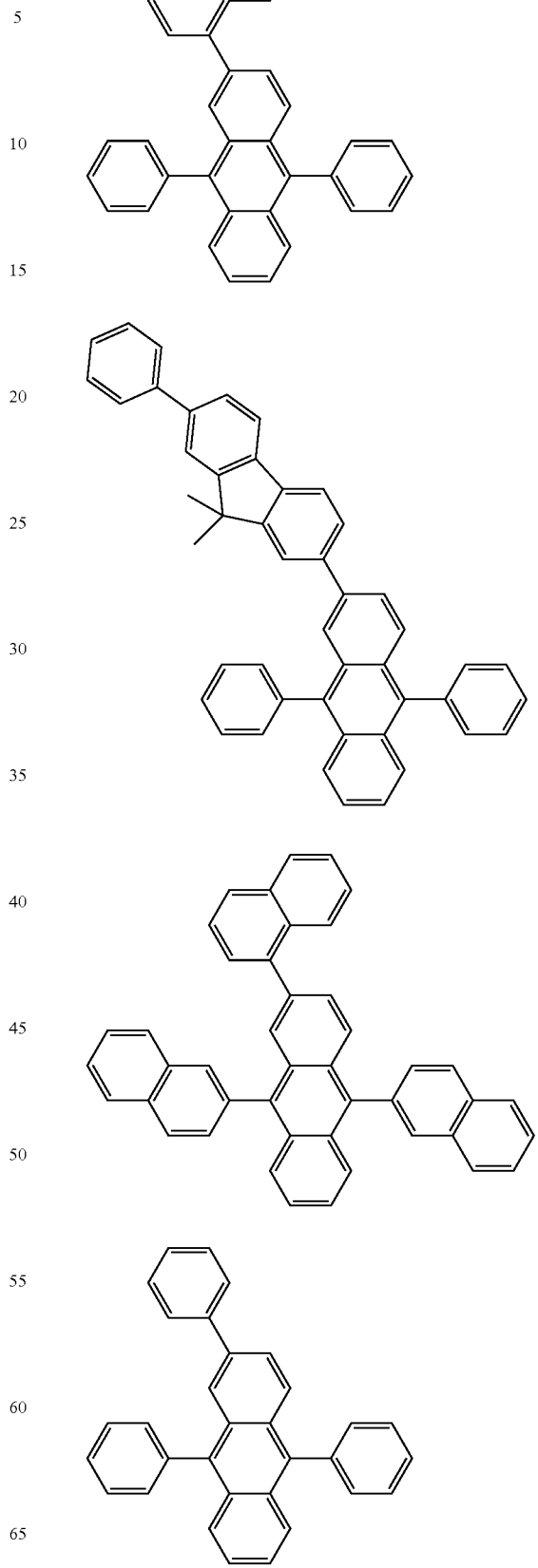

205
-continued
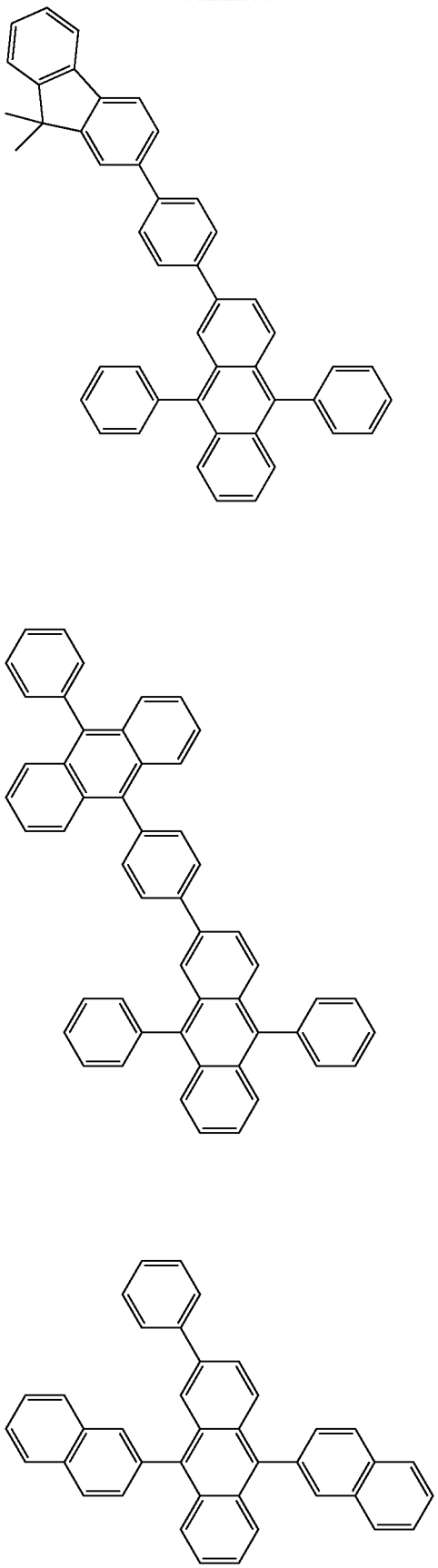
206
-continued
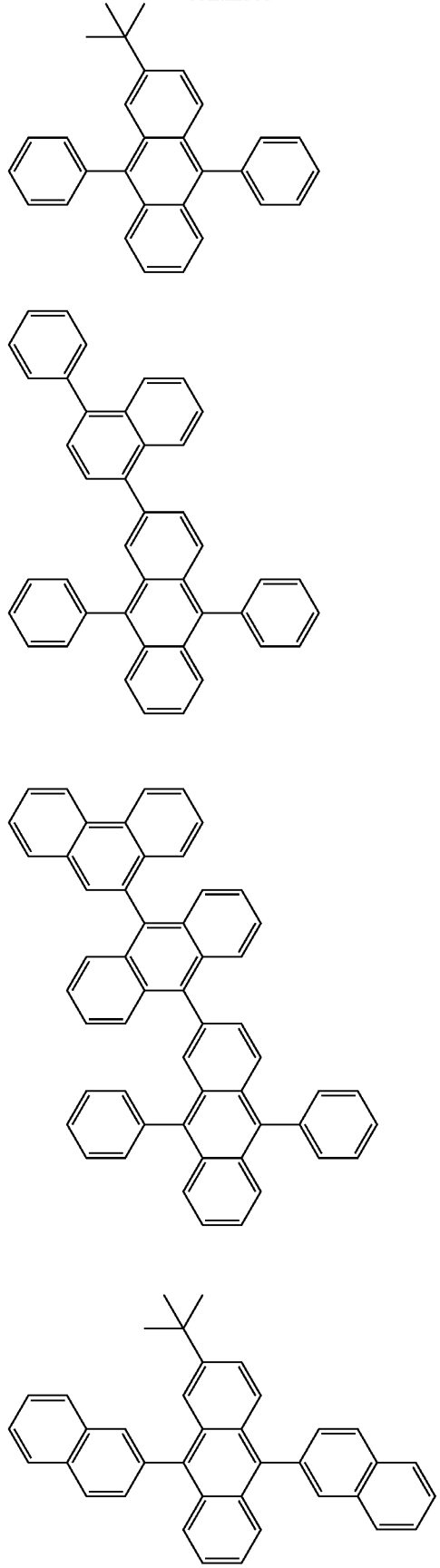

207
-continued
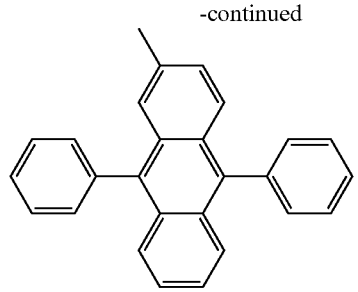
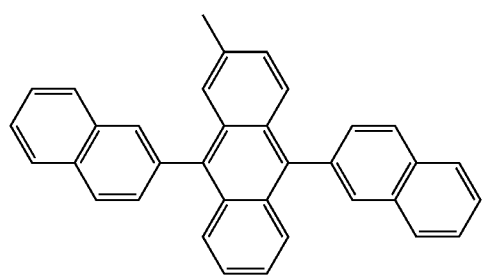
[Chem. 62]
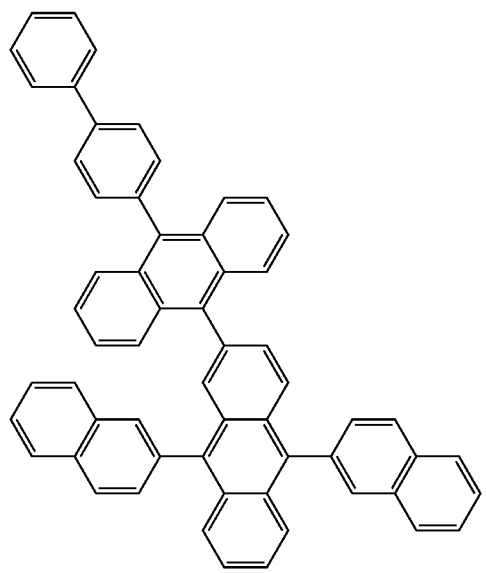
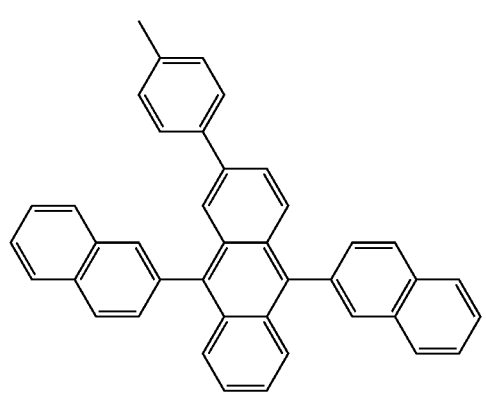
208
-continued
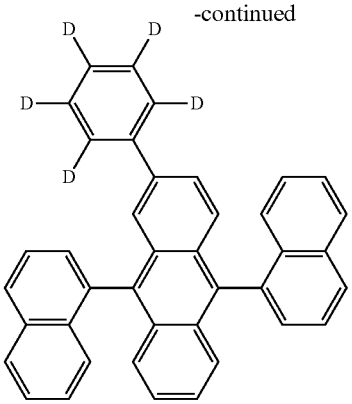
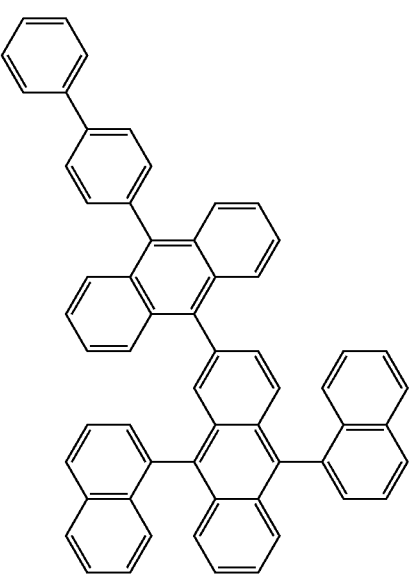
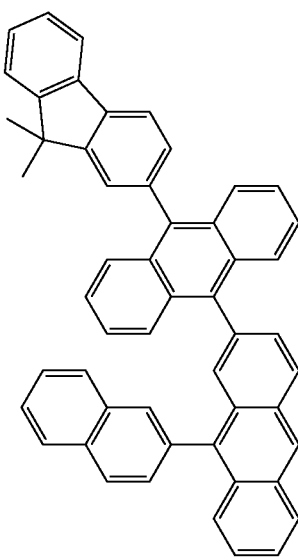

209
-continued
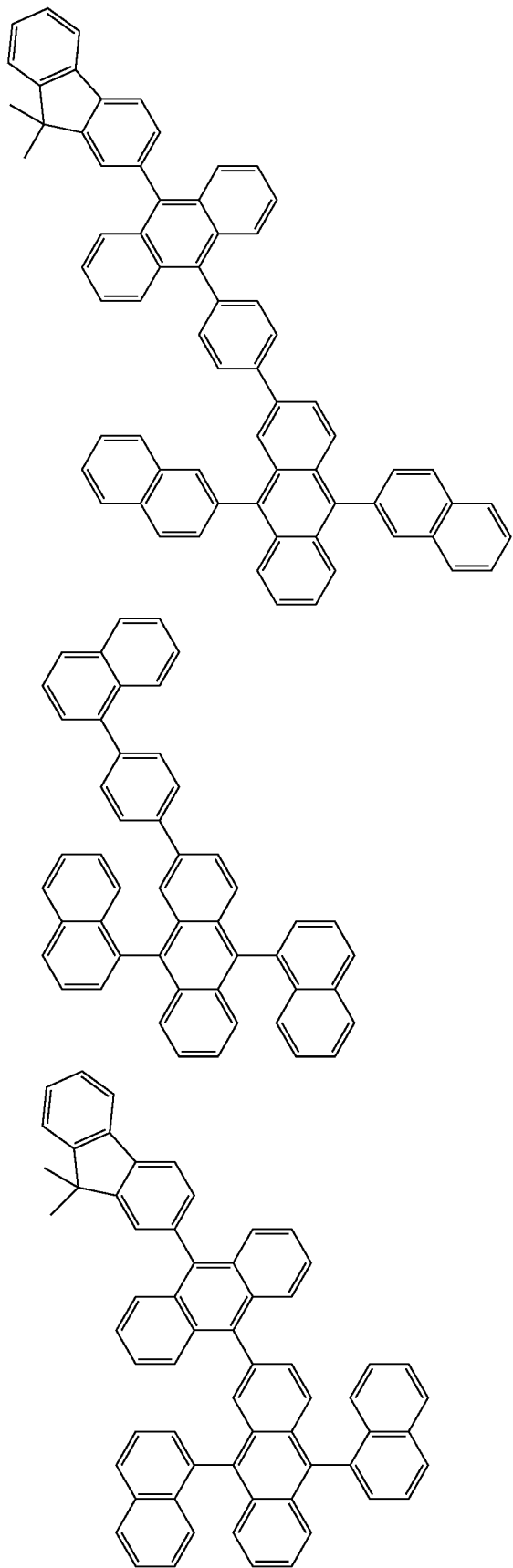
210
-continued
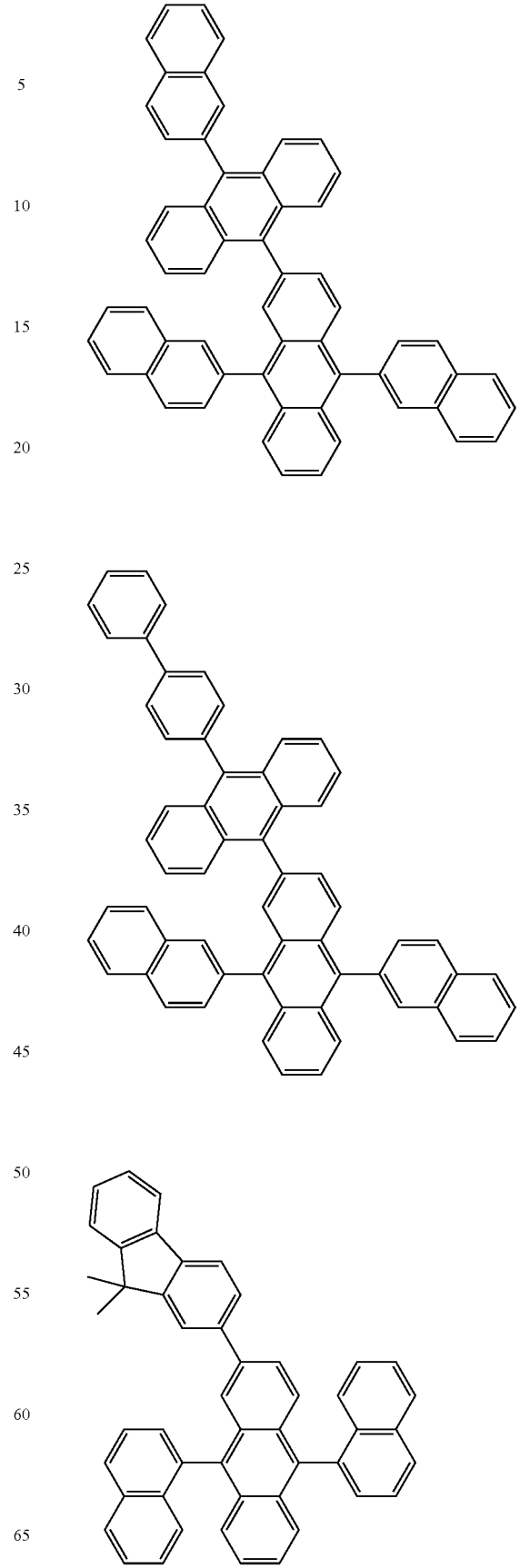

211
-continued
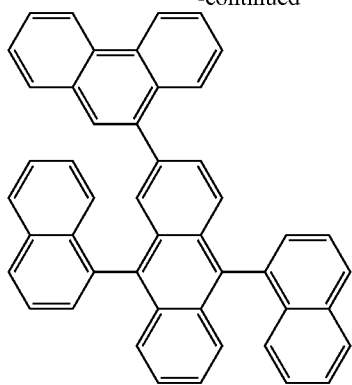
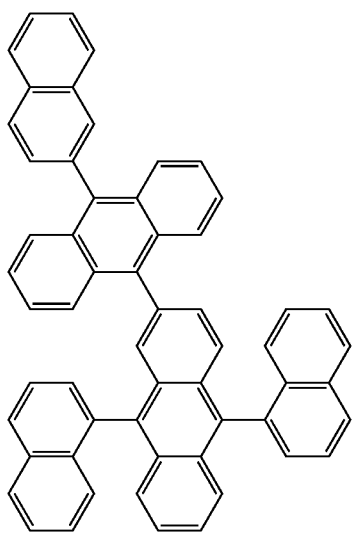
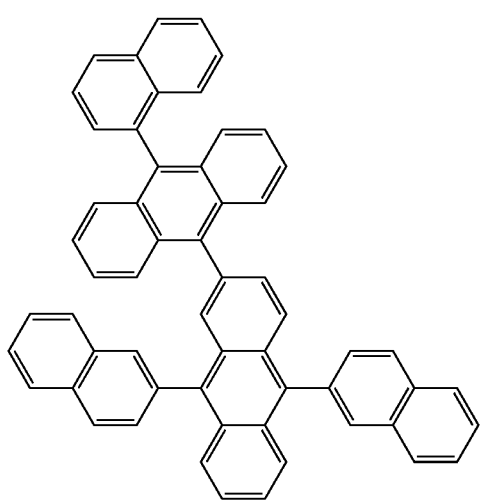
212
-continued
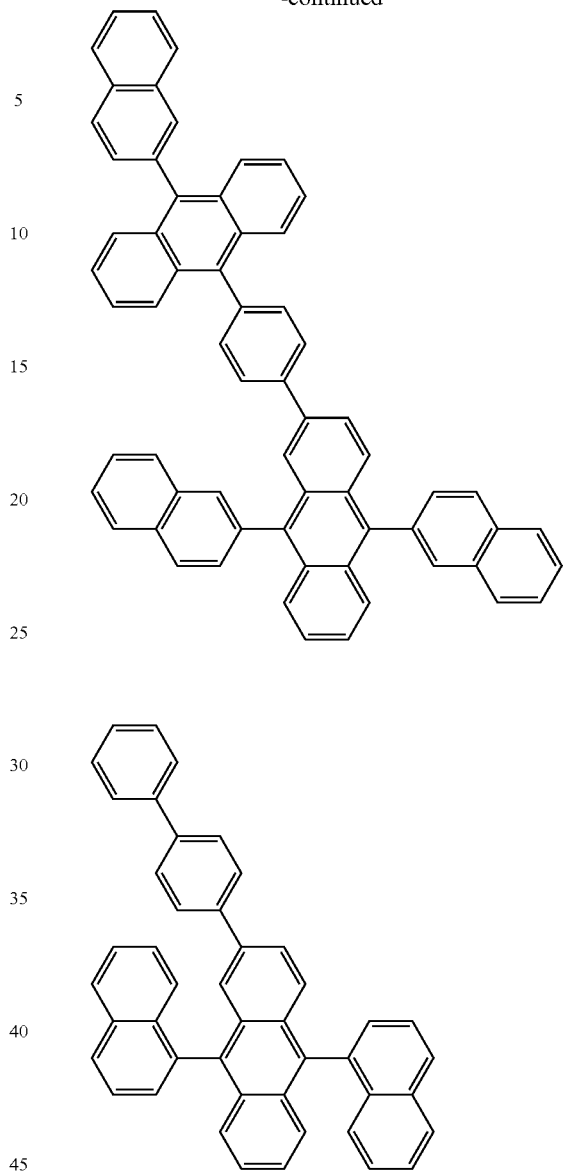
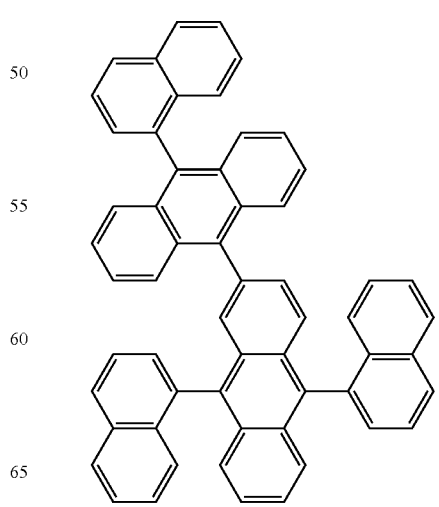

213
-continued
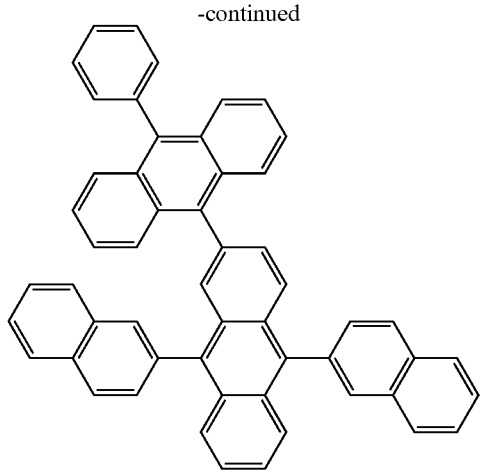
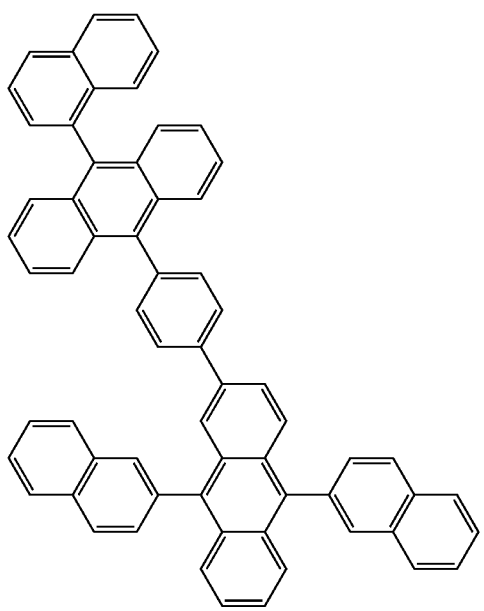
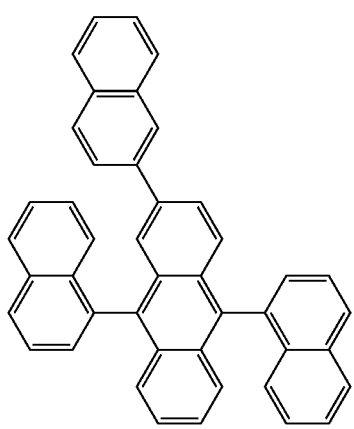
214
-continued
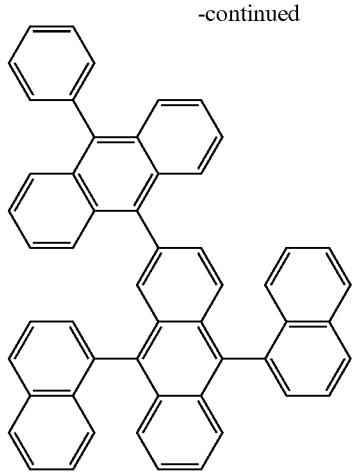
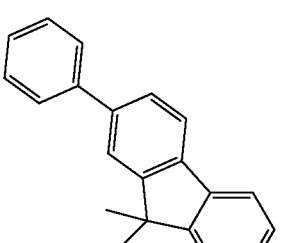
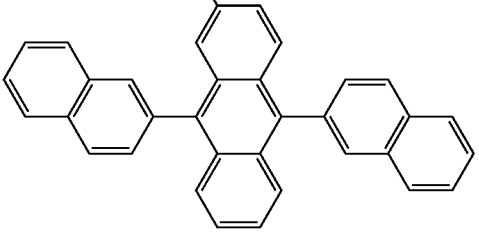
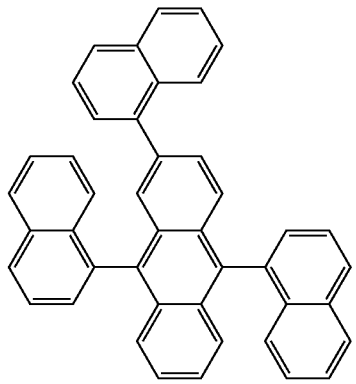

215
-continued
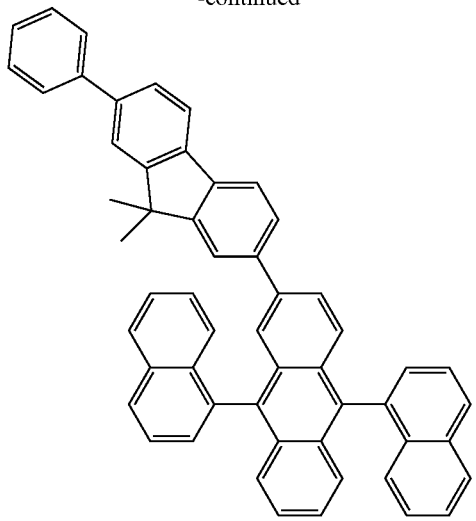
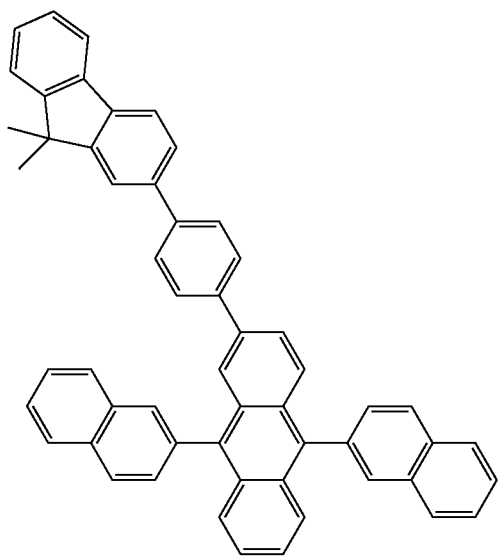
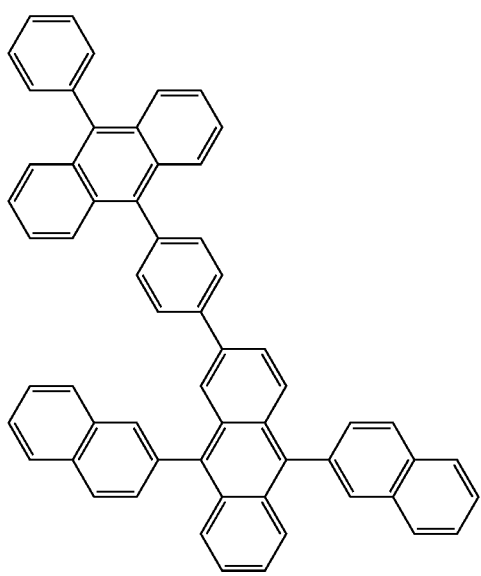
216
-continued
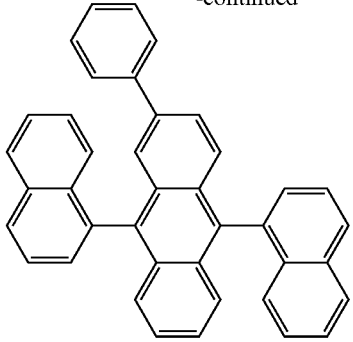
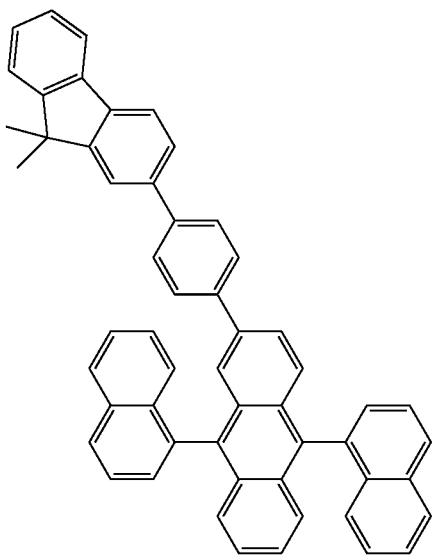
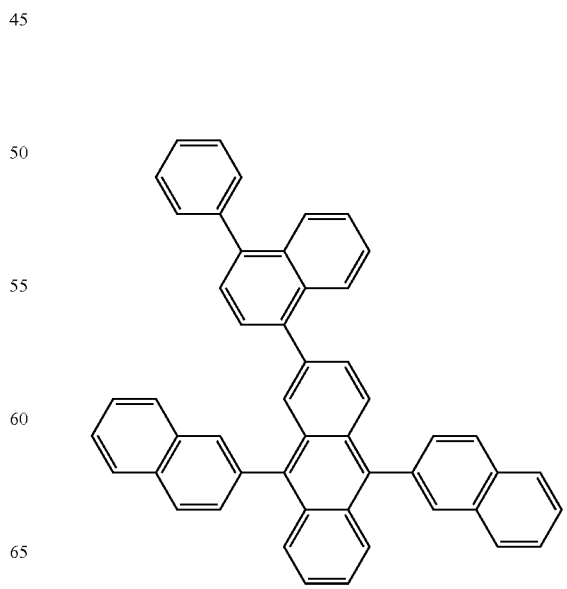

217
-continued
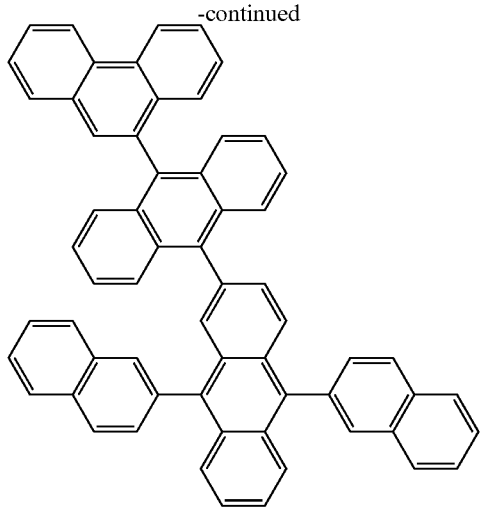
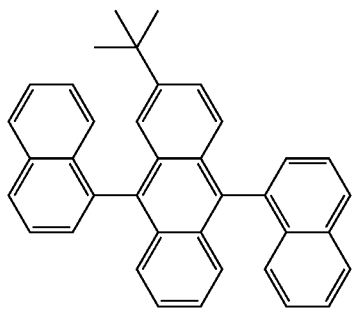
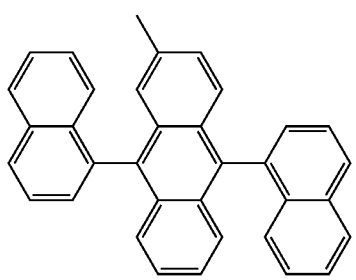
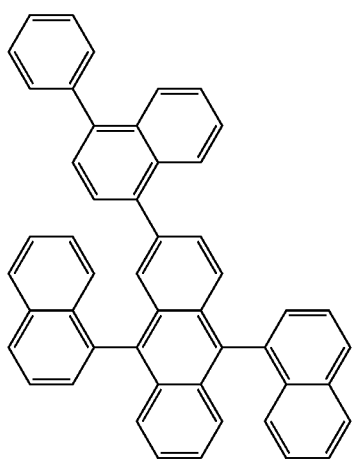
218
[Chem. 63]
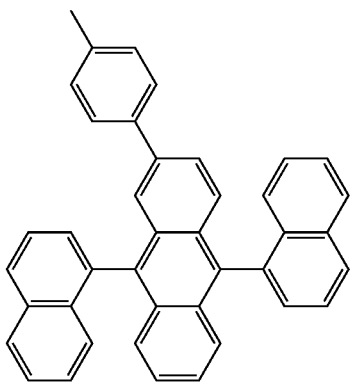
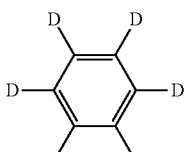
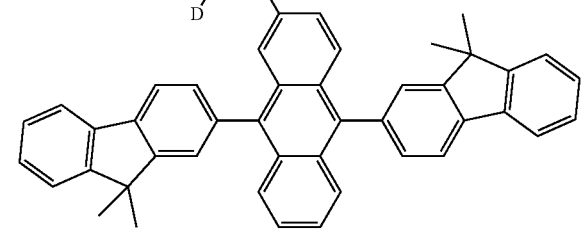
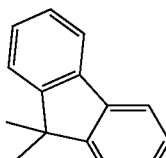
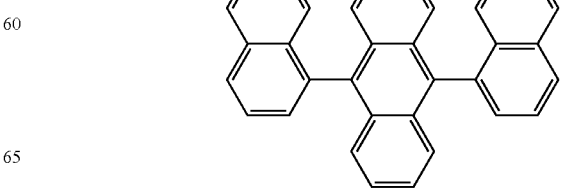

219
-continued
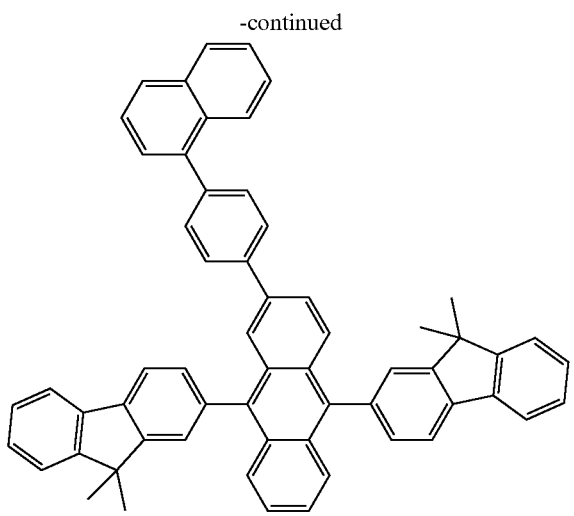
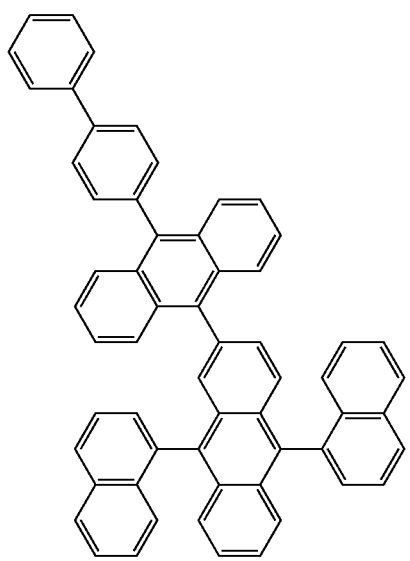
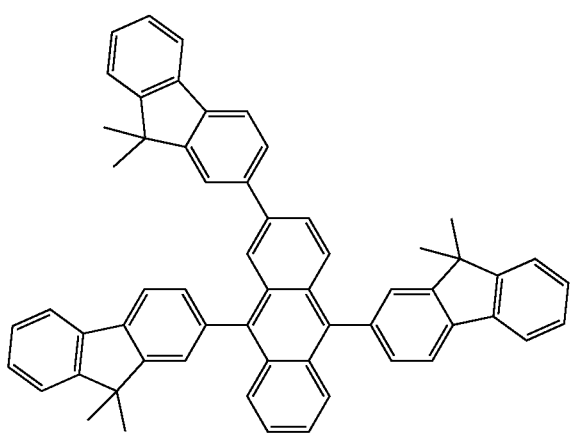
220
-continued
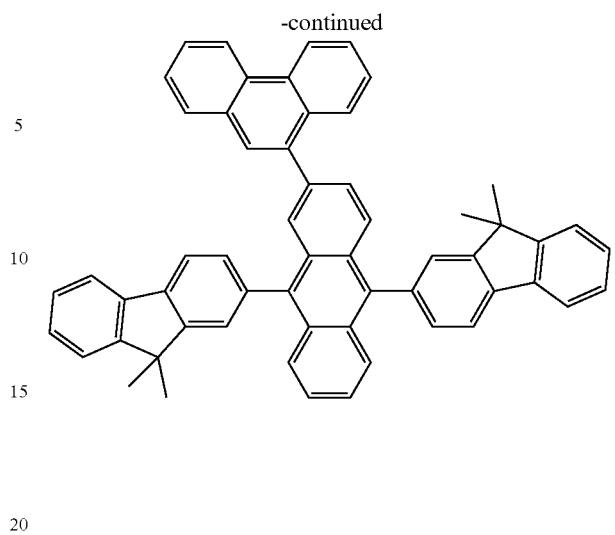
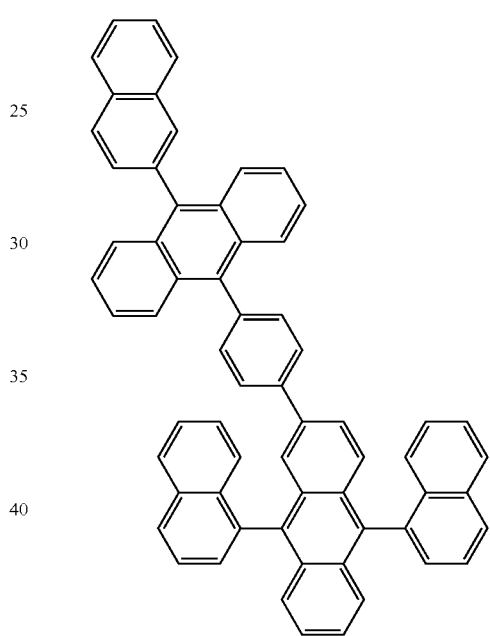
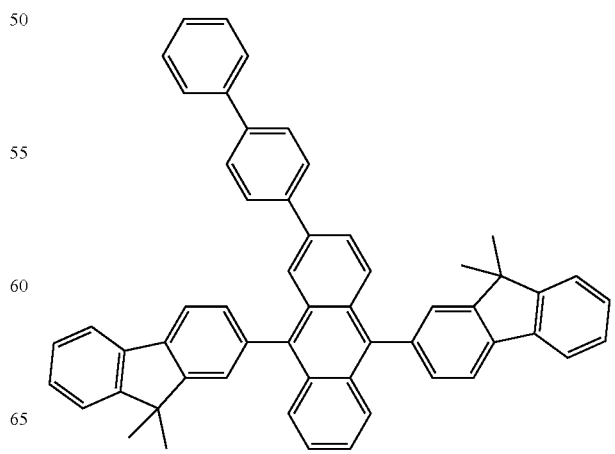

221
-continued
222
-continued
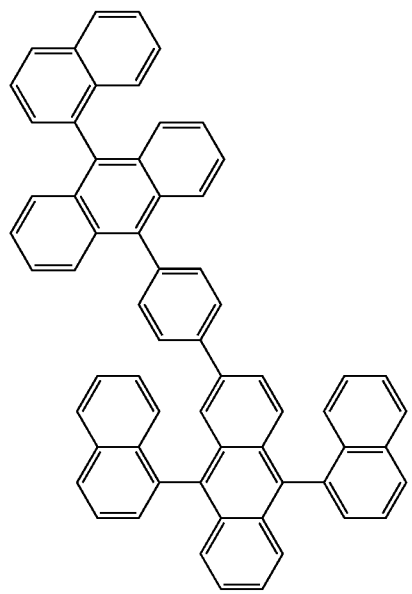

223
-continued
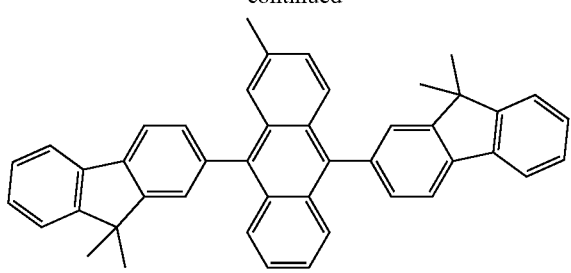
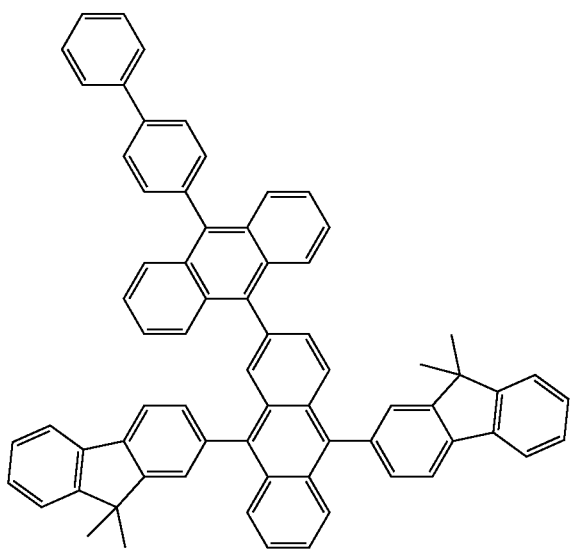
[Chem. 64]
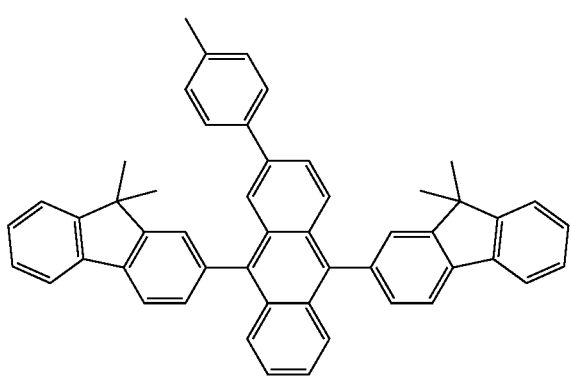
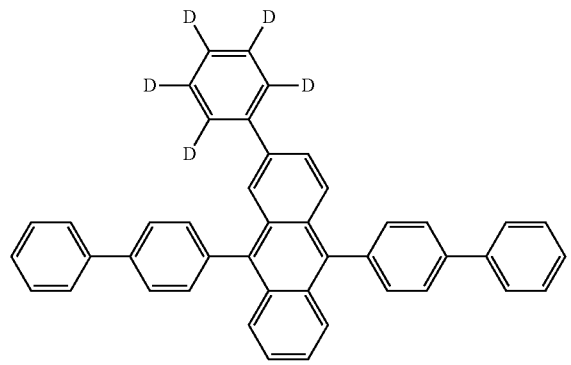
224
-continued
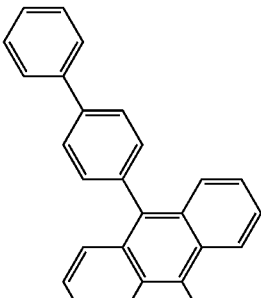
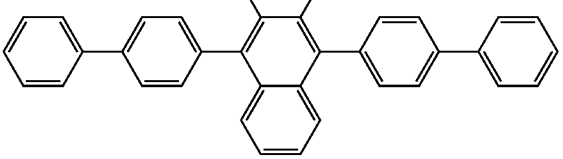
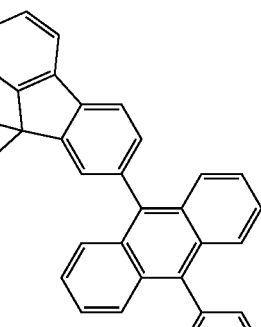
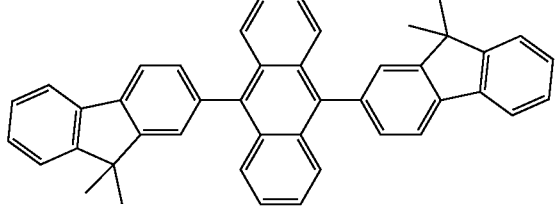
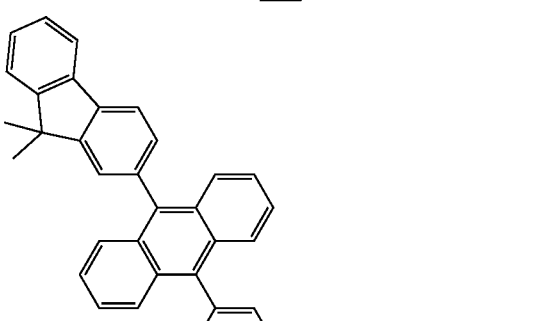
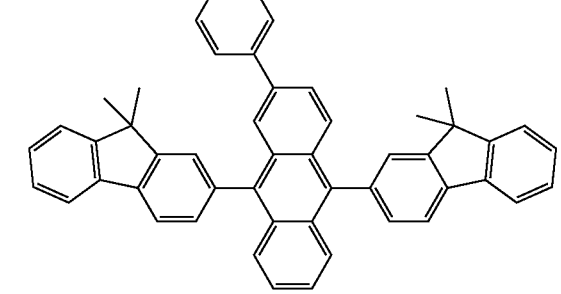

225
-continued
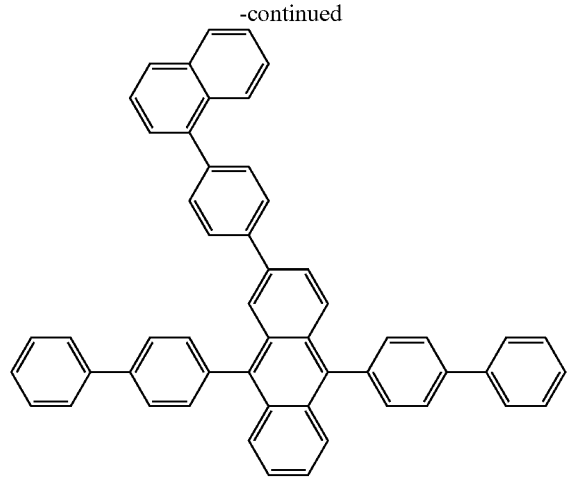
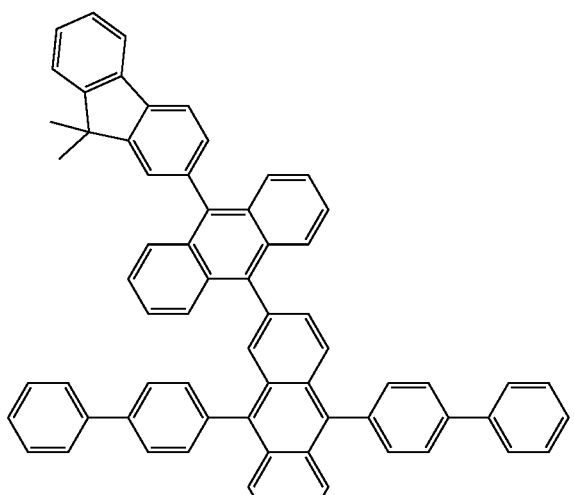
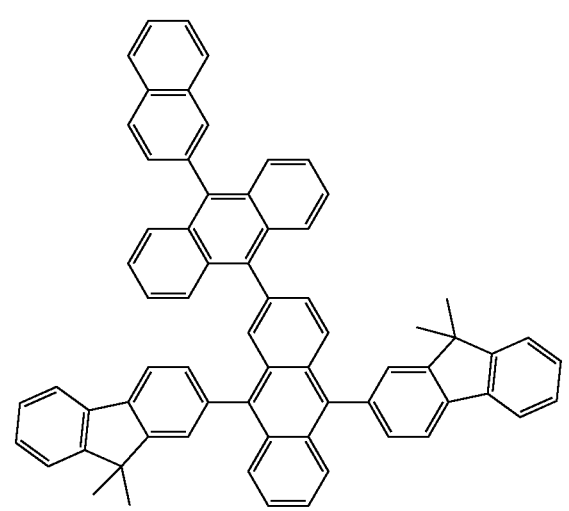
226
-continued
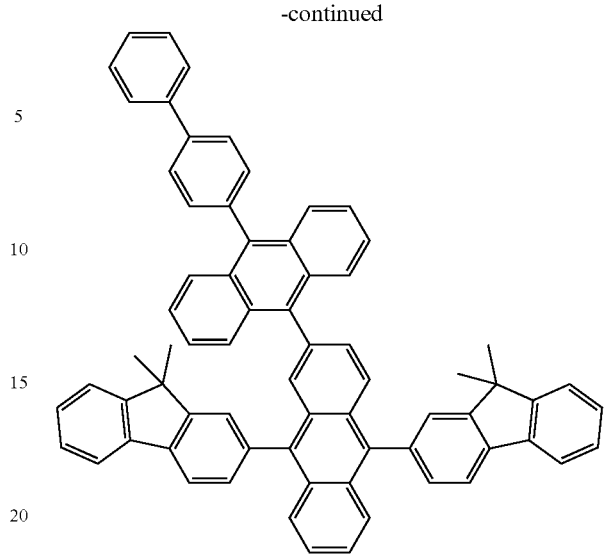
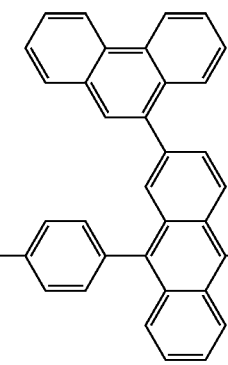

227
-continued
228
-continued
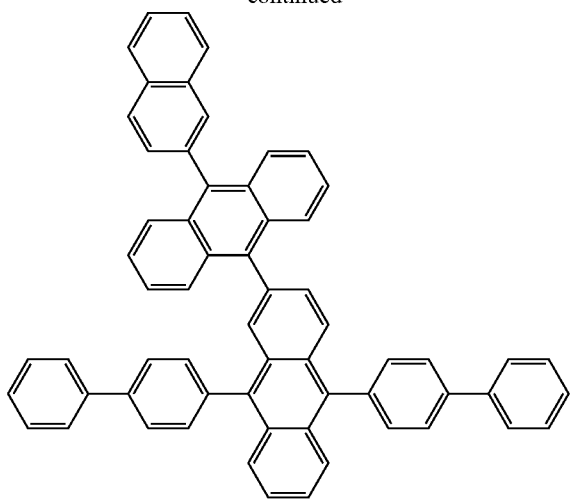
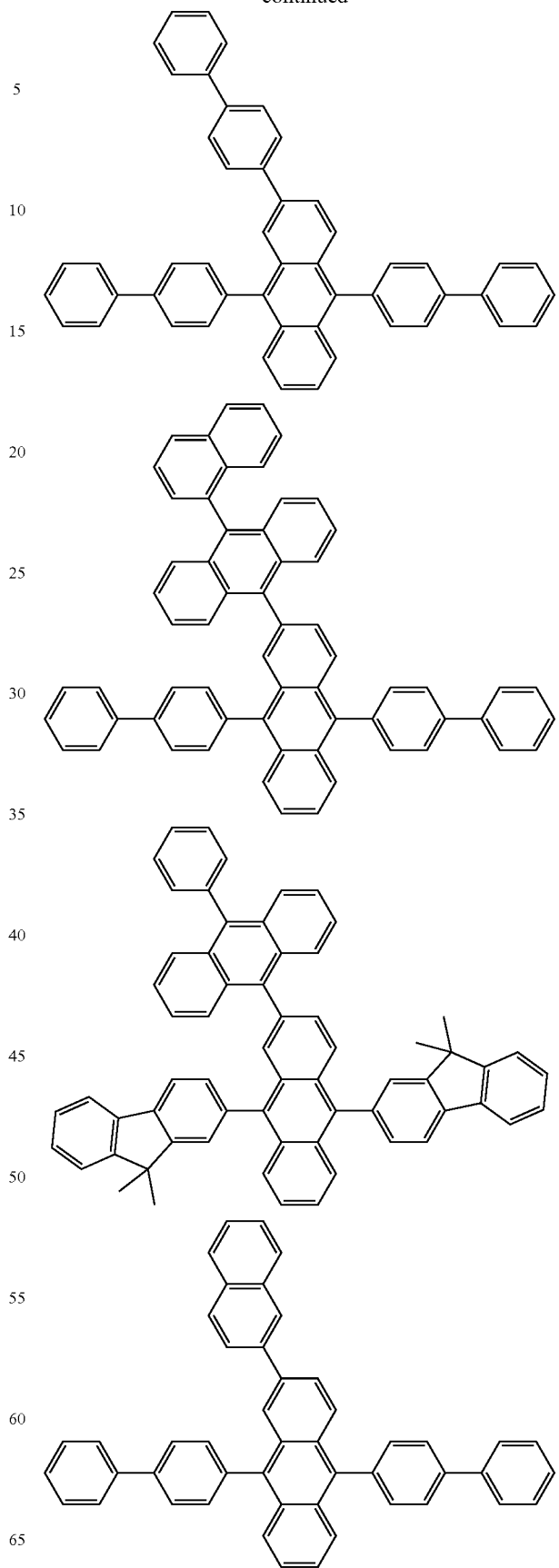

229
-continued
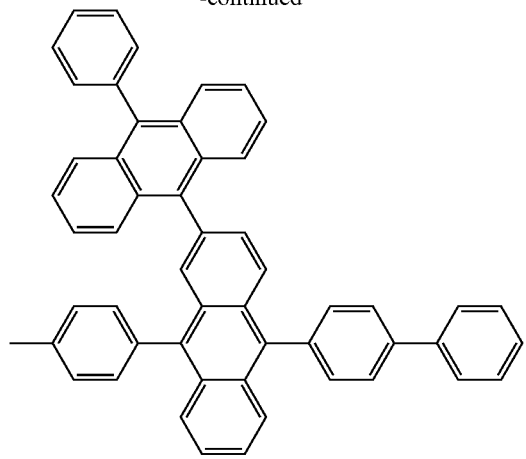
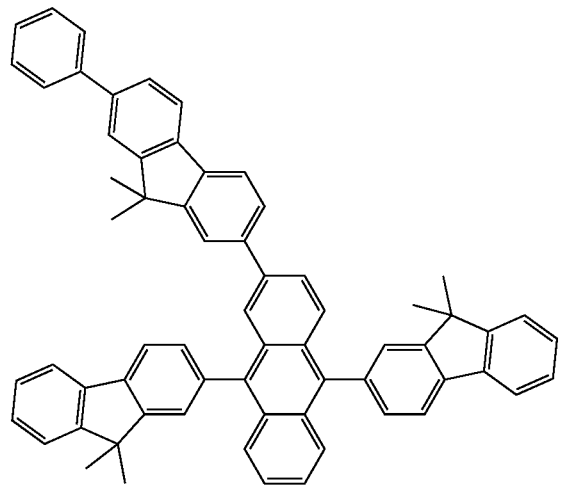
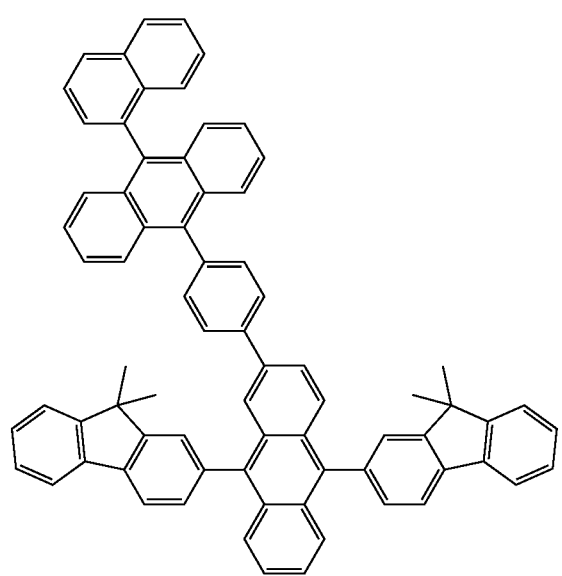
230
-continued
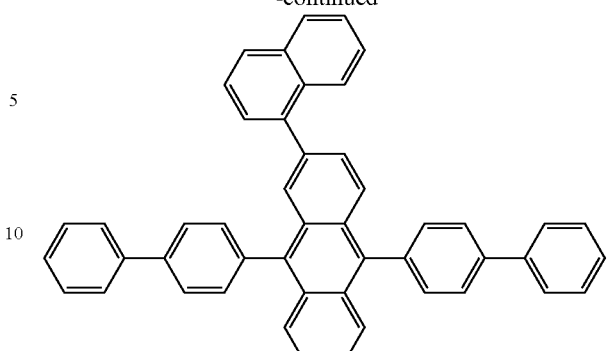
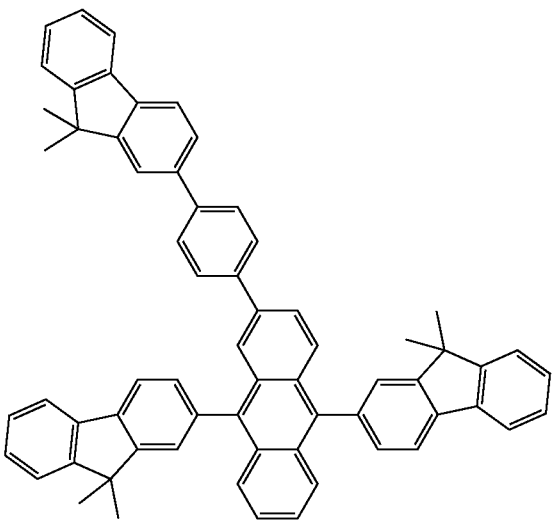

231
-continued
232
-continued
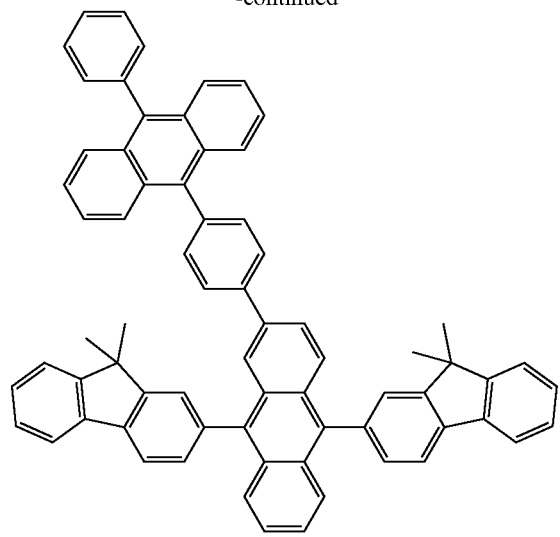
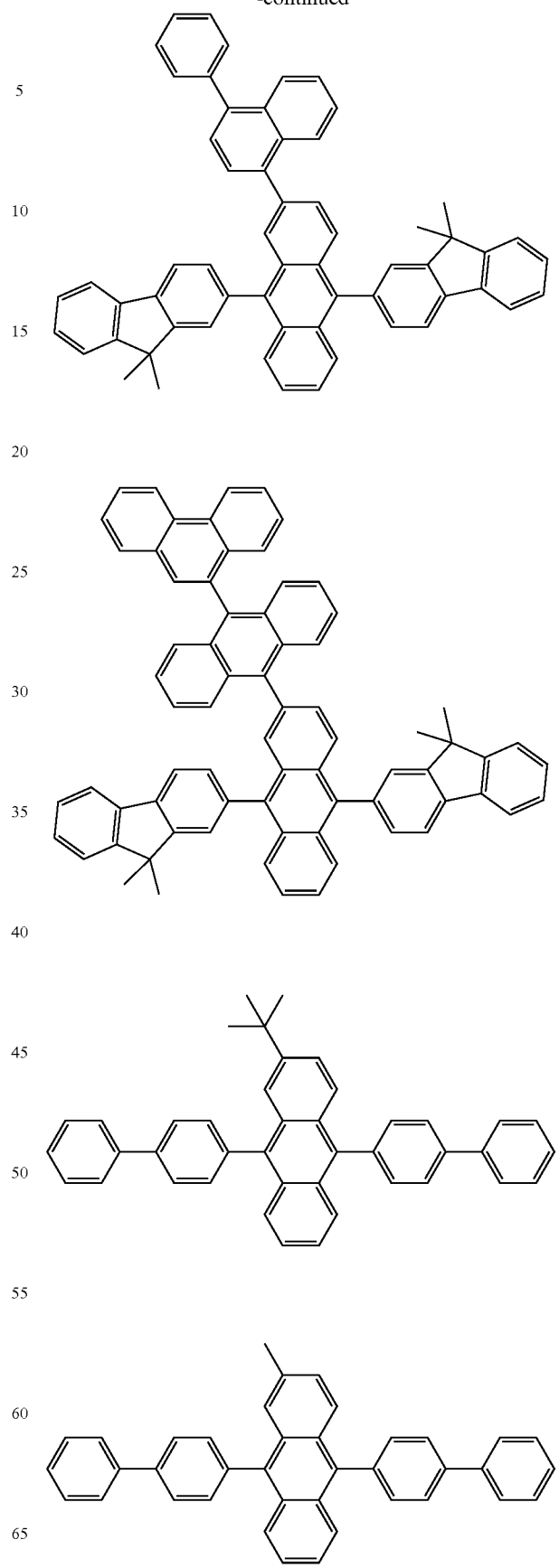

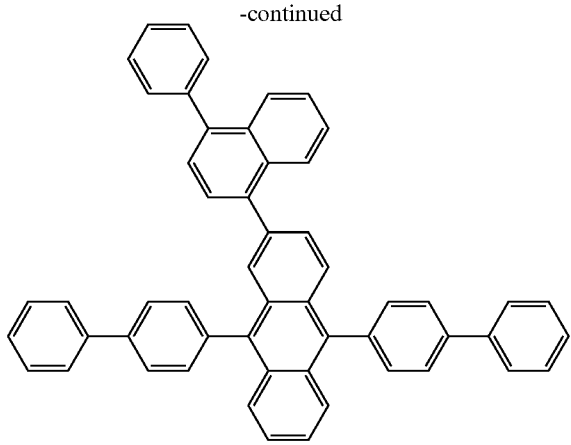
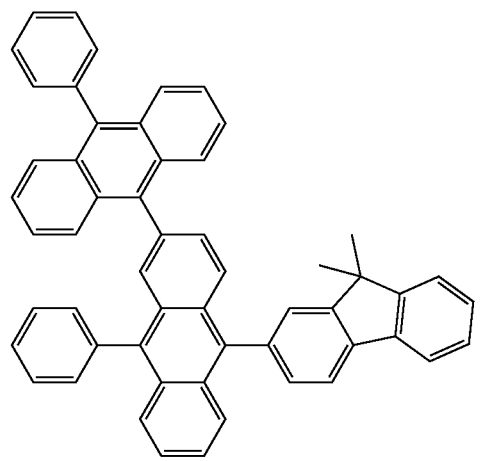
[Chem. 65]
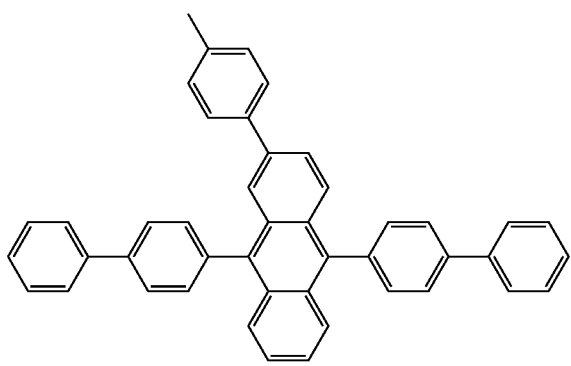
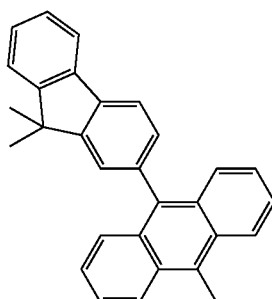
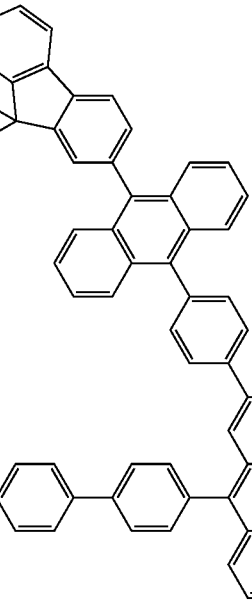
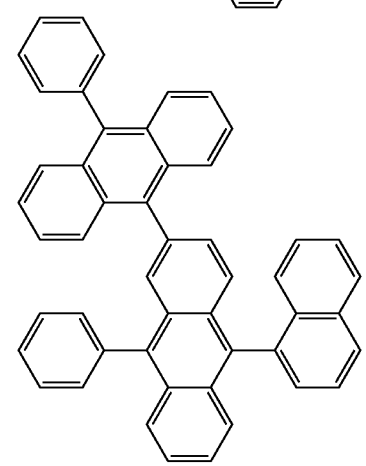
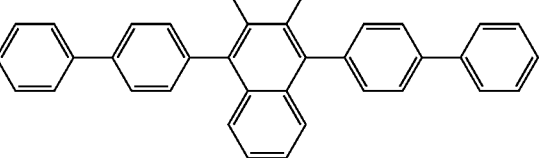
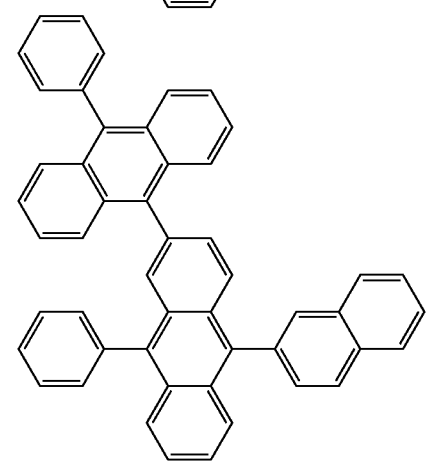
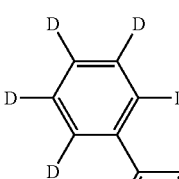
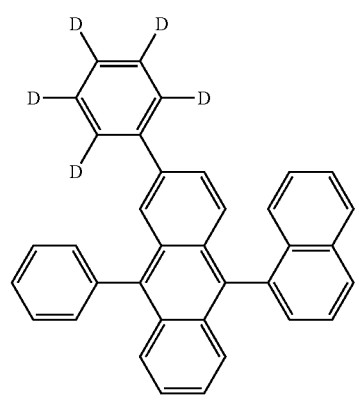

235
-continued
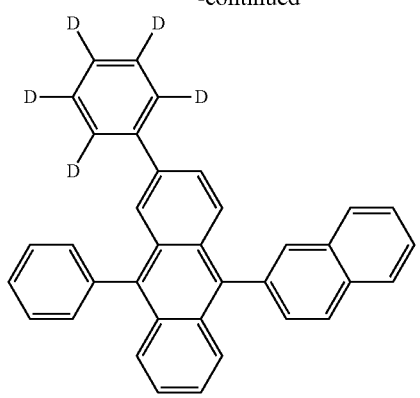
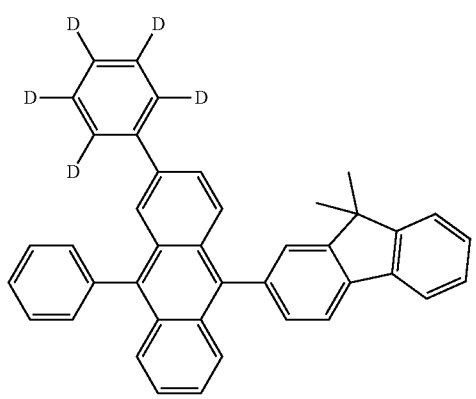
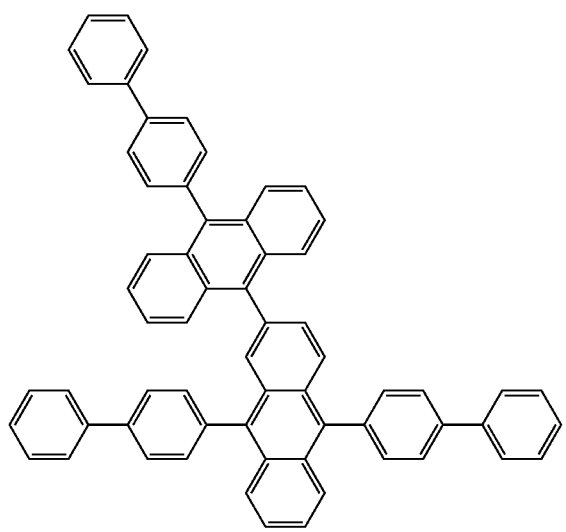
236
-continued
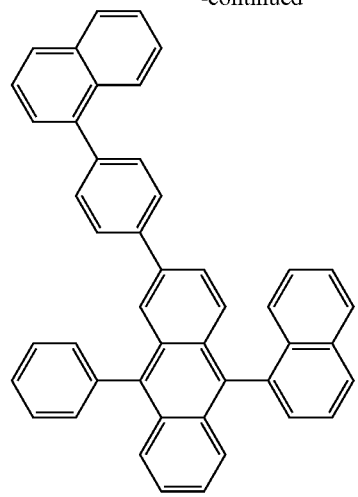
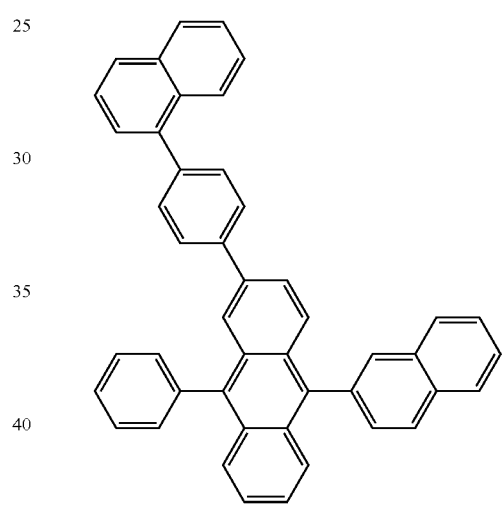
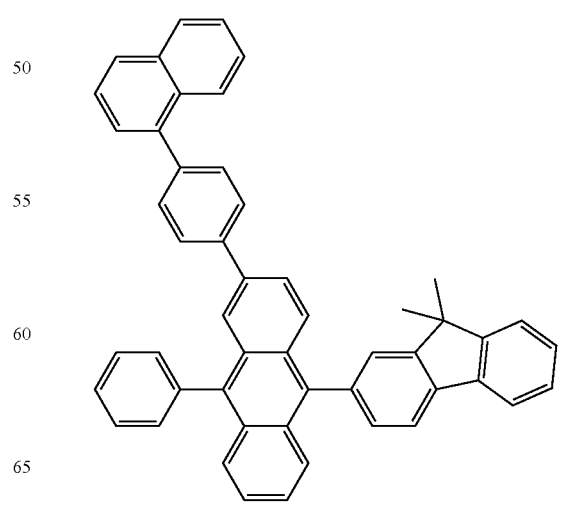

237
-continued
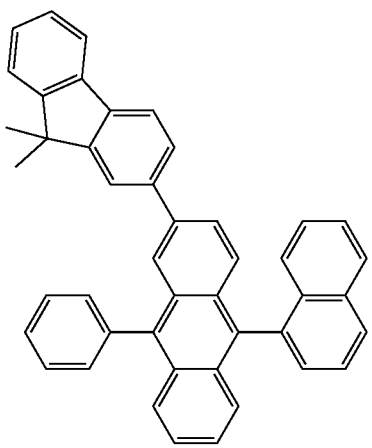
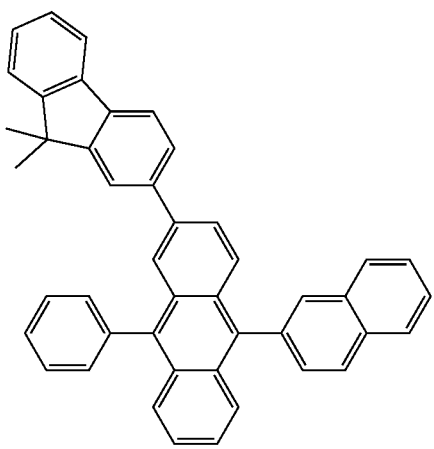
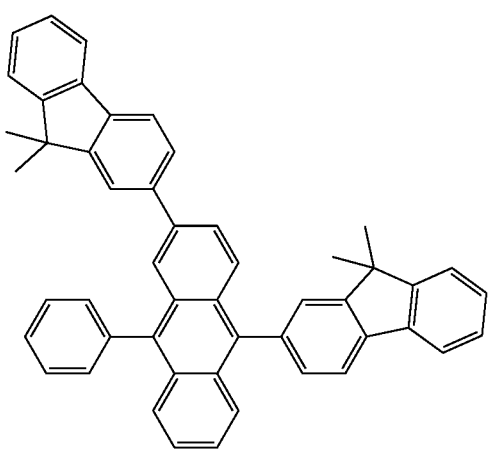
238
-continued
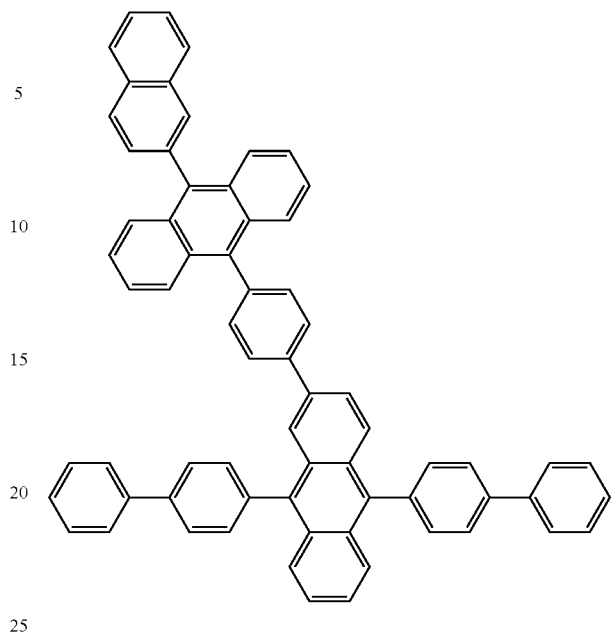
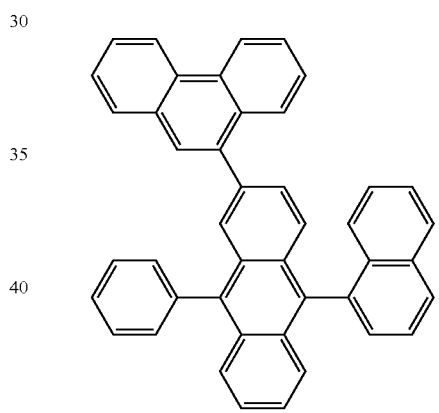
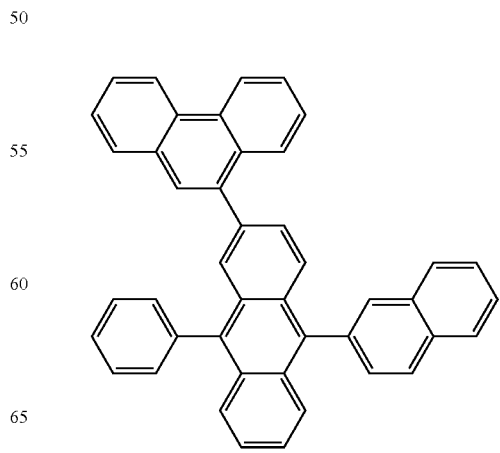

239
-continued
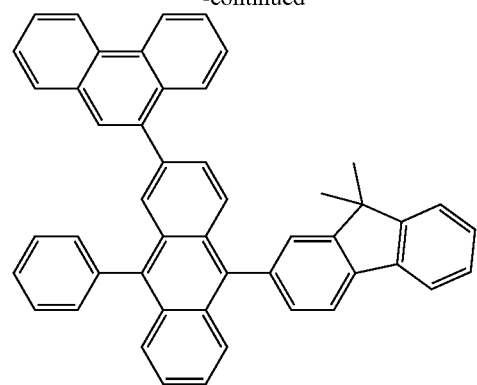
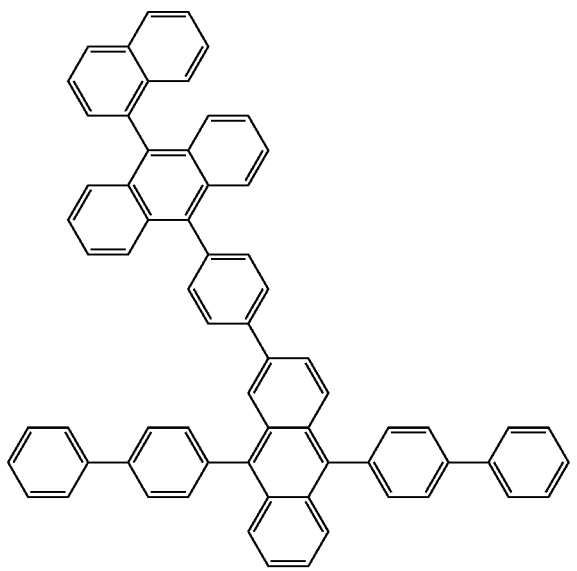
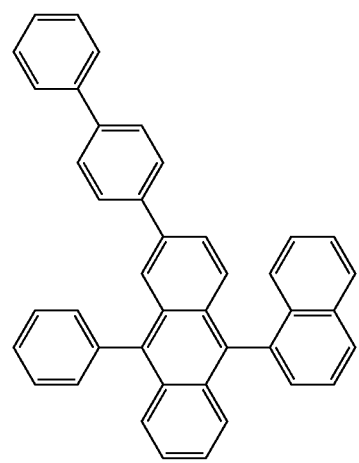
240
-continued
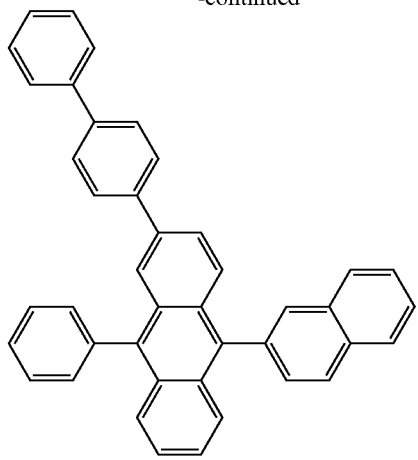
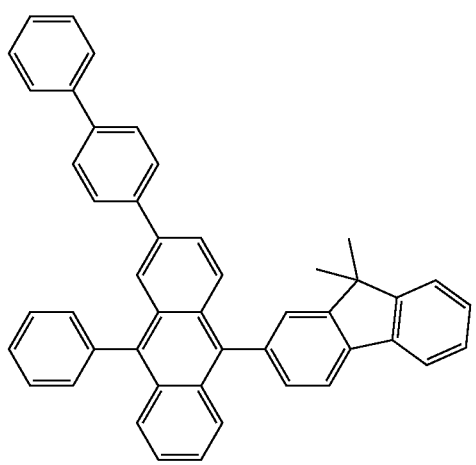
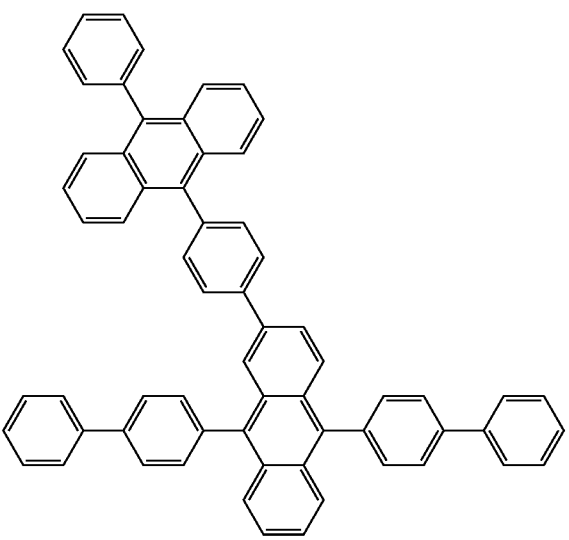

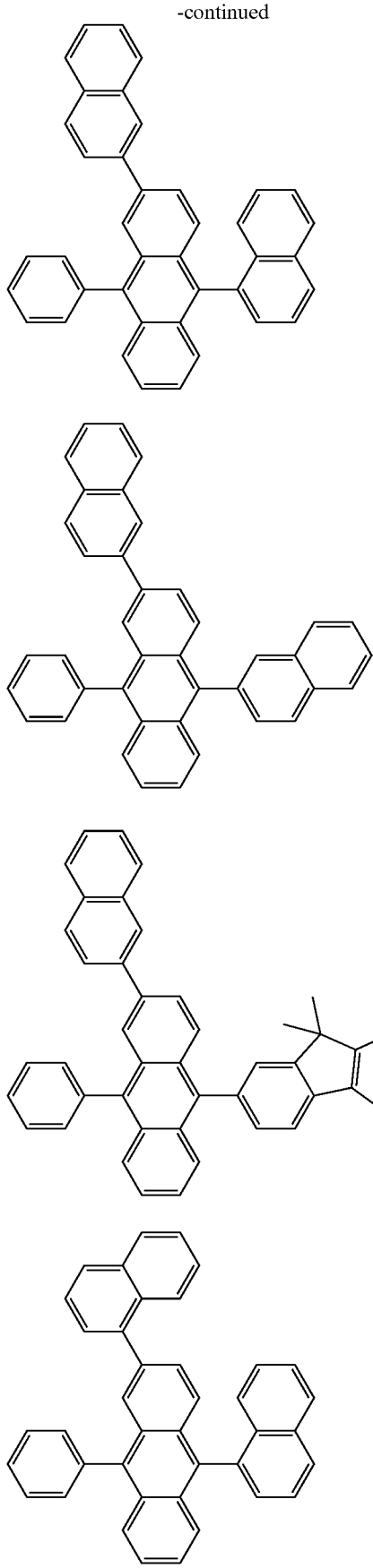
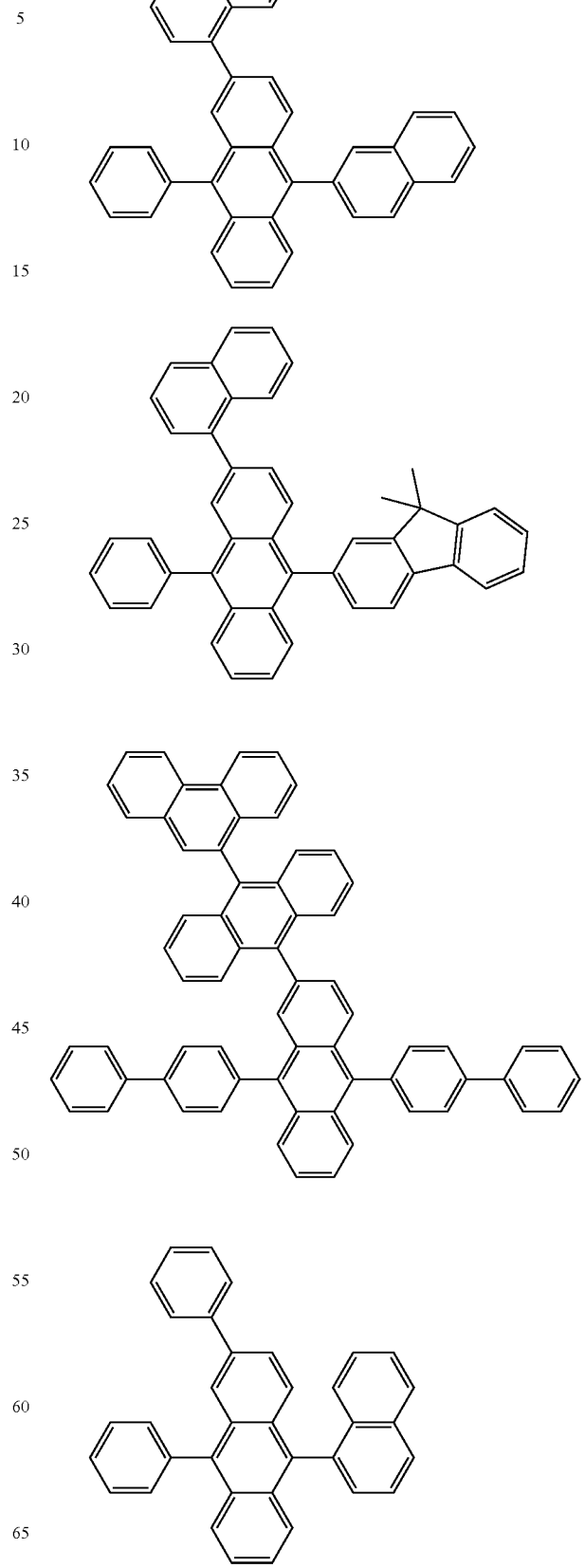

-continued
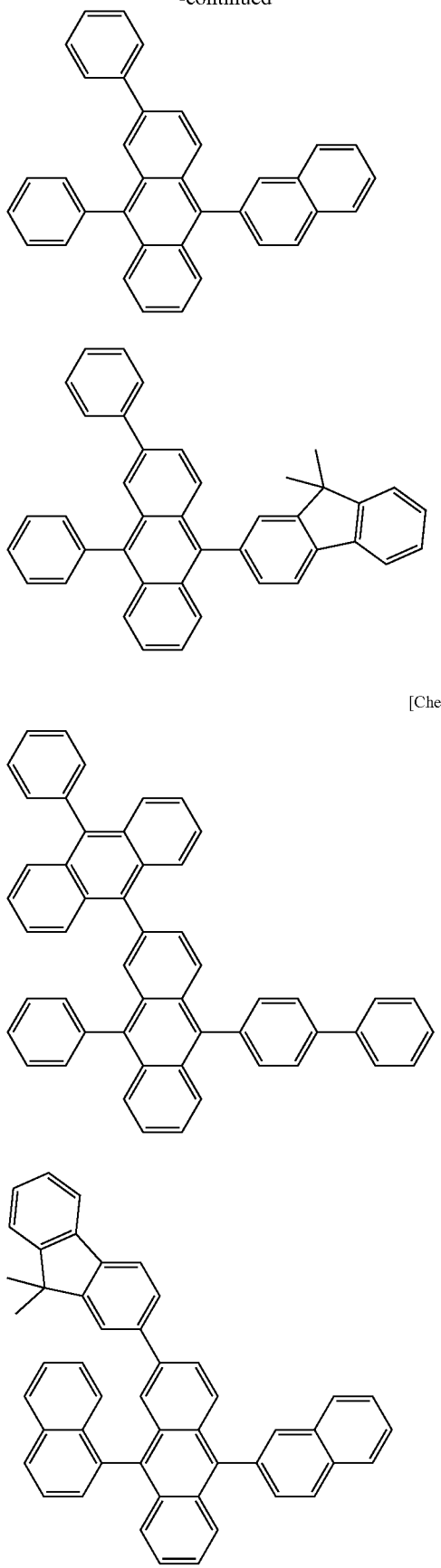
[Chem. 66]
-continued
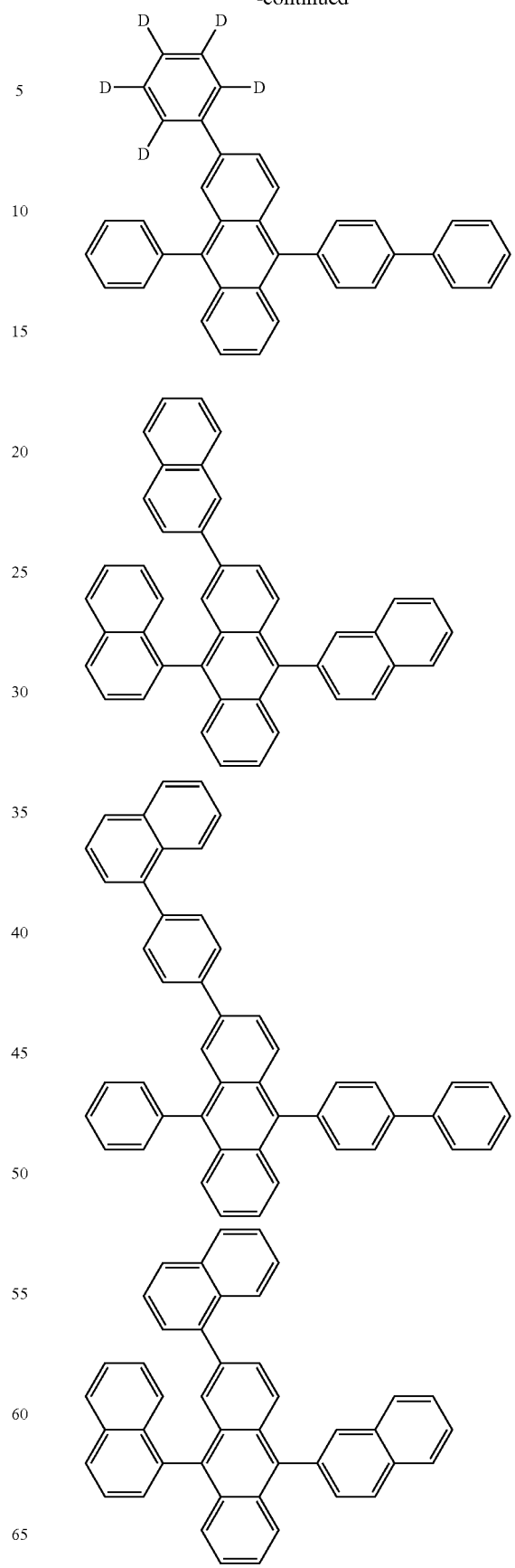

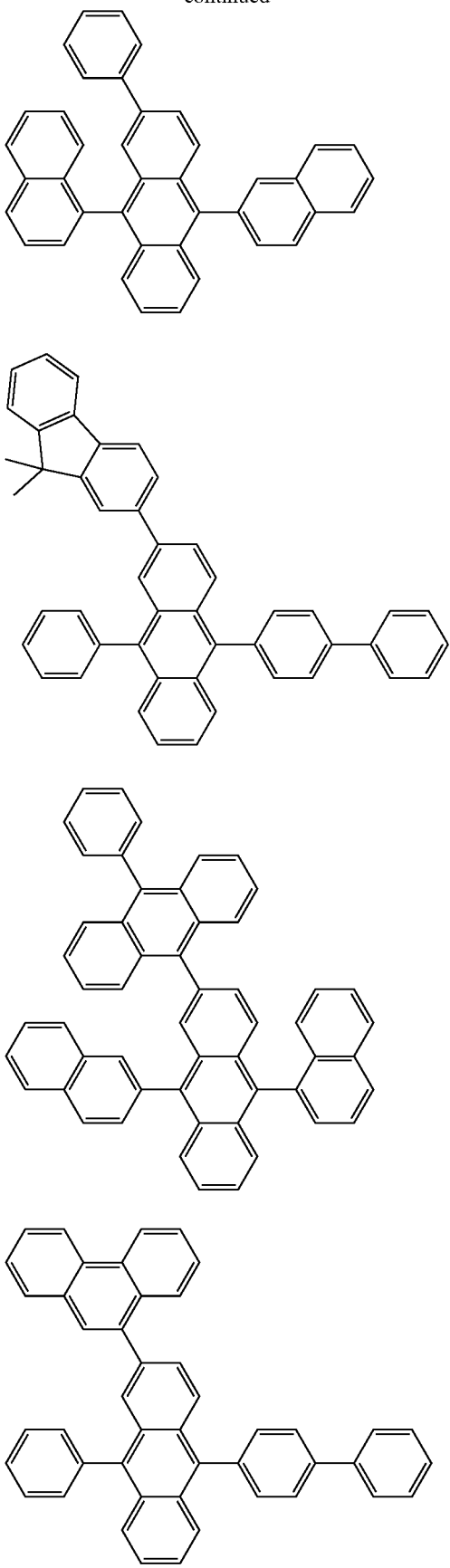
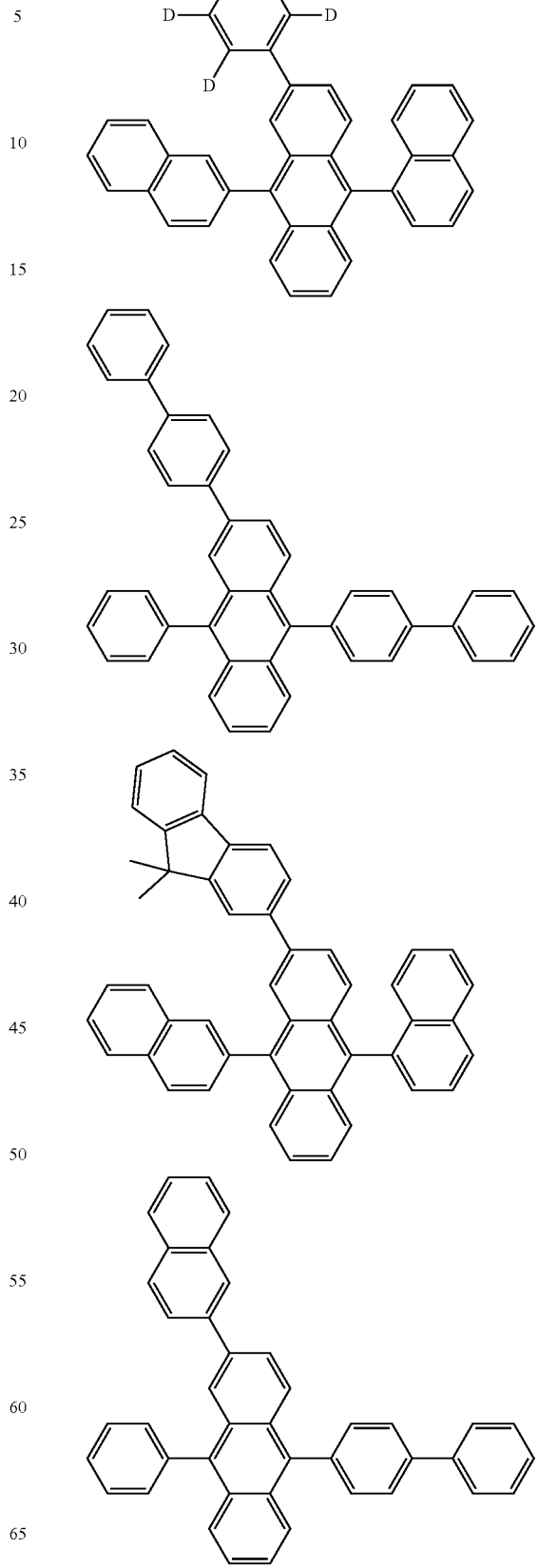

-continued
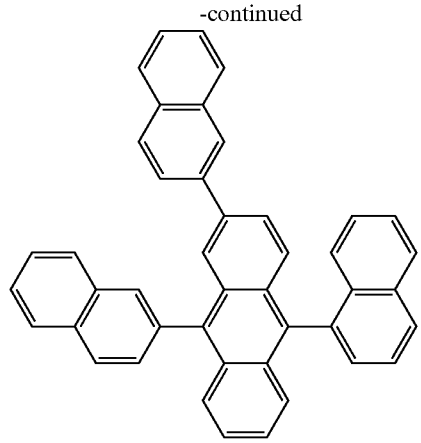
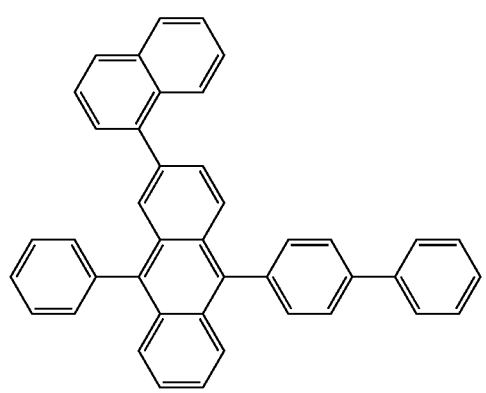
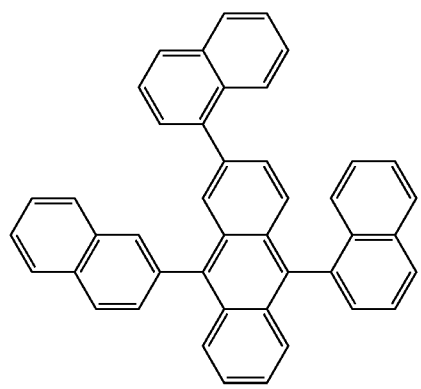
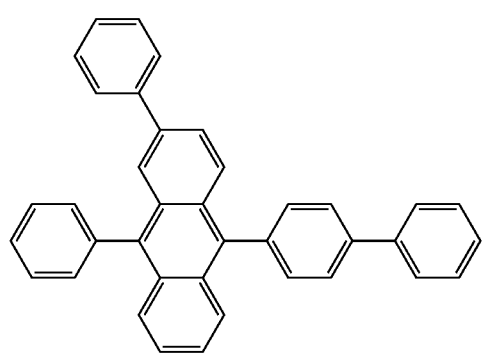
-continued
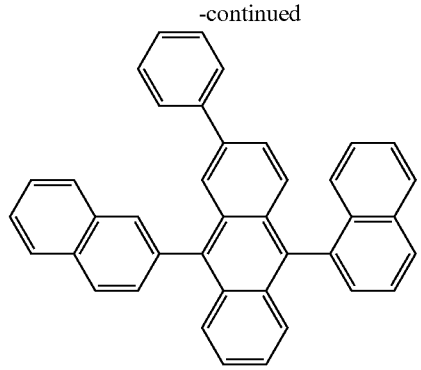
[Chem. 67]
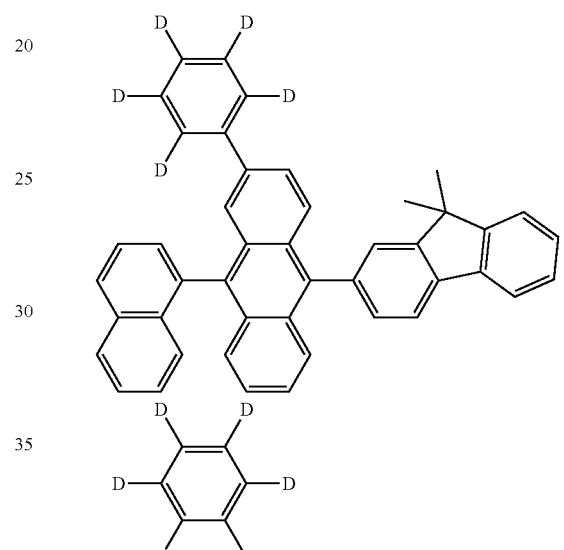
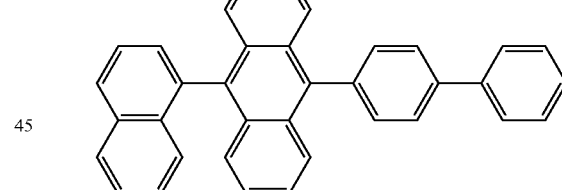
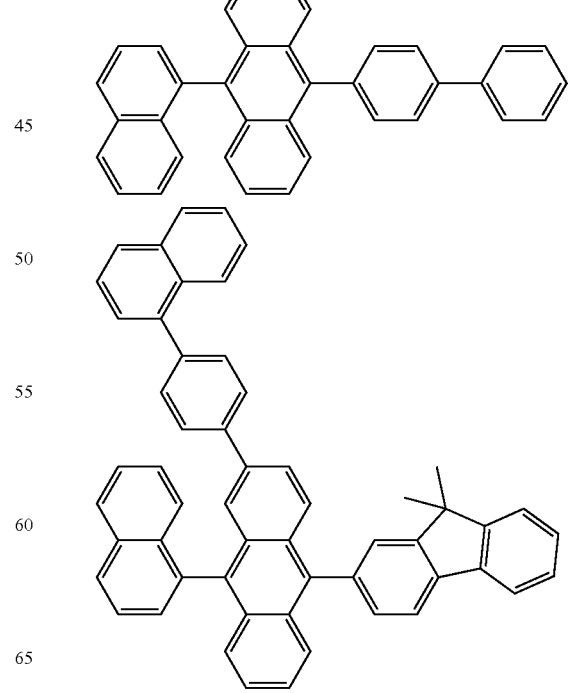

249
-continued
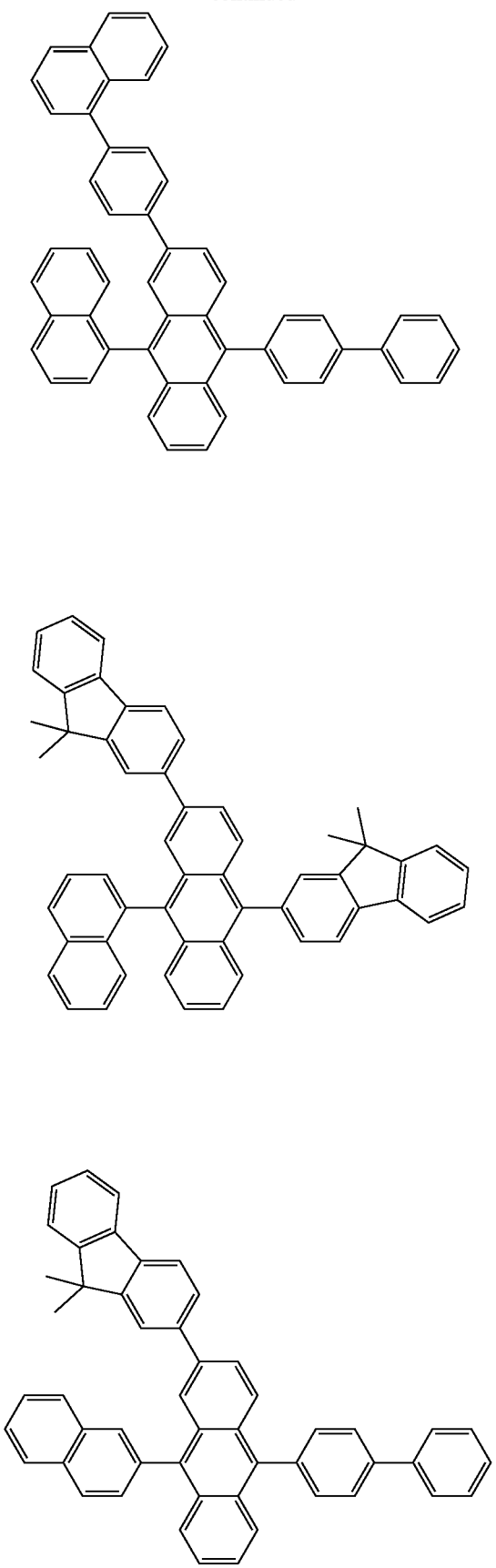
250
-continued
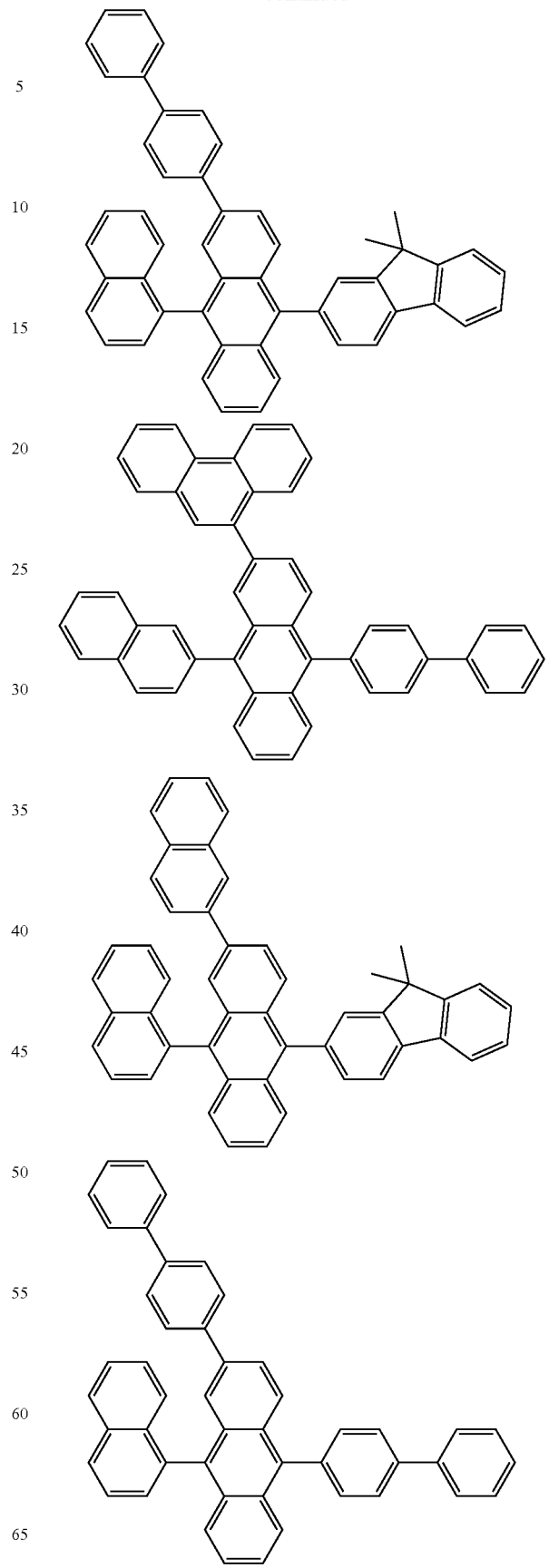

251
-continued
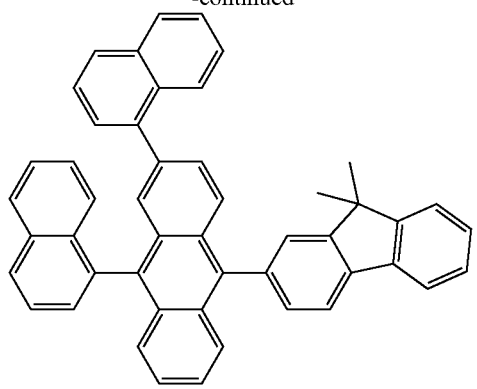
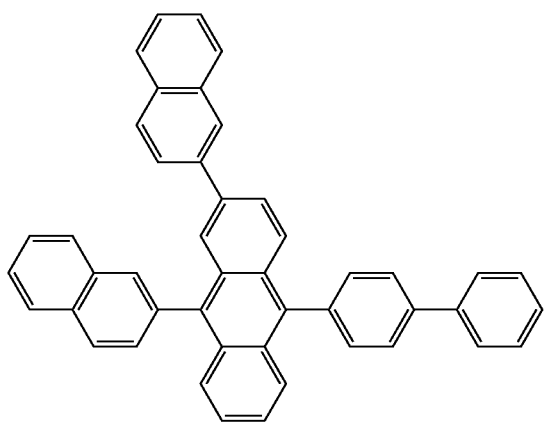
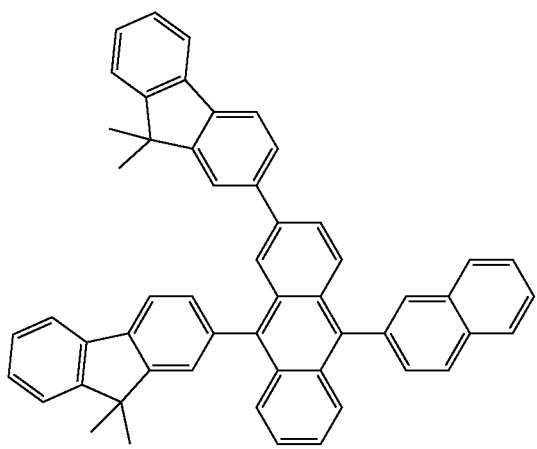
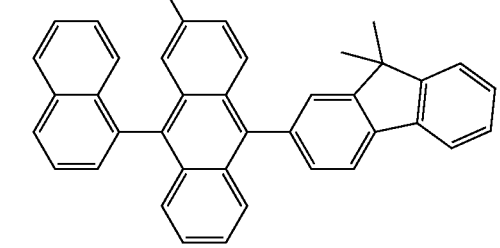
252
-continued
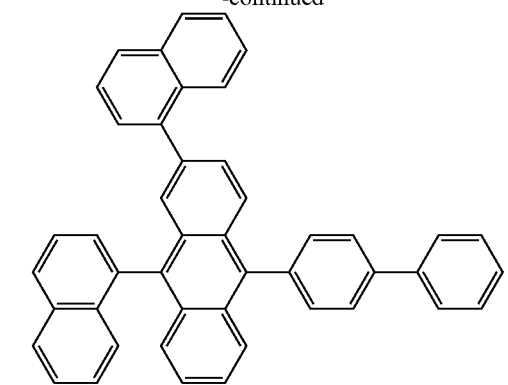
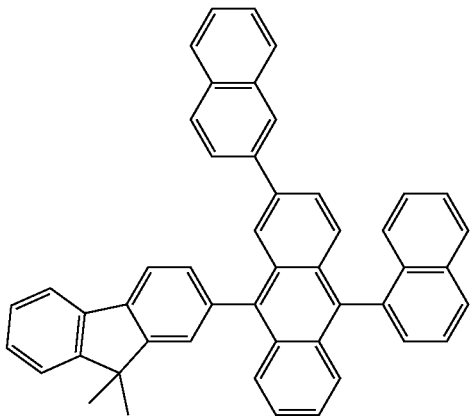
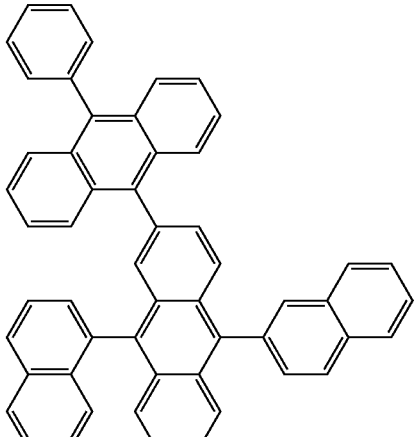
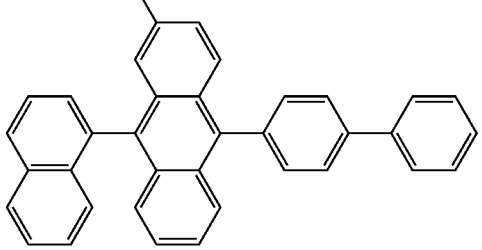

253
-continued
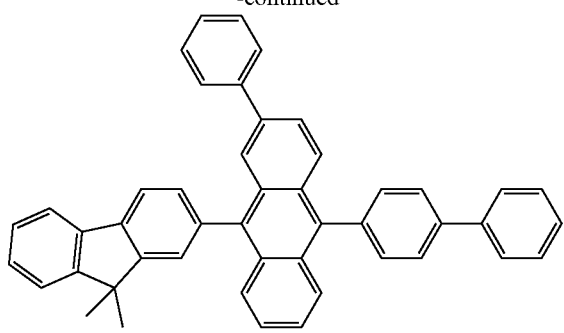
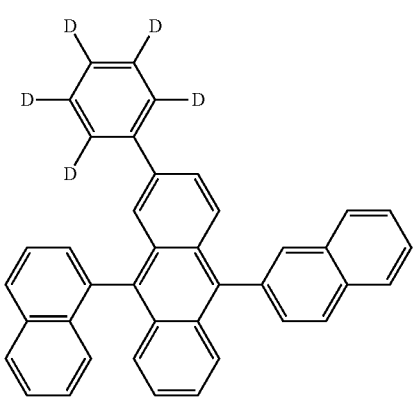
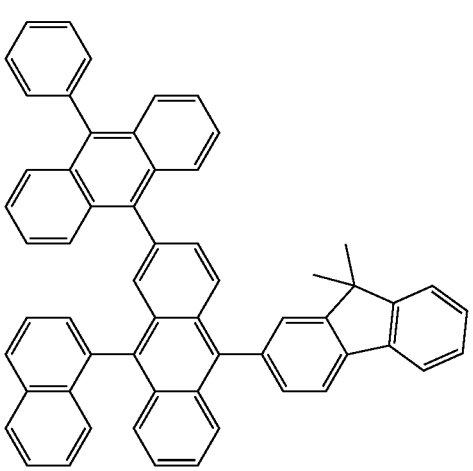
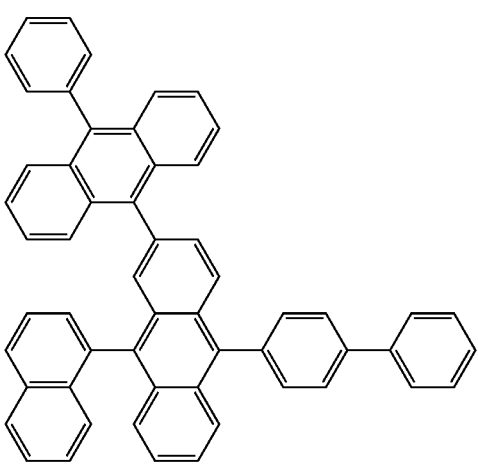
254
-continued
[Chem. 68]
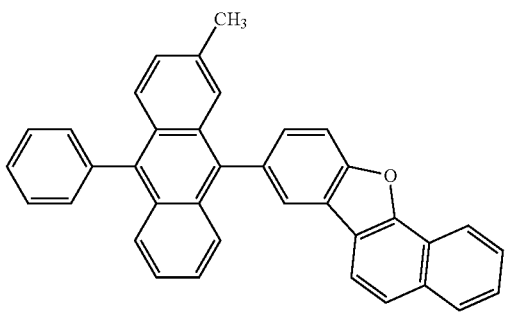
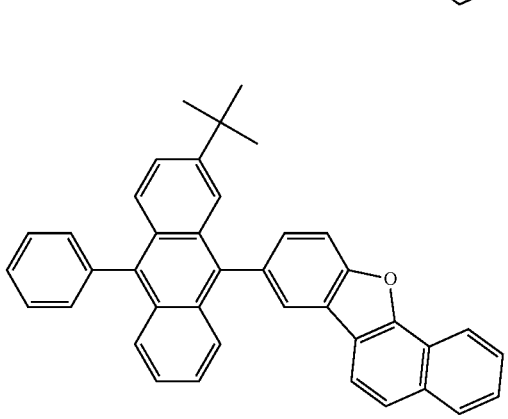
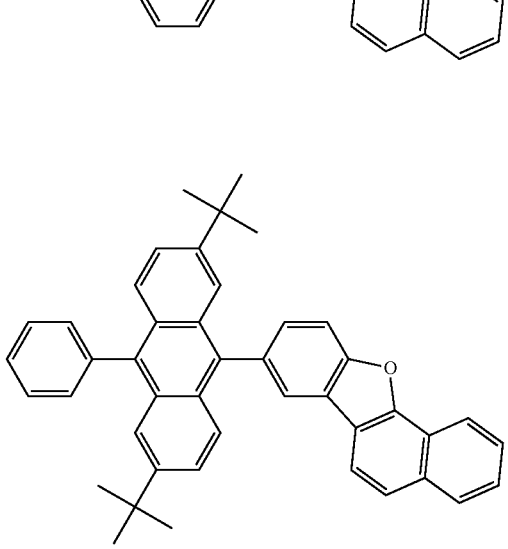
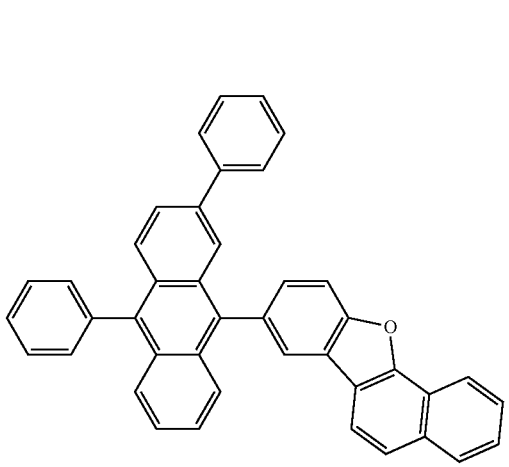

-continued
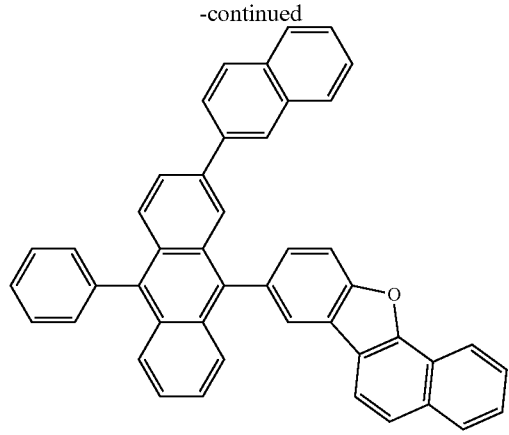
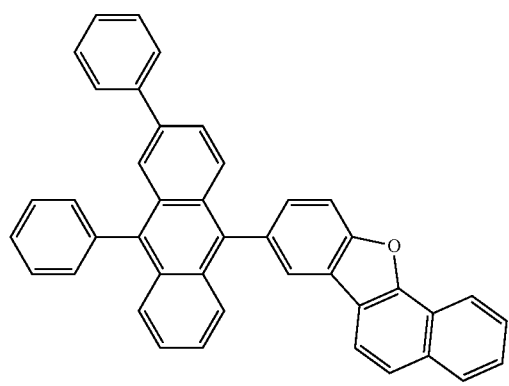
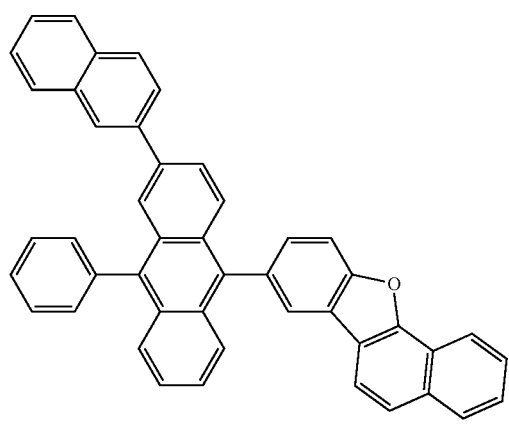
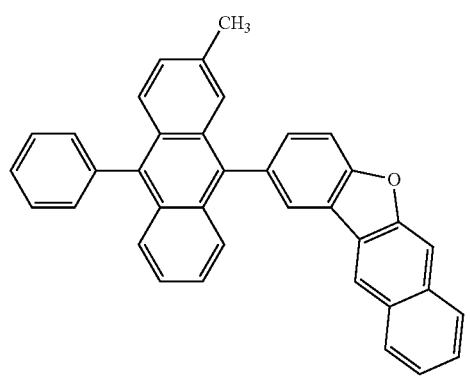
-continued
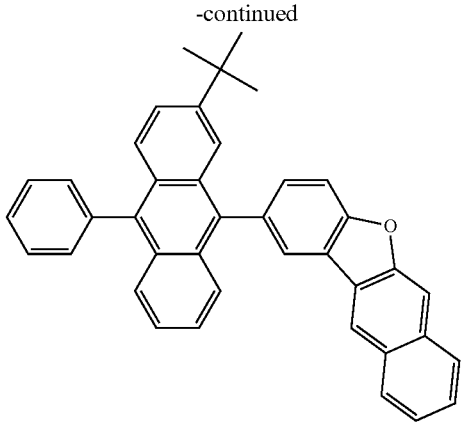
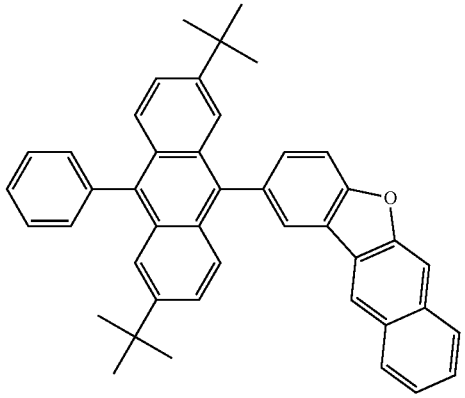
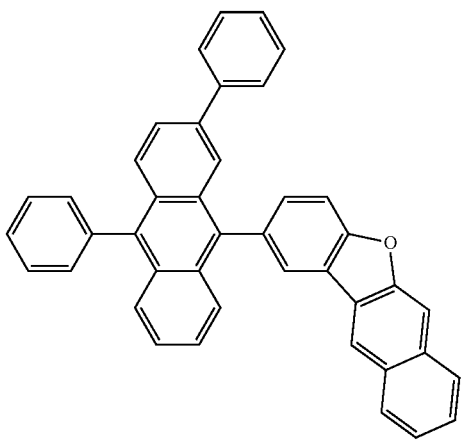
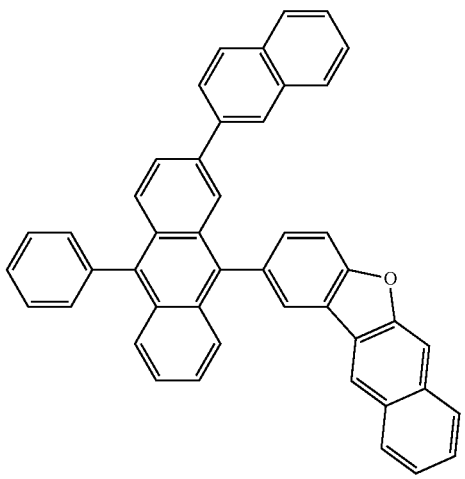

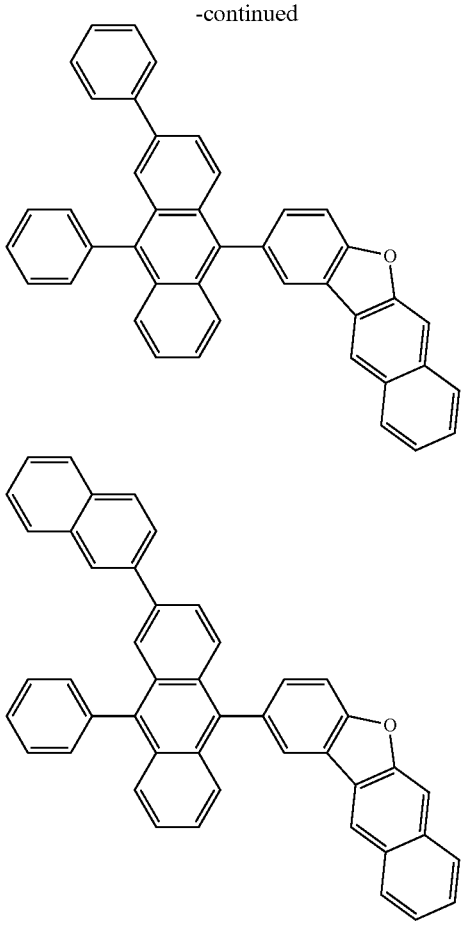

Examples of the host material other than the aforementioned anthracene derivative include a metal complex, such as an aluminum complex, a beryllium complex, and a zinc complex; a heterocyclic compound, such as indole derivative, a pyridine derivative, a pyrimidine derivative, a triazine derivative, a quinoline derivative, an isoquinoline derivative, a quinazoline derivative, a dibenzofuran derivative, a dibenzothiophene derivative, an oxadiazole derivative, a benzimidazole derivative, and a phenanthroline derivative; a condensed aromatic compound, such as a naphthalene derivative, a triphenylene derivative, a carbazole derivative, a phenanthrene derivative, a pyrene derivative, a chrysene derivative, a naphthacene derivative, and a fluoranthene derivative; and an aromatic amine compound, such as a triarylamine derivative and a condensed polycyclic aromatic amine derivative. The host material may be used as a combination of plural kinds thereof.

Specific examples of the metal complex include tris(8-quinolinolato) aluminum(III) (abbr: Alq), tris(4-methyl-8-quinolinolato) aluminum(III) (abbr: Almq3), bis(10-hydroxybenzo[h]quinolinato) beryllium(II) (abbr: BeBq2), bis (2-methyl-8-quinolinolato) (4-phenylphenolato) aluminum (III) (abbr: BAlq), bis(8-quinolinolato) zinc(II) (abbr: Znq), bis[2-(2-benzoxazolyl)phenolato] zinc(II) (abbr: ZnPBO), and bis[2-(2-benzothiazolyl)phenolato] zinc(II) (abbr: ZnBTZ).

Specific examples of the heterocyclic compound include 2-(4-biphenylyl)-5-(4-tert-butylphenyl)-1,3,4-oxadiazole (abbr: PBD), 1,3-bis[5-(p-tert-butylphenyl)-1,3,4-oxadiazol-2-yl]benzene (abbr: OXD-7), 3-(4-biphenylyl)-4-phenyl-5-(4-tert-butylphenyl)-1,2,4-triazole (abbr: TAZ), 2,2',2"-(1,3,5-benzentriyl)tris(1-phenyl-1H-benzimidazol) (abbr: TPBI), bathophenanthroline (abbr: BPhen), and bathocuproine (abbr: BCP).

Examples of the condensed aromatic compound include 9-[4-(10-phenyl-9-anthryl)phenyl]-9H-carbazole (abbr: CzPA), 3,6-diphenyl-9-[4-(10-phenyl-9-anthryl)phenyl]-9H-carbazole (abbr: DPCzPA), 9,10-bis(3,5-diphenylphenyl)anthracene (abbr: DPPA), 9,10-di(2-naphthyl)anthracene (abbr: DNA), 2-tert-butyl-9,10-di(2-naphthyl) anthracene (abbr: t-BuDNA), 9,9'-bianthryl (abbr: BANT), 9,9'-(stilben-3,3'-diypdiphenanthrene (abbr: DPNS), 9,9'-(stilben-4,4'-diypdiphenanthrene (abbr: DPNS2), 3,3',3"-(benzen-1,3,5-triyl)tripyrene (abbr: TPB3), 9,10-diphenylanthracene (abbr: DPAnth), and 6,12-dimethoxy-5,11-diphenylchrysene.

Specific examples of the aromatic amine compound include N,N-diphenyl-9-[4-(10-phenyl-9-anthryl)phenyl]-9H-carbazole-3-amine (abbr: CzA1PA), 4-(10-phenyl-9-anthryl)triphenylamine (abbr: DPhPA), N,9-diphenyl-N-[4-(10-phenyl-9-anthryl)phenyl]-9H-carbazole-3-amine (abbr: PCAPA), N,9-diphenyl-N-{4-[4-(10-phenyl-9-anthryl)phenyl]phenyl}-9H-carbazole-3-amine (abbr: PCAPBA), N-(9,10-diphenyl-2-anthryl)-N,9-diphenyl-9H-carbazole-3-amine (abbr: 2PCAPA), 4,4'-bis[N-(1-naphthyl)-N-phenylamino]biphenyl (abbr: NPB or α-NPD), N,N'-bis(3-methylphenyl)-N,N'-diphenyl-[1,1'-biphenyl]-4,4'-diamine (abbr: TPD), 4,4'-bis[N-(9,9-dimethylfluoren-2-yl)-N-phenylamino]biphenyl (abbr: DFLDPBi), and 4,4'-bis[N-(spiro-9,9'-bifluoren-2-yl)-N-phenylamino]biphenyl (abbr: BSPB).

The fluorescent host is preferably a compound having a singlet level that is higher than the fluorescent dopant, and examples thereof include a heterocyclic compound and a condensed aromatic compound. Preferred examples of the condensed aromatic compound include an anthracene derivative, a pyrene derivative, a chrysene derivative, and a naphthacene derivative.

The phosphorescent host is preferably a compound having a triplet level that is higher than the phosphorescent dopant, and examples thereof include a metal complex, a heterocyclic compound, and a condensed aromatic compound. Among these, an indole derivative, a carbazole derivative, a pyridine derivative, a pyrimidine derivative, a triazine derivative, a quinoline derivative, an isoquinoline derivative, a quinazoline derivative, a dibenzofuran derivative, a dibenzothiophene derivative, a naphthalene derivative, a triphenylene derivative, a phenanthrene derivative, and a fluoranthene derivative.

(Electron Transport Layer)

The electron transport layer is a layer containing a substance having a high electron transport capability. The substance having a high electron transport capability is preferably a substance having an electron mobility of $10^{-6}$ cm$^2$/Vs or more, and examples thereof include a metal complex, an aromatic heterocyclic compound, an aromatic hydrocarbon compound, and a high-molecular weight compound.

Examples of the metal complex include an aluminum complex, a beryllium complex, and a zinc complex. Specific examples thereof include tris(8-quinolinolato) aluminum (III) (abbr: Alq), tris(4-methyl-8-quinolinolato) aluminum (abbr: Almq3), bis(10-hydroxybenzo[h]quinolinato) beryllium (abbr: BeBq2), bis(2-methyl-8-quinolinolato) (4-phenylphenolato) aluminum(III) (abbr: BAlq), bis(8-quinolinolato) zinc(II) (abbr: Znq), bis[2-(2-benzoxazolyl)phenolato] zinc(II) (abbr: ZnPBO), and bis[2-(2-benzothiazolyl)phenolato] zinc(II) (abbr: ZnBTZ).

Examples of the aromatic heterocyclic compound include an imidazole derivative, such as a benzimidazole derivative, an imidazopyridine derivative, and a benzimidazophenanthridine derivative; an azine derivative, such as a pyrimidine derivative and a triazine derivative; and a compound containing a nitrogen-containing 6-membered ring (including a compound having a phosphine oxide substituent on a heterocyclic ring), such as a quinoline derivative, an isoquinoline derivative, and a phenanthroline derivative. Specific examples thereof include 2-(4-biphenylyl)-5-(4-tert-butylphenyl)-1,3,4-oxadiazole (abbr: PBD), 1,3-bis[5-(p-tert-butylphenyl)-1,3,4-oxadiazol-2-yl]benzene (abbr: OXD-7), 3-(4-tert-butylphenyl)-4-phenyl-5-(4-biphenylyl)-1,2,4-triazole (abbr: TAZ), 3-(4-tert-butylphenyl)-4-(4-ethylphenyl)-5-(4-biphenylyl)-1,2,4-triazole (abbr: p-EtTAZ), bathophenanthroline (abbr: BPhen), bathocuproine (abbr: BCP), and 4,4'-bis(5-methylbenzoxazol-2-yl)stilbene (abbr: BzOs).

Examples of the aromatic hydrocarbon compound include an anthracene derivative and a fluoranthene derivative.

Examples of the high-molecular weight compound include poly[(9,9-dihexylfluoren-2,7-diyl)-co-(pyridin-3,5-diyl)] (abbr: PF-Py), and poly[(9,9-dioctylfluoren-2,7-diyl)-co-(2,2'-bipyridin-6,6'-diyl)] (abbr: PF-BPy).

A substance other than the above may be used in the electron transport layer, as far as the substance has a higher electron transport capability than a hole transport capability.

The electron transport layer may be a single layer or may be two or more layers laminated. In this case, it is preferred that a substance that has a larger energy gap among the substances having a high electron transport capability is disposed on the side near the light emitting layer.

For example, as shown in FIG. 2, the structure may include the first electron transport layer 7a on the side of the anode and the second electron transport layer 7b on the side of the cathode.

The electron transport layer may contain, for example, a metal, such as an alkali metal, magnesium, an alkaline earth metal, and an alloy containing two or more metals among these; and a metal compound, such as an alkali metal compound, e.g., 8-quinolinolatolithium (abbr: Liq), and an alkaline earth metal compound. In the case where the electron transport layer contains a metal, such as an alkali metal, magnesium, an alkaline earth metal, and an alloy containing two or more metals among these, the content thereof is not particularly limited, and is preferably 0.1 to 50% by mass, more preferably 0.1 to 20% by mass, and further preferably 1 to 10% by mass.

In the case where the electron transport layer contains a metal compound, such as an alkali metal compound and an alkaline earth metal compound, the content thereof is preferably 1 to 99% by mass, and more preferably 10 to 90% by mass. In the case where the electron transport layer includes plural layers, the layer on the side of the light emitting layer may be formed only with the metal compound.

(Electron Injection Layer)

The electron injection layer is a layer containing a substance having a high electron injection capability, and has a function injecting electrons from the cathode to the light emitting layer efficiently. Examples of the substance having a high electron injection capability include an alkali metal, magnesium, an alkaline earth metal, and a compound thereof. Specific examples thereof include lithium, cesium, calcium, lithium fluoride, cesium fluoride, calcium fluoride, and lithium oxide. In addition, a substance having an electron transport capability, to which an alkali metal, magnesium, an alkaline earth metal, or a compound thereof is added, such as Alq having magnesium added thereto, may also be used.

In the electron injection layer, a composite material containing an organic compound and a donative compound may be used. The composite material is excellent in electron injection capability and electron transport capability since the organic compound receives electrons from the donative compound.

The organic compound is preferably a substance excellent in transport capability of the received electrons, and examples thereof used include a metal complex and an aromatic heterocyclic compound that are the aforementioned substances having a high electron transport capability.

It suffices that the donative compound is a substance capable of donating electrons to the organic compound, and examples thereof include an alkali metal, magnesium, an alkaline earth metal, and a rare earth metal. Specific examples thereof include lithium, cesium, magnesium, calcium, erbium, and ytterbium. An alkali metal oxide and an alkaline earth metal oxide are preferred, and specific examples thereof include lithium oxide, calcium oxide, and barium oxide. A Lewis base, such as magnesium oxide, may also be used. An organic compound, such as tetrathiafulvalene (abbr: TTF), may also be used.

(Cathode)

The cathode used is preferably, for example, a metal, an alloy, a conductive compound, or a mixture thereof, having a small work function (which may be specifically 3.8 eV or less). Examples of the material of the cathode include an alkali metal, such as lithium and cesium; magnesium; an alkaline earth metal, such as calcium and strontium; an alloy containing these metals (such as magnesium-silver and aluminum-lithium); a rare earth metal, such as europium and ytterbium; and an alloy containing a rare earth metal.

The cathode is generally formed by a vacuum vapor deposition method or a sputtering method. In the case where a silver paste or the like is used, a coating method and an ink-jet method may be used.

In the case where the electron injection layer is provided, the cathode may be formed with various conductive materials, such as aluminum, silver, ITO, graphene, and indium-tin oxide containing silicon or silicon oxide, irrespective of the work function thereof. The conductive materials can be formed into a film by a sputtering method, an ink-jet method, a spin coating method, or the like.

(Insulating Layer)

The organic EL device tends to suffer pixel defects due to leakage and short circuit since an electric field is applied to the thin film. For preventing the same, a thin film insulating layer may be inserted between the pair of electrodes.

Specific examples of the substance used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture of the substances may be used in insulating layer, and a laminate of plural layers containing these substance may also be used.

(Space Layer)

In the case where, for example, the fluorescent light emitting layer and the phosphorescent light emitting layer are laminated, a space layer may be provided between the layers for the prevention of diffusion of excitons formed in the phosphorescent light emitting layer to the phosphorescent light emitting layer and the control of the carrier balance. The space layer may also be provided between plural phosphorescent light emitting layers.

The space layer is provided between plural light emitting layers, and therefor is preferably formed with a substance that has both an electron transport capability and a hole transport capability. The space layer preferably has a triplet energy of 2.6 eV or more from the standpoint of the prevention of diffusion of the triplet energy in the adjacent phosphorescent light emitting layers.

Examples of the substance used in the space layer include the similar substances as the aforementioned substances used in the hole transport layer.

(Electron Block Layer, Hole Block Layer, and Exciton Block Layer)

An electron block layer, a hole block layer, and an exciton (triplet) block layer may be provided adjacent to the light emitting layer.

The electron block layer is a layer having a function blocking electrons from leaking from the light emitting layer to the hole transport layer. The hole block layer is a layer having a function blocking holes from leaking from the light emitting layer to the electron transport layer. The exciton block layer is a layer having a function blocking excitons formed in the light emitting layer from diffusing to the adjacent layer, so as to confine the excitons in the light emitting layer.

(Method for Forming Layers)

The method for forming the layers of the organic EL device is not particularly limited unless otherwise described. The forming method may be a known method, such as a dry film forming method and a wet film forming method. Specific examples of the dry film forming method include a vacuum vapor deposition method, a sputtering method, a plasma method, and an ion-plating method. Specific examples of the wet film forming method include a spin coating method, a dipping method, a flow coating method, and an ink-jet method.

(Film Thickness)

The film thicknesses of the layers of the organic EL device are not particularly limited unless otherwise described. With a too small film thickness, a defect, such as a pinhole, tends to occur to fail to provide a sufficient light emission luminance. With a too large film thickness, on the other hand, a high driving voltage is required to deteriorate the efficiency. In this standpoint, the film thickness is generally preferably 5 nm to 10 μm, and more preferably 10 nm to 0.2 μm.

[Electronic Device]

The electronic device according to one embodiment of the present invention includes the organic EL device according to one embodiment of the present invention described above. Specific examples of the electronic device include a display component of an organic EL display panel module; a display device of a television set, a mobile phone, a personal computer, and the like; and a light emitting device of an illumination equipment and an automobile lighting equipment.

EXAMPLES

One embodiment of the present invention will be described in more detail with reference to examples below, but the present invention is not limited thereto.

A synthesis example of the compound (1) according to one embodiment of the present invention will be shown below.

(Synthesis Example 1) Synthesis of Compound 2

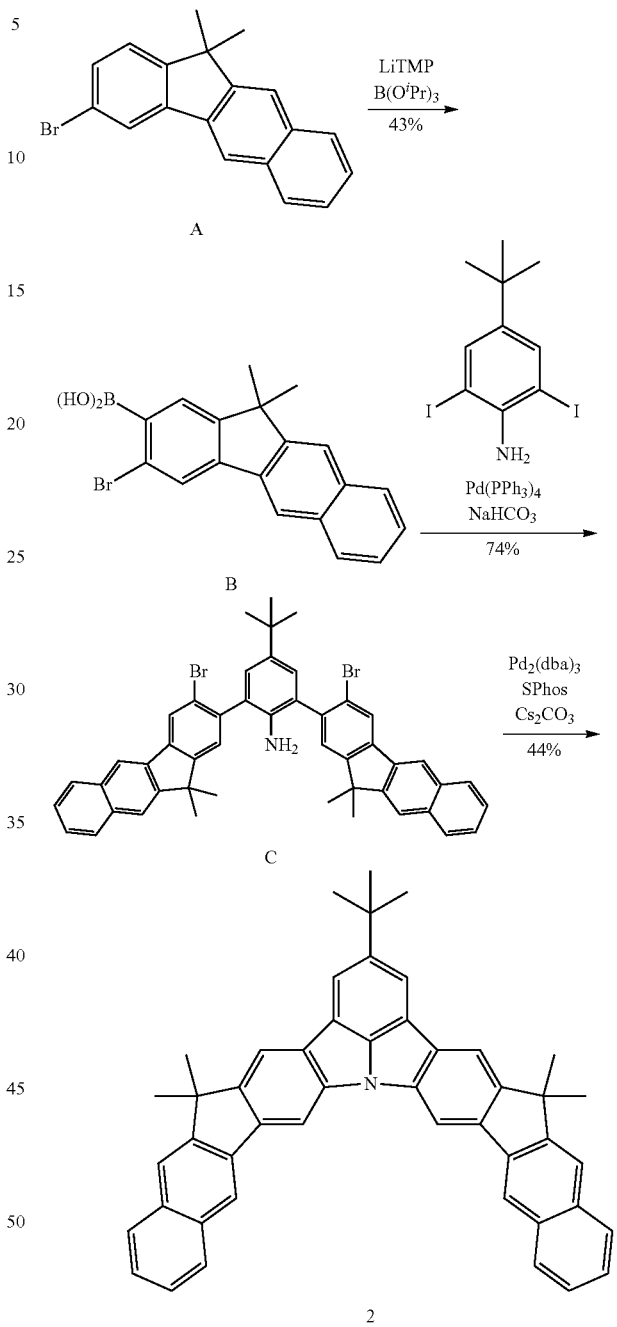

(1-1) Synthesis of Intermediate B

Under an argon atmosphere, 7.00 g (49.6 mmol) of 2,2,6,6-tetramethylpiperidine (TMP) was dissolved in 70 mL of anhydrous tetrahydrofuran (THF), and cooled to −48° C. with a dry ice/acetone bath. 32 mL (1.55 mol/L, 49.6 mmol) of a hexane solution of n-butyl lithium (n-BuLi) was added thereto, and after agitating at −40° C. for 20 minutes, cooled to −70° C. 17 mL (73.7 mmol) of triisopropoxyborane (B(O$^i$Pr)$_3$) was added dropwise thereto, and after the lapse of 5 minutes, 50 mL of a THF solution having 8.00 g

263

(24.8 mmol) of the compound A dissolved therein was added thereto, followed by agitating in a cooling bath for 10 hours. 150 mL of hydrochloric acid having a concentration of 10% by mass was added to the reaction mixture, and after agitating at room temperature for 30 minutes, the mixture was extracted with 200 mL of ethyl acetate. The organic layer was washed with 30 mL of a saturated sodium chloride aqueous solution, and dried over magnesium sulfate, and then the solvent was distilled off, followed by drying under reduced pressure, so as to provide 7.02 g of a yellow solid matter. The solid matter was purified by column chromatography to provide 3.87 g of a white solid matter (yield: 43%). The resulting solid matter was the intermediate B as the target product, and the mass spectrum analysis thereof revealed m/e=367 for the molecular weight of 367.04.

(1-2) Synthesis of Intermediate C

Under an argon atmosphere, 3.87 g (10.5 mmol) of the intermediate C, 1.92 g (4.79 mmol) of 4-tert-butyl-2,6-diiodoaniline, 0.55 g (0.48 mmol) of tetrakis(triphenylphosphine) palladium(0) (Pd(PPh$_3$)$_4$), and 3.2 g (38 mmol) of sodium hydrogen carbonate (NaHCO$_3$) were added to 60 mL of 1,2-dimethoxyethane to provide a suspension liquid, to which 30 mL of water was added, and the suspension liquid was refluxed for 11 hours. The reaction mixture was extracted with 250 mL of dichloromethane, and the organic layer was concentrated to provide a brown oily matter. The oily matter was purified by column chromatography to provide 2.80 g of a white solid matter (yield: 74%). The resulting solid matter was the intermediate C as the target product, and the mass spectrum analysis thereof revealed m/e=791 for the molecular weight of 791.65.

(1-3) (Synthesis of Compound 2)

Under an argon atmosphere, 2.80 g (3.54 mmol) of the intermediate C, 0.13 g (0.14 mmol) of tris(dibenzylideneacetone) dipalladium(0) (Pd$_2$(dba)$_3$), 0.23 g (0.56 mmol) of 2-dicyclohexylphosphino-2',6'-dimethoxybiphenyl (SPhos), and 6.9 g (21 mmol) of cesium carbonate (Cs$_2$CO$_3$) were added to 280 mL of anhydrous xylene to provide a suspension liquid, which was refluxed for 10 hours. The reaction mixture was purified by column chromatography to provide 0.99 g of a white solid matter (yield: 44%). The resulting solid matter was the compound 2 as the target product, and the mass spectrum analysis thereof revealed m/e=629 for the molecular weight of 629.83.

(Synthesis Example 2) Synthesis of Compound 3

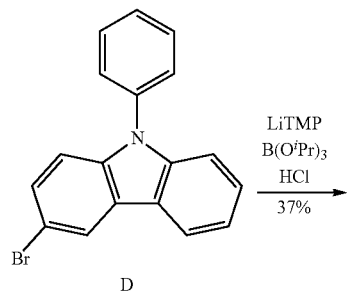

264

-continued

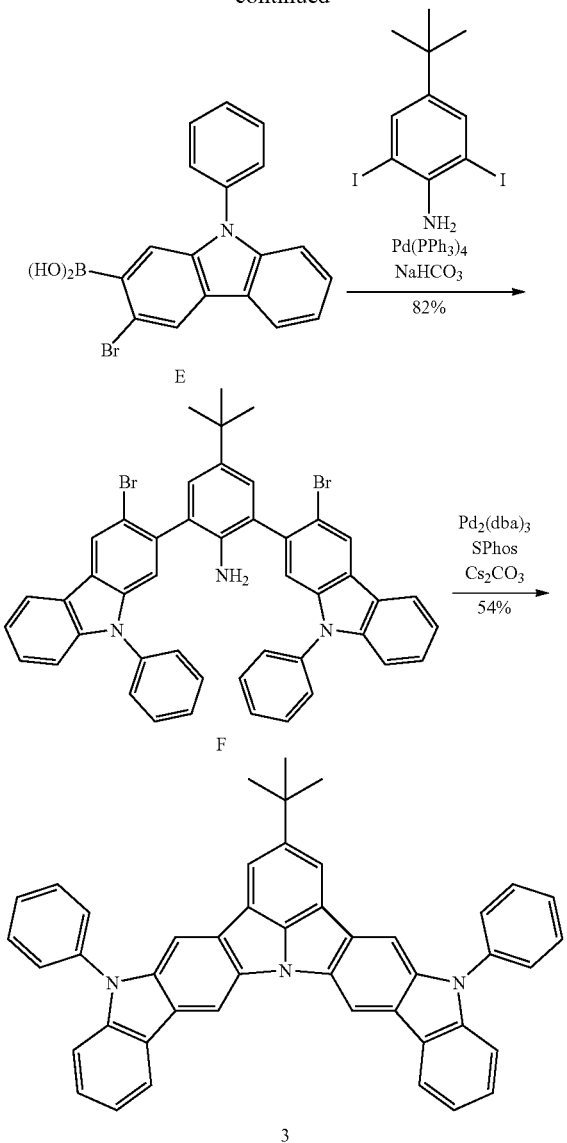

(2-1) Synthesis of Intermediate E

Under an argon atmosphere, 8.80 g (62.4 mmol) of 2,2,6,6-tetramethylpiperidine (TMP) was dissolved in 90 mL of anhydrous tetrahydrofuran (THF), and cooled to −50° C. with a dry ice/acetone bath. 40.3 mL (1.55 mol/L, 62.5 mmol) of a hexane solution of n-butyl lithium (n-BuLi) was added thereto, and after agitating at −50° C. for 30 minutes, cooled to −70° C. 20.0 mL (86.7 mmol) of triisopropoxyborane (B(O$^i$Pr)$_3$) was added dropwise thereto, and after the lapse of 5 minutes, 45 mL of a THF solution having 10.1 g (31.4 mmol) of the compound D dissolved therein was added thereto, followed by agitating in a cooling bath for 10 hours. 130 mL of hydrochloric acid having a concentration of 10% by mass was added to the reaction mixture, and after agitating at room temperature for 30 minutes, the mixture was extracted with 200 mL of ethyl acetate. The organic layer was washed with 30 mL of a saturated sodium chloride aqueous solution, and dried over magnesium sulfate, and then the solvent was distilled off, followed by drying under reduced pressure, so as to provide 10.6 g of a yellow amorphous solid matter. The solid matter was purified by column chromatography to provide 4.20 g of a pale yellow solid matter (yield: 37%). The resulting solid matter was the intermediate E as the target product, and the mass spectrum analysis thereof revealed m/e=366 for the molecular weight of 366.02.

(2-2) Synthesis of Intermediate F

Under an argon atmosphere, 4.20 g (11.5 mmol) of the intermediate E, 2.00 g (4.99 mmol) of 4-tert-butyl-2,6-diiodoaniline, 0.58 g (0.50 mmol) of tetrakis(triphenylphosphine) palladium(0) (Pd(PPh$_3$)$_4$), and 3.5 g (42 mmol) of sodium hydrogen carbonate (NaHCO$_3$) were added to 70 mL of 1,2-dimethoxyethane to provide a suspension liquid, to which 35 mL of water was added, and the suspension liquid was refluxed for 11 hours. The reaction mixture was extracted with 250 mL of dichloromethane, and dried over magnesium sulfate, and then the solvent was distilled off, followed by drying under reduced pressure, so as to provide 5.6 g of a yellow amorphous solid matter. The solid matter was purified by column chromatography to provide 3.25 g of a white solid matter (yield: 82%). The resulting solid matter was the intermediate F as the target product, and the mass spectrum analysis thereof revealed m/e=789 for the molecular weight of 789.6.

(2-3) Synthesis of Compound 3

Under an argon atmosphere, 3.25 g (4.12 mmol) of the intermediate F, 0.15 g (0.16 mmol) of tris(dibenzylideneacetone) dipalladium(0) (Pd$_2$(dba)$_3$), 0.27 g (0.66 mmol) of 2-dicyclohexylphosphino-2',6'-dimethoxybiphenyl (SPhos), and 8.10 g (24.8 mmol) of cesium carbonate (Cs$_2$CO$_3$) were added to 320 mL of anhydrous xylene to provide a suspension liquid, which was refluxed for 11 hours. The reaction mixture was filtered to provide a filtrate, from which the solvent was distilled off, followed by drying under reduced pressure, so as to provide 3.27 g of a brown solid matter. The solid matter was purified by column chromatography to provide 1.40 g of a yellow solid matter. The resulting solid matter was recrystallized from 40 mL of toluene to provide 1.14 g of yellow plate-like crystals (yield: 54%). The resulting solid matter was the compound 3 as the target product, and the mass spectrum analysis thereof revealed m/e=627 for the molecular weight of 627.77.

(Synthesis Example 3) Synthesis of Compound 4

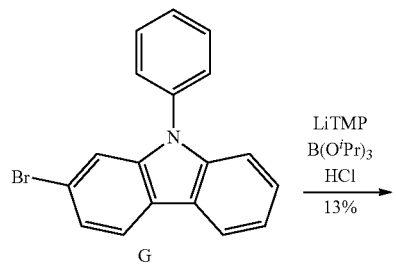

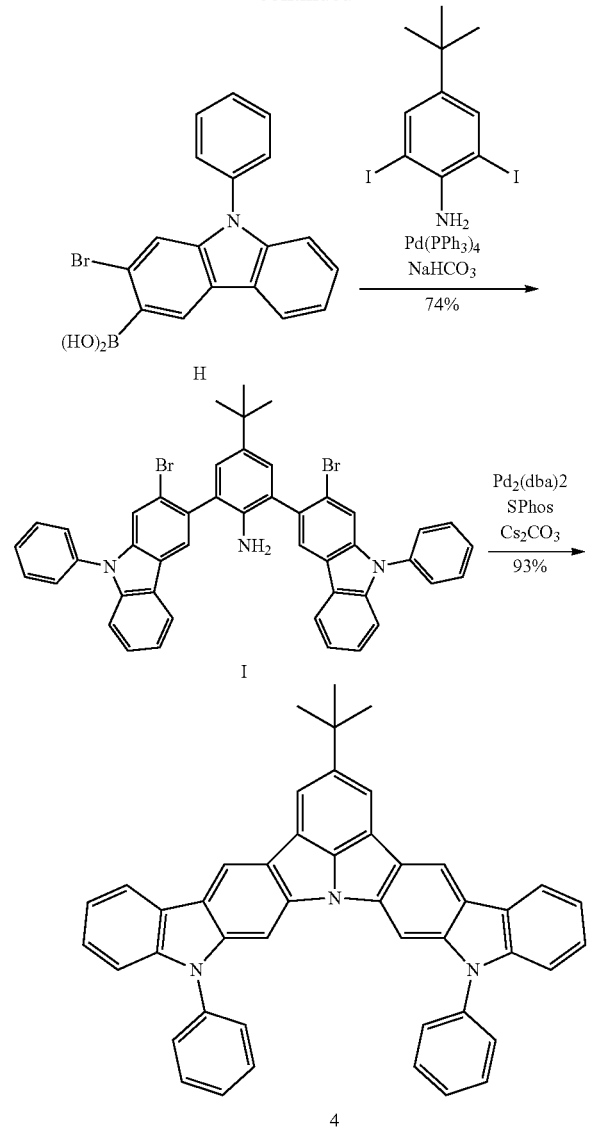

(3-1) Synthesis of Intermediate H

Under an argon atmosphere, 8.80 g (62.4 mmol) of 2,2,6,6-tetramethylpiperidine (TMP) was dissolved in 90 mL of anhydrous tetrahydrofuran (THF), and cooled to −50° C. with a dry ice/acetone bath. 40.3 mL (1.55 mol/L, 62.5 mmol) of a hexane solution of n-butyl lithium (n-BuLi) was added thereto, and after agitating at −50° C. for 30 minutes, cooled to −70° C. 20.0 mL (86.7 mmol) of triisopropoxyborane (B(O$^i$Pr)$_3$) was added dropwise thereto, and after the lapse of 5 minutes, 40 mL of a THF solution having 10.0 g (31.0 mmol) of the compound G dissolved therein was added thereto, followed by agitating in a cooling bath for 10 hours. 130 mL of hydrochloric acid having a concentration of 10% by mass was added to the reaction mixture, and after agitating at room temperature for 30 minutes, the mixture was extracted with 200 mL of ethyl acetate. The organic layer was washed with 30 mL of a saturated sodium chloride aqueous solution, and dried over magnesium sulfate, and then the solvent was distilled off, followed by drying under reduced pressure, so as to provide 8.7 g of a brown amorphous solid matter. The solid matter was purified by column chromatography to provide 1.42 g of a yellow solid matter (yield: 13%). The resulting solid matter was the intermediate H as the target product, and the mass spectrum analysis thereof revealed m/e=366 for the molecular weight of 366.02.

(3-2) Synthesis of Intermediate I

Under an argon atmosphere, 1.42 g (3.88 mmol) of the intermediate H, g (1.77 mmol) of 4-tert-butyl-2,6-diiodoaniline, 0.20 g (0.17 mmol) of tetrakis(triphenylphosphine) palladium(0) (Pd(PPh$_3$)$_4$), and 1.2 g (14 mmol) of sodium hydrogen carbonate (NaHCO$_3$) were added to 25 mL of 1,2-dimethoxyethane to provide a suspension liquid, to which 12 mL of water was added, and the suspension liquid was refluxed for 11 hours. The reaction mixture was extracted with 200 mL of dichloromethane, and dried over magnesium sulfate, and then the solvent was distilled off, followed by drying under reduced pressure, so as to provide 2.0 g of a yellow amorphous solid matter. The solid matter was purified by column chromatography to provide 1.04 g of a white solid matter (yield: 74%). The resulting solid matter was the intermediate I as the target product, and the mass spectrum analysis thereof revealed m/e=789 for the molecular weight of 789.6.

(3-3) Synthesis of Compound 4

Under an argon atmosphere, 1.04 g (1.32 mmol) of the intermediate I, 0.05 g (0.055 mmol) of tris(dibenzylideneacetone) dipalladium(0) (Pd$_2$(dba)$_3$), 0.09 g (0.22 mmol) of 2-dicyclohexylphosphino-2',6'-dimethoxybiphenyl (SPhos), and 2.60 g (7.98 mmol) of cesium carbonate (Cs$_2$CO$_3$) were added to 100 mL of anhydrous xylene to provide a suspension liquid, which was refluxed for 10 hours. The reaction mixture was filtered, and the filtered product was washed with water and methanol, and dried under reduced pressure to provide a brown solid matter. The solid matter was purified by column chromatography to provide 0.78 g of a yellow solid matter (yield: 94%). The resulting solid matter was the compound 4 as the target product, and the mass spectrum analysis thereof revealed m/e=627 for the molecular weight of 627.77.

[Production of Organic EL Device]

The compounds used in Examples and Comparative Examples below are shown below.

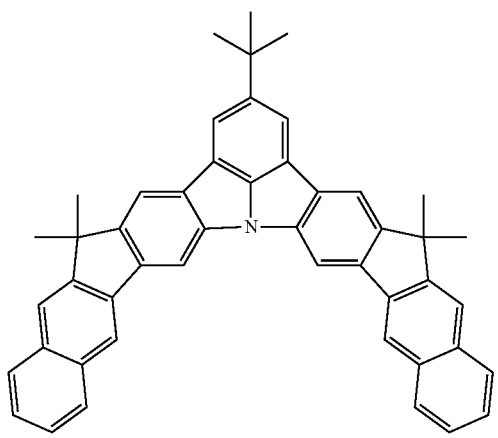

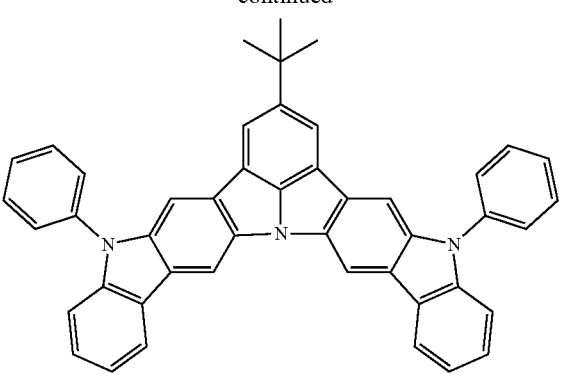

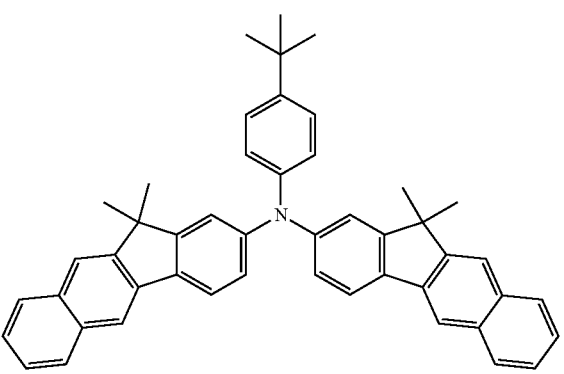

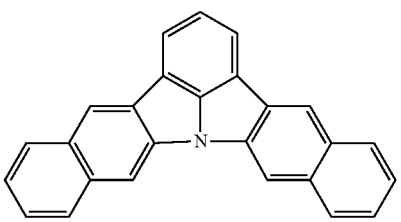

Compound 2
Compound 3
Comparative Compound 1
Comparative Compound 2

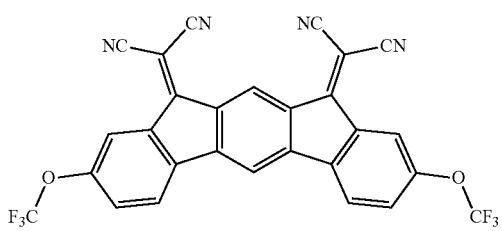

HI-1

HT-1
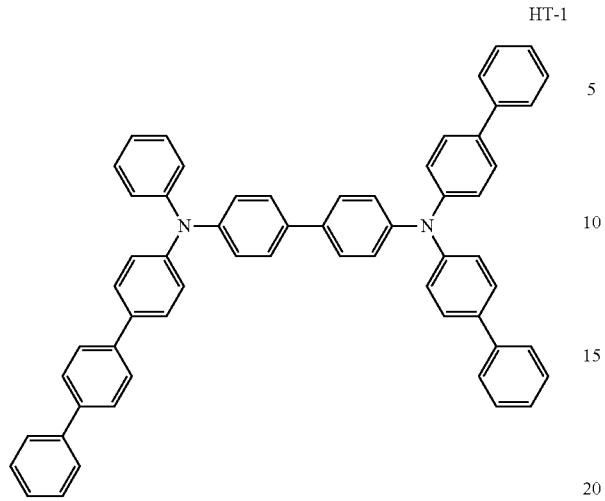
HT-2
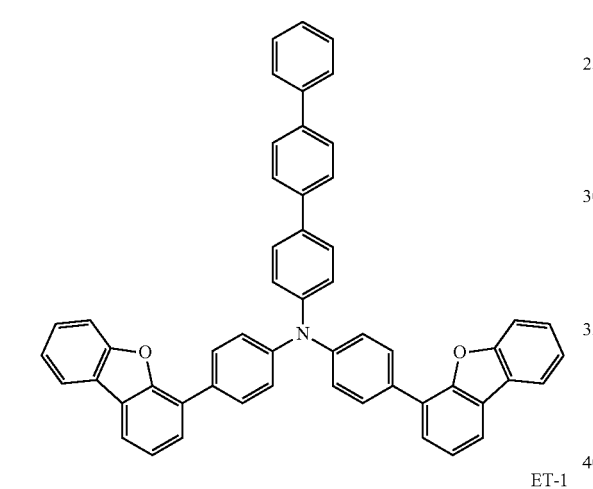
ET-1
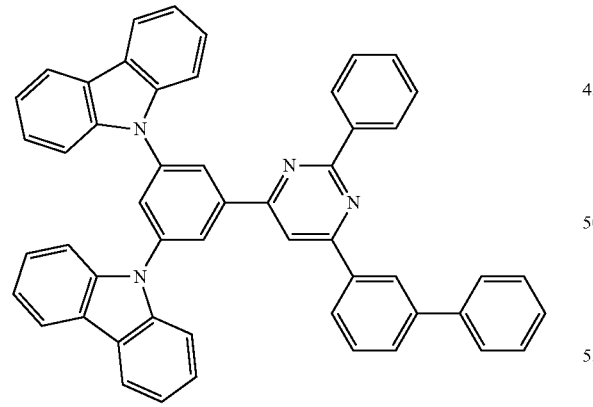
ET-2
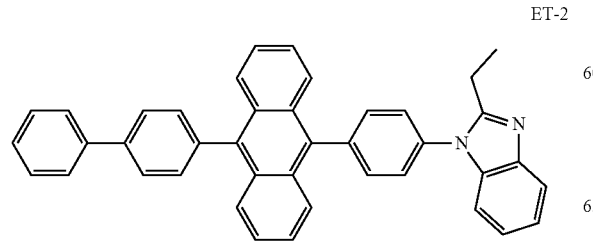
BD-1
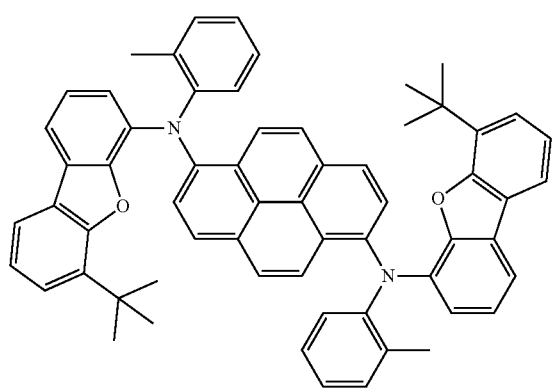
BH-1
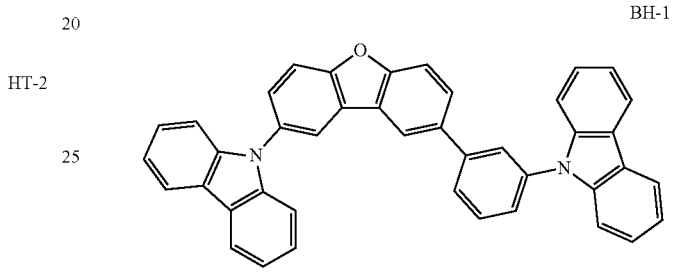
BH-2
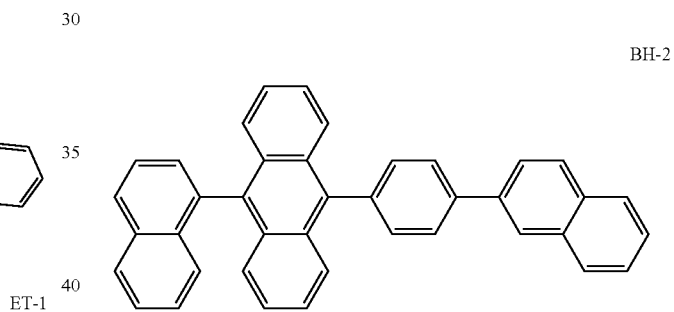
BH-3
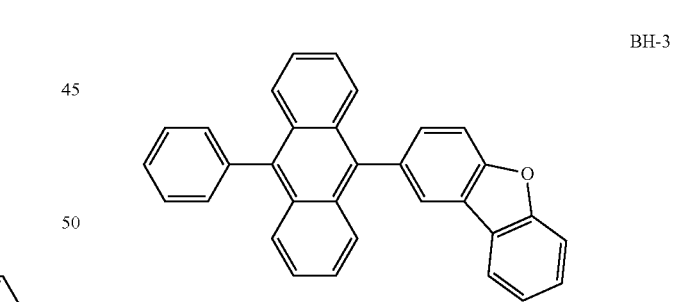
BH-4
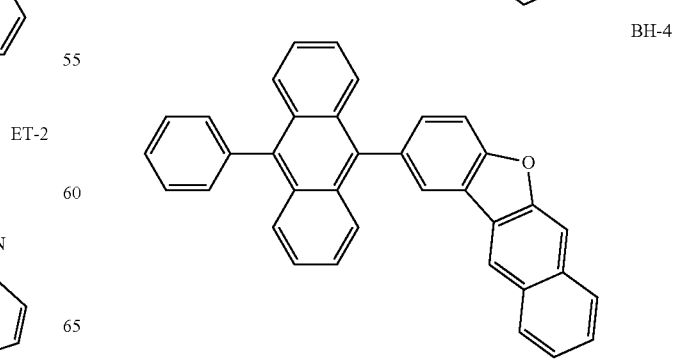

-continued

BH-5

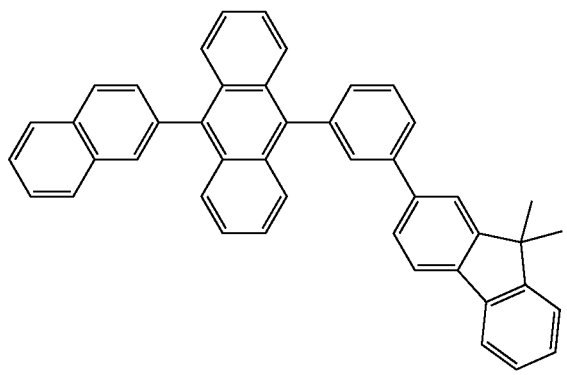

The organic EL devices produced in Examples and Comparative Examples below were evaluated in such a manner that the organic EL device was driven with a direct current at a constant current of a current density of 10 mA/cm² at room temperature (25° C.), and the light emission spectrum was measured with a spectral radiance meter ("CS-1000", produced by Konica Minolta, Inc.).

The main peak wavelength and the CIE 1931 chromaticity coordinate (x,y) were obtained from the resulting light emission spectrum. The external quantum efficiency EQE (%) was obtained on the assumption that the Lambertian radiation was performed.

Example 1

A glass substrate of 25 mm×75 mm×1.1 mm in thickness having an ITO transparent electrode (anode) (produced by Geomatec Co., Ltd., ITO film thickness: 130 nm) was subjected to ultrasonic cleaning in isopropyl alcohol for 5 minutes, and then subjected to UV ozone cleaning for 30 minutes.

The cleaned glass substrate having a transparent electrode was mounted on a substrate holder of a vacuum vapor deposition equipment.

The compound HI-1 was vapor-deposited on the electrode pattern forming surface of the glass substrate to cover the transparent electrode, so as to form a hole injection layer having a film thickness of 5 nm. On the hole injection layer, the compound HT-1 was vapor-deposited to form a first hole transport layer having a film thickness of 80 nm. On the first hole transport layer, the compound 2 was vapor-deposited to form a second hole transport layer having a thickness of 10 nm. On the second hole transport layer, the compound BH-2 (host material) and BD-1 (dopant material, concentration: 4% by mass) were vapor-co-deposited to form a light emitting layer having a film thickness of 25 nm. On the light emitting layer, the compound ET-1 was vapor-deposited to form a first electron transport layer having a film thickness of 10 nm. On the first electron transport layer, the compound ET-2 was vapor-deposited to form a second electron transport layer having a film thickness of 15 nm. On the second electron transport layer, lithium fluoride (LiF) was vapor-deposited to form an electron injection layer having a film thickness of 1 nm. On the electron injection layer, aluminum (Al) was vapor-deposited to form a metal cathode having a film thickness of 80 nm, and thus an organic EL device was produced.

The summary of the laminated structure of the organic EL device is as follows. The numeral in parenthesis shows the film thickness (nm).

ITO (130)/HI-1 (5)/HT-1 (80)/Compound 2 (10)/BH-2 and BD-1 (25/4% by mass)/ET-1 (10)/ET-2 (15)/LiF (1)/Al (80)

The organic EL device showed blue light emission with a main peak wavelength of 454 nm and had an external quantum efficiency of 6.5%.

Comparative Example 1

An organic EL device was produced in the same manner as in Example 1 except that the comparative compound 1 was used instead of the compound 2 in Example 1.

The summary of the laminated structure of the organic EL device is as follows. The numeral in parenthesis shows the film thickness (nm).

ITO (130)/HI-1 (5)/HT-1 (80)/Comparative Compound 1 (10)/B H-2 and BD-1 (25/4% by mass)/ET-1 (10)/ET-2 (15)/LiF (1)/Al (80)

The organic EL device showed blue light emission with a main peak wavelength of 455 nm and had an external quantum efficiency of 2.4%.

It is understood from the evaluation results above that the case using the compound 2 in the hole transport layer provided the organic EL device having a higher efficiency than the case using the comparative compound 1.

Example 2

An organic EL device was produced in the same manner as in Example 1 except that the second hole transport layer was formed by using the compound HT-2 instead of the compound 2, and the light emitting layer was formed by using the compound BH-1 instead of the compound BH-2 and using the compound 2 instead of the compound BD-1, in Example 1.

The summary of the laminated structure of the organic EL device is as follows. The numeral in parenthesis shows the film thickness (nm).

ITO (130)/HI-1 (5)/HT-1 (80)/HT-2 (10)/BH-1 and Compound 2 (25/4% by mass)/ET-1 (10)/ET-2 (15)/LiF (1)/Al (80)

The organic EL device showed blue light emission with a main peak wavelength of 434 nm and the chromaticity coordinate (x,y)=(0.155,0.043).

It is understood from the evaluation results above that the compound 2 can be used not in the hole transport layer but in the light emitting layer.

Example 3

An organic EL device was produced in the same manner as in Example 2 except that the light emitting layer was formed by using the compound BH-2 instead of the compound BH-1 and using the compound 3 instead of the compound 2 in Example 2.

The summary of the laminated structure of the organic EL device is as follows. The numeral in parenthesis shows the film thickness (nm).

ITO (130)/HI-1 (5)/HT-1 (80)/HT-2 (10)/BH-2 and Compound 3 (25/4% by mass)/ET-1 (10)/ET-2 (15)/LiF (1)/Al (80)

The organic EL device had an external quantum efficiency of 7.5%.

Example 4

An organic EL device was produced in the same manner as in Example 3 except that the light emitting layer was formed by using the compound BH-3 instead of the compound BH-2 in Example 3.

The summary of the laminated structure of the organic EL device is as follows. The numeral in parenthesis shows the film thickness (nm).

ITO (130)/HI-1 (5)/HT-1 (80)/HT-2 (10)/BH-3 and Compound 3 (25/4% by mass)/ET-1 (10)/ET-2 (15)/LiF (1)/Al (80)

The organic EL device had an external quantum efficiency of 7.1%.

Example 5

An organic EL device was produced in the same manner as in Example 3 except that the light emitting layer was formed by using the compound BH-4 instead of the compound BH-2 in Example 3.

The summary of the laminated structure of the organic EL device is as follows. The numeral in parenthesis shows the film thickness (nm).

ITO (130)/HI-1 (5)/HT-1 (80)/HT-2 (10)/BH-4 and Compound 3 (25/4% by mass)/ET-1 (10)/ET-2 (15)/LiF (1)/Al (80)

The organic EL device had an external quantum efficiency of 7.0%.

Example 6

An organic EL device was produced in the same manner as in Example 3 except that the light emitting layer was formed by using the compound BH-5 instead of the compound BH-2 in Example 3.

The summary of the laminated structure of the organic EL device is as follows. The numeral in parenthesis shows the film thickness (nm).

ITO (130)/HI-1 (5)/HT-1 (80)/HT-2 (10)/BH-5 and Compound 3 (25/4% by mass)/ET-1 (10)/ET-2 (15)/LiF (1)/Al (80)

The organic EL device had an external quantum efficiency of 7.0%.

Comparative Example 2

An organic EL device was produced in the same manner as in Example 3 except that the comparative compound 2 was used instead of the compound 3 in Example 3.

The summary of the laminated structure of the organic EL device is as follows. The numeral in parenthesis shows the film thickness (nm).

ITO (130)/HI-1 (5)/HT-1 (80)/HT-2 (10)/BH-2 and Comparative Compound 2 (25/4% by mass)/ET-1 (10)/ET-2 (15)/LiF (1)/Al (80)

The organic EL device had an external quantum efficiency of 6.4%.

Comparative Example 3

An organic EL device was produced in the same manner as in Example 5 except that the comparative compound 3 was used instead of the compound 3 in Example 5.

The summary of the laminated structure of the organic EL device is as follows. The numeral in parenthesis shows the film thickness (nm).

ITO (130)/HI-1 (5)/HT-1 (80)/HT-2 (10)/BH-4 and Comparative Compound 2 (25/4% by mass)/ET-1 (10)/ET-2 (15)/LiF (1)/Al (80)

The organic EL device had an external quantum efficiency of 4.8%.

It is understood from the evaluation results above that the case using the compound 3 in the light emitting layer provided the organic EL device having a higher efficiency than the case using the comparative compound 2.

The external quantum efficiencies of the organic EL devices in Example 1 and Comparative Example 1 are shown in Table 1, and the external quantum efficiencies of the organic EL devices in Examples 3 to 6 and Comparative Examples 2 and 3 are shown in Table 2.

TABLE 1

| | Material of second hole transport layer | Material of light emitting layer | | External quantum efficiency EQE (%) |
|---|---|---|---|---|
| | | Host material | Dopant material | |
| Example 1 | Compound 2 | BH-2 | BD-1 | 6.5 |
| Comparative Example 1 | Comparative Compound 1 | BH-2 | BD-1 | 2.4 |

TABLE 2

| | Material of second hole transport layer | Material of light emitting layer | | External quantum efficiency EQE (%) |
|---|---|---|---|---|
| | | Host material | Dopant material | |
| Example 3 | HT-2 | BH-2 | Compound 3 | 7.5 |
| Example 4 | HT-2 | BH-3 | Compound 3 | 7.1 |
| Example 5 | HT-2 | BH-4 | Compound 3 | 7.0 |
| Example 6 | HT-2 | BH-5 | Compound 3 | 7.0 |
| Comparative Example 2 | HT-2 | BH-2 | Comparative Compound 2 | 6.4 |
| Comparative Example 3 | HT-2 | BH-4 | Comparative Compound 2 | 4.8 |

REFERENCE SIGN LIST

1, 11: Organic EL device

2: Substrate

3: Anode

4: Cathode

5: Light emitting layer

6: Hole transport band (Hole transport layer)

6a: First hole transport layer

6b: Second hole transport layer

7: Electron transport band (Electron transport layer)

7a: First electron transport layer

7b: Second electron transport layer

10, 20: Light emitting unit

The invention claimed is:

1. A compound represented by the following formula (1):

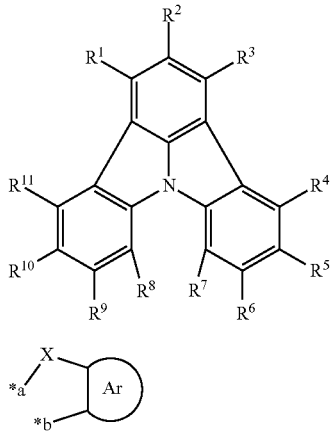
(1)

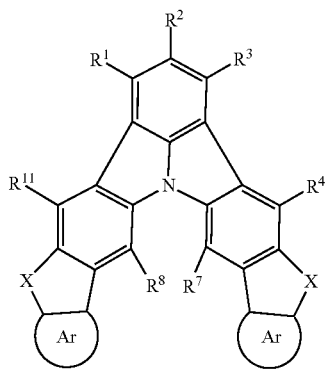
(11)

wherein in the formula (1):
in $R^5$ and $R^6$, one member of the pair represents a single bond bonded to *a of a group represented by the formula (11), and the other member represents a single bond bonded to *b of the group represented by the formula (11);
in $R^9$ and $R^{10}$, one member of the pair represents a single bond bonded to *a of a group represented by the formula (11), and the other member represents a single bond bonded to *b of the group represented by the formula (11);
$R^1$ to $R^4$, $R^7$, $R^8$, and $R^{11}$ each independently represent a hydrogen atom or a substituted or unsubstituted alkyl group having 1 to 5 carbon atoms;
X represents a group represented by —C($R^{31}$)($R^{32}$)—, or a group represented by —$NR^{33}$—;
Ar represents a substituted or unsubstituted benzene ring or a substituted or unsubstituted naphthalene ring, wherein any substituents on the substituted benzene ring or the substituted naphthalene ring are unsubstituted alkyl groups having 1 to 5 carbon atoms;
$R^{31}$ and $R^{32}$ each independently represent an unsubstituted alkyl group having 1 to 5 carbon atoms, or an unsubstituted phenyl group; and
$R^{33}$ is an unsubstituted phenyl group.

2. The compound according to claim 1, wherein the compound is represented by any of the following formulae (2-1) to (2-3):

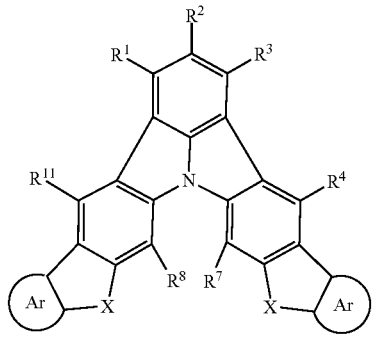
(2-1)

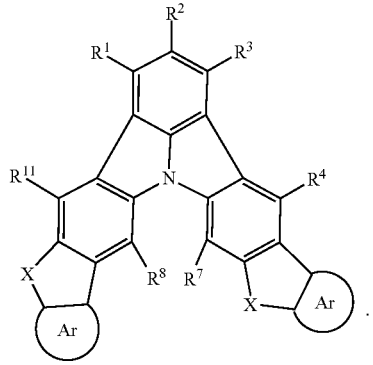
(2-2)

(2-3)

3. The compound according to claim 2, wherein the compound is represented by the formula (2-1).

4. The compound according to claim 2, wherein the compound is represented by the formula (2-2).

5. The compound according to claim 1, wherein X represents a group represented by —C($R^{31}$)($R^{32}$)—.

6. The compound according to claim 1, wherein the group represented by the formula (11) is represented by any of the following formulae (11-1) to (11-4):

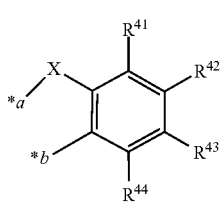
(11-1)

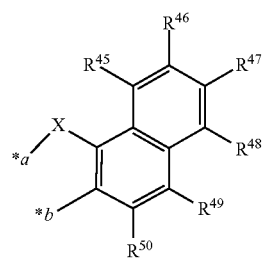
(11-2)

-continued

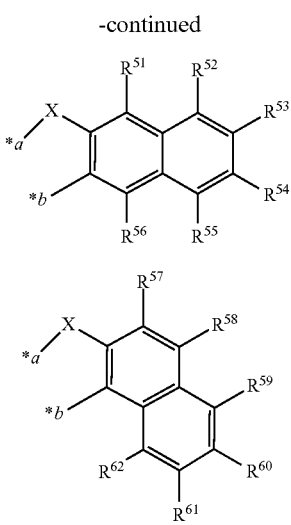

wherein in the formulae (11-1) to (11-4), $R^{41}$ to $R^{62}$ have the same definitions as any of $R^1$ to $R^4$, $R^7$, $R^8$, and $R^{11}$.

7. A compound represented by the following formula (1):

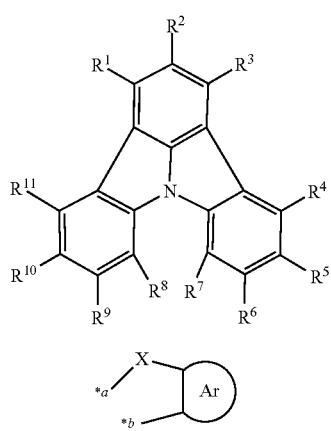

wherein in the formula (1);
in one member of the pair represents a single bond bonded to *a of a group represented by the formula (11), and the other member represents a single bond bonded to *b of the group represented by the formula (11);
in $R^9$ and $R^{10}$, one member of the pair represents a single bond bonded to *a of a group represented by the formula (11), and the other member represents a single bond bonded to *b of the group represented by the formula (11);
$R^1$ to $R^4$, $R^7$, $R^8$, and $R^{11}$ each independently represent a hydrogen atom or a substituted or unsubstituted alkyl group having 1 to 5 carbon atoms;
X represents a group represented by —C($R^{31}$)($R^{32}$)—, or a group represented by —$NR^{33}$—;
Ar represents a substituted or unsubstituted benzene ring or a substituted or unsubstituted naphthalene ring, wherein any substituents on the substituted benzene ring or the substituted naphthalene ring are unsubstituted alkyl groups having 1 to 5 carbon atoms;
$R^{31}$ and $R^{32}$ each independently represent an unsubstituted alkyl group having 1 to 5 carbon atoms, or an unsubstituted phenyl group or $R^{31}$ and $R^{32}$ form a substituted or unsubstituted ring structure, or $R^{33}$ forms a substituted or unsubstituted ring structure with at least one selected from adjacent $R^1$ to $R^{11}$ and Ar, or $R^{33}$ represents an unsubstituted phenyl group.

8. A material for an organic electroluminescent device, comprising the compound according to claim 1.

9. An organic electroluminescent device comprising an anode, a cathode, and an organic layer provided therebetween, the organic layer including a light emitting layer, at least one layer of the organic layer including the compound according to claim 1.

10. The organic electroluminescent device according to claim 9, wherein the light emitting layer includes the compound.

11. The organic electroluminescent device according to claim 9, wherein:
the organic layer includes a hole transport layer; and
the hole transport layer includes a compound that represented by the following formula (1);

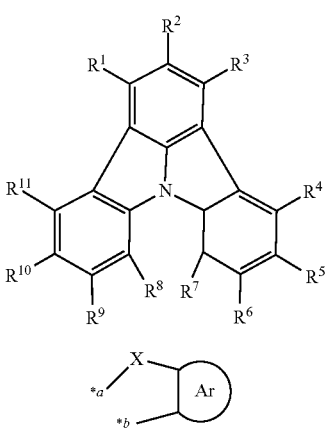

wherein in the formula (1):
in $R^5$ and $R^6$, one member of the pair represents a single bond bonded to *a of a group represented by the formula (11), and the other member represents a single bond bonded to *b of the group represented by the formula (11);
in $R^9$ and $R^{10}$, one member of the pair represents a single bond bonded to *a of a group represented by the formula (11), and the other member represents a single bond bonded to *b of the group represented by the formula (11);
$R^1$ to $R^4$, $R^7$, $R^8$, and $R^{11}$ each independently represent a hydrogen atom, or a substituted or unsubstituted alkyl group having 1 to 5 carbon atoms;
X represents a group represented by —C($R^{31}$)($R^{32}$)— or a group represented by —$NR^{33}$—;
Ar represents a substituted or unsubstituted benzene ring or a substituted or unsubstituted naphthalene ring, wherein any substituents on the substituted benzene ring or the substituted naphthalene ring are unsubstituted alkyl groups having 1 to 5 carbon atoms;
$R^{31}$ and $R^{32}$ each independently represent an unsubstituted alkyl group having 1 to 5 carbon atoms, or an unsubstituted phenyl group; and
$R^{33}$ represents an unsubstituted phenyl group.

12. The organic electroluminescent device according to claim 9, wherein at least one layer of the organic layer contains the compound and a compound represented by the following formula (31):

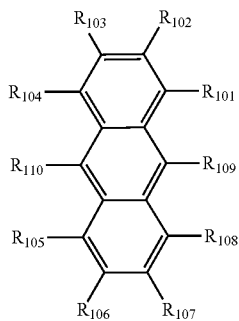

(31)

wherein in the formula (31), at least one of $R_{101}$ to $R_{110}$ represents a group represented by the following formula (41), in which in the case where two or more groups represented by the following formula (41) exist, the two or more groups represented by the following formula (41) may be the same as or different from each other:

-$L_{101}$-$Ar_{101}$ (41)

wherein in the formula (41),
$L_{101}$ represents
a single bond,
a substituted or unsubstituted arylene group having 6 to 30 ring carbon atoms, or a substituted or unsubstituted divalent heterocyclic group having 5 to 30 ring atoms,
$Ar_{101}$ represents
a substituted or unsubstituted aryl group having 6 to 50 ring carbon atoms, or
a substituted or unsubstituted monovalent heterocyclic group having 5 to 50 ring atoms,
in $R_{101}$ to $R_{110}$ that do not represent a group represented by the formula (41), one or more combination of two or more adjacent groups forms a substituted or unsubstituted saturated or unsaturated ring or does not form the ring,
$R_{101}$ to $R_{110}$ that do not represent a group represented by the formula (41) and do not form the ring each independently represent
a hydrogen atom, a halogen atom, a cyano group, a nitro group,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group having 6 to 50 ring carbon atoms, or a substituted or unsubstituted monovalent heterocyclic group having 5 to 50 ring atoms, and
$R_{901}$ to $R_{907}$ each independently represent
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms, in which in the case where two or more groups represented by $R_{901}$ to $R_{907}$ exist, the two or more groups represented by $R_{901}$ to $R_{907}$ may be the same as or different from each other.

13. The organic electroluminescent device according to claim 12, wherein the compound represented by the formula (31) is a compound represented by the following formula (31-1) or (31-2):

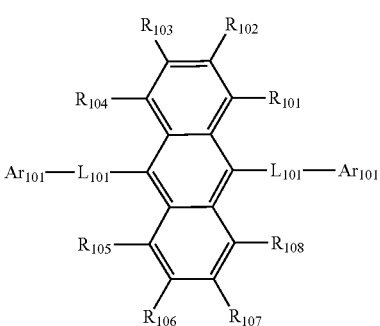

(31-1)

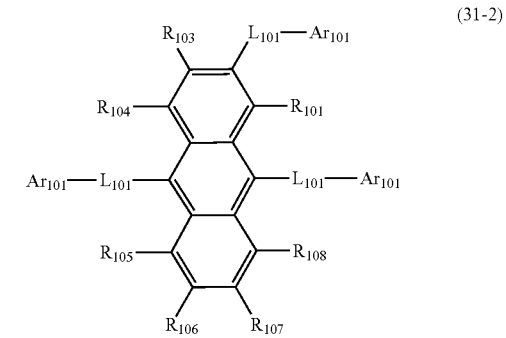

(31-2)

wherein in the formula (31-1), $R_{101}$ to $R_{108}$, $L_{101}$, and $Ar_{101}$ have the same definitions as in the formula (31), and in the formula (31-2), $R_{101}$, $R_{103}$ to $R_{108}$, $L_{101}$, and $Ar_{101}$ have the same definitions as in the formula (31).

14. The organic electroluminescent device according to claim 12, wherein the compound represented by the formula (31) is a compound represented by the following formula (31-3):

(31-3)

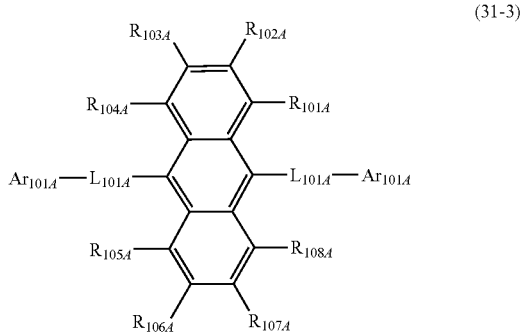

wherein in the formula (31-3), $R_{101A}$ to $R_{108A}$ each independently represent a hydrogen atom or a substituted or unsubstituted aryl group having 6 to 50 ring carbon atoms, $L_{101A}$ represents a single bond or a substituted or unsubstituted arylene group having 6 to 30 ring carbon atoms, in which the two groups represented by $L_{101A}$ may be the same as or different from each other, and $Ar_{101A}$ represents a substituted or unsubstituted aryl group having 6 to 50 ring carbon atoms, in which the two groups represented by $Ar_{101A}$ may be the same as or different from each other.

15. The organic electroluminescent device according to claim 12, wherein the compound represented by the formula (31) is a compound represented by the following formula (31-4):

(31-4)

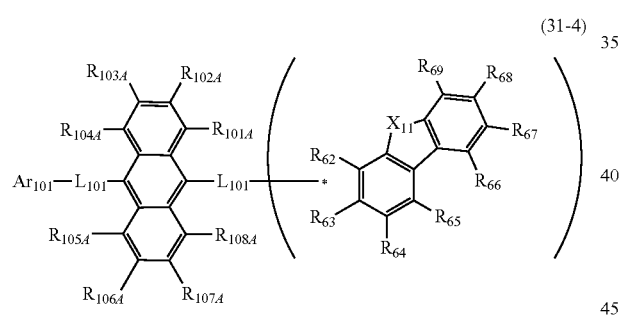

wherein in the formula (31-4), $L_{101}$ and $Ar_{101}$ have the same definitions as in the formula (31), $R_{101A}$ to $R_{108A}$ each independently represent a hydrogen atom or a substituted or unsubstituted aryl group having 6 to 50 ring carbon atoms, $X_{11}$ represents an oxygen atom (—O—), a sulfur atom (—S—), —C($R_{91}$)($R_{92}$)—, or —N$R_{61}$—, $R_{91}$ and $R_{92}$ have the same definition as $R^{31}$ and $R^{32}$, $R_{61}$ represents a hydrogen atom, a substituted or unsubstituted alkyl group having 1 to 50 carbon atoms, or a substituted or unsubstituted aryl group having 6 to 50 ring carbon atoms, one of $R_{62}$ to $R_{69}$ represents a bond bonded to $L_{101}$, in $R_{62}$ to $R_{69}$ that are not bonded to $L_{101}$, one or more combination of two or more adjacent groups forms a substituted or unsubstituted saturated or unsaturated ring or does not form the ring, $R_{62}$ to $R_{69}$ that are not bonded to $L_{101}$ and do not form the ring each independently represent a hydrogen atom, a substituted or unsubstituted alkyl group having 1 to 50 carbon atoms, or a substituted or unsubstituted aryl group having 6 to 50 ring carbon atoms.

16. The organic electroluminescent device according to claim 12, wherein the compound represented by the formula (31) is a compound represented by the following formula (31-6H):

(31-6H)

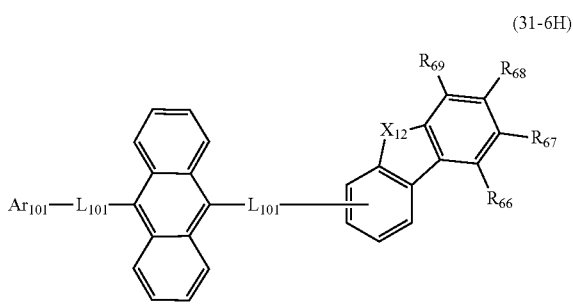

wherein in the formula (31-6H), $L_{101}$ and $Ar_{101}$ have the same definitions as in the formula (31), $R_{66}$ to $R_{69}$ have the same definitions as in the formula (31-4), $X_{12}$ represents an oxygen atom (—O—), a sulfur atom (—S—), or —C($R_{91}$)($R_{92}$)—, and $R_{91}$ and $R_{92}$ have the same definition as $R^{31}$ and $R^{32}$.

17. The organic electroluminescent device according to claim 15, wherein the compound represented by the formula (31) is a compound represented by the following formula (31-7):

(31-7)

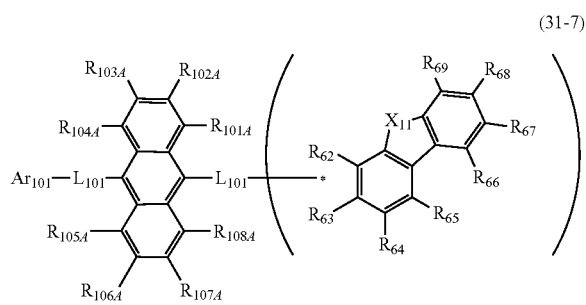

wherein in the formula (31-7), $L_{101}$ and $Ar_{101}$ have the same definitions as in the formula (31), $R_{101A}$ to $R_{108A}$ have the same definitions as in the formula (31-4), $X_{11}$ has the same definition as in the formula (31-4), and $R_{62}$ to $R_{69}$ have the same definitions as in the formula (31-4), provided that any one of the combinations of $R_{66}$ and $R_{67}$, $R_{67}$ and $R_{68}$, and $R_{68}$ and $R_{69}$ forms a substituted or unsubstituted saturated or unsaturated ring through bonding the members thereof.

18. The organic electroluminescent device according to claim 12, wherein the compound represented by the formula (31) is a compound represented by the following formula (31-8):

(31-8)

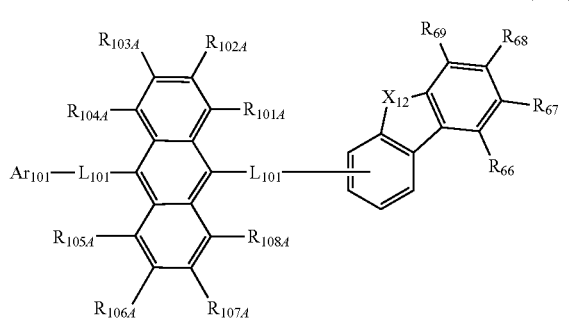

wherein in the formula (31-8), $L_{101}$ and $Ar_{101}$ have the same definitions as in the formula (31), $R_{101A}$ to $R_{108A}$ have the same definitions as in the formula (31-4), $X_{12}$ represents an oxygen atom (—O—), a sulfur atom (—S—), or —C($R_{91}$)($R_{92}$)—, $R_{91}$ and $R_{92}$ have the same definition as $R^{31}$ and $R^{32}$, and $R_{66}$ to $R_{69}$ have the same definitions as in the formula (31-4), provided that any one of the combinations of $R_{66}$ and $R_{67}$, $R_{67}$ and $R_{68}$, and $R_{68}$ and $R_{69}$ forms a substituted or unsubstituted saturated or unsaturated ring through bonding the members thereof.

19. The organic electroluminescent device according to claim 17, wherein any one of the combinations of $R_{66}$ and $R_{67}$, $R_{67}$ and $R_{68}$, and $R_{68}$ and $R_{69}$ forms a ring represented by the following formula (31-8-1) or (31-8-2) through bonding the members thereof, and $R_{66}$ to $R_{69}$ that do not form a ring represented by the following formula (31-8-1) or (31-8-2) do not form a substituted or unsubstituted saturated or unsaturated ring:

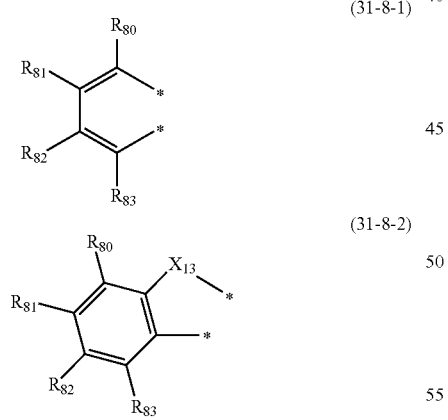

wherein in the formulae (31-8-1) and (31-8-2), two bonds * are bonded to any one of the combinations of $R_{66}$ and $R_{67}$, $R_{67}$ and $R_{68}$, and $R_{68}$ and $R_{69}$, $R_{80}$ to $R_{83}$ each independently represent a hydrogen atom, a substituted or unsubstituted alkyl group having 1 to 50 carbon atoms, or a substituted or unsubstituted aryl group having 6 to 50 ring carbon atoms, $X_{13}$ represents an oxygen atom (—O—), a sulfur atom (—S—), or —C($R_{91}$)($R_{92}$)—, and $R_{91}$ and $R_{92}$ have the same definition as $R^{31}$ and $R^{32}$.

20. The organic electroluminescent device according to claim 15, wherein the compound represented by the formula (31) is a compound represented by the following formula (31-9):

(31-9)

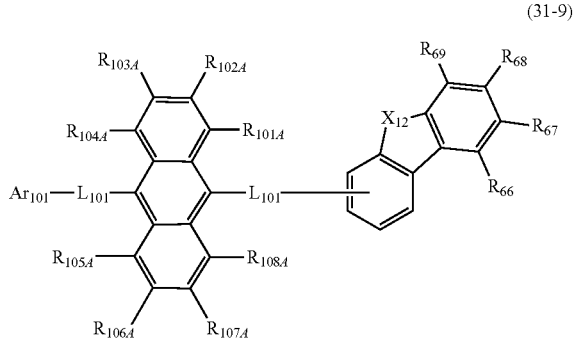

wherein in the formula (31-9), $L_{101}$ and $Ar_{101}$ have the same definitions as in the formula (31), $R_{101A}$ to $R_{108A}$ have the same definitions as in the formula (31-4), $R_{66}$ to $R_{69}$ have the same definitions as in the formula (31-4), provided that $R_{66}$ and $R_{67}$, $R_{67}$ and $R_{68}$, and $R_{68}$ and $R_{69}$ each are not bonded to each other and do not form a substituted or unsubstituted saturated or unsaturated ring, $X_{12}$ represents an oxygen atom (—O—), a sulfur atom (—S—), or —C($R_{91}$)($R_{92}$)—, and $R_{91}$ and $R_{92}$ have the same definition as $R^{31}$ and $R^{32}$.

21. The organic electroluminescent device according to claim 12, wherein the compound represented by the formula (31) is a compound represented by the following formula (31-4A):

(31-4A)

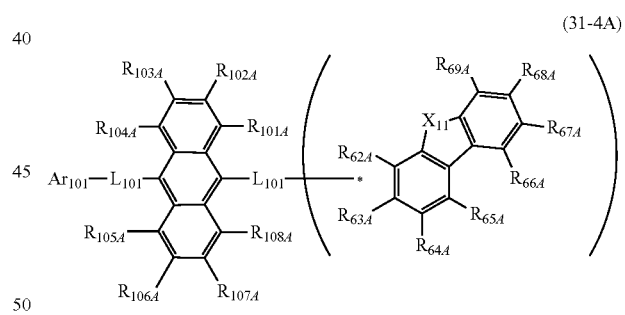

wherein in the formula (31-4A), $L_{101}$ and $Ar_{101}$ have the same definitions as in the formula (31), $R_{101A}$ to $R_{108A}$ each independently represent a hydrogen atom or a substituted or unsubstituted aryl group having 6 to 50 ring carbon atoms, $X_{11}$ represents an oxygen atom (—O—), a sulfur atom (—S—), —C($R_{91}$)($R_{92}$)—, or —$NR_{61}$—, $R_{91}$ and $R_{92}$ have the same definition as $R^{31}$ and $R^{32}$, $R_{61}$ represents a hydrogen atom, a substituted or unsubstituted alkyl group having 1 to 50 carbon atoms, or a substituted or unsubstituted aryl group having 6 to 50 ring carbon atoms, in $R_{62A}$ to $R_{69A}$, any one combination of two adjacent groups forms a ring represented by the following formula (31-4A-1):

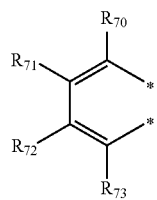 (31-4A-1)

wherein in the formula (31-4A-1), two bonds * are bonded to adjacent two of $R_{62A}$ to $R_{69A}$ respectively, one of $R_{70}$ to $R_{73}$ represents a bond bonded to $L_{101}$, $R_{70}$ to $R_{73}$ that are not bonded to $L_{101}$ each independently represent a hydrogen atom, a substituted or unsubstituted alkyl group having 1 to 50 carbon atoms, or a substituted or unsubstituted aryl group having 6 to 50 ring carbon atoms, in $R_{62A}$ to $R_{69A}$ that do not form the ring represented by the formula (31-4A-1), one or more combination of two or more adjacent groups forms a substituted or unsubstituted saturated or unsaturated ring or does not form the ring, and $R_{62A}$ to $R_{69A}$ that do not form the ring represented by the formula (31-4A-1) and do not form the substituted or unsubstituted saturated or unsaturated ring each independently represent a hydrogen atom, a substituted or unsubstituted alkyl group having 1 to 50 carbon atoms, or a substituted or unsubstituted aryl group having 6 to 50 ring carbon atoms.

22. An electronic device comprising the organic electroluminescent device according to claim 9.

* * * * *